US008404466B2

(12) United States Patent
Baier et al.

(10) Patent No.: US 8,404,466 B2
(45) Date of Patent: Mar. 26, 2013

(54) METABOLICALLY ENHANCED PHOTOAUTOTROPHIC ETHANOL PRODUCING HOST CELLS, METHOD FOR PRODUCING THE HOST CELLS, CONSTRUCTS FOR THE TRANSFORMATION OF THE HOST CELLS, AND METHOD OF PRODUCING ETHANOL USING THE HOST CELLS

(75) Inventors: Kerstin Baier, Kleinmachnow (DE); Ulf Duhring, Fredersdorf (DE); Christine Oesterhelt, Berlin (DE); Karl Ziegler, Zeuthen (DE); Heike Enke, Berlin (DE)

(73) Assignee: Algenol Biofuels Inc., Bonita Springs, FL (US)

( * ) Notice: Subject to any disclaimer, the term of this patent is extended or adjusted under 35 U.S.C. 154(b) by 0 days.

(21) Appl. No.: 13/372,456

(22) Filed: Feb. 13, 2012

(65) Prior Publication Data
US 2012/0142066 A1    Jun. 7, 2012

Related U.S. Application Data

(63) Continuation of application No. PCT/EP2009/060526, filed on Aug. 13, 2009.

(51) Int. Cl.
C12P 7/06 (2006.01)
C12P 21/06 (2006.01)
C12P 19/34 (2006.01)
C12N 1/00 (2006.01)
C12N 1/20 (2006.01)
C12N 1/12 (2006.01)
C12N 15/00 (2006.01)
C07H 21/04 (2006.01)

(52) U.S. Cl. ........... 435/161; 435/243; 435/252.3; 435/257.2; 435/320.1; 435/69.1; 435/91.1; 536/23.1; 536/23.2

(58) Field of Classification Search ............ 435/161, 435/243, 252.3, 257.2, 320.1, 69.1, 91.1; 536/23.1, 23.2
See application file for complete search history.

(56) References Cited

U.S. PATENT DOCUMENTS

| 5,000,000 | A | 3/1991 | Ingram et al. |
| 5,270,175 | A | 12/1993 | Moll |
| 6,306,639 | B1 | 10/2001 | Woods et al. |
| 6,699,696 | B2 | 3/2004 | Woods et al. |
| 7,314,974 | B2 | 1/2008 | Cao et al. |
| 2009/0155871 | A1 | 6/2009 | Fu et al. |
| 2009/0203070 | A1* | 8/2009 | Devroe et al. ............... 435/69.1 |
| 2010/0003739 | A1 | 1/2010 | Duhring et al. |
| 2010/0068776 | A1 | 3/2010 | Woods et al. |
| 2010/0297736 | A1* | 11/2010 | Duhring et al. ............. 435/252.3 |
| 2011/0008861 | A1* | 1/2011 | Berry et al. .................. 435/161 |

FOREIGN PATENT DOCUMENTS

| EP | 1854889 | 11/2007 |
| WO | WO 9839457 | 9/1998 |
| WO | WO 2009/062190 | 5/2009 |
| WO | WO 2009078712 | 6/2009 |
| WO | WO 2009/098089 | 8/2009 |
| WO | WO 2011/018116 | 2/2011 |

OTHER PUBLICATIONS

Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Dias et al., Antisense oligonucleotides: Basic concepts and mechanisms. Mol. Cancer Therap., 2002, vol. 1: 347-355.*
Kisselev L., Polypeptide release factors in prokaryotes and eukaryotes: same function, different structure. Structure, 2002, vol. 10: 8-9.*
Kurreck J., Antisense technologies, Eur. J. Biochem., 2003, vol. 270: 1628-1644.*
Sen et al., Developments in directed evolution for improving enzyme functions. Appl. Biochem. Biotechnol., 2007, vol. 143: 212-223.*
Whisstock et al., Prediction of protein function from protein sequence. Q. Rev. Biophysics., 2003, vol. 36 (3): 307-340.*
Wishart et al., A single mutation converts a novel phosphotyrosine binding domain into a dual-specificity phosphatase. J. Biol. Chem., 1995, vol. 270(45): 26782-26785.*
Guo et al., Protein tolerance to random amino acid change. PNAS., 2004, vol. 101 (25): 9205-9210.*
Bowie et al., "Deciphering the Message in Protein Sequences: Tolerance to Amino Acid Substitution," Science 247:1306-1310 (1990).
Office Action for U.S. Appl. No. 12/368,060 dated Feb. 7, 2012.
Office Action for U.S. Appl. No. 12/368,160 dated May 25, 2010.
Amendment and Response to Office Action for U.S. Appl. No. 12/368,160, dated Nov. 24, 2010.
Supplemental Amendment and Response to Office Action for U.S. Appl. No. 12/368,160, dated Apr. 18, 2011.
Office Action for U.S. Appl. No. 12/368,160 dated Sep. 27, 2011.
Amendment and Response to Office Action for U.S. Appl. No. 12/368,160 dated Dec. 16, 2011.

(Continued)

*Primary Examiner* — Ganapathirama Raghu
(74) *Attorney, Agent, or Firm* — Lawrence B. Ebert; David J. Lorenz; Suzanne G. Jepson

(57) ABSTRACT

One embodiment of the invention provides a metabolically enhanced photoautotrophic, ethanol producing host cell comprising:
at least two first metabolic enhancements reducing the enzymatic activity or affinity of at least two endogenous host cell enzymes involved in acetate and lactate fermentation,
the first metabolic enhancements resulting in an enhanced level of biosynthesis of acetaldehyde, pyruvate, acetyl-CoA or precursors thereof compared to the respective wild type host cell,
at least one second metabolic enhancement different from the first metabolic enhancement comprising an overexpressed enzyme for the formation of ethanol.

21 Claims, 82 Drawing Sheets

OTHER PUBLICATIONS

Notice of Allowance/Allowability for U.S. Appl. No. 12/368,160 dated Jan. 30, 2012.
International Search Report for No. PCT/EP2009/000892 dated Jan. 7, 2010.
International Preliminary Report on Patentability and Written Opinion for PCT/EP2009/000892 dated Aug. 10, 2010.
Deng, M-D et al., "Ethanol Synthesis by Genetic Engineering in Cyanobacteria," Applied and Environmental Microbiology, 65: 523-528 (1999).
NCBI Database Accession No. P73162, Nov. 1, 1997.
NCBI Database Accession No. P72661, Oct. 31, 2006.
NCBI Database Accession No. Q55383, Aug. 16, 2004.
Ncbi Database Accession No. P73662, May 30, 2000.
NCBI Database Accession No. BAA10564, Dec. 22, 2010.
NCBI Database Accession No. X52328.1, Jan. 29, 2002.
NCBI Database Accession No. X06404, Mar. 10, 2001.
NCBI Database Accession No. M77789, Aug. 7, 2008.
NCBI Database Accession No. X06403, Nov. 14, 2006.
NCBI Database Accession No. P74586, Oct. 31, 2006.
NCBI Database Accession No. AF100176, Dec. 1, 2000.
Nakamura et al., "CyanoBase, the Genome Database for *Synechocystis* sp. Strain PCC6803: Status for the Year 2000," Nucleic Acids Research 18:72 (2000).
Gfeller et al.,"Fermentative Metabolism of *Chlamydomonas reinhardtii*," Plant Physiology 75:212-218 (1984).
Duran et al., "The Efficient Functioning of Photosynthesis and Respiration in *Synechocystis* sp. PCC 6803 Strictly Requires the Presence of either Cytochrome c6 or Plastocyanin," Journal of Biological Chemistry 279:7229-7233 (2004).
Singh et al., "The Heat Shock Response in the Cyanobacterium *Synechocystis* sp. Strain PCC 6803 and Regulation of Gene Expression by HrcA and SigB," Arch Microbiol. 186:273-286 (2006).
Imamura et al., "Antagonistic Dark/light-induced SigB/SigD, Group 2 Sigma Factors, Expression Through Redox Potential and their Roles in Cyanobacteria," FEBS Lett. 554:357-362 (2003).
Imamura et al., "Growth Phase-dependent Activation of Nitrogen-related Genes by a Control Network of Group 1 and Group 2 Sigma Factors in a Cyanobacterium," Jour. Biol. Chem. 281:2668-2675 (2006).
Samartzidou et al., "Transcriptional and Posttranscriptional Control of mRNA from IrtA, a Light-repressed Transcript in *Synechococcus* sp. PCC 7002," Plant Physiol. 117:225-234 (1998).
Agrawal et al., "Light-dependent and Rhythmic psbA Transcripts in Homologous/heterologous Cyanobacterial Cells," Biochem. Biophys. Res. Commun. 255:47-53 (1999).
Mohamed et al., "Influence of Light on Accumulation of Photosynthesis-specific Transcripts in the Cyanobacterium *Synechocystis* 6803," Plant Mol. Biol. 13:693-700 (1989).
Herranen et al., "Regulation of Photosystem I Reaction Center Genes in *Synechocystis* sp. Strain PCC 6803 During Light Acclimation," Plant Cell Physiol. 46:1484-1493 (2005).
Muramatsu et al., "Characterization of High-light-responsive Promoters of the psaAB Genes in *Synechocystis* sp. PCC 6803," Plant Cell Physiol. 47:878-890 (2006).
Marin et al., "Gene Expression Profiling Reflects Physiological Processes in Salt Acclimation of *Synechocystis* sp. strain PCC 6803," Plant Physiol. 136:3290-3300 (2004).
Marin et al., "Salt-dependent Expression of Glucosylglycerol-phosphate Synthase, Involved in Osmolyte Synthesis in the Cyanobacterium *Synechocystis* sp. Strain PCC 6803," Jour. Bacteriol. 184:2870-2877 (2002).
Qi et al., "Application of the *Synechococcus* nirA Promoter to Establish an Inducible Expression System for Engineering the Synechocystis Tocopherol Pathway," Appl. Environ. Microbiol. 71:5678-5684 (2005).
Maeda et al., "cis-acting Sequences Required for NtcB-dependent, Nitrite-responsive Positive Regulation of the Nitrate Assimilation Operon in the Cyanobacterium *Synechococcus* sp. Strain PCC 7942," Jour. Bacteriol. 180:4080-4088 (1998).
Ghassemian et al., "Cloning, Sequencing and Transcriptional Studies of the Genes for Cytochrome c-553 and Plastocyanin from *Anabaena* sp. PCC 7120," Microbiology 140:1151-1159 (1994).
Buikema et al., "Expression of the Anabaena hetR gene from a Copper-regulated Promoter Leads to Heterocyst Differentiation under Repressing Conditions," Proc. Natl. Acad. Sci. U S A. 98:2729-2734 (2001).
Fang et al., "Expression of the Heat Shock Gene hsp16.6 and Promoter Analysis in the Cyanobacterium, *Synechocystis* sp. PCC 6803," Curr Microbiol. 49:192-198 (2004).
Suzuki et al., "The Heat Shock Response of *Synechocystis* sp. PCC 6803 Analyzed by Transcriptomics and Proteomics," Jour. Exp. Bot. 57:1573-1578 (2006).
He et al., "The High Light-inducible Polypeptides in *Synechocystis* PCC6803. Expression and Function in High Light," Jour. Biol. Chem. 276:306-314 (2001).
Kappell et al., "The Response Regulator RpaB Binds the High Light Regulatory 1 Sequence Upstream of the High-light-inducible hliB Gene from the Cyanobacterium *Synechocystis* PCC 6803," Arch. Microbiol. 187:337-342 (2007).
Mary et al., "Effects of High Light on Transcripts of Stress-associated Genes for the Cyanobacteria *Synechocystis* sp. PCC 6803 and *Prochlorococcus* MED4 and MIT9313," Microbiology 150:1271-1281 (2004).
International Preliminary Report and Written Opinion for PCT/EP2009/060526 dated Feb. 14, 2012.
Branden et al., "Introduction to Protein Structure," Garland Publishing Inc., New York, p. 247 (1991).
Juntarajumnong et al., "Two-component Signal Transduction in *Synechococcus* sp. PCC 6803 under Phosphate Limitation: Role of Acetyl Phosphate," Jour. Biochem. Mol. Biol. 40:708-714 (2007).
Kaneko et al., "Sequence Analysis of the Genome of the Unicellular Cyanobacterium *Synechocystis* sp. Strain PCC 6803. II Sequence Determination of the Entire Genome and Assignment of Potential Protein-coding Regions," DNA Research, 3:109-136 (1996).
Seffernick et al., "Melamine Deaminase and Atrazine Chlorohydrolase: 98 Percent Identical but Functionally Different," Jour. Bacteriol. 183:2405-2410 (2001).
Spreitzer et al., "Rubisco: Structure, Regulatory Interactions, and Possibilities for a Better Enzyme," Annu. Rev. Plant Biol. 53:449-475 (2002).
Wahlund et al., "Bioconversion of CO2 to Ethanol and Other Compounds," Am. Chem. Soc. Div. Fuel Chem. 41:1403-1406 (1996).
Witkowski et al., "Conversion of a Beta-Ketoacyl Synthase to a Malonyl Decarboxylase by Replacement of the Active-Site Cysteine with Glutamine," Biochemistry 38:11643-11650 (1999).
Dexter et al., "Metabolic Engineering of Cyanobacteria for Ethanol Production," Energy Env. Science 2:857-864 (2009).
Beutler et al. in: Methods in Enzymatic Analysis (Bergmeyer, H.U. ed.) 3rd ed. vol. 6:598-606, Verlag Chemie, Weinheim, Germany (1984).
Häusler et al., "Determination of Low-abundant Metabolites in Plant Extracts by NAD(P)H Fluorescence with a Microtiter Plate Reader," Anal. Biochem. 281:1-8 (2000).
Fu et al., "Genome-scale Modeling of *Synechocystis* sp. PCC 6803 and Prediction of Pathway Insertion," Journal of Chemical Technology & Biotechnology 84:473-483 (2009).
NCBI Database Accession No. P74690, Mar. 15, 2005.
Amichay et al., "Construction of a *Synechocystis* PCC6803 Mutant Suitable for the Study of Variant Hexadecameric Ribulose Bisphosphate Carboxylase/Oxygenase Enzymes" Plant Mol. Biol. 23:465-476 (1993).

* cited by examiner

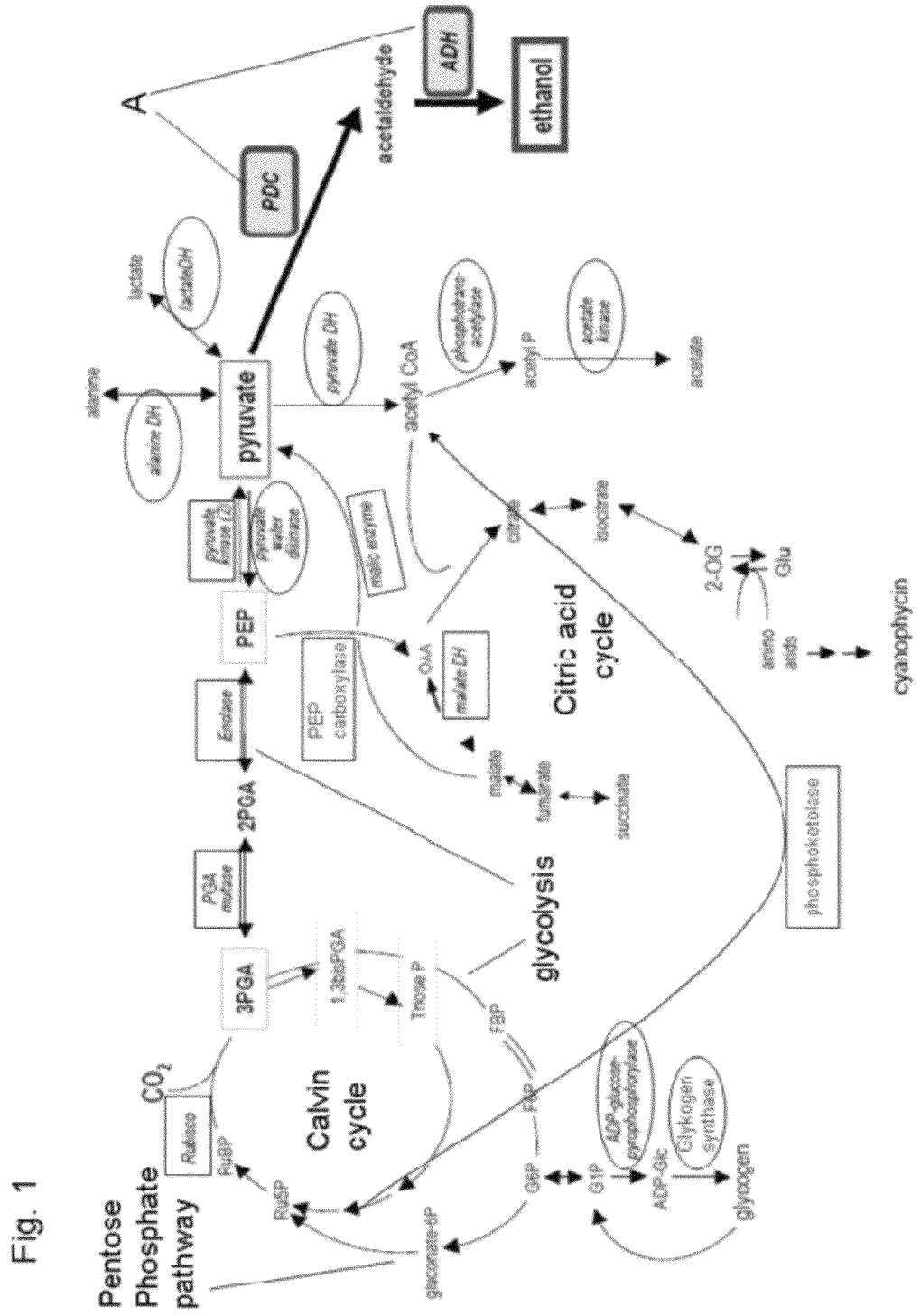

```
MVSLTPNPSYSVSLLLELPNHAGTLASVTQAIADAGGSFGQISLIESNLKLTRREIAVDA
SSSEHAEKIIGAVKALDNVKLLKVSDRTFDLHRQGKISVVSRIPLTSQSDLAMAYTPGVG
RICRAIAEDPEKVYSLTIKSNTVAVVTDGSAVLGLGNLGPEAALPVMEGKAMLFKEFAQL
DAFPICLDTQDTEEIIRTVKAIAPVFGGVNLEDIAAPRCFEIEARLKKELNIPVFHDDQH
GTAIVTLAALLNALKFVGKAMAAVRIVINGAGAAGLAIAELLKESGATDIWICDSKGIVG
KHRTDLNSKKQSFAVDAEGTLADAMAGADVFLGVSAPGVVTKEMVQSMAKDPIVFAMANP
IPEIQPELIQEDAAVIATGRSDYPNQINNVLAFPGVFRGAIDCRASIITTTMCIEAAKAI
ASLVHSNTLDSEHIIPSVFDNRVATTVASAVQLAARNEGVAGQ
```

Fig. 4 (SEQ ID NO. 1)

```
   1 CACCTAAATT GTAAGCGTTA ATATTTTGTT AAAATTCGCG TTAAATTTTT
  51 GTTAAATCAG CTCATTTTTT AACCAATAGG CCGAAATCGG CAAAATCCCT
 101 TATAAATCAA AAGAATAGAC CGAGATAGGG TTGAGTGTTG TTCCAGTTTG
 151 GAACAAGAGT CCACTATTAA AGAACGTGGA CTCCAACGTC AAAGGGCGAA
 201 AAACCGTCTA TCAGGGCGAT GGCCCACTAC GTGAACCATC ACCCTAATCA
 251 AGTTTTTTGG GGTCGAGGTG CCGTAAAGCA CTAAATCGGA ACCCTAAAGG
 301 GAGCCCCCGA TTTAGAGCTT GACGGGGAAA GCCGGCGAAC GTGGCGAGAA
 351 AGGAAGGGAA GAAAGCGAAA GGAGCGGGCG CTAGGGCGCT GGCAAGTGTA
 401 GCGGTCACGC TGCGCGTAAC CACCACACCC GCCGCGCTTA ATGCGCCGCT
 451 ACAGGGCGCG TCCCATTCGC CATTCAGGCT GCGCAACTGT TGGGAAGGGC
 501 GATCGGTGCG GGCCTCTTCG CTATTACGCC AGCTGGCGAA AGGGGGATGT
 551 GCTGCAAGGC GATTAAGTTG GGTAACGCCA GGGTTTTCCC AGTCACGACG
 601 TTGTAAAACG ACGGCCAGTG AATTGTAATA CGACTCACTA TAGGGCGAAT
 651 TGGAGGCCAG TGCTGGAGGA ATATGATTTT GTCATCCTCG ACTGTGCCCC
 701 TGGTTATAAT CTGTTGACCC GCAGTGGCAT TGCGGCCAGC GACTTTTATC
 751 TGTTGCCGGC TCGTCCTGAA CCCCTATCGG TGGTGGGGAT GCAGTTACTG
 801 GAAAGAAGAA TTGAGAAACT GAAGGAAAGC CATAAGGCCT CCGATGATCC
 851 CCTGAATATC AATCTGATCG GAGTGGTGTT TATTCTGTCC GGCGGCGGTT
 901 TGATGAGTCG CTACTATAAC CAGGTAATGC GGCGGGTACA AACGGATTTC
 951 ACCCCGGGAC AACTTTTTCA GCAGTCCATT CCCATGGATG TCAATGTGGC
1001 TAAGGCAGTG GATAGCTTTA TGCCGGTGGT TACCTCCATG CCCAATACGG
1051 CGGGTTCAAA AGCTTTTATT AAATTAACCC AGGAATTTTT ACAGAAAGTA
1101 GAAGCTTTTG GCTAAAGCAA AGCCCCCATT GATTAACAAC GGGAGGGGTA
1151 CCGAGGTGCT GCTGAAGTTG CCCGCAACAG AGAGTGGAAC CAACCGGTGA
1201 TACCACGATA CTATGACTGA GAGTCAACGC CATGAGCGGC CTCATTTCTT
1251 ATTCTGAGTT ACAACAGTCC GCACCGCTGT CCGGTAGCTC CTTCCGGTGG
1301 GCGCGGGGCA TGACTATCGT CGCCGCACTT ATGACTGTCT TCTTTATCAT
1351 GCAACTCGTA GGACAGGTGC CGGCAGCGCC CAACAGTCCC CCGGCCACGG
1401 GGCCTGCCAC CATACCCACG CCGAAACAAG CGCCCTGCAC CATTATGTTC
1451 CGGATCTGCA TCGCAGGATG CTGCTGGCTA CCCTGTGGAA CACCTACATC
1501 TGTATTAACG AAGCGCTAAC CGTTTTTATC AGGCTCTGGG AGGCAGAATA
1551 AATGATCATA TCGTCAATTA TTACCTCCAC GGGGAGAGCC TGAGCAAACT
1601 GGCCTCAGGC ATTTGAGAAG CACACGGTCA CACTGCTTCC GGTAGTCAAT
1651 AAACCGGTAA ACCAGCAATA GACATAAGCG GCTATTTAAC GACCCTGCCC
1701 TGAACCGACG ACCGGGTCGA ATTTGCTTTC GAATTTCTGC CATTCATCCG
1751 CTTATTATCA CTTATTCAGG CGTAGCACCA GGCGTTTAAG GGCACCAATA
1801 ACTGCCTTAA AAAAATTACG CCCCGCCCTG CCACTCATCG CAGTACTGTT
1851 GTAATTCATT AAGCATTCTG CCGACATGGA AGCCATCACA GACGGCATGA
1901 TGAACCTGAA TCGCCAGCGG CATCAGCACC TTGTCGCCTT GCGTATAATA
1951 TTTGCCCATG GTGAAAACGG GGGCGAAGAA GTTGTCCATA TTGGCCACGT
```

Fig. 4-1A

```
2001 TTAAATCAAA ACTGGTGAAA CTCACCCAGG GATTGGCTGA GACGAAAAAC
2051 ATATTCTCAA TAAACCCTTT AGGGAAATAG GCCAGGTTTT CACCGTAACA
2101 CGCCACATCT TGCGAATATA TGTGTAGAAA CTGCCGGAAA TCGTCGTGGT
2151 ATTCACTCCA GAGCGATGAA AACGTTTCAG TTTGCTCATG GAAAACGGTG
2201 TAACAAGGGT GAACACTATC CCATATCACC AGCTCACCGT CTTTCATTGC
2251 CATACGGAAT TCCGGATGAG CATTCATCAG GCGGGCAAGA ATGTGAATAA
2301 AGGCCGGATA AAACTTGTGC TTATTTTTCT TTACGGTCTT TAAAAAGGCC
2351 GTAATATCCA GCTGAACGGT CTGGTTATAG GTACATTGAG CAACTGACTG
2401 AAATGCCTCA AAATGTTCTT TACGATGCCA TTGGGATATA TCAACGGTGG
2451 TATATCCAGT GATTTTTTC TCCATTTTAG CTTCCTTAGC TCCTGAAAAT
2501 CTCGATAACT CAAAAAATAC GCCCGGTAGT GATCTTATTT CATTATGGTG
2551 AAAGTTGGAA CCTCTTACCT CGGTACCCCT CATCGGGGC TGTGTTGGCC
2601 GAGACGGCAC TGAGGATTTT ACTCTCCATG GCATTCCAAG GAATATCTAC
2651 CCAACTCACC TGCTCCGGCG GATTGTTCCG CTCAAAAGTA CTAATCAAGT
2701 CGTCAAAATA CTTATTAAAT TTGGCTGCA ATTGCATAGT CCAAAAGCTG
2751 ACTTTCCCCT CCATGCTCTG GGGGGAATTG CTCTGGCAAC TGATTAATCC
2801 ACTGAGCAAC AGCCCAAGAC ACGCAAACAA AAACCAACGT CTTGGCGATC
2851 GCCATCGGCA CCATGAAACC ATCGTAAAAG CTGGGGAAAG AATAAAAAAC
2901 AGTGGTTCAG GAATTGCATT GCCATGGCCA CTTCACAAAC CTAGCCAATT
2951 TTAGCTTGAC CGCAACTTTG ACAGATTGTC TTTTGACTTT GCCTGGACCG
3001 CCTCCCATAA TACCTTCGCG TCTTGAAGAC TTTATCCTTG AAAGGAGAAC
3051 ATATGTTTCT CGGCAAAAAT TAATTATCGA TTGGCTGGAA CCTGGTCAAA
3101 CCAGGGCTTT TCATCCATTG GAAAAGCGAT TTTGATCATC TAGGGTCAGG
3151 AGCAAAGATC TGATCAAATA TTGATCATTT ATTAGGAAAG CTGAACTTTC
3201 ACCACTTTAT TTTTGGCTTC CTCTACTTTG GGCAAAGTCA AAGTTAGGAT
3251 ACCGGCATCG TAATTAGCTT TAACTTCTGT GTTTTGGATT GCTCCAGGTA
3301 CAGGAATAAC CCGGCGGAAA CTGCCATAGC GGAACTCTGT GCGCCGCACC
3351 CCATCTTTTT CGGTGCTATG GGTATCCTGG CGATCGCCGC TGACGGTCAC
3401 CGCATCCCTG GCGGCTTGGA TGTCCAAATT ATCGGGGTCC ATGCCAGGTA
3451 ATTCTAGTTT GAGCACATAG GCTTCTTCAG TTTCAGTTAG TTCTGCTTTA
3501 GGATTAAACC CTTGGCGATC GCCGTGGCGG TCCGTAGGGA CAAAAACTTC
3551 TTCAAACAGT TGGTTCATCT GCTGCTGGAA ATTATCCATT TCCCGCAGGG
3601 GATTGTAAAG AATGAGAGAC ATAATGTTAA CTCCTGATGT GTGGAAGGAA
3651 TTGATTACCC TTGAATGGTT CTATCTTAAA ATTTCCCCTT CCAGGTTAGA
3701 TTCGGTTTTC AGGAAAGAAG GTGGGGGGAT TGCCGAAATT ACATTTCTAG
3751 CCGCAATTTT TAGTAAAAAA AAGATGAGTT TTTACCTCAC CTTAAGTAAA
3801 TATTTGAGTG GCAAAACAAA ATGGTAAAAA TAGCTAAGCT TCCACCGCCC
3851 TATGGATTTT TGGAAGGAAG TCTTAGGTTG TGAAAAACTA AAAAACCAA
3901 CCATAGGAAT GGAGACCTTT ACCCAACAAG TTGACCCCTA GGTAACAAAT
3951 CCAAACCACC GTAAAACCGC TGGCGGCCAA AATAGCGGGC TTGCGGCCTT
```

Fig. 4-1A (Continued)

```
4001 GCCAACCTTT GGTAATGCGG GCATGGAGAT AGGCGGCAAA TACTAGCCAG
4051 GTGATTAGGG CCCGGTACCC AGCTTTTGTT CCCTTTAGTG AGGGTTAATT
4101 TCGAGCTTGG CGTAATCATG GTCATAGCTG TTTCCTGTGT GAAATTGTTA
4151 TCCGCTCACA ATTCCACACA ACATACGAGC CGGAAGCATA AAGTGTAAAG
4201 CCTGGGGTGC CTAATGAGTG AGCTAACTCA CATTAATTGC GTTGCGCTCA
4251 CTGCCCGCTT TCCAGTCGGG AAACCTGTCG TGCCAGCTGC ATTAATGAAT
4301 CGGCCAACGC GCGGGGAGAG GCGGTTTGCG TATTGGGCGC TCTTCCGCTT
4351 CCTCGCTCAC TGACTCGCTG CGCTCGGTCG TTCGGCTGCG GCGAGCGGTA
4401 TCAGCTCACT CAAAGGCGGT AATACGGTTA TCCACAGAAT CAGGGGATAA
4451 CGCAGGAAAG AACATGTGAG CAAAAGGCCA GCAAAAGGCC AGGAACCGTA
4501 AAAAGGCCGC GTTGCTGGCG TTTTTCCATA GGCTCCGCCC CCCTGACGAG
4551 CATCACAAAA ATCGACGCTC AAGTCAGAGG TGGCGAAACC CGACAGGACT
4601 ATAAAGATAC CAGGCGTTTC CCCCTGGAAG CTCCCTCGTG CGCTCTCCTG
4651 TTCCGACCCT GCCGCTTACC GGATACCTGT CCGCCTTTCT CCCTTCGGGA
4701 AGCGTGGCGC TTTCTCATAG CTCACGCTGT AGGTATCTCA GTTCGGTGTA
4751 GGTCGTTCGC TCCAAGCTGG GCTGTGTGCA CGAACCCCCC GTTCAGCCCG
4801 ACCGCTGCGC CTTATCCGGT AACTATCGTC TTGAGTCCAA CCCGGTAAGA
4851 CACGACTTAT CGCCACTGGC AGCAGCCACT GGTAACAGGA TTAGCAGAGC
4901 GAGGTATGTA GGCGGTGCTA CAGAGTTCTT GAAGTGGTGG CCTAACTACG
4951 GCTACACTAG AAGGACAGTA TTTGGTATCT GCGCTCTGCT GAAGCCAGTT
5001 ACCTTCGGAA AAAGAGTTGG TAGCTCTTGA TCCGGCAAAC AAACCACCGC
5051 TGGTAGCGGT GGTTTTTTTG TTTGCAAGCA GCAGATTACG CGCAGAAAAA
5101 AAGGATCTCA AGAAGATCCT TTGATCTTTT CTACGGGGTC TGACGCTCAG
5151 TGGAACGAAA ACTCACGTTA AGGGATTTTG GTCATGAGAT TATCAAAAAG
5201 GATCTTCACC TAGATCCTTT TAAATTAAAA ATGAAGTTTT AAATCAATCT
5251 AAAGTATATA TGAGTAAACT TGGTCTGACA GTTACCAATG CTTAATCAGT
5301 GAGGCACCTA TCTCAGCGAT CTGTCTATTT CGTTCATCCA TAGTTGCCTG
5351 ACTCCCCGTC GTGTAGATAA CTACGATACG GGAGGGCTTA CCATCTGGCC
5401 CCAGTGCTGC AATGATACCG CGAGACCCAC GCTCACCGGC TCCAGATTTA
5451 TCAGCAATAA ACCAGCCAGC CGGAAGGGCC GAGCGCAGAA GTGGTCCTGC
5501 AACTTTATCC GCCTCCATCC AGTCTATTAA TTGTTGCCGG GAAGCTAGAG
5551 TAAGTAGTTC GCCAGTTAAT AGTTTGCGCA ACGTTGTTGC CATTGCTACA
5601 GGCATCGTGG TGTCACGCTC GTCGTTTGGT ATGGCTTCAT TCAGCTCCGG
5651 TTCCCAACGA TCAAGGCGAG TTACATGATC CCCCATGTTG TGCAAAAAAG
5701 CGGTTAGCTC CTTCGGTCCT CCGATCGTTG TCAGAAGTAA GTTGGCCGCA
5751 GTGTTATCAC TCATGGTTAT GGCAGCACTG CATAATTCTC TTACTGTCAT
5801 GCCATCCGTA AGATGCTTTT CTGTGACTGG TGAGTACTCA ACCAAGTCAT
5851 TCTGAGAATA GTGTATGCGG CGACCGAGTT GCTCTTGCCC GGCGTCAATA
5901 CGGGATAATA CCGCGCCACA TAGCAGAACT TTAAAAGTGC TCATCATTGG
5951 AAAACGTTCT TCGGGGCGAA AACTCTCAAG GATCTTACCG CTGTTGAGAT
```

Fig. 4-1A (Continued)

```
6001 CCAGTTCGAT GTAACCCACT CGTGCACCCA ACTGATCTTC AGCATCTTTT
6051 ACTTTCACCA GCGTTTCTGG GTGAGCAAAA ACAGGAAGGC AAAATGCCGC
6101 AAAAAAGGGA ATAAGGGCGA CACGGAAATG TTGAATACTC ATACTCTTCC
6151 TTTTTCAATA TTATTGAAGC ATTTATCAGG GTTATTGTCT CATGAGCGGA
6201 TACATATTTG AATGTATTTA GAAAAATAAA CAAATAGGGG TTCCGCGCAC
6251 ATTTCCCCGA AAAGTGC
```

Fig. 4-1A (Continued)

```
   1 ATGGTTAGC CTCACCCCCA ATCCGAGTTA TAGCGTCAGC CTACTGTTGG
  51 AACTCCCCAA CCACGCCGGA ACTTTGGCCA GCGTTACCCA GGCGATCGCC
 101 GATGCGGGGG GCAGTTTTGG GCAAATTTCC CTGATTGAGA GTAACTTAAA
 151 ACTCACCCGG CGGGAAATTG CGGTGGATGC TTCCAGCAGT GAGCACGCCG
 201 AAAAAATTAT TGGGGCAGTG AAAGCTCTGG ATAATGTCAA ATTGCTGAAG
 251 GTGTCCGATC GCACCTTTGA TTTACACCGT CAGGGCAAAA TTAGCGTGGT
 301 TAGTCGCATT CCCCTCACCT CCCAATCGGA TTTGGCCATG GCCTATACCC
 351 CAGGGGTGGG GCGCATCTGT CGGCGATCG CCGAAGATCC GGAAAAGGTT
 401 TATTCCCTGA CCATTAAAAG CAATACGGTG GCGGTGGTGA CCGATGGCAG
 451 TGCGGTGTTG GGGTTGGGTA ACCTGGGGCC GGAAGCGGCT TTACCAGTGA
 501 TGGAAGGCAA GGCCATGTTA TTCAAGGAAT TTGCCCAACT GGACGCTTTT
 551 CCCATCTGTT TGGATACCCA GGATACGGAG GAAATTATTC GCACCGTCAA
 601 GGCGATCGCC CCGGTGTTTG GCGGCGTAAA TTTGGAAGAC ATTGCCGCTC
 651 CCCGGTGTTT TGAAATTGAA GCCCGGCTGA AAAAAGAATT AAATATTCCT
 701 GTATTTCACG ATGATCAGCA CGGCACCGCC ATTGTTACCC TGGCCGCTTT
 751 GTTAAATGCC CTCAAATTTG TTGGTAAAGC CATGGCCGCT GTCCGCATTG
 801 TCATCAACGG CGCTGGGGCT GCTGGGTTGG CGATCGCCGA ATTGCTCAAG
 851 GAATCCGGAG CCACCGATAT TTGGATTTGC GACTCCAAGG GCATTGTGGG
 901 CAAACATCGC ACCGATTTAA ACAGCAAAAA ACAGAGCTTT GCGGTGGATG
 951 CGGAAGGGAC TTTAGCCGAT GCTATGGCTG GAGCTGATGT GTTTTTAGGG
1001 GTGAGTGCGC CGGGGGTAGT GACCAAGGAA ATGGTGCAAT CCATGCCCAA
1051 GGACCCGATT GTGTTTGCCA TGGCCAACCC TATCCCCGAA ATTCAGCCGG
1101 AATTAATCCA AGAGGATGCG GCGGTTATTG CCACGGGGCG CAGTGATTAC
1151 CCCAACCAAA TTAACAATGT GCTTGCCTTT CCGGGGGTTT TCCGGCGAGC
1201 CATTGACTGT AGAGCTAGCA TTATTACCAC CACCATGTGC ATCGAAGCGG
1251 CCAAGGCGAT CGCCTCTTTG GTGCACAGCA ACACCCTAGA TAGTGAGCAT
1301 ATTATTCCTT CGGTTTTTGA CAATCGGGTC GCCACTACCG TAGCCAGTGC
1351 AGTGCAGTTG GCCGCCCGCA ATGAAGGGGT GGCCGGTCAA TAGTTAATCG
1401 GGAATTGTTA AACCTTTACT GGTCAACCAT TCCTGATTGT AAAGACGGGA
1451 TTGGTAACGG GCTCCTCCGT CACAAAGTAC GGTAACAATG GTATGCCCCG
1501 GCCCAAGTTT TTTGGCCAAT TGGTAAGCCG CTCCCACATT AATAT
```

Fig. 6 (SEQ ID NO. 4)

```
MNILEYAPIACQSWQVTVVGAGNVGRTLAQRLVQQNVANVVLLDIVPGLPQGIALDLMAA
QSVEEYDSKIIGTNEYEATAGSDVVVITAGLPRRPGMSRDDLLGKNANIVAQGAREALRY
SPNAILIVVTNPLDVMTYLAWKVTGLPSQRVMGMAGVLDSARLKAFIAMKLGACPSDINT
LVLGGHGDLMLPLPRYCTVSGVPITELIPPQTIEELVERTRNGGAEIAALLQTGTAYYAP
ASSAAVMVESILRNQSRILPAATYLDGAYGLKDIFLGVPCRLGCRGVEDILEVQLTPEEK
AALHLSAEAVRLNIDVALAMVSDG
```

Fig. 7 (SEQ ID NO. 5)

```
  1 ATGAATATT TTGGAGTATG CTCCGATCGC CTGTCAGTCC TGGCAGGTTA
 51 CCGTGGTCGG CGCTGGCAAT GTGGGCGGA CCCTTGCCCA GACGTTAGTG
101 CAGCAAAATG TCGCCAACGT AGTTTTGTTG GACATTGTGC CAGGCTTACC
151 CCAGGGCATT GCCTTGGATT TGATGGCCGC CCAGAGCGTG GAGGAATACG
201 ACAGCAAAAT CATTGGCACC AATGAATACG AGGCCACCGC CGGCTCCGAT
251 GTGGTGGTAA TTACCGCTGG TCTACCCCGC AGGCCCGGCA TGAGTCGGGA
301 TGATTTGTTG GGCAAAAACG CCAACATTGT GGCCCAGGGG GCCCGGGAAG
351 CATTGCGTTA TTCCCCCAAC GCCATTTTGA TTGTGGTCAC CAATCCCCTG
401 GATGTAATGA CCTATTTGGC CTGGAAAGTA ACTGGTTTAC CTTCCCAACG
451 GGTTATGGGC ATGGCGGGGG TGTTGGACTC GGCTCGGCTC AAGGCCTTCA
501 TTGCGATGAA ATTAGGGGCC TGTCCTTCTG ATATCAACAC CTTAGTGCTG
551 GGCGGGCACG GAGATTTGAT GCTGCCCTTG CCACGATACT GCACCGTCAG
601 CGGGGTTCCC ATTACCGAAT TAATACCCCC CCAAACCATT GAAGAGTTGG
651 TGGAGCGTAC CCGTAACGGT GGGGCTGAAA TTGCCGCCTT ACTACAAACG
701 GGCACAGCCT ATTATGCGCC GGCCTCTTCC GCTGCGGTGA TGGTGGAGTC
751 CATTTTACGC AATCAGTCTA GAATTCTCCC CGCCGCCACC TACCTTGATG
801 GTGCCTATGG ATTGAAGGAC ATTTTCCTTG GAGTGCCCTG CCGTTTGGGG
851 TGTCGAGGAG TGGAAGATAT TCTCGAAGTG CAATTAACCC CTGAAGAAAA
901 AGCTGCCCTC CATCTTTCTG CAGAAGCAGT TCGCCTTAAT ATTGATGTGG
951 CGTTGGCCAT GGTTAGCGAC GGT   CACG ATAACGGACA GTGCCAATAC
1001 CGTTTTTTCA CCGAGGTTAG GGCTTAT
```

Fig. 9 (SEQ ID NO. 8)

```
   1 T■■GTTAGC CTCACCCCCA ATCCGAGTTA TAGCGTCAGC CTACTGTTGG
  51 AACTCCCCAA CCACGCCGGA ACTTTGGCCA GCGTTACCCA GGCGATCGCC
 101 GATGCGGGGG GCAGTTTTGG GCAAATTTCC CTGATTGAGA GTAACTTAAA
 151 ACTCACCCGG CGGGAAATTG CGGTGGATGC TTCCAGCAGT GAGCACGCCG
 201 AAAAAATTAT TGGGGCAGTG AAAGCTCTGG ATAATGTCAA ATTGCTGAAG
 251 GTGTCCGATC GCACCTTTGA TTTACACCGT CAGGGCAAAA TTAGCGTGGT
 301 TAGTCGCATT CCCCTCACCT CCCAATCGGA TTTGGCCATG GCCTATACCC
 351 CAGGGGTGGG GCGCATCTGT CGGGCGATCG CCGAAGATCC GGAAAAGGTT
 401 TATTCCCTGA CCATTAAAAG CAATACGGTG GCGGTGGTGA CCGATGGCAG
 451 TGCGGTGTTG GGGTTGGGTA ACCTGGGGCC GGAAGCGGCT TTACCAGTGA
 501 TGGAAGGCAA GGCCATGTTA TTCAAGGAAT TGCCCAACT GGACGCTTTT
 551 CCCATCTGTT TGGATACCCA GGATACGGAG GAAATTATTC GCACCGTCAA
 601 GGCGATCGCC CCGGTGTTTG GCGGCGTAAA TTTGGAAGAC ATTGCCGCTC
 651 CCCGGTGTTT TGAAATTGAA GCCCGGCTGA AAAAGAATT AAATATTCCT
 701 GTATTTCACG ATGATCAGCA CGGCACCGCC ATTGTTACCC TGGCCGCTTT
 751 GTTAAATGCC CTCAAATTTG TTGGTAAAGC CATGGCCGCT GTCCGCATTG
 801 TCATCAACGG CGCTGGGGCT GCTGGGTTGG CGATCGCCGA ATTGCTCAAG
 851 GAATCCGGAG CCACCGATAT TTGGATTTGC GACTCCAAGG GCATTGTGGG
 901 CAAACATCGC ACCGATTTAA ACAGCAAAAA ACAGAGCTTT GCGGTGGATG
 951 CGGAAGGGAC TTTAGCCGAT GCTATGGCTG GAGCTGATGT GTTTTTAGGG
1001 GTGAGTGCGC CGGGGGTAGT GACCAAGGAA ATGGTGCAAT CCATGGCCAA
1051 GGACCCGATT GTGTTTGCCA TGGCCAACCC TATCCCCGAA ATTCAGCCGG
1101 AATTAATCCA AGAGGATGCG GCGGTTATTG CCACGGGGCG CAGTGATTAC
1151 CCCAACCAAA TTAACAATGT GCTTGCCTTT CCGGGGGTTT TCCGGGGAGC
1201 CATTGACTGT AGAGCTAGCA TTATTACCAC CACCATGTGC ATCGAAGCGG
1251 CCAAGGCGAT CGCCTCTTTG GTGCACAGCA ACACCCTAGA TAGTGAGCAT
1301 ATTATTCCTT CGGTTTTTGA CAATCGGGTC GCCACTACCG TAGCCAGTGC
1351 AGTGCAGTTG GCCGCCCGCA ATGAAGGGGT GGCCGGTCAA ■■TTAATCG
1401 GGAATTGTTA AACCTTTACT GGTCAACCAT TCCTGATTGT AAAGACGGGA
1451 TTGGTAACGG GCTCCTCCGT CACAAAGTAC GGTAACAATG GTATGCCCCG
1501 GCCCAAGTTT TTTGGCCAAT TGGTAAGCCG CTCCCACATT AATATCGATT
1551 TTTCTCCACC ATCAACACCC CGGAGGGTGC C■■AATATT TTGGAGTATG
1601 CTCCGATCGC CTGTCAGTCC TGGCAGGTTA CCGTGGTCGG CGCTGGCAAT
1651 GTGGGGCGGA CCCTTGCCCA GAGGTTAGTG CAGCAAAATG TCGCCAACGT
1701 AGTTTTGTTG GACATTGTGC CAGGCTTACC CCAGGGCATT GCCTTGGATT
1751 TGATGGCCGC CCAGAGCGTG GAGGAATACG ACAGCAAAAT CATTGGCACC
1801 AATGAATACG AGGCCACCGC CGGCTCCGAT GTGGTGGTAA TTACCGCTGG
```

Fig. 11

```
1851 TCTACCCCGC AGGCCCGGCA TGAGTCGGGA TGATTTGTTG GGCAAAAACG
1901 CCAACATTGT GGCCCAGGGG GCCCGGGAAG CATTGCGTTA TTCCCCCAAC
1951 GCCATTTTGA TTGTGGTCAC CAATCCCCTG GATGTAATGA CCTATTTGGC
2001 CTGGAAAGTA ACTGGTTTAC CTTCCCAACG GGTTATGGGC ATGGCGGGGG
2051 TGTTGGACTC GGCTCGGCTC AAGGCCTTCA TTGCGATGAA ATTAGGGGCC
2101 TGTCCTTCTG ATATCAACAC CTTAGTGCTG GGCGGGCACG GAGATTTGAT
2151 GCTGCCCTTG CCACGATACT GCACCGTCAG CGGGGTTCCC ATTACCGAAT
2201 TAATACCCCC CCAAACCATT GAAGAGTTGG TGGAGCGTAC CCGTAACGGT
2251 GGGGCTGAAA TTGCCGCCTT ACTACAAACG GGCACAGCCT ATTATGCGCC
2301 GGCCTCTTCC GCTGCGGTGA TGGTGGAGTC CATTTTACGC AATCAGTCTA
2351 GAATTCTCCC CGCCGCCACC TACCTTGATG GTGCCTATGG ATTGAAGGAC
2401 ATTTTCCTTG GAGTGCCCTG CCGTTTGGGG TGTCGAGGAG TGGAAGATAT
2451 TCTCGAAGTG CAATTAACCC CTGAAGAAAA AGCTGCCCTC CATCTTTCTG
2501 CAGAAGCAGT TCGCCTTAAT ATTGATGTGG CGTTGGCCAT GGTTAGCGAC
2551 GGT    CACG ATAACGGACA GTGCCAATAC CGTTTTTTCA CCGAGGTTAG
2601 GGCTTA
                    (SEQ ID NO. 13)
```

Fig. 11 (Continued)

```
   1 CACCTAAATT GTAAGCGTTA ATATTTTGTT AAAATTCGCG TTAAATTTTT
  51 GTTAAATCAG CTCATTTTTT AACCAATAGG CCGAAATCGG CAAAATCCCT
 101 TATAAATCAA AAGAATAGAC CGAGATAGGG TTGAGTGTTG TTCCAGTTTG
 151 GAACAAGAGT CCACTATTAA AGAACGTGGA CTCCAACGTC AAAGGGCGAA
 201 AAACCGTCTA TCAGGGCGAT GGCCCACTAC GTGAACCATC ACCCTAATCA
 251 AGTTTTTTGG GGTCGAGGTG CCGTAAAGCA CTAAATCGGA ACCCTAAAGG
 301 GAGCCCCCGA TTTAGAGCTT GACGGGGAAA GCCGGCGAAC GTGGCGAGAA
 351 AGGAAGGGAA GAAAGCGAAA GGAGCGGGCG CTAGGGCGCT GGCAAGTGTA
 401 GCGGTCACGC TGCGCGTAAC CACCACACCC GCCGCGCTTA ATGCGCCGCT
 451 ACAGGGCGCG TCCCATTCGC CATTCAGGCT GCGCAACTGT TGGGAAGGGC
 501 GATCGGTGCG GGCCTCTTCG CTATTACGCC AGCTGGCGAA AGGGGGATGT
 551 GCTGCAAGGC GATTAAGTTG GGTAACGCCA GGGTTTTCCC AGTCACGACG
 601 TTGTAAAACG ACGGCCAGTG AATTGTAATA CGACTCACTA TAGGGCGAAT
 651 TGGAGGCCAG TGCTGGAGGA ATATGATTTT GTCATCCTCG ACTGTGCCCC
 701 TGGTTATAAT CTGTTGACCC GCAGTGGCAT TGCGGCCAGC GACTTTTATC
 751 TGTTGCCGGC TCGTCCTGAA CCCCTATCGG TGGTGGGGAT GCAGTTACTG
 801 GAAAGAAGAA TTGAGAAACT GAAGGAAAGC CATAAGGCCT CCGATGATCC
 851 CCTGAATATC AATCTGATCG GAGTGGTGTT TATTCTGTCC GGCGGCGGTT
 901 TGATGAGTCG CTACTATAAC CAGGTAATGC GGCGGGTACA AACGGATTTC
 951 ACCCCGGGAC AACTTTTTCA GCAGTCCATT CCCATGGATG TCAATGTGGC
1001 TAAGGCAGTG GATAGCTTTA TGCCGGTGGT TACCTCCATG CCCAATACGG
1051 CGGGTTCAAA AGCTTTTATT AAATTAACCC AGGAATTTTT ACAGAAAGTA
1101 GAAGCTTTTG CTAAAGCAA AGCCCCCATT GATTAACAAC GGGAGGGGTA
1151 CCGAGGTGCT GCTGAAGTTG CCCGCAACAG AGAGTGGAAC CAACCGGTGA
1201 TACCACGATA CTATGACTGA GAGTCAACGC CATGAGCGGC CTCATTTCTT
1251 ATTCTGAGTT ACAACAGTCC GCACCGCTGT CCGGTAGCTC CTTCCGGTGG
1301 GCGCGGGGCA TGACTATCGT CGCCGCACTT ATGACTGTCT TCTTTATCAT
1351 GCAACTCGTA GGACAGGTGC CGGCAGCGCC AACAGTCCC CCGGCCACGG
1401 GGCCTGCCAC CATACCCACG CCGAAACAAG CGCCCTGCAC CATTATGTTC
1451 CGGATCTGCA TCGCAGGATG CTGCTGGCTA CCCTGTGGAA CACCTACATC
1501 TGTATTAACG AAGCGCTAAC CGTTTTTATC AGGCTCTGGG AGGCAGAATA
1551 AATGATCATA TCGTCAATTA TTACCTCCAC GGGGAGAGCC TGAGCAAACT
1601 GGCCTCAGGC ATTTGAGAAG CACACGGTCA CACTGCTTCC GGTAGTCAAT
1651 AAACCGGTAA ACCAGCAATA GACATAAGCG CTATTTAAC GACCCTGCCC
1701 TGAACCGACG ACCGGGTCGA ATTGCTTTC GAATTCTGC CATTCATCCG
1751 CTTATTATCA CTTATTCAGG CGTAGCACCA GGCGTTTAAG GGCACCAATA
1801 ACTGCCTTAA AAAATTACG CCCCGCCCTG CCACTCATCG CAGTACTGTT
                              Fig. 13
```

```
1851 GTAATTCATT AAGCATTCTG CCGACATGGA AGCCATCACA GACGGCATGA
1901 TGAACCTGAA TCGCCAGCGG CATCAGCACC TTGTCGCCTT GCGTATAATA
1951 TTTGCCCATG GTGAAAACGG GGGCGAAGAA GTTGTCCATA TTGGCCACGT
2001 TTAAATCAAA ACTGGTGAAA CTCACCCAGG GATTGGCTGA GACGAAAAAC
2051 ATATTCTCAA TAAACCCTTT AGGGAAATAG GCCAGGTTTT CACCGTAACA
2101 CGCCACATCT TGCGAATATA TGTGTAGAAA CTGCCGGAAA TCGTCGTGGT
2151 ATTCACTCCA GAGCGATGAA AACGTTTCAG TTTGCTCATG GAAAACGGTG
2201 TAACAAGGGT GAACACTATC CCATATCACC AGCTCACCGT CTTTCATTGC
2251 CATACGGAAT TCCGGATGAG CATTCATCAG GCGGGCAAGA ATGTGAATAA
2301 AGGCCGGATA AAACTTGTGC TTATTTTTCT TTACGGTCTT TAAAAAGGCC
2351 GTAATATCCA GCTGAACGGT CTGGTTATAG GTACATTGAG CAACTGACTG
2401 AAATGCCTCA AAATGTTCTT TACGATGCCA TTGGGATATA TCAACGGTGG
2451 TATATCCAGT GATTTTTTTC TCCATTTTAG CTTCCTTAGC TCCTGAAAAT
2501 CTCGATAACT CAAAAAATAC GCCCGGTAGT GATCTTATTT CATTATGGTG
2551 AAAGTTGGAA CCTCTTACCT CGGTACCCCT CATCGGGGGC TGTGTTGGCC
2601 GAGACGGCAC TGAGGATTTT ACTCTCCATG GCATTCCAAG GAATATCTAC
2651 CCAACTCACC TGCTCCGGCG GATTGTTCCG CTCAAAAGTA CTAATCAAGT
2701 CGTCAAAATA CTTATTAAAT TTTGGCTGCA ATTGCATAGT CCAAAAGCTG
2751 ACTTTCCCCT CCATGCTCTG GGGGGAATTG CTCTGGCAAC TGATTAATCC
2801 ACTGAGCAAC AGCCCAAGAC ACGCAAACAA AAACCAACGT CTTGGCGATC
2851 GCCATCGGCA CCATGAAACC ATCGTAAAAG CTGGGGAAAG AATAAAAAAC
2901 AGTGGTTCAG GAATTGCATT GCCATGGCCA CTTCACAAAC CTAGCCAATT
2951 TTAGCTTGAC CGCAACTTTG ACAGATTGTC TTTTGACTTT GCCTGGACCG
3001 CCTCCCATAA TACCTTCGCG TCTTGAAGAC TTTATCCTTG AAAGGAGAAC
3051 ATATGTTTCT CGGCAAAAAT TAATTATCGA TTGGCTGGAA CCTGGTCAAA
3101 CCAGGGCTTT TCATCCATTG GAAAAGCGAT TTTGATCATC TAGGGTCAGG
3151 AGCAAAGATC TGATCAAATA TTGATCATTT ATTAGGAAAG CTGAACTTTC
3201 ACCACTTTAT TTTTGGCTTC CTCTACTTTG GGCAAAGTCA AAGTTAGGAT
3251 ACCGGCATCG TAATTAGCTT TAACTTCTGT GTTTTGGATT GCTCCAGGTA
3301 CAGGAATAAC CCGGCGGAAA CTGCCATAGC GGAACTCTGT GCGCCGCACC
3351 CCATCTTTTT CGGTGCTATG GGTATCCTGG CGATCGCCGC TGACGGTCAC
3401 CGCATCCCTG GCGGCTTGGA TGTCCAAATT ATCGGGGTCC ATGCCAGGTA
3451 ATTCTAGTTT GAGCACATAG GCTTCTTCAG TTTCAGTTAG TTCTGCTTTA
3501 GGATTAAACC CTTGGCGATC GCCGTGGCGG TCCGTAGGGA CAAAAACTTC
3551 TTCAAACAGT TGGTTCATCT GCTGCTGGAA ATTATCCATT TCCCGCAGGG
3601 GATTGTAAAG AATGAGAGAC ATAATGTTAA CTCCTGATGT GTGGAAGGAA
3651 TTGATTACCC TTGAATGGTT CTATCTTAAA ATTTCCCCTT CCAGGTTAGA
```
Fig. 13 (Continued)

```
3701 TTCGGTTTTC AGGAAAGAAG GTGGGGGGAT TGCCGAAATT ACATTTCTAG
3751 CCGCAATTTT TAGTAAAAAA AAGATGAGTT TTTACCTCAC CTTAAGTAAA
3801 TATTTGAGTG GCAAAACAAA ATGGTAAAAA TAGCTAAGCT TCCACCGCCC
3851 TATGGATTTT TGGAAGGAAG TCTTAGGTTG TGAAAAACTA TAAAAACCAA
3901 CCATAGGAAT GGAGACCTTT ACCCAACAAG TTGACCCCTA GGTAACAAAT
3951 CCAAACCACC GTAAACCGC TGGCGGCCAA AATAGCGGGC TTGCGGCCTT
4001 GCCAACCTTT GGTAATGCGG GCATGGAGAT AGGCGGCAAA TACTAGCCAG
4051 GTGATTAGGG CCCGGTACCC AGCTTTTGTT CCCTTTAGTG AGGGTTAATT
4101 TCGAGCTTGG CGTAATCATG GTCATAGCTG TTTCCTGTGT GAAATTGTTA
4151 TCCGCTCACA ATTCCACACA ACATACGAGC CGGAAGCATA AAGTGTAAAG
4201 CCTGGGGTGC CTAATGAGTG AGCTAACTCA CATTAATTGC GTTGCGCTCA
4251 CTGCCCGCTT TCCAGTCGGG AAACCTGTCG TGCCAGCTGC ATTAATGAAT
4301 CGGCCAACGC GCGGGGAGAG GCGGTTTGCG TATTGGGCGC TCTTCCGCTT
4351 CCTCGCTCAC TGACTCGCTG CGCTCGGTCG TTCGGCTGCG GCGAGCGGTA
4401 TCAGCTCACT CAAAGGCGGT AATACGGTTA TCCACAGAAT CAGGGGATAA
4451 CGCAGGAAAG AACATGTGAG CAAAAGGCCA GCAAAAGGCC AGGAACCGTA
4501 AAAAGGCCGC GTTGCTGGCG TTTTTCCATA GGCTCCGCCC CCTGACGAG
4551 CATCACAAAA ATCGACGCTC AAGTCAGAGG TGGCGAAACC CGACAGGACT
4601 ATAAAGATAC CAGGCGTTTC CCCCTGGAAG CTCCCTCGTG CGCTCTCCTG
4651 TTCCGACCCT GCCGCTTACC GGATACCTGT CCGCCTTTCT CCCTTCGGGA
4701 AGCGTGGCGC TTTCTCATAG CTCACGCTGT AGGTATCTCA GTTCGGTGTA
4751 GGTCGTTCGC TCCAAGCTGG GCTGTGTGCA CGAACCCCCC GTTCAGCCCG
4801 ACCGCTGCGC CTTATCCGGT AACTATCGTC TTGAGTCCAA CCCGGTAAGA
4851 CACGACTTAT CGCCACTGGC AGCAGCCACT GGTAACAGGA TTAGCAGAGC
4901 GAGGTATGTA GGCGGTGCTA CAGAGTTCTT GAAGTGGTGG CCTAACTACG
4951 GCTACACTAG AAGGACAGTA TTTGGTATCT GCGCTCTGCT GAAGCCAGTT
5001 ACCTTCGGAA AAAGAGTTGG TAGCTCTTGA TCCGGCAAAC AAACCACCGC
5051 TGGTAGCGGT GGTTTTTTTG TTTGCAAGCA GCAGATTACG CGCAGAAAAA
5101 AAGGATCTCA AGAAGATCCT TTGATCTTTT CTACGGGGTC TGACGCTCAG
5151 TGGAACGAAA ACTCACGTTA AGGGATTTTG GTCATGAGAT TATCAAAAAG
5201 GATCTTCACC TAGATCCTTT TAAATTAAAA ATGAAGTTTT AAATCAATCT
5251 AAAGTATATA TGAGTAAACT TGGTCTGACA GTTACCAATG CTTAATCAGT
5301 GAGGCACCTA TCTCAGCGAT CTGTCTATTT CGTTCATCCA TAGTTGCCTG
5351 ACTCCCCGTC GTGTAGATAA CTACGATACG GGAGGGCTTA CCATCTGGCC
5401 CCAGTGCTGC AATGATACCG CGAGACCCAC GCTCACCGGC TCCAGATTTA
5451 TCAGCAATAA ACCAGCCAGC CGGAAGGGCC GAGCGCAGAA GTGGTCCTGC
5501 AACTTTATCC GCCTCCATCC AGTCTATTAA TTGTTGCCGG GAAGCTAGAG
```
FIG. 13 (Continued)

```
5551 TAAGTAGTTC GCCAGTTAAT AGTTTGCGCA ACGTTGTTGC CATTGCTACA
5601 GGCATCGTGG TGTCACGCTC GTCGTTTGGT ATGGCTTCAT TCAGCTCCGG
5651 TTCCCAACGA TCAAGGCGAG TTACATGATC CCCCATGTTG TGCAAAAAAG
5701 CGGTTAGCTC CTTCGGTCCT CCGATCGTTG TCAGAAGTAA GTTGGCCGCA
5751 GTGTTATCAC TCATGGTTAT GGCAGCACTG CATAATTCTC TTACTGTCAT
5801 GCCATCCGTA AGATGCTTTT CTGTGACTGG TGAGTACTCA ACCAAGTCAT
5851 TCTGAGAATA GTGTATGCGG CGACCGAGTT GCTCTTGCCC GGCGTCAATA
5901 CGGGATAATA CCGCGCCACA TAGCAGAACT TTAAAAGTGC TCATCATTGG
5951 AAAACGTTCT TCGGGGCGAA AACTCTCAAG GATCTTACCG CTGTTGAGAT
6001 CCAGTTCGAT GTAACCCACT CGTGCACCCA ACTGATCTTC AGCATCTTTT
6051 ACTTTCACCA GCGTTTCTGG GTGAGCAAAA ACAGGAAGGC AAAATGCCGC
6101 AAAAAAGGGA ATAAGGGCGA CACGGAAATG TTGAATACTC ATACTCTTCC
6151 TTTTTCAATA TTATTGAAGC ATTTATCAGG GTTATTGTCT CATGAGCGGA
6201 TACATATTTG AATGTATTTA GAAAAATAAA CAAATAGGGG TTCCGCGCAC
6251 ATTTCCCCGA AAAGTGC
```

(SEQ ID NO. 14)

Fig. 13 (Continued)

```
MGSTLVGKCTSLGVFSMVTSPFSLSPFGQARSTVTGNPLDPTELNQMHGFWRAANYLAVGM
IYLRDNPLLREPLQPEQIKHRLLGHWGSSPGISFLYTHLNRIIRKFDQDMLYMVGPGHGAP
GFLGPCYLEGSYSRFFAECSEDEDGMKRFFKQFSFPGGIGSHCTPETPGSIHEGGELGYCL
SHAYGAAFDNPNLIVVGLACDCESETGPLATSWHSNKFINPIRDGAVLPVLHLNGYKINNP
SVLSRISHEELKALFEGYGYTPYFVEGSDPESMHQAMAATLDHCVSEIHQIQQEARSTGIA
VRPRWPMVVMRTPKGWTGPDYVDGHKVEGFWRSHQVPMGGMHENPAHLQQLEAWMRSYKPE
ELFDEQGTLKPGFKAIAPEGDKRLGSTPYANGGLLRRGLKMPDFRQYGIDVDQPGTIEAPN
TAPLGVFLRDVMANNMTNFRLFGPDENSSNKLHAVYEVSKKFWIAEYLEEDQDGGELSPDG
RVMEMLSEHTLEGWLEAYLLTGRHGFFATYESFAHVITSMVNQHAKWLDICRHLNWRADIS
SLNILMTSTVWRQDHNGFTHQDPGFLDVILNKSPDVVRIYLPPDVNSLLSVADHCLQSKNY
INIIVCDKQAHLQYQDMTSAIRNCTKGVDIWEWASNDAGTEPDVVMAAAGDIPTKEALAAT
AMLRQFFPNLRIRFVSVIDLLKLQPESEHPHGLSDRDFDSLFTTDKPIIFNFHAYPWLIHR
LTYRRTNHGNLHVRGYKEKGNINTPMDLAIQNQIDRFSLAIDVIDRLPQLRVAGAHIKEML
KDMQIDCTNYAYEHGIDMPEIVNWRWPL

Fig. 14 (SEQ ID NO. 15)
```

```
MTSSLYLSTTEARSGKSLVVLGILDLILKKTTRIAYFRPIIQDPVNGKHDNNIILVLENF
RLQQTYTDSFGLYFHEAVSLASDGAIDQVLDRILAKYRHLADQVDFILCEGSDYLGEESA
FEFDLNTTIAKMLNCPILLLGNAMGNTIADSLQPIDMALNSYDQESCQVVGVIINRVQPE
LATEIQAQLEQRYGDRPMVLCTIPQDIMLKSLRLREIVSGLNAQVLSGADLLDNLVYHHL
VVAMHIAHALHWLHEKNTLIITPGDRGDILGVMQAHRSLNYPSIAGILLTADYHPEPAI
MKLIEGLPDAPPLLLTSTHTHETSARLETLHPALSPTDNYKIRHSIALFQQQIDGEKLLN
YLKTIRSKGITPKLFLYNLVQAATAAQRHLVLPEGEEIRILKAAASLINHGIVRLTLLGN
IEAIEQTVKINHIDLDLSKVRLINPKTSPDRERYAETYYQLRKHKGVTLAMARDILTDIS
YFGTMMVHLGEADGMVSGSVNTTQHTVRPALQIIKTQPGFSLVSSVFFMCLEDRVLVYGD
CAVNPDPNAEQLAEIALTSAATAKNFGIEPRVALLSYSSGSSGQGADVEKVRQATAIAKE
REPDLALEGPIQYDAAVDSTVAAQKMPGSAVAGKATVFIFPDLNTGNNTYKAVQRETKAI
AIGPILCGLNKPVNDLSRGCLVEDIINTVVITALQVK
```

Fig. 15 (SEQ ID NO. 16)

```
   1  cccgggtacc cctcatcggg ggctgtgttg gccgagacgg cactgaggat
  51  tttactctcc atggcattcc aaggaatatc tacccaactc acctgctccg
 101  gcggattgtt ccgctcaaaa gtactaatca agtcgtcaaa atacttatta
 151  aattttggct gcaattgcat agtccaaaag ctgactttcc cctccatgct
 201  ctgggggggaa ttgctctggc aactgattaa tccactgagc aacagcccaa
 251  gacacgcaaa caaaaaccaa cgtcttggcg atcgccatcg gcaccatgaa
 301  accatcgtaa aagctgggga aagaataaaa aacagtggtt caggaattgc
 351  attgccatgg ccacttcaca aacctagcca attttagctt gaccgcaact
 401  ttgacagatt gtcttttgac tttgcctgga ccgcctccca taataccttc
 451  gcgtcttgaa gactttatcc ttgaaaggag aacatatggt tacatccccc
 501  ttttccctta gtccctttgg tcaagctaga tccaccgtca ctggcaatcc
 551  ccttgacccg acagaactta accaaatgca cggttttttgg cgggcagcca
 601  actacttggc agtgggcatg atttatctgc gggataatcc ccttttgcgg
 651  gaaccgcttc aaccggaaca gatcaagcat cgcctgttgg gtcactgggg
 701  ttctagtccc ggcattagtt ttctctacac ccatctcaac cgcattatca
 751  ggaaatttga ccaggatatg ctgtacatgg tggggcctgg ccacggcgca
 801  ccaggctttt tggggccctg ctacctagaa gggagctatt ctcgcttttt
 851  tgccgagtgt agtgaagatg aggacggcat gaagcgcttt ttcaaacaat
 901  tttcctttcc cggtggcatt ggcagtcatt gcactcccga aaccccctggt
 951  tccatccacg aggggggaga attgggctac tgcctatccc atgcctatgg
1001  cgctgccttt gataatccca atttaattgt ggtcggttta gcggggggatg
1051  gggagtcgga acaggcccc ttggctacct cctggcattc caataagttt
1101  attaacccga ttcgggatgg ggcagtttta ccggttctgc atctcaatgg
1151  gtacaagatt aacaatccaa gtgttttatc tcgcattagc catgaagaat
1201  taaaggcttt atttgaaggt tacggttata cccctactt tgttgaaggc
1251  tctgacccgg aatctatgca ccaagccatg gcagccacgt ggatcattg
1301  tgtgagcgaa attcatcaaa tccaacaaga agctcgtagt acgggcattg
1351  ccgtgcgccc ccgttggccc atggttgtga tgcggactcc caagggatgg
1401  acggggcctg actatgttga tggccataag gtagaaggtt tttggcgatc
1451  gcaccaagtt cccatggggg gcatgcacga gaatccagcc catttgcaac
1501  agttggaagc ttggatgcgg agttataagc cggaagaatt gttcgacgag
1551  caaggtactt taaaaccggg atttaaggcg atcgccccgg agggagataa
1601  gcgtttaggc tctactccct acgccaatgg tggtttgtta cggcggggtt
1651  tgaaaatgcc ggactttcgt caatatggta ttgatgtgga ccaaccaggc
1701  accatcgaag cccctaatac tgcaccctg ggagtatttc tgcgggatgt
1751  gatggccaac aacatgacca atttccgcct gtttggcccc gatgaaaata
```

Fig. 17

1801 gttccaataa actccatgcc gtctacgagg ttagcaaaaa attctggatt
1851 gctgaatatc tagaagaaga ccaggatggg ggggaattaa gtcccgatgg
1901 tcgggtgatg gaaatgttaa gcgagcacac cttagaaggt tggttagagg
1951 cctatctttt aaccgggcgt cacggctttt cgccaccta tgaatccttt
2001 gcccatgtga tcacttccat ggttaaccaa cacgctaaat ggttggatat
2051 ttgtcgacac ctcaactggc gggcagatat ttcctcgtta aatatcttga
2101 tgacgtccac cgtgtggcga caggatcaca acgggtttac ccaccaagat
2151 cccggttttc tcgatgtcat tctcaataaa agccccgatg tggtgcgaat
2201 ttatttaccc cccgatgtta attctctgct ttccgtagcg gaccattgtt
2251 tacagagcaa aaactacatc aacatcatcg tttgcgataa gcaagcccac
2301 ctgcaatacc aggacatgac ttccgctatc cgtaactgca ctaaaggggt
2351 ggacatttgg gaatgggcca gtaatgatgc cggtacggaa ccggatgtgg
2401 tgatggcagc ggcgggggat attcccacca aagaggcctt ggcggccaca
2451 gccatgctaa ggcaattttt tcctaatctg agaattcgct tgtcagcgt
2501 gattgatttg ctcaaactgc aaccggaatc ggagcatccc catggcctga
2551 gcgatcggga ttttgactcc ctctttacca ccgataaacc gattattttt
2601 aacttccacg cctatccctg gttaattcat cggttgacct atcgacggac
2651 taaccatggc aatctccatg tgcggggcta caaggaaaag ggcaacatca
2701 acaccccat ggatttagcg attcaaaacc agattgaccg tttcagcctc
2751 gccattgatg tgatcgatcg cctgccccaa ttgcgggtgg ccggagccca
2801 catcaaggaa atgctcaagg atatgcagat tgactgcacc aactacgcct
2851 acgaacacgg cattgatatg ccagaaatcg ttaattggcg ctggcccctc
2901 tagaccttaa ctaaaatccc tgacatcgtt ctagtttctg ttccaatagg
2951 ttagctaggc catgggggac aacagatctg gatacgttga ggttatttaa
3001 attatgacga gttcccttta tttaagcacc accgaagccc gcagcggtaa
3051 atctctagta gtattgggca ttttagactt aattctcaaa aaaccaccc
3101 gtattgccta ttttcgtccc attattcaag acccagttaa tggcaaacat
3151 gataacaaca ttattctggt gctggaaaat tttcgtctcc aacaaccta
3201 taccgattcc tttggtttgt atttccatga gcggtgagt ttagcctccg
3251 atggagctat tgatcaggta ttagaccgaa ttttggctaa atatcgccat
3301 ttggcagatc aagtagattt tattctctgt gaaggctcag actatttggg
3351 ggaggaatcg gcttttgaat ttgatctcaa caccacgatc gccaagatgt
3401 tgaactgccc catttgctg ttgggcaatg ccatgggcaa caccattgcc
3451 gatagtttgc aacccatcga tatggccctg aatagctatg accaagagtc
3501 ttgtcaggtg gtgggggtaa tcattaaccg agtgcagccc gaattagcca
3551 cagaaattca agcccaactg gaacagcgtt atggcgatcg cccgatggtg Fig. 17 (Continued)

```
3601  ttgggcacta ttccccagga cattatgctc aaaagtctgc gcctgaggga
3651  aattgtcagc gggctcaatg cccaagtact cagcggtgcg gatttgctcg
3701  ataacttggt ctatcaccat ttagtggtgg cgatgcacat tgcccacgcc
3751  ctccattggt tgcacgaaaa aaatacccta attattaccc ctggcgatcg
3801  gggcgacatc attctggggg tgatgcaggc ccaccgctcc ctcaactatc
3851  ccagcattgc cggtattttg ctcactgcag attaccatcc gaaccggcc
3901  attatgaaac taattgaagg gctacccgac gcccctcccc tgttgctgac
3951  tagcacccac acccatgaaa cttccgcccg tttggaaact ctccaccctg
4001  ccctgagccc tacggataat tataaaattc gccacagtat tgcgctgttt
4051  caacaacaaa ttgatgggga gaaattactc aattaccta aaaccatccg
4101  cagtaaaggt attaccccca aactgtttct ctacaattta gttcaagccg
4151  ccaccgccgc ccaacgacat attgtcctac cggaagggga agaaattcgt
4201  attctcaagg cggccgctag cttaattaac cacggcattg tccgtttgac
4251  tttactcggt aacattgagg cgatcgagca acggtaaaa attaatcaca
4301  ttgacttaga tttgagcaaa gttcgcctca ttaatcctaa aactagccca
4351  gaccgagagc gctacgccga aacctattac cagctacgta aacataaggg
4401  ggtaaccctg gccatggctc gggatatcct caccgatatt tcctattttg
4451  gaacgatgat ggtgcatttg ggagaggccg atggcatggt ttctggctcc
4501  gtcaatacca cccaacatac cgtgcgtcct gctttacaaa ttattaaaac
4551  ccagccaggt ttttccttgg tttcttcagt ctttttatg tgtttagaag
4601  accgagtttt ggtctatgga gattgtgctg ttaatcccga tcccaatgca
4651  gaacagttag cagaaattgc ccttacttct gcggctacgg ccaagaattt
4701  tggcattgag cccagggtag ctctattgtc ctattcttcc ggttcttctg
4751  ggcaaggggc cgatgtggaa aaagtgcggc aagccacggc gatcgccaag
4801  gaaagagagc cagatttagc attggaaggg ccgatccagt atgatgcggc
4851  ggtggattcc acagtggcgg cccaaaaaat gcctgggtca gcggtggcgg
4901  gtaaagcaac ggtgtttatt tttcccgatt taaataccgg taacaatact
4951  tacaaggcag tgcaaagaga acaaaggcg atcgccattg gccccatttt
5001  acaaggatta aataaaccag ttaatgatct aagtcggggt tgtttagtgg
5051  aggatattat taatacggtg gtaattacag ctttgcaagt taaataattt
5101  tactcttaat tagttaaaat gatcccttga attccttga ttttgccctc
5151  caaactacca atagctgggc cgaaaattgg catcatttaa aatcaccaac
5201  gtgtccccgg acggagctag cacaaacaga cccttaccat aggcatagct
5251  gaccacttct tggcttaaca ccatggctgc cactgcacct aaagctttaa
5301  catcccggta gcgggcata aactgtttga atttacccaa ccgttccaga
5351  tgctcgagca accgatcttt ctagaagatc tcgag
```

Fig. 17 (Continued)

(SEQ ID NO. 21)

Fig. 17 (Continued)

```
MNTAKTVVAEQRDFFRQGKTKSVQDRLTALAKLKTQIQAQEEEIIKALKQDFGKPTFESYV
NEILGVIREINYYQKHLQQWSKPQRVGTNLMVFPASAQLRPEPLGVVLIISPWNYPFYLCL
MPLIGAIAAGNCVVVKPSEYTPAISGVITRLIQNVFSPAWATVVEGDETISQQLLQEKFDH
IFFTCSPRVGRLIMAAAAEQLTPVTLELGGKSPCVVDREINLQETAKRIMWGKLVNAGQTC
VAPDYLLVEQSCLEQLLPALQQAIQMLFGENPAHSPDYTRIVNQQQWSRLVSLLSHGKVIT
RGDHNEGDRYIAPTLIIDPDLNSPLMQEEIFGPILPILTYQSLSEAIDFINIKPKPLALYF
FSNNRQKQEEILQSTSSGSVCLNDILLHLIVTDLPFGGVGESGMGRYHGKATFDTLSNYKS
ILRRPFWGETNLRYSPYGKKMNLIKKLFS
```

Fig. 18 (SEQ ID NO. 22)

```
   1  ctgcaggtcg actctagagg atccccgggt accccdtcatc gggggctgtg
  51  ttggccgaga cggcactgag gattttactc tccatggcat tccaaggaat
 101  atctacccaa ctcacctgct ccggcggatt gttccgctca aagtactaa
 151  tcaagtcgtc aaaatactta ttaaattttg gctgcaattg catagtccaa
 201  aagctgactt tcccctccat gctctggggg gaattgctct ggcaactgat
 251  taatccactg agcaacagcc caagacacgc aaacaaaaac caacgtcttg
 301  gcgatcgcca tcggcaccat gaaaccatcg taaaagctgg ggaaagaata
 351  aaaaacagtg gttcaggaat tgcattgcca tggccacttc acaaacctag
 401  ccaattttag cttgaccgca actttgacag attgtctttt gactttgcct
 451  ggaccgcctc ccataatacc ttcgcgtctt gaagactttta tccttgaaag
 501  gagaacatat gaatactgct aaaactgttg ttgctgagca aagggacttt
 551  tttcgtcagg gcaaaactaa atcagtccaa gatagattaa cagctctagc
 601  aaaattaaaa acgcaaattc aagcccagga agaggaaatt attaaggccc
 651  ttaagcaaga ttttggtaag cccacctttg aaagctatgt aaacgaaatt
 701  ttggggggtaa ttagggaaat taattattat caaaaacatc ttcagcaatg
 751  gtctaagccc caacgggtag gtacgaatct gatggttttt cctgccagtg
 801  cccagttaag accagaaccc cttggtgtag tgctaattat tagccccctgg
 851  aattatcctt tttatctttg tttaatgccc ttgatcgggg cgatcgccgc
 901  tggaaattgt gtggtggtaa agccgtcgga atatactcca gctattagtg
 951  gggtaattac cagattaatc caaaatgtat tttccccggc ttgggcaaca
1001  gtggtggagg gagatgaaac cattagccaa caattgttac aggaaaaatt
1051  tgaccatatt ttctttaccg gcagccctag ggtgggtcgg ttaattatgg
1101  cagctgcggc agagcaatta accccagtta cgttggaatt ggggggtaaa
1151  tctccctgtg tggtggatag ggaaatcaac ctccaggaaa cagccaaacg
1201  cattatgtgg ggcaagctag tcaatgctgg ccaaacctgt gtggcaccgg
1251  attatttatt ggtggagcaa tcctgcttag aacaactttt accagcttta
1301  caacaggcaa ttcagatgct tttcggggaa atccagccc atagccctga
1351  ctacactcgc attgttaacc aacaacaatg gtcacggtta gttagtttat
1401  taagccatgg caaagtaatt acaaggggag atcataacga aggcgatcgc
1451  tacattgccc caactttaat catcgatcca gatttaaatt ctcccttaat
1501  gcaagaggaa atatttggcc caatttttgcc aattttaact tatcagagtt
1551  tgtcagaagc aatagatttt attaacatca aacctaaacc attggcactt
1601  tatttttta gcaataatcg gcaaaaacag gaggaaattt tgcaatctac
1651  cagttccggt agtgttttgtt tgaacgatat tttgcttcat ttaactgtga
1701  cagacttacc ctttggtggg gtgggagaaa gtggtatggg acgctaccat
1751  ggcaaggcta cttttgacac attgagcaat tataaaagca ttttacgacg
```

Fig. 20

```
1801  acccttttgg ggggaaacta atttacgcta ttctccctat ggcaaaaaaa
1851  tgaatttaat caaaaagttg ttctcctagg attattcatg gccgaccgtc
1901  cccagttgag tattattatt cccgtgttta atgaagcaaa aattttacaa
1951  aagtctccga ctgaaaatac cagacaatat ttgggacaat ttaccgagga
2001  tcaacggata gaaattttaa ttattgatgg gggcagtcag gatagcacag
2051  tggagttatg ccagacctat gctgattctt tacctcgag
```

(SEQ ID NO. 25)

Fig. 20 (Continued)

```
MKFLILNAGSSSQKSCLYELTGDRLPETIPEPLWEAFIDWTVLANQGRLTVETAGQKQVI
ILETGDRQQGIARMLDTLVTGDDAVLKSLAEIDLVGHRVVHGGTDHAEATLITPEVQQAI
ADLIPLAPAHNPAHLEGIEAISALLVLGEVPQIAVFDTAFHRTIPTPAAEYPIPQAWTNL
GIRRYGFHGTSHKYCAQKTAEILGKPLADLKLITCHIGNGASLTAIKNGVSIDTTMGFTP
LEGLMMGARSGSIDPAILLFLQETQGLTPAEINTTLNKKSGLLGVSGLSADLRTILQAKA
EGNEQACLAYVMYIHRFRSCLGQMIASLEGLDTLVFTAGVGENAATVRADVCQAFEFLGL
KLDPELNNRSPRDTVISHSDSLVTVLIVHTEEDWAIAQDCWHWWHSQGQRKQS
```

Fig. 21 (SEQ ID NO. 26)

```
   1  ACTAGTAGTG CAGAAATTTT GAGCGATCTG GAAGCCACCA TTGCCTACGC
  51  CCAAACTTTA CCCAACGTTA AACCGGAAGA AGTAGGATTA ATTGGTTTTT
 101  GTTTTGGTGG TTGGATTGTC TATTTAGGGG CTAGTTTACC CACAGTCAAG
 151  GCCACGGCTT CCTTTTACGG CGCGGGTATT CCCCATTGGG CTCCAGGGAC
 201  AGCGGAACCG CCCATTACCT ATACCGATAA AATTCAGGGC ACTTTATACG
 251  CCTTCTTCGG CTTGGAAGAT ACCAGCATTC CATGGCAGA TACGGAGCAG
 301  ATTGAACAGG CTTTAACCAA GTATCAGGTG AACCATAAAA TTTTCCGTTA
 351  CCCAGGCGCA GACCATGGCT TTTTCTGTGA CCAAGGGCT AGCTATAACG
 401  CCGAAGCGGC CGCCGATGCT TGGCAAAAAG TGAAACAACT TTTCCAAACC
 451  GAATTGAAAT GAATTCCTG ATTCTCAATG CCGGTTCCAG CAGTCAAAAA
 501  AGTTGTCTTT ATGAGCTGAC TGGCGATCGC CTACCGGAGA CGATACCGGA
 551  GCCCTTATGG GAGGCTTTCA TTGATTGGAC GGTGTTGGCA AATCAGGGGC
 601  GGTTGACCTG CAGGGGGGGG GGGGAAAGCC ACGTTGTGTC TCAAAATCTC
 651  TGATGTTACA TTGCACAAGA TAAAAATATA TCATCATGAA CAATAAAACT
 701  GTCTGCTTAC ATAAACAGTA ATACAAGGGG TGTTATGAGC CATATTCAAC
 751  GGGAAACGTC TTGCTCGAGG CCGCGATTAA ATTCCAACAT GGATGCTGAT
 801  TTATATGGGT ATAAATGGGC TCGCGATAAT GTCGGGCAAT CAGGTGCGAC
 851  AATCTATCGA TTGTATGGGA AGCCCGATGC GCCAGAGTTG TTTCTGAAAC
 901  ATGGCAAAGG TAGCGTTGCC AATGATGTTA CAGATGAGAT GGTCAGACTA
 951  AACTGGCTGA CGGAATTTAT GCCTCTTCCG ACCATCAAGC ATTTTATCCG
1001  TACTCCTGAT GATGCATGGT TACTCACCAC TGCGATCCCC GGGAAAACAG
1051  CATTCCAGGT ATTAGAAGAA TATCCTGATT CAGGTGAAAA TATTGTTGAT
1101  GCGCTGGCAG TGTTCCTGCG CCGGTTGCAT TCGATTCCTG TTTGTAATTG
1151  TCCTTTTAAC AGCGATCGCG TATTTCGTCT CGCTCAGGCG CAATCACGAA
1201  TGAATAACGG TTTGGTTGAT GCGAGTGATT TGATGACGA GCGTAATGGC
1251  TGGCCTGTTG AACAAGTCTG GAAAGAAATG CATAAGCTTT TGCCATTCTC
1301  ACCGGATTCA GTCGTCACTC ATGGTGATTT CTCACTTGAT AACCTTATTT
1351  TTGACGAGGG GAAATTAATA GGTTGTATTG ATGTTGGACG AGTCGGAATC
1401  GCAGACCGAT ACCAGGATCT TGCCATCCTA TGGAACTGCC TCGGTGAGTT
1451  TTCTCCTTCA TTACAGAAAC GGCTTTTTCA AAAATATGGT ATTGATAATC
1501  CTGATATGAA TAAATTGCAG TTTCATTTGA TGCTCGATGA GTTTTTCTAA
1551  TCAGAATTGG TTAATTGGTT GTAACACTGG CAGAGCATTA CGCTGACTTG
1601  ACGGGACGGC GGCTTTGTTG AATAAATCGA ACTTTTGCTG AGTTGAAGGA
1651  TCAGATCACG CATCTTCCCG ACAACGCAGA CCGTTCCGTG GCAAAGCAAA
1701  AGTTCAAAAT CACCAACTGG TCCACCTACA ACAAAGCTCT CATCAACCGT
1751  GGCTCCCTCA CTTTCTGGCT GGATGATGGG GCGATTCAGG CCTGGTATGA
1801  GTCAGCAACA CCTTCTTCAC GAGGCAGACC TCAGCGCCCC CCCCCCCCTG
```

Fig. 23

```
1851  CAGGTCAACC CCGGCGGAAA TTAACACCAC CCTCAATAAA AAATCCGGTT
1901  TGCTCGGAGT CTCTGGGCTG TCGGCGGATC TTCGTACCAT TTTGCAGGCC
1951  AAAGCAGAGG GTAATGAACA AGCTCAATTG GCTTATGTCA TGTATATCCA
2001  TCGCTTCCGG AGTTGTTTGG GGCAAATGAT TGCTTCCTTG GAAGGTTTGG
2051  ATACGTTGGT GTTTACCGCC GGGGTGGGGG AAAATGCCGC CACTGTGCGG
2101  GCAGATGTTT GCCAAGCTTT TGAATTTCTA GGTTTAAAAC TTGATCCAGA
2151  GTTGAATAAC CGATCGCCAA GGGATACTGT CATTTCTCAC TCCGACTCCT
2201  TGGTGACGGT GTTGATTGTC CACACCGAAG AAGATTGGGC GATCGCCCAG
2251  GATTGTTGGC ACTGGTGGCA TAGCCAGGGA CAGAGAAAGC AATCGTAAAT
2301  TGCGAAAATG TTAGAAAATG GCTGTGAAGA TAAATGTTGA ATTAGGCTAA
2351  ATTTCCTTGG CTAGAGTCCG CATCCGCCAA CACGTCAACC CCCTCAGTGA
2401  AAAATATCGG CAGGTGTTGG CCTGTCCCGA TTGGGCCACC GTTTATGACG
2451  ATGTCCAACG ACCATTGCAT CTAGATATTG GCTGTGCCCG GGGTCGCTTT
2501  CCCCTCAAAA TGGCTCAACA ACACCCGAC TGGAATTTTT TAGGGGTGGA
2551  AATCCGTCAA CCCTTGGTGC TAGAGGCCAA CGAAACCGGC GATCGTCTGG
2601  GGTTAAAAAA TCTCCATTAC CTGTTTGGCA ACATCAATGT GGAGCCAGAA
2651  AAATTCTTTT CCGCCTTTCC CCCCACTCTG CAACGGGTCA GCATCCAATT
2701  TCCCGATCCC TGGTTTAAGC AACGACATAA TAAACGCCGA GTGGCCCAAC
2751  CAGAACTAGT
```

(SEQ ID NO. 29)

Fig. 23 (Continued)

```
MTSSLYLSTTEARSGKSLVVLGILDLILKKTTRIAYFRPIIQDPVNGKHDNNIILVLENF
RLQQTYTDSFGLYFHEAVSLASDGAIDQVLDRILAKYRHLADQVDFILCEGSDYLGEESA
FEFDLNTTIAKMLNCPILLLGNAMGNTIADSLQPIDMALNSYDQESCQVVGVIINRVQPE
LATEIQAQLEQRYGDRPMVLGTIPQDIMLKSLRLREIVSGLNAQVLSGADLLDNLVYHHL
VVAMHIAHALHWLHEKNTLIITPGDRGDIILGVMQAHRSLNYPSIAGILLTADYHPEPAI
MKLIEGLPDAPPLLLTSTHTHETSARLETLHPALSPTDNYKIRHSIALFQQQIDGEKLLN
YLKTIRSKGITPKLFLYNLVQAATAAQRHIVLPEGEEIRILKAAASLINHGIVRLTLLGN
IEAIEQTVKINHIDLDLSKVRLINPKTSPDRERYAETYYQLRKHKGVTLAMARDILTDIS
YFGTMMVHLGEADGMVSGSVNTTQHTVRPALQIIKTQPGFSLVSSVFFMCLEDRVLVYGD
CAVNPDFNAEQLAEIALTSAATAKNFGIEPRVALLSYSSGSSGQGADVEKVRQATAIAKE
REPDLALEGPIQYDAAVDSTVAAQKMPGSAVAGKATVFIFPDLNTGNNTYKAVQRETKAI
AIGPILQGLNKPVNDLSRGCLVEDIINTVVITALQVK
```

Fig. 24 (SEQ ID NO. 30)

```
   1 TTGGCCAAAA AACAAGGTTT ACTGGGTTTT ACCGCTGATG TTTTACTGGA
  51 AAATCGAGCC ATGTTGCATC TATTTGAGAA GATGAACTTT CGCATGGAAC
 101 GACGTATGAG CGAAGGGGTT TACGAATTAA AAATGTTTTT TAGTTGAGCC
 151 GTCTTCTTTC TGCTAATTTA TTGAAGGAAT TTTTGATGCT GGCGTTAGTA
 201 ATTTTACCGC TTCTTAGATT TATTAAAATC TCGTCATAAA ACTTTACTGA
 251 CTAGCGGTTT ATTTTCTGGC TAAAAGCGCT ATCACTTAAG TAGGTGGAAT
 301 TGGCAGATTT GTAGTAGTTG ATACTTAACT TTTTAGGGAA TATCGCTGTG
 351 GGAAAAATCG AGATCATTTT CCCAGAAAAA TCATTGCTGG ATACGTTGAG
 401 GTTATTTAAA TTATGACGAG TTCCCTTTAT TTAAGCACCA CCGAAGCCCG
 451 CAGCGGTAAA TCTCTAGTAG TATTGGGCAT TTTAGACTTA ATTCTCAAAA
 501 AAACCACCCG TATTGCCTAT TTTCGTCCCA TTATTCAAGA CCCAGTTAAT
 551 GGCAAACATG ATAACAACAT TATTCTGGTG CTGGAAAATT TTCGTCTCCA
 601 ACAAACCTAT ACCGATTCCT TTGGTTTGTA TTTCCATGAA GCGGTGAGTT
 651 TAGCCTCCGA TGGAGCTATT GATCAGGTAT TAGACCGAAT TTTGGCTAAA
 701 TATCGCCATT TGGCAGATCA AGTAGATTTT ATTCTCTGTG AAGGCTCAGA
 751 CTATTTGGGG GAGGAATCGG CTTTTGAATT TGATCTCAAC ACCACGATCG
 801 CCAAGATGTT GAACTGCCCC ATTTTGCTGT TGGGCAATGC CATGGGCAAC
 851 ACCATTGCCG ATAGTTTGCA ACCCATCGAT TTTCCATGGC AGCTGAGAAT
 901 ATTGTAGGAG ATCTTCTAGA AGATCCTGT GACGGAAGTT AACTTCGCAG
 951 AATAAATAAA TCCTGGTGTC CCTGTTGATA CCGGGAAGCC CTGGGCCAAC
1001 TTTTGGCGAA AATGAGACGT TGATCGGCAC GTAAGAGGTT CCAACTTTCA
1051 CCATAATGAA ATAAGATCAC TACCGGGCGT ATTTTTTGAG TTATCGAGAT
1101 TTTCAGGAGC TAAGGAAGCT AAAATGGAGA AAAAAATCAC TGGATATACC
1151 ACCGTTGATA TATCCCAATG GCATCGTAAA GAACATTTTG AGGCATTTCA
1201 GTCAGTTGCT CAATGTACCT ATAACCAGAC CGTTCAGCTG GATATTACGG
1251 CCTTTTTAAA GACCGTAAAG AAAAATAAGC ACAAGTTTTA TCCGGCCTTT
1301 ATTCACATTC TTGCCCGCCT GATGAATGCT CATCCGGAAT TCCGTATGGC
1351 AATGAAAGAC GGTGAGCTGG TGATATGGGA TAGTGTTCAC CCTTGTTACA
1401 CCGTTTTCCA TGAGCAAACT GAAACGTTTT CATCGCTCTG GAGTGAATAC
1451 CACGACGATT TCCGGCAGTT TCTACACATA TATTCGCAAG ATGTGGCGTG
1501 TTACGGTGAA AACCTGGCCT ATTTCCCTAA AGGGTTTATT GAGAATATGT
1551 TTTTCGTCTC AGCCAATCCC TGGGTGAGTT TCACCAGTTT TGATTTAAAC
1601 GTGGCCAATA TGGACAACTT CTTCGCCCCC GTTTTCACCA TGGGCAAATA
1651 TTATACGCAA GGCGACAAGG TGCTGATGCC GCTGGCGATT CAGGTTCATC
1701 ATGCCGTTTG TGATGGCTTC CATGTCGGCA GAATGCTTAA TGAATTACAA
1751 CAGTACTGCG ATGAGTGGCA GGGCGGGGCG TAATTTTTTT AAGGCAGTTA
1801 TTGGTGCCCT TAAACGCCTG GTTGCTACGC CTGAATAAGT GATAATAAGC
```

Fig. 26

```
1851 GGTTGACTGG CAGAAATTCG ATCTTGCTGA AAAACTCGAG CCATCCGGAA
1901 GATCTGGCGG CCGCTCTCCC TATAGTGAGT CGTATTACGC CGGATGGATA
1951 TGGTGTTCAG GCACAAGTGT TAAAGCAGTT GATTTTATTC ACTATGATGA
2001 AAAAAACAAT GAATGGAACC TGCTCCAAGT TAAAAATAGA GATAATACCG
2051 AAAACTCATC GAGTAGTAAG ATTAGAGATA ATACAACAAT AAAAAAATGG
2101 TTTAGAACTT ACTCACAGCG TGATGCTACT AATTGGGACA ATTTTCCAGA
2151 TGAAGTATCA TCTAAGAATT TAAATGAAGA AGACTTCAGA GCTTTTGTTA
2201 AAAATTATTT GGCAAAAATA ATATAATTCG GCTGCAGATT ACCATCCCGA
2251 ACCGGCCATT ATGAAACTAA TTGAAGGGCT ACCCGACGCC CCTCCCCTGT
2301 TGCTGACTAG CACCCACACC CATGAAACTT CCGCCCGTTT GGAAACTCTC
2351 CACCCTGCCC TGAGCCCTAC GGATAATTAT AAAATTCGCC ACAGTATTGC
2401 GCTGTTTCAA CAACAAATTG ATGGGGAGAA ATTACTCAAT TACCTTAAAA
2451 CCATCCGCAG TAAAGGTATT ACCCCCAAAC TGTTTCTCTA CAATTTAGTT
2501 CAAGCCGCCA CCGCCGCCCA ACGACATATT GTCCTACCGG AAGGGGAAGA
2551 AATTCGTATT CTCAAGGCGG CCGCTAGCTT AATTAACCAC GGCATTGTCC
2601 GTTTGACTTT ACTCGGTAAC ATTGAGGCGA TCGAGCAAAC GGTAAAAATT
2651 AATCACATTG ACTTAGATTT GAGCAAAGTT CGCCTCATTA ATCCTAAAAC
2701 TAGCCCAGAC CGAGAGCGCT ACGCCGAAAC CTATTACCAG CTACGTAAAC
2751 ATAAGGGGGT AACCCTGGCC ATGGCTCGGG ATATCCTCAC CGATATTTCC
2801 TATTTTGGAA CGATGATGGT GCATTTGGGA GAGGCCGATG GCATGGTTTC
2851 TGGCTCCGTC AATACCACCC AACATACCGT GCGTCCTGCT TTACAAATTA
2901 TTAAAACCCA GCCAGGTTTT TCCTTGGTTT CTTCAGTCTT TTTTATGTGT
2951 TTAGAAGACC GAGTTTTGGT CTATGGAGAT TGTGCTGTTA ATCCCGATCC
3001 CAATGCAGAA CAGTTAGCAG AAATTGCCCT TACTTCTGCG GCTACGGCCA
3051 AGAATTTTGG CATTGAGCCC AGGGTAGCTC TATTGTCCTA TTCTTCCGGT
3101 TCTTCTGGGC AAGGGGCCGA TGTGGAAAAA GTGCGGCAAG CCACGGCGAT
3151 CGCCAAGGAA AGAGAGCCAG ATTTAGCATT GGAAGGGCCG ATCCAGTATG
3201 ATGCGGCGGT GGATTCCACA GTGGCGGCCC AAAAAATGCC TGGGTCAGCG
3251 GTGGCGGGTA AAGCAACGGT GTTTATTTTT CCCGATTTAA ATACCGGTAA
3301 CAATACTTAC AAGGCAGTGC AAAGAGAAAC AAAGGCGATC GCCATTGGCC
3351 CCATTTTACA AGGATTAAAT AAACCAGTTA ATGATCTAAG TCGGGGTTGT
3401 TTAGTGGAGG ATATTATTAA TACGGTGGTA ATTACAGCTT GCAAGTTAA
3451 ATAATTTTAC TCTTAATTAG TTAAATGAT CCCTTGAATT ACCTTGATTT
3501 TGCCCTCCAA ACTACCAATA GCTGGGCCGA AAATTGGCAT CATTTAAAAT
3551 CACCAACGTG TCCCCGGACG GAGCTAGCAC AAACAGACCC TTACCATAGG
3601 CATAGCTGAC CACTTCTTGG CTTAACACCA TGGCTGCCAC TGCACCTAAA
3651 GCTT
```

Fig. 26 (Continued)

(SEQ ID NO. 33)

Fig. 26 (Continued)

```
MKIAFFSSKAYDRQFFQQANHPHQREMVFFDAQLNLDTAILAEDCPVICLFVNDQAPAPV
LEKLAACGTKLIALRSAGYNNVDLKTAADLGLKVVHVPSYSPHAVAEHTVGLILALNRKL
YRAYNRVRDDNFSLEGLLGFDLHGTTVGVIGTGKIGLAFAQIMNGFGCHLLGYDAFPNDK
FTAIGQALYVSLNELLAHSDIISLHCPLLPETHYLINTNTIAQMKPGVMLINTSRGHLID
TQAVIQGIKSHKIGFLGIDVYEEEEELFFIDHSDTIIQDDTFQLLQSFPNVMITAHQGFF
THNALQTIAATTLANIAEFEQNKPLTYQVICPH
```

Fig. 27 (SEQ ID NO. 34)

```
   1  GGAGCTCCAC CGCGGTGGCG GCCGCTCTAG CTAAAGGGAA GCTGAAAATG
  51  CATCACAGCC AAACACAGGA GTTGGAGGCC AAACCCTACA GTTGCCCCAG
 101  TGTGAGTCAA TATCTACCGC TACGGCAATC GCCAGAGCTA GGGGAGTATT
 151  AAATAATACA AATGCAGGAA GAATCAGAAA ATTTCTTTTA AGATTGGAAA
 201  AAATACCCTT GACTAAATAG TGCTCTAAGA GCCTGTTTAA CAAGCCCCCC
 251  TGGCCCCCAA ATTTGGGGTG AAGCTGGGTG AAAGTACCCC ATTATTGGGG
 301  GATTTAGGGG GCGGAATAAA ACTTTCCAAA CACGTTCTAA ACTACTTCCC
 351  ATAATCGTCA TGAAAATCGC TTTTTTTAGC AGTAAAGCCT ATGATCGTCA
 401  ATTTTTCCAA CAAGCAAACC ACCCCCATCA ACGGGAAATG GTCTTTTTTG
 451  ATGCCCAACT CAACCTTGAT ACCGCTATTT TAGCGGAGGA TTGCCCCGTT
 501  ATTTGCCTCT TCGTTAATGA CCAAGCTCCT GCCCCGGTGC TAGAAAAGTT
 551  AGCTGCCCAG GGCACAAAAT TAATCGCTCT GCGCAGTGCG GGCTATAATA
 601  ATGTTGACCT CAAAACAGCC GCAGATCCGT CGACCTGCAG CCTTGCTCTA
 651  GAGCTCGAAT TGACATAAGC CTGTTCGGTT CGTAAACTGT AATGCAAGTA
 701  GCGTATGCGC TCACGCAACT GGTCCAGAAC CTTGACCGAA CGCAGCGGTG
 751  GTAACGGCGC AGTGGCGGTT TTCATGGCTT GTTATGACTG TTTTTTTGTA
 801  CAGTCTATGC CTCGGGCATC CAAGCAGCAA GCGCGTTACG CCGTGGGTCG
 851  ATGTTTGATG TTATGGAGCA GCAACGATGT TACGCAGCAG CAACGATGTT
 901  ACGCAGCAGG GCAGTCGCCC TAAAACAAAG TTAGGTGGCT CAAGTATGGG
 951  CATCATTCGC ACATGTAGGC TCGGCCCTGA CCAAGTCAAA TCCATGCGGG
1001  CTGCTCTTGA TCTTTTCGGT CGTGAGTTCG GAGACGTAGC CACCTACTCC
1051  CAACATCAGC CGGACTCCGA TTACCTCGGG AACTTGCTCC GTAGTAAGAC
1101  ATTCATCGCG CTTGCTGCCT TCGACCAAGA AGCGGTTGTT GGCGCTCTCG
1151  CGGCTTACGT TCTGCCCAGG TTTGAGCAGC CGCGTAGTGA GATCTATATC
1201  TATGATCTCG CAGTCTCCGG CGAGCACCGG AGGCAGGGCA TTGCCACCGC
1251  GCTCATCAAT CTCCTCAAGC ATGAGGCCAA CGCGCTTGGT GCTTATGTGA
1301  TCTACGTGCA AGCAGATTAC GGTGACGATC CCGCAGTGGC TCTCTATACA
1351  AAGTTGGGCA TACGGAAGA AGTGATGCAC TTTGATATCG ACCCAAGTAC
1401  CGCCACCTAA CAATTCGTTC AAGCCGAGAT CGGCTTCCCG GCCGCGGAGT
1451  TGTTCGGTAA ATTGTCACAA CGCCGCGGCC AATTCGAGCT CGGTACCCAA
1501  CGCTCGGTTG CCGCCGGGCG TTTTTTATTC CACCGGTTGG TTCCACTCTC
1551  TGTTGCGGGC AACTTCAGCA GCACCTCGGT ACCCCTCCCG TTGTTAATCA
1601  ATGGGGGCTT TGCTTTAGCC AAAAGCTTCT ACTTTCTGTA AAAATTCCTG
1651  GGTTAATTTA ATAAAAGCTT TTGAACCCGC CGTATTGGGC ATGGAGGTAA
1701  CCACCGGCAT AAAGCTATCC ACTGCCTTAG CCACATTGAC ATCCATGGGA
1751  ATGGACTGCT GAAAAAGTTG TCCCAACTAA AGATAACGTT AAATTTTTTA
```

Fig. 31

```
1801  GCCTTTTATT ACCAGATATT TTTCCTAAAA ATGAAGCAAC GATAGTATTA
1851  ACGGCACTAC CTTGGTGATC GATAGTACGA TAAATCGTAG CTGTTACTAG
1901  GTTTTACTAA CCGGCGACTT CTGCCTTTTG TTGTCGCATC AACTTGACGA
1951  ACTTCTCGAA CAGATAATCG GCATCATGGG GTCCAGGGCT GGCCTCCGGG
2001  TGGTACTGCA CCGAGAAAAA GGGCAATTCT TTATGGCGTA GCCCCGCCAC
2051  CGTTTTATCG TTGAGGTTGA AATGGGTAAT TTCCACTTCT TCGGCCAGGG
2101  AACCTTCCGT CACCGCAAAA CCATGGTTCT GGCTGGTAAT TTCCACCTGT
2151  TGCTCCAGGC CACAGGGTTG ATTGAGCCCT CGATGACCAA ATTTGAGCTT
2201  AAAGGTCTCC GCTCCCAGGG ATATCAAGCT TATCGATACC GTCGAC
```

(SEQ ID NO. 37)

Fig. 31 (Continued)

```
   1 ATGAATTCTT ATACTGTCGG TACCTATTTA GCGGAGCGGC TTGTCCAGAT
  51 TGGTCTCAAG CATCACTTCG CAGTCGCGGG CGACTACAAC CTCGTCCTTC
 101 TTGACAACCT GCTTTTGAAC AAAAACATGG AGCAGGTTTA TTGCTGTAAC
 151 GAACTGAACT GCGGTTTCAG TGCAGAAGGT TATGCTCGTG CCAAAGGCGC
 201 AGCAGCAGCC GTCGTTACCT ACAGCGTCGG TGCGCTTTCC GCATTTGATG
 251 CTATCGGTGG CGCCTATGCA GAAAACCTTC CGGTTATCCT GATCTCCGGT
 301 GCTCCGAACA ACAATGATCA CGCTGCTGGT CACGTTGTGC ATCACGCTCT
 351 TGGCAAAACC GACTATCACT ATCAGTTGGA AATGGCCAAG AACATCACGG
 401 CCGCAGCTGA AGCGATTTAC ACCCCAGAAG AAGCTCCGGC TAAAATCGAT
 451 CACGTGATTA AAACTGCTCT TCGTGAGAAG AAGCCGGTTT ATCTCGAAAT
 501 CGCTTGCAAC ATTGCTTCCA TGCCCTGCGC CGCTCCTGGA CCGGCAAGCG
 551 CATTGTTCAA TGACGAAGCC AGCGACGAAG CTTCTTTGAA TGCAGCGGTT
 601 GAAGAAACCC TGAAATTCAT CGCCAACCGC GACAAAGTTG CCGTCCTCGT
 651 CGGCAGCAAG CTGCGCGCAG CTGGTGCTGA GAAGCTGCT GTCAAATTTG
 701 CTGATGCTCT CGGTGGCGCA GTTGCTACCA TGGCTGCTGC AAAAAGCTTC
 751 TTCCCAGAAG AAAACCCGCA TTACATCGGT ACCTCATGGG GTGAAGTCAG
 801 CTATCCGGGC GTTGAAAAGA CGATGAAAGA AGCCGATGCG GTTATCGCTC
 851 TGGCTCCTGT CTTCAACGAC TACTCCACCA CTGGTTGGAC GGATATTCCT
 901 GATCCTAAGA AACTGGTTCT CGCTGAACCG CGTTCTGTCG TCGTTAACGG
 951 CGTTCGCTTC CCCAGCGTTC ATCTGAAAGA CTATCTGACC CGTTTGGCTC
1001 AGAAAGTTTC CAAGAAAACC GGTGCTTTGG ACTTCTTCAA ATCCCTCAAT
1051 GCAGGTGAAC TGAAGAAAGC CGCTCCGGCT GATCCGAGTG CTCCGTTGGT
1101 CAACGCAGAA ATCGCCCGTC AGGTCGAAGC TCTTCTGACC CCGAACACGA
1151 CGGTTATTGC TGAAACCGGT GACTCTTGGT TCAATGCTCA GCGCATGAAG
1201 CTCCCGAACG GTGCTCGCGT TGAATATGAA ATGCAGTGGG GTCACATCGG
1251 TTGGTCCGTT CCTGCCGCCT TCGGTTATGC CGTCGGTGCT CCGGAACGTC
1301 GCAACATCCT CATGGTTGGT GATGGTTCCT TCCAGCTGAC GGCTCAGGAA
1351 GTCGCTCAGA TGGTTCGCCT GAAACTGCCG GTTATCATCT TCTTGATCAA
1401 TAACTATGGT TACACCATCG AAGTTATGAT CCATGATGGT CCGTACAACA
1451 ACATCAAGAA CTGGGATTAT GCCGGTCTGA TGGAAGTGTT CAACGGTAAC
1501 GGTGGTTATG ACAGCGGTGC TGGTAAAGGC CTGAAGGCTA AACCGGTGG
1551 CGAACTGGCA GAAGCTATCA AGGTTGCTCT GGCAAACACC GACGGCCCAA
1601 CCCTGATCGA ATGCTTCATC GGTCGTGAAG ACTGCACTGA AGAATTGGTC
1651 AAATGGGGTA AGCGCGTTGC TGCCGCCAAC AGCCGTAAGC CTGTTAACAA
1701 GCTCCTC░░░ TTTTTGGGGA TCAATTCGAG CTCGGTACCC AAACTAGTAT
1751 GTAGGGTGAG GTTATAGCT░ ░░GCTTCTTC AACTTTTTAT ATTCCTTTCG
1801 TCAACGAAAT GGGCGAAGGT TCGCTTGAAA AAGCAATCAA GGATCTTAAC
```

Fig. 33

```
1851 GGCAGCGGCT TTAAAAATGC GCTGATCGTT TCTGATGCTT TCATGAACAA
1901 ATCCGGTGTT GTGAAGCAGG TTGCTGACCT GTTGAAAGCA CAGGGTATTA
1951 ATTCTGCTGT TTATGATGGC GTTATGCCGA ACCCGACTGT TACCGCAGTT
2001 CTGGAAGGCC TTAAGATCCT GAAGGATAAC AATTCAGACT TCGTCATCTC
2051 CCTCGGTGGT GGTTCTCCCC ATGACTGCGC CAAAGCCATC GCTCTGGTCG
2101 CAACCAATGG TGGTGAAGTC AAAGACTACG AAGGTATCGA CAAATCTAAG
2151 AAACCTGCCC TGCCTTTGAT GTCAATCAAC ACGACGGCTG GTACGGCTTC
2201 TGAAATGACG CGTTTCTGCA TCATCACTGA TGAAGTCCGT CACGTTAAGA
2251 TGGCCATTGT TGACCGTCAC GTTACCCCGA TGGTTTCCGT CAACGATCCT
2301 CTGTTGATGG TTGGTATGCC AAAAGGCCTG ACCGCCGCCA CCGGTATGGA
2351 TGCTCTGACC CACGCATTTG AAGCTTATTC TTCAACGGCA GCTACTCCGA
2401 TCACCGATGC TTGCGCCTTG AAGGCTGCGT CCATGATCGC TAAGAATCTG
2451 AAGACCGCTT GCGACAACGG TAAGGATATG CCAGCTCGTG AAGCTATGGC
2501 TTATGCCCAA TTCCTCGCTG GTATGGCCTT CAACAACGCT TCGCTTGGTT
2551 ATGTCCATGC TATGGCTCAC CAGTTGGGCG GCTACTACAA CCTGCCGCAT
2601 GGTGTCTGCA ACGCTGTTCT GCTTCCGCAT GTTCTGGCTT ATAACGCCTC
2651 TGTCGTTGCT GGTCGTCTGA AGACGTTGG TGTTGCTATG GGTCTCGATA
2701 TCGCCAATCT CGGTGATAAA GAAGGCGCAG AAGCCACCAT TCAGGCTGTT
2751 CGCGATCTGG CTGCTTCCAT TGGTATTCCA GCAAATCTGA CCGAGCTGGG
2801 TGCTAAGAAA GAAGATGTGC CGCTTCTTGC TGACCACGCT CTGAAAGATG
2851 CTTGTGCTCT GACCAACCCG CGTCAGGGTG ATCAGAAAGA AGTTGAAGAA
2901 CTCTTCCTGA GCGCTTTC         TTTCAAAAC AGGAAAACGG TTTTCCGTCC
2951 TGTCTTGATT TTCAAGCAAA CAATGCCTCC GATTTCTAAT CGGAGGCATT
3001 TGTTTTTGTT TATTGCAAAA ACAAAAAATA TTGTTACAAA TTTTTACAGG
3051 CTATTAAGCC TACCGTCATA AATAATTTGC CATTTGGGGA TCC
```

(SEQ ID NO. 40)

Fig. 33 (Continued)

```
MNSYTVGTYLAERLVQIGLKHHFAVAGDYNLVLLDNLLLNKNMEQVYCCN  50
ELNCGFSAEGYARAKGAAAAVVTYSVGALSAFDAIGGAYAENLPVILISG 100
APNNNDHAAGHVLHHALGKTDYHYQLEMAKNITAAAEAIYTPEEAPAKID 150
HVIKTALREKKPVYLEIACNIASMPCAAPGPASALFNDEASDEASLNAAV 200
EETLKFIANRDKVAVLVGSKLRAAGAEEAAVKFADALGGAVATMAAAKSF 250
FPEENPHYIGTSWGEVSYPGVEKTMKEADAVIALAPVFNDYSTTGWTDIP 300
DPKKLVLAEPRSVVVNGVRFPSVHLKDYLTRLAQKVSKKTGALDFFKSLN 350
AGELKKAAPADPSAPLVNAEIARQVEALLTPNTTVIAETGDSWFNAQRMK 400
LPNGARVEYEMQWGHIGWSVPAAFGYAVGAPERRNILMVGDGSFQLTAQE 450
VAQMVRLKLPVIIFLINNYGYTIEVMIHDGPYNNIKNWDYAGLMEVFNGN 500
GGYDSGAGKGLKAKTGGELAEAIKVALANTDGPTLIECFIGREDCTEELV 550
KWGKRVAAANSRKPVNKLL
```

Fig. 35 (SEQ ID NO. 41)

```
MASSTFYIPFVNEMGEGSLEKAIKDLNGSGFKNALIVSDAFMNKSGVVKQ  50
VADLLKAQGINSAVYDGVMPNPTVTAVLEGLKILKDNNSDFVISLGGGSP 100
HDCAKAIALVATNGGEVKDYEGIDKSKKPALPLMSINTTAGTASEMTRFC 150
IITDEVRHVKMAIVDRHVTPMVSVNDPLLMVGMPKGLTAATGMDALTHAF 200
EAYSSTAATPITDACALKAASMIAKNLKTACDNGKDMPAREAMAYAQFLA 250
GMAFNNASLGYVHAMAHQLGGYYNLPHGVCNAVLLPHVLAYNASVVAGRL 300
KDVGVAMGLDIANLGDKEGAEATIQAVRDLAASIGIPANLTELGAKKEDV 350
PLLADHALKDACALTNPRQGDQKEVEELFLSAF
```

Fig. 36 (SEQ ID NO. 42)

```
GTCGACGGGAATTGCTCTGGCAACTGATTAATCCACTGAGCAACAG
CCCAAGACACGCAAACAAAAACCAACGTCTTGGCGATCGCCATCGGCACCATGAAACCAT
CGTAAAAGCTGGGGAAAGAATAAAAAACAGTGGTTCAGGAATTGCATTGCCATGGCCACT
TCACAAACCTAGCCAATTTTAGCTTGACCGCAACTTTGACAGATTGTCTTTTGACTTTGC
CTGGACCGCCTCCCATAATACCTTCGCGTCTTGAAGACTTTATCCTTGAAAGGAGAACTA
                      ATGAATTC
```

Fig. 37 (SEQ ID NO. 43)

```
   1 GTCGACGAAT TTCTGCCATT CATCCGCTTA TTATCACTTA TTCAGGCGTA
  51 GCACCAGGCG TTTAAGGGCA CCAATAACTG CCTTAAAAAA ATTACGCCCC
 101 GCCCTGCCAC TCATCGCAGT ACTGTTGTAA TTCATTAAGC ATTCTGCCGA
 151 CATGGAAGCC ATCACAGACG GCATGATGAA CCTGAATCGC CAGCGGCATC
 201 AGCACCTTGT CGCCTTGCGT ATAATATTTG CCCATGGTGA AAACGGGGGC
 251 GAAGAAGTTG TCCATATTGG CCACGTTTAA ATCAAAACTG GTGAAACTCA
 301 CCCAGGGATT GGCTGAGACG AAAACATAT TCTCAATAAA CCCTTTAGGG
 351 AAATAGGCCA GGTTTTCACC GTAACACGCC ACATCTTGCG AATATATGTG
 401 TAGAAACTGC CGGAAATCGT CGTGGTATTC ACTCCAGAGC GATGAAAACG
 451 TTTCAGTTTG CTCATGGAAA ACGGTGTAAC AAGGGTGAAC ACTATCCCAT
 501 ATCACCAGCT CACCGTCTTT CATTGCCATA CGGAATTCCG GATGAGCATT
 551 CATCAGGCGG GCAAGAATGT GAATAAAGGC CGGATAAAAC TTGTGCTTAT
 601 TTTTCTTTAC GGTCTTTAAA AAGGCCGTAA TATCCAGCTG AACGGTCTGG
 651 TTATAGGTAC ATTGAGCAAC TGACTGAAAT GCCTCAAAAT GTTCTTTACG
 701 ATGCCATTGG GATATATCAA CGGTGGTATA TCCAGTGATT TTTTTCTCCA
 751 TTTTAGCTTC CTTAGCTCCT GAAAATCTCG ATAACTCAAA AAATACGCCC
 801 GGTAGTGATC TTATTTCATT ATGGTGAAAG TTGGAACCTC TTACGTGCCG
 851 ATCAACGTCT CATTTTCGCC AAAAGTTGGC CCAGGGCTTC CCGGTATCAA
 901 CAGGGACACC AGGATTTATT TATTCTGCGA AGTGATCTTC CGTCACAGGT
 951 ATTTATTCGA AGACGAAAGG GCCTCGTGAT ACGCCTATTT TTATAGGTTA
1001 ATGTCATGAT AATAATGGTT TCTTAGACGT CAGGTGGCAC TTTTCGGGGA
1051 AATGTGCGCG GAACCCCTAT TTGTTTATTT TTCTAAATAC ATTCAAATAT
1101 GTATCCGCTC ATGAGACAAT AACCCTGATA AATGCTTCAA TAATATTGAA
1151 AAAGGAAGAG TATGAGTATT CAACATTTCC GTGTCGCCCT TATTCCCTTT
1201 TTTGCGGCAT TTTGCCTTCC TGTTTTTGCT CACCCAGAAA CGCTGGTGAA
1251 AGTAAAAGAT GCTGAAGATC AGTTGGGTGC ACGAGTGGGT TACATCGAAC
1301 TGGATCTCAA CAGCGGTAAG ATCCTTGAGA GTTTTCGCCC CGAAGAACGT
1351 TTTCCAATGA TGAGCACTTT TAAAGTTCTG CTATGTGGCG CGGTATTATC
1401 CCGTGTTGAC GCCGGGCAAG AGCAACTCGG TCGCCGCATA CACTATTCTC
1451 AGAATGACTT GGTTGAGTAC TCACCAGTCA CAGAAAAGCA TCTTACGGAT
1501 GGCATGACAG TAAGAGAATT ATGCAGTGCT GCCATAACCA TGAGTGATAA
1551 CACTGCGGCC AACTTACTTC TGACAACGAT CGGAGGACCG AAGGAGCTAA
1601 CCGCTTTTTT GCACAACATG GGGGATCATG TAACTCGCCT TGATCGTTGG
1651 GAACCGGAGC TGAATGAAGC CATACCAAAC GACGAGCGTG ACACCACGAT
1701 GCCTGCAGGA GCAGAAGAGC ATACATCTGG AAGCAAAGCC AGGAAAGCGG
1751 CCTATGGAGC TGTGCGGCAG CGCTCAGTAG GCAATTTTTC AAAATATTGT
1801 TAAGCCTTTT CTGAGCATGG TATTTTTCAT GGTATTACCA ATTAGCAGGA
```

Fig. 38

```
1851 AAATAAGCCA TTGAATATAA AAGATAAAAA TGTCTTGTTT ACAATAGAGT
1901 GGGGGGGGTC AGCCTGCCGC CTTGGGCCGG GTGATGTCGT ACTTGCCCGC
1951 CGCGAACTCG GTTACCGTCC AGCCCAGCGC GACCAGCTCC GGCAACGCCT
2001 CGCGCACCCG CTGGCGGCGC TTGCGCATGG TCGAACCACT GGCCTCTGAC
2051 GGCCAGACAT AGCCGCACAA GGTATCTATG GAAGCCTTGC CGGTTTTGCC
2101 GGGGTCGATC CAGCCACACA GCCGCTGGTG CAGCAGGCGG GCGGTTTCGC
2151 TGTCCAGCGC CCGCACCTCG TCCATGCTGA TGCGCACATG CTGGCCGCCA
2201 CCCATGACGG CCTGCGCGAT CAAGGGGTTC AGGGCACGT ACAGGCGCCC
2251 GTCCGCCTCG TCGCTGGCGT ACTCCGACAG CAGCCGAAAC CCCTGCCGCT
2301 TGCGGCCATT CTGGGCGATG ATGGATACCT TCCAAAGGCG CTCGATGCAG
2351 TCCTGTATGT GCTTGAGCGC CCCACCACTA TCGACCTCTG CCCCGATTTC
2401 CTTTGCCAGC GCCCGATAGC TACCTTTGAC CACATGGCAT TCAGCGGTGA
2451 CGGCCTCCCA CTTGGGTTCC AGGAACAGCC GGAGCTGCCG TCCGCCTTCG
2501 GTCTTGGGTT CCGGGCCAAG CACTAGGCCA TTAGGCCCAG CCATGGCCAC
2551 CAGCCCTTGC AGGATGCGCA GATCATCAGC GCCCAGCGGC TCCGGGCCGC
2601 TGAACTCGAT CCGCTTGCCG TCGCCGTAGT CATACGTCAC GTCCAGCTTG
2651 CTGCGCTTGC GCTCGCCCCG CTTGAGGGCA CGGAACAGGC CGGGGGCCAG
2701 ACAGTGCGCC GGGTCGTGCC GGACGTGGCT GAGGCTGTGC TTGTTCTTAG
2751 GCTTCACCAC GGGGCACCCC CTTGCTCTTG CGCTGCCTCT CCAGCACGGC
2801 GGGCTTGAGC ACCCCGCCGT CATGCCGCCT GAACCACCGA TCAGCGAACG
2851 GTGCGCCATA GTTGGCCTTG CTCACACCGA AGCGGACGAA GAACCGGCGC
2901 TGGTCGTCGT CCACACCCCA TTCCTCGGCC TCGGCGCTGG TCATGCTCGA
2951 CAGGTAGGAC TGCCAGCGGA TGTTATCGAC CAGTACCGAG CTGCCCCGGC
3001 TGGCCTGCTG CTGGTCGCCT GCGCCCATCA TGGCCGCGCC CTTGCTGGCA
3051 TGGTGCAGGA ACACGATAGA GCACCCGGTA TCGGCGGCGA TGGCCTCCAT
3101 GCGACCGATG ACCTGGGCCA TGGGCCGCT GGCGTTTTCT TCCTCGATGT
3151 GGAACCGGCG CAGCGTGTCC AGCACCATCA GGCGGCGGCC CTCGGCGGCG
3201 CGCTTGAGGC CGTCGAACCA CTCCGGGGCC ATGATGTTGG GCAGGCTGCC
3251 GATCAGCGGC TGGATCAGCA GGCCGTCAGC CACGGCTTGC CGTTCCTCGG
3301 CGCTGAGGTG CGCCCCAAGG GCGTGCAGGC GGTGATGAAT GGCGGTGGGC
3351 GGGTCTTCGG CGGGCAGGTA GATCACCGGG CCGGTGGGCA GTTCGCCCAC
3401 CTCCAGCAGA TCCGGCCCGC CTGCAATCTG TGCGGCCAGT TGCAGGGCCA
3451 GCATGGATTT ACCGGCACCA CCGGGCGACA CCAGCGCCCC GACCGTACCG
3501 GCCACCATGT TGGGCAAAAC GTAGTCCAGC GGTGGCGGCG CTGCTGCGAA
3551 CGCCTCCAGA ATATTGATAG CTTATGGGT AGCCATTGAT TGCCTCCTTT
3601 GCAGGCAGTT GGTGGTTAGG CGCTGGCGGG GTCACTACCC CCGCCCTGCG
3651 CCGCTCTGAG TTCTTCCAGG CACTCGCGCA GCGCCTCGTA TTCGTCGTCG
```

Fig. 38 (Continued)

```
3701 GTCAGCCAGA ACTTGCGCTG ACGCATCCCT TTGGCCTTCA TGCGCTCGGC
3751 ATATCGCGCT GGCGTACAG CGTCAGGGCT GGCCAGCAGG TCGCCGGTCT
3801 GCTTGTCCTT TTGGTCTTTC ATATCAGTCA CCGAGAAACT GCCGGGGCC
3851 GAAAGGCTTG TCTTCGCGGA ACAAGGACAA GGTGCAGCCG TCAAGGTTAA
3901 GGCTGGCCAT ATCAGCGACT GAAAGCGGC CAGCCTCGGC CTTGTTTGAC
3951 GTATAACCAA AGCCACCGGG CAACCAATAG CCCTTGTCAC TTTTGATCAG
4001 GTAGACCGAC CCTGAAGCGC TTTTTTCGTA TTCCATAAAA CCCCCTTCTG
4051 TGCGTGAGTA CTCATAGTAT AACAGGCGTG AGTACCAACG CAAGCACTAC
4101 ATGCTGAAAT CTGGCCCGCC CCTGTCCATG CCTCGCTGGC GGGGTGCCGG
4151 TGCCCGTGCC AGCTCGGCCC GCGCAAGCTG GACGCTGGGC AGACCCATGA
4201 CCTTGCTGAC GGTGCGCTCG ATGTAATCCG CTTCGTGGCC GGGCTTGCGC
4251 TCTGCCAGCG CTGGGCTGGC CTCGGCCATG GCCTTGCCGA TTTCCTCGGC
4301 ACTGCGGCCC CGGCTGGCCA GCTTCTGCGC GGCGATAAAG TCGCACTTGC
4351 TGAGGTCATC ACCGAAGCGC TTGACCAGCC CGGCCATCTC GCTGCGGTAC
4401 TCGTCCAGCG CCGTGCGCCG GTGGCGGCTA AGCTGCCGCT CGGGCAGTTC
4451 GAGGCTGGCC AGCCTGCGGG CCTTCTCCTG CTGCCGCTGG GCCTGCTCGA
4501 TCTGCTGGCC AGCCTGCTGC ACCAGCGCCG GGCCAGCGGT GGCGGTCTTG
4551 CCCTTGGATT CACGCAGCAG CACCCACGGC TGATAACCGG CGCGGGTGGT
4601 GTGCTTGTCC TTGCGGTTGG TGAAGCCCGC CAAGCGGCCA TAGTGGCGGC
4651 TGTCGGCGCT GGCCGGGTCG GCGTCGTACT CGCTGGCCAG CGTCCGGGCA
4701 ATCTGCCCCC GAAGTTCACC GCCTGCGGCG TCGGCCACCT TGACCCATGC
4751 CTGATAGTTC TTCGGGCTGG TTTCCACTAC CAGGGCAGGC TCCCGGCCCT
4801 CGGCTTTCAT GTCATCCAGG TCAAACTCGC TGAGGTCGTC CACCAGCACC
4851 AGACCATGCC GCTCCTGCTC GGCGGGCCTG ATATACACGT CATTGCCCTG
4901 GGCATTCATC CGCTTGAGCC ATGGCGTGTT CTGGAGCACT TCGGCGGCTG
4951 ACCATTCCCG GTTCATCATC TGGCCGGTGG TGGCGTCCCT GACGCCGATA
5001 TCGAAGCGCT CACAGCCCAT GGCCTTGAGC TGTCGGCCTA TGGCCTGCAA
5051 AGTCCTGTCG TTCTTCATCG GGCCACCAAG CGCAGCCAGA TCGAGCCGTC
5101 CTCGGTTGTC AGTGGCGTCA GGTCGAGCAA GAGCAACGAT GCGATCAGCA
5151 GCACCACCGT AGGCATCATG GAAGCCAGCA TCACGGTTAG CCATAGCTTC
5201 CAGTGCCACC CCCGCGACGC GCTCCGGGCG CTCTGCGCGG CGCTGCTCAC
5251 CTCGGCGGCT ACCTCCCGCA ACTCTTTGGC CAGCTCCACC CATGCCGCCC
5301 CTGTCTGGCG CTGGGCTTTC AGCCACTCCG CCGCCTGCGC CTCGCTGGCC
5351 TGCTGGGTCT GGCTCATGAC CTGCCGGGCT TCGTCGGCCA GTGTCGCCAT
5401 GCTCTGGGCC AGCGGTTCGA TCTGCTCCGC TAACTCGTTG ATGCCTCTGG
5451 ATTTCTTCAC TCTGTCGATT GCGTTCATGG TCTATTGCCT CCCGGTATTC
5501 CTGTAAGTCG ATGATCTGGG CGTTGGCGGT GTCGATGTTC AGGGCCACGT
```

Fig. 38 (Continued)

```
5551 CTGCCCGGTC GGTGCGGATG CCCCGGCCTT CCATCTCCAC CACGTTCGGC
5601 CCCAGGTGAA CACCGGGCAG GCGCTCGATG CCCTGCGCCT CAAGTGTTCT
5651 GTGGTCAATG CGGGCGTCGT GGCCAGCCCG CTCTAATGCC CGGTTGGCAT
5701 GGTCGGCCCA TGCCTCGCGG GTCTGCTCAA GCCATGCCTT GGGCTTGAGC
5751 GCTTCGGTCT TCTGTGCCCC GCCCTTCTCC GGGGTCTTGC CGTTGTACCG
5801 CTTGAACCAC TGAGCGGCGG GCCGCTCGAT GCCGTCATTG ATCCGCTCGG
5851 AGATCATCAG GTGGCAGTGC GGGTTCTCGC CGCCACCGGC ATGGATGGCC
5901 AGCGTATACG GCAGGCGCTC GGCACCGGTC AGGTGCTGGG CGAACTCGGA
5951 CGCCAGCGCC TTCTGCTGGT CGAGGGTCAG CTCGACCGGC AGGGCAAATT
6001 CGACCTCCTT GAACAGCCGC CCATTGGCGC GTTCATACAG GTCGGCAGCA
6051 TCCCAGTAGT CGGCGGGCCG CTCGACGAAC TCCGGCATGT GCCCGGATTC
6101 GGCGTGCAAG ACTTCATCCA TGTCGCGGGC ATACTTGCCT TCGCGCTGGA
6151 TGTAGTCGGC CTTGGCCCTG GCCGATTGGC CGCCCGACCT GCTGCCGGTT
6201 TTCGCCGTAA GGTGATAAAT CGCCATGCTG CCTCGCTGTT GCTTTTGCTT
6251 TTCGGCTCCA TGCAATGGCC CTCGGAGAGC GCACCGCCCG AAGGGTGGCC
6301 GTTAGGCCAG TTTCTCGAAG AGAAACCGGT AAGTGCGCCC TCCCCTACAA
6351 AGTAGGGTCG GGATTGCCGC CGCTGTGCCT CCATGATAGC CTACGAGACA
6401 GCACATTAAC AATGGGGTGT CAAGATGGTT AAGGGGAGCA ACAAGGCGGC
6451 GGATCGGCTG GCCAAGCTCG AAGAACAACG AGCGCGAATC AATGCCGAAA
6501 TTCAGCGGGT GCGGGCAAGG GAACAGCAGC AAGAGCGCAA GAACGAAACA
6551 AGGCGCAAGG TGCTGGTGGG GGCCATGATT TTGGCCAAGG TGAACAGCAG
6601 CGAGTGGCCG GAGGATCGGC TCATGGCGGC AATGGATGCG TACCTTGAAC
6651 GCGACCACGA CCGCGCCTTG TTCGGTCTGC CGCCACGCCA GAAGGATGAG
6701 CCGGGCTGAA TGATCGACCG AGACAGGCCC TGCGGGGCTG CACACGCGCC
6751 CCCACCCTTC GGGTAGGGGG AAAGGCCGCT AAAGCGGCTA AAAGCGCTCC
6801 AGCGTATTTC TGCGGGGTTT GGTGTGGGGT TTAGCGGGCT TTGCCCGCCT
6851 TTCCCCCTGC CGCGCAGCGG TGGGGCGGTG TGTAGCCTAG CGCAGCGAAT
6901 AGACCAGCTA TCCGGCCTCT GGCCGGGCAT ATTGGGCAAG GGCAGCAGCG
6951 CCCCACAAGG GCGCTGATAA CCGCGCCTAG TGGATTATTC TTAGATAATC
7001 ATGGATGGAT TTTTCCAACA CCCCGCCAGC CCCCGCCCCT GCTGGGTTTG
7051 CAGGTTTGGG GGCGTGACAG TTATTGCAGG GGTTCGTGAC AGTTATTGCA
7101 GGGGGGCGTG ACAGTTATTG CAGGGGTTCG TGACAGTTAG TACGGGAGTG
7151 ACGGGCACTG GCTGGCAATG TCTAGCAACG GCAGGCATTT CGGCTGAGGG
7201 TAAAAGAACT TTCCGCTAAG CGATAGACTG TATGTAAACA CAGTATTGCA
7251 AGGACGCGGA ACATGCCTCA TGTGGCGGCC AGGACGGCCA GCCGGGATCG
7301 GGATACTGGT CGTTACCAGA GCCACCGACC CGAGCAAACC CTTCTCTATC
7351 AGATCGTTGA CGAGTATTAC CCGGCATTCG CTGCGCTTAT GGCAGAGCAG
```

Fig. 38 (Continued)

```
7401 GGAAAGGAAT TGCCGGGCTA TGTGCAACGG GAATTTGAAG AATTTCTCCA
7451 ATGCGGGCGG CTGGAGCATG GCTTTCTACG GGTTCGCTGC GAGTCTTGCC
7501 ACGCCGAGCA CCTGGTCGCT TTCAGCTGTA ATCCGGGCAG CGCAACGGAA
7551 CATTCATCAG TGTAAAAATG GAATCAATAA AGCCCTGCGC AGCGCGCAGG
7601 GTCAGCCTGA ATACGCGTTT AATGACCAGC ACAGTCGTGA TGGCAAGGTC
7651 AGAATAGCGC TGAGGTCTGC CTCGTGAAGA AGGTGTTGCT GACTCATACC
7701 AGGCCTGAAT CGCCCCATCA TCCAGCCAGA AAGTGAGGGA GCCACGGTTG
7751 ATGAGAGCTT TGTTGTAGGT GGACCAGTTG GTGATTTTGA ACTTTTGCTT
7801 TGCCACGGAA CGGTCTGCGT TGTCGGGAAG ATGCGTGATC TGATCCTTCA
7851 ACTCAGCAAA AGTTCGATTT ATTCAACAAA GCCACGTTGT GTCTCAAAAT
7901 CTCTGATGTT ACATTGCACA AGATAAAAAT ATATCATCAT GAACAATAAA
7951 ACTGTCTGCT TACATAAACA GTAATACAAG GGGTGTTATG AGCCATATTC
8001 AACGGGAAAC GTCTTGCTCG AGGCCGCGAT TAAATTCCAA CATGGATGCT
8051 GATTTATATG GGTATAAATG GGCTCGCGAT AATGTCGGGC AATCAGGTGC
8101 GACAATCTAT CGATTGTATG GGAAGCCCGA TGCGCCAGAG TTGTTTCTGA
8151 AACATGGCAA AGGTAGCGTT GCCAATGATG TTACAGATGA GATGGTCAGA
8201 CTAAACTGGC TGACGGAATT TATGCCTCTT CCGACCATCA AGCATTTTAT
8251 CCGTACTCCT GATGATGCAT GGTTACTCAC CACTGCGATC CCCGGGAAAA
8301 CAGCATTCCA GGTATTAGAA GAATATCCTG ATTCAGGTGA AAATATTGTT
8351 GATGCGCTGG CAGTGTTCCT GCGCCGGTTG CATTCGATTC CTGTTTGTAA
8401 TTGTCCTTTT AACAGCGATC GCGTATTTCG TCTCGCTCAG GCGCAATCAC
8451 GAATGAATAA CGGTTTGGTT GATGCGAGTG ATTTTGATGA CGAGCGTAAT
8501 GGCTGGCCTG TTGAACAAGT CTGGAAAGAA ATGCATAAGC TTTTGCCATT
8551 CTCACCGGAT TCAGTCGTCA CTCATGGTGA TTTCTCACTT GATAACCTTA
8601 TTTTTGACGA GGGGAAATTA ATAGGTTGTA TTGATGTTGG ACGAGTCGGA
8651 ATCGCAGACC GATACCAGGA TCTTGCCATC CTATGGAACT GCCTCGGTGA
8701 GTTTTCTCCT TCATTACAGA AACGGCTTTT TCAAAAATAT GGTATTGATA
8751 ATCCTGATAT GAATAAATTG CAGTTTCATT TGATGCTCGA TGAGTTTTTC
8801 TAATCAGAAT TGGTTAATTG GTTGTAACAC TGGCAGAGCA TTACGCTGAC
8851 TTGACGGGAC GGCGGCTTTG TTGAATAAAT CGAACTTTTG CTGAGTTGAA
8901 GGATCAGATC ACGCATCTTC CCGACAACGC AGACCGTTCC GTGGCAAAGC
8951 AAAAGTTCAA AATCACCAAC TGGTCCACCT ACAACAAAGC TCTCATCAAC
9001 CGTGGCTCCC TCACTTTCTG GCTGGATGAT GGGGCGATTC AGGCCTGGTA
9051 TGAGTCAGCA ACACCTTCTT CACGAGGCAG ACCTCAGCGC TATTCTGACC
9101 TTGCCATCAC GACTGTGCTG GTCATTAAAC GCGTATTCAG GCTGACCCTG
9151 CGCGCTGCGC AGGGCTTTAT TGATTCCATT TTTACACTGA TGAATGTTCC
9201 GTTGCGCTGC CCGGATTACA GATCCTCTAG ATCTAGAAGA ACAGCAAGGC
```

Fig. 38 (Continued)

```
9251 CGCCAATGCC TGACGATGCG TGGAGACCGA AACCTTGCGC TCGTTCGCCA
9301 GCCAGGACAG AAATGCCTCG ACTTCGCTGC TGCCCAAGGT TGCCGGGTGA
9351 CGCACACCGT GGAAACGGAT GAAGGCACGA ACCCAGTGGA CATAAGCCTG
9401 TTCGGTTCGT AAGCTGTAAT GCAAGTAGCG TATGCGCTCA CGCAACTGGT
9451 CCAGAACCTT GACCGAACGC AGCGGTGGTA ACGGCGCAGT GGCGGTTTTC
9501 ATGGCTTGTT ATGACTGTTT TTTTGGGGTA CAGTCTATGC CTCGGGCATC
9551 CAAGCAGCAA GCGCGTTACG CCGTGGGTCG ATGTTTGATG TTATGGAGCA
9601 GCAACGATGT TACGCAGCAG GGCAGTCGCC CTAAAACAAA GTTAAACATC
9651 ATGAGGGAAG CGGTGATCGC CGAAGTATCG ACTCAACTAT CAGAGGTAGT
9701 TGGCGTCATC GAGCGCCATC TCGAACCGAC GTTGCTGGCC GTACATTTGT
9751 ACGGCTCCGC AGTGGATGGC GGCCTGAAGC CACACAGTGA TATTGATTTG
9801 CTGGTTACGG TGACCGTAAG GCTTGATGAA ACAACGCGGC GAGCTTTGAT
9851 CAACGACCTT TTGGAAACTT CGGCTTCCCC TGGAGAGAGC GAGATTCTCC
9901 GCGCTGTAGA AGTCACCATT GTTGTGCACG ACGACATCAT TCCGTGGCGT
9951 TATCCAGCTA AGCGCGAACT GCAATTTGGA GAATGGCAGC GCAATGACAT
10001 TCTTGCAGGT ATCTTCGAGC CAGCCACGAT CGACATTGAT CTGGCTATCT
10051 TGCTGACAAA AGCAAGAGAA CATAGCGTTG CCTTGGTAGG TCCAGCGGCG
10101 GAGGAACTCT TTGATCCGGT TCCTGAACAG GATCTATTTG AGGCGCTAAA
10151 TGAAACCTTA ACGCTATGGA ACTCGCCGCC CGACTGGGCT GGCGATGAGC
10201 GAAATGTAGT GCTTACGTTG TCCCGCATTT GGTACAGCGC AGTAACCGGC
10251 AAAATCGCGC CGAAGGATGT CGCTGCCGAC TGGGCAATGG AGCGCCTGCC
10301 GGCCCAGTAT CAGCCCGTCA TACTTGAAGC TAGACAGGCT TATCTTGGAC
10351 AAGAAGAAGA TCGCTTGGCC TCGCGCGCAG ATCAGTTGGA AGAATTTGTC
10401 CACTACGTGA AAGGCGAGAT CACCAAGGTA GTCGGCAAAT AATGTCTAAC
10451 AATTCGTTCA AGCCGACGCC GCTTCGCGGC GCGGCTTAAC TCAAGCTCTA
10501 GA
```

(SEQ ID NO. 44)

Fig. 38 (Continued)

```
GAGCTCTCTGGATAAAACTAATAAACTCTATTACCC
ATGATTAAAGCCTACGCTGCCCTGGAAGCCAACGGAAAACTCCAACCCTTTGAATACGAC
CCCGGTGCCCTGGGTGCTAATGAGGTGGAGATTGAGGTGCAGTATTGTGGGGTGTGCCAC
AGTGATTTGTCCATGATTAATAACGAATGGGGCATTTCCAATTACCCCCTAGTGCCGGGT
CATGAGGTGGTGGGTACTGTGGCCGCCATGGGCGAAGGGGTGAACCATGTTGAGGTGGGG
GATTTAGTGGGGCTGGGTTGGCATTCGGGCTACTGCATGACCTGCCATAGTTGTTTATCT
GGCTACCACAACCTTTGTGCCACGGCGGAATCGACCATTGTGGGCCACTACGGTGGCTTT
GGCGATCGGGTTCGGGCCAAGGGAGTCAGCGTGGTGAAATTACCTAAAGGCATTGACCTA
GCCAGTGCCGGGCCCCTTTTCTGTGGAGGAATTACCGTTTTCAGTCCTATGGTGGAACTG
AGTTTAAAGCCCACTGCAAAAGTGGCAGTGATCGGCATTGGGGGCTTGGGCCATTTAGCG
GTGCAATTTCTCCGGGCCTGGGGCTGTGAAGTGACTGCCTTTACCTCCAGTGCCAGGAAG
CAAACGGAAGTGTTGGAATTGGGCGCTCACCACATACTAGATTCCACCAATCCAGAGGCG
ATCGCCAGTGCGGAAGGCAAATTTGACTA?ATTATCTCCACTGTGAACCTGAAGCTTGAC
TGGAACTTATACATCAGCACCCTGGCGCCCCAGGGACATTTCCACTTTGTTGGGGTGGTG
TTGGAGCCTTTGGATCTAAATCTTTTTCCCCTTTTGATGGGACAACGCTCCGTTTCTGCC
TCCCCAGTGGGTAGTCCCGCCACCATTGCCACCATGTTGGACTTTGCTGTGCGCCATGAC
ATTAAACCCGTGGTGGAACAATTTAGCTT?GATCAGATCAACGAGCCGATCGCCCATCTA
GAAAGCGGCAAAGCCCATTATCGGGTAGTGCTCAGCCATAGTAAAAATGACCTCTGCAAA
GGTTGCTTCTGGGTCCGTGGAATGGTCAAACGGAGTCGATCTCAGTTTTGATACGCTCTA
                TCTGGAAAGCTTGACATTCGATCTGCAG

Fig. 41 (SEQ ID NO. 47)
```

```
MIKAYAALEANGKLQPFEYDPGALGANEVEIEVQYCGVCHSDLSMINNEWGISNYPLVPG
HEVVGTVAAMGEGVNHVEVGDLVGLGWHSGYCMTCHSCLSGYHNLCATAESTIVGHYGGF
GDRVRAKGVSVVKLPKGIDLASAGPLFCGGITVFSPMVELSLKPTAKVAVIGIGGLGHLA
VQFLRAWGCEVTAFTSSARKQTEVLELGAHHILDSTNPEAIASAEGKFDYIISTVNLKLD
WNLYISTLAPQGHFHFVGVVLEPLDLNLFPLLMGQRSVSASPVGSPATIATMLDFAVRHD
IKPVVEQFSFDQINEAIAHLESGKAHYRVVLSHSKN
```

Fig. 42 (SEQ ID NO. 48)

```
GAATTCCCCAACCTTGACCAGTGACCCCCCCGTTCAAAGCCTTGCCGATCTGGAAGGG
CTGATTGAGCGCGTCCAACGGGCGCAGAGTCAGTACGCCCAATTTACCCAAGAGCAAGTG
GATCACATTTTCCACGAAGCAGCCATGGCGGCCAACCAAGCCCGGATTCCCCTGGCCAAA
CAAGCCGTAGCCGAAACGGGCATGGGGGTTGTCGAAGATAAAGTTATTAAAAATCACTTT
GCTTCGGAATACATCTACAACAAGTACAAAAATGAGAAAACCTGCGGCGTCATTGAGGAT
GACCCCATCTTTGGTATCCAAAAAATTGCTGAACCGGTGGGGATCATTGCCGGTGTGGTG
CCGGTCACGAACCCCACTTCAACGACCATCTTTAAGGCACTGATTGCCCTGAAGACTCGC
AATGGCATTATCTTTTCGCCCCACCCCCGGGCAAAGGCCTGTACGGTTGCAGCGGCCAAG
GTAGTGTTGGATGCAGCGGTCGCTGCCGGCGCACCCCCCGATATTATTGGCTGGATTGAT
GAGCCGACGATTGAACTCTCCCAAGCCCTGATGCAGCACCCGCAGATCAAGCTGATTTTG
GCCACGGGGGGACCAGGTATGGTCAAGGCAGCCTATTCCTCTGGCCATCCGGCGATCGGG
GTCGGGGCCGGGAATACCCCCGTGCTCATTGATGCCACAGCCGATATTCCCACGGCAGTG
AGTTCGATTCTCCTCAGTAAGGCCTTTGACAATGGCATGATCTGTGCCTCGGAGCAGGCA
GTGATTGTTGTGGATGAGATTTATGACGCACTTAAAGCTGAGTTTCAACGGCGAGGGGCC
TACCTTCTCTCCCCTGAGGAACGGCAGCAGGTGGCACAACTACTGCTGAAGGATGGTCGC
CTCAATGCCGCCATTGTTGGTCAATCGGCCGCCACCATTGCCGCAATGGCCAATATCCAA
GTACCGCCAGAAACCCGGGTACTCATTGGCGAGGTGAGTGAAGTGGGGCCGCAGGAGCCA
TTTTCCTATGAGAAACTCTGTCCGGTATTGGCGTTATATCGGGCACCCCAGTTCCATAAA
GGGGTGGAGATTGCGGCCCAGTTGGTGAATTTTGGGGGCAAGGGGCATACATCTGTGCTC
TATACCGATCCCCGCAATCAAGATGATATTGCCTATTTCAAATACCGCATGCAAACGGCG
CGGGTTCTGATTAACACCCCTTCTTCCCAGGGGGCAATTGGCGATCTCTACAACTTCAAG
TTAGATCCGTCGCTAACCCTTGGTTGTGGTACGTGGGGCGGCAACGTCACATCGGAAAAT
GTTGGTCCCCGTCACTTGCTGAATATTAAAACGGTGAGCGATCGCCGGGAAAATATGCTT
TGGTTTCGGGTGCCGCCCAAGATCTACTTCAAACCCGGCTGTTTGCCCATTGCCCTGCGG
GAGCTGGCGGGGAAAAAACGCGCCTTCCTCGTGACGGATAAACCCCTCTTTGACTTGGGG
ATCACTGAACCGATTGTCCATACCCTCGAAGAACTGGGCATCAAGTATGACATCTTCCAT
GAAGTGGAACCAGATCCAACCCTCAGTACCGTTAACCGCGGTCTAGGGTTGCTGCGGCAA
TATCAGCCGGATGTGATTGTTGCTGTGGGGGGTGGCTCACCTATGGATGCAGCCAAGGTG
ATGTGGCTGTTGTATGAGCATCCGGAGGTGGAGTTTGACGGCCTTGCGATGCGCTTCATG
GATATTCGCAAGCGGGTGTATCAACTGCCTCCCTTGGGTCAAAAGGCAATCCTGGTGGCT
ATTCCCACCACCTCGGGGACGGGTTCAGAGGTGACCCCCTTTGCCGTGGTTACCGACGAT
CGCGTGGGGATTAAATATCCCTTGGCAGACTATGCCCTTACGCCAACGATGGCGATTGTG
GATCCCGACTTGGTGCTGCACATGCCCAAGAAACTGACGGCCTACGGTGGCATTGATGCG
CTGACCCATGCCCTGGAGGCCTATGTGTCGGTGCTCTCGACGGAGTTTACGGAGGGACTG
GCTCTAGAGGCCATTAAACTGCTCTTTACCTACCTACCCCGTGCCTATCGCTTGGGGGCG
GCGGATCCGGAGGCACGGGAGAAGGTCCACTATGCGGCGACGATCGCTGGCATGGCCTTT
GCGAATGCCTTCTTGGGGGTCTGCCACTCGCTGGCCCACAAACTAGGCTCCACCTTCCAC
GTGCCCCACGGCTTGGCGAATGCACTCATGATTTCCATGTGATTCGCTACAATGCCACG
GATGCTCCCCTGAAGCAGGCGATTTTCCCGCAGTACAAGTATCCCCAAGCGAAGGAGCGC
TATGCCCAAATTGCCGACTTCCTCGAATTGGGGGGCACGACCCCAGAGGAAAAAGTGGAG
```

Fig. 44A

```
CGTCTCATTGCGGCAATTGAGGATTTGAAAGCCCAATTAGAAATTCCCGCCACGATTAAG
GAGGCCCTCAACAGTGAGGATCAAGCGTTCTATGAGCAGGTGGAGAGCATGGCCGAACTG
GCCTTTGACGATCAGTGCACGGGGGCCAATCCCCGCTATCCGCTGATCCAAGACCTCAAG
GAGTTGTATATCCTGGCCTATATGGGGTGTCGGCGGGATGCGGCAGCCTACTATGGGGGG
GAGGCAACGGGGAGT░░░TGTGGCGTTATATTCCCCCTTTGCAGCTCCAGCGAAGGTGC
           AAATGGCGGTGGATTCCTGGCTCTGGCAGCGGAGCGATCGC░░░░░░
```

Fig. 44A (Continued)

```
MNSPTLTSDPPVQSLADLEGLIERVQRAQSQYAQFTQEQVDHIFHEAAMA
ANQARIPLAKQAVAETGMGVVEDKVIKNHFASEYIYNKYKNEKTCGVIED
DPIFGIQKIAEPVGIIAGVVPVTNPTSTTIFKALIALKTRNGIIFSPHPR
AKACTVAAAKVVLDAAVAAGAPPDIIGWIDEPTIELSQALMQHPQIKLIL
ATGGPGMVKAAYSSGHPAIGVGAGNTPVLIDATADIPTAVSSILLSKAFD
NGMICASEQAVIVVDEIYDALKAEFQRRGAYLLSPEERQQVAQLLLKDGR
LNAAIVGQSAATIAAMANIQVPPETRVLIGEVSEVGPQEPFSYEKLCPVL
ALYRAPQFHKGVEIAAQLVNFGGKGHTSVLYTDPRNQDDIAYFKYRMQTA
RVLINTPSSQGAIGDLYNFKLDPSLTLGCGTWGGNVTSENVGPRHLLNIK
TVSDRRENMLWFRVPPKIYFKPGCLPIALRELAGKKRAFLVTDKPLFDLG
ITEPIVHTLEELGIKYDIFHEVEPDPTLSTVNRGLGLLRQYQPDVIVAVG
GGSPMDAAKVMWLLYEHPEVEFDGLAMRFMDIRKRVYQLPPLGQKAILVA
IPTTSGTGSEVTPFAVVTDDRVGIKYPLADYALTPTMAIVDPDLVLHMPK
KLTAYGGIDALTHALEAYVSVLSTEFTEGLALEAIKLLFTYLPRAYRLGA
ADPEAREKVHYAATIAGMAFANAFLGVCHSLAHKLGSTFHVPHGLANALM
TSHVIRYNATDAPLKQAIFPQYKYPQAKERYAQIADFLELGGTTPEEKVE
RLIAAIEDLKAQLEIPATIKEALNSEDQAFYEQVESMAELAFDDQCTGAN
PRYPLIQDLKELYILAYMGCRRDAAAYYGGEATGS

Fig. 44B
```

```
GTCGACGGGAATTGCTCTGGCAACTGATTAATCCACTGAGCAACAG
CCCAAGACACGCAAACAAAAACCAACGTCTTGGCGATCGCCATCGGCACCATGAAACCAT
CGTAAAAGCTGGGGAAAGAATAAAAAAACAGTGGTTCAGGAATTGCATTGCCATGGCCACT
TCACAAACCTAGCCAATTTTAGCTTGACCGCAACTTTGACAGATTGTCTTTTGACTTTGC
CTGGACCGCCTCCCATAATACCTTCGCGTCTTGAAGACTTTATCCTTGAAAGGAGAACTA
ATGAATTC
```

Fig. 45A

GTCGACTGTCCGACCAATTGGTTCATCAAAGTTGATTTACCCACATTGGGACGGCCGACA
ATGGCCACAAAGCCGGAACGAAAACCCGCAGGAGCCTGGGGAATAGTTGCAATGGTTGCG
GTGGTGTTGGGAATATCCATTGAAAAAATCAAGCCTAAAAATTCCTTAGTTTATGGAGGG
TCAAGCGGAAAAACGTTAAAAACTCCACTGAGTTAATCAACCAGAGGAAAAAGTCAAGGA
GGTAAACTATCCGCCTGGAAAACGGCTTGCCAGCTTGACAAAAAAATATGTTGGGTTAAC
CCCACTGTGCCATTCGGTAATCCTTCATCTTGGCCCTTGTGGAATCCCTTAATGATTCGT
CATCATGGTGATATTGATTTTTTGGGTATCTTTTTAGCTATGCGGCTGTAGGAGCGTGGT
ATTGGTTTCGGCGGTAACGCCCCAGCCTAGAACCACAAAAATTATTATTTATTCCCGAAC
CTTGTCACCATTTGCGGCGTCTAAAGGCCCACTCGTTAGGACACGGTGTAAAAAAAATTG
ACGACTGCACTACCCTATTCTCCACCATCAATGACTTAGTCTAAGACATTTTTGGGAAAG
ATGAATTC

Fig. 45B

```
                              GTCGACGCTGATGTGACGGTTAAGGGAGGCGGA
ATTAAACTGGGTAAGGACGTAAATTTTAACGATTTCTGAGTTGATGCAATTACTGACGGG
AATATCGATGAGGCGATACTTTCCGGCCAAGGGAACTGCGGGTTTGGCTCTGAGTTTGGT
TAAAGGATAGAGGCGGGTCCCGGCCCCACCGCCCAGGATAATCGCTAAGACACGTTTCAC
AAGCAGACCTCTCGATTGCCAACAACACACTTCGAAGTCAAGTTTAGAACCGAGGGGGAC
ATCTGGAAAGGGAATCTGGACGGAAATTCCGGCTAACCAGCGGGTTTTAATGCCCCAAGC
AAGAATGGCGATCGCCGTTGGGATTCGGAGCTGAGTTGTCAGATCACTGTGGGGGTACGG
ATAACCGAAATGGCAAAGGTCGGAAACTGCCGCTGAGTAAACTGTCCCTGGCTTCGTATG
ATGATGGGGTTACCCCCATTGCTGGGGCGCTGGGCAAATCTGGGGAGCTGACTAGGTTCC
TGGAAGTTTTGCTAATCCACTAAATTTCCTAACAATCCTAAACATTAAATCTAAAGACCT
                          ATGAATTC
```

Fig. 45C

```
GTCGACCCAACAACATTAGTCCGTCCTCCCGTTGGCGATCGC
GCTGTTTGGCTCTGACCCATCGCCGCTGATATTGCCAAGCTTGGCAGTAGGGCACAAGTC
CGAACGATAATAAACGACAGGAAGGATTGGCCATGGCGCTACAAAGGAAACGGAATCAAA
CTAAAGTTCAAAGTTGGCAGAAATTAAGAAACGTAAAGAGATGCAAAGGAAAGTCAAAAT
CACCTGACCGATTAGGTCTTATTCAATACATAGTGCTAATCTGAAGATAGTCTTAGGAGT
TAATTATTTACCACCACAATTTTCTGGAAAACTTTACCTCTACCCTAGGGATGATTAAAA
GTAAACTAGAGAATAACAAGGTTGGGTTTATAATTCATCACCAAGCTCAAATTTATGGTG
TTTTTTCAATGATCCATGCTTTTGATATCTTTAGCAGAAAGGCATTTTAAGTAATGATTC
CACCTCACTGTTTCTCGGAAAAATTGCCCAATCTAACTTAGTTTTTATAACTTAAGTTTA
GATCTGCGGAAAACCAACCATTGCTCATTTTTTATTAATTTTACGAAGGGAGAATTTAGT
ATGAATTC
```

Fig. 45D

GTCGACAGAATCCTTGCCCAGATG
CAGGCCTTCTGGCGATCGCCATGGTGAGCAACGATTGCGGCTTTAGCGTTCCAGTGGATA
TTTGCTGGGGGTTAATGAAACATTGTGGCGGAACCCAGGGACAATGTGACCAAAAAATTC
AGGGATATCAATAAGTATTAGGTATATGGATCATAATTGTATGCCCGACTATTGCTTAAA
CTGACTGACCACTGACCTTAAGAGTAATGGCGTGCAAGGCCCAGTGATCAATTTCATTAT
TTTTCATTATTTCATCTCCATTGTCCCTGAAAATCAGTTGTGTCGCCCCTCTACACAGCC
CAGAACTATGGTAAAGGCGCACGAAAAACCGCCAGGTAAACTCTTCTCAACCCCCAAAAC
GCCCTCTGTTTACCCATGGAAAAAACGACAATTACAAGAAAGTAAAACTTATGTCATCTA
TAAGCTTCGTGTATATTAACTTCCTGTTACAAAGCTTTACAAAACTCTCATTAATCCTTT
AGACTAAGTTTAGTCAGTTCCAATCTGAACATCGACAAATACATAAGGAATTATAACCAA
ATGAATTC

Fig. 45E

GTCGACATCAGGAATTGTAATTAGA
AAGTCCAAAAATTGTAATTTAAAAAACAGTCAATGGAGAGCATTGCCATAAGTAAAGGCA
TCCCCTGCGTGATAAGATTACCTTCAGAAAACAGATAGTTGCTGGGTTATCGCAGATTTT
TCTCGCAACCAAATAACTGTAAATAATAACTGTCTCTGGGGCGACGGTAGGCTTTATATT
GCCAAATTTCGCCCGTGGGAGAAAGCTAGGCTATTCAATGTTTATGGAGGACTGACCTAG
ATGAATTC

Fig. 45F

GTCGACATTTCTTAAAATTAAAGCTGTTATAGCAACAACATTGATTAATTTCTATCTAAT
TTTTGACGGTGCCCATTGCTATCAGTTGTAAGTTGATGAAAATGCTGTAAATTTTTGTAA
CAAAGTTCAACTTTGTCTTGACTTTTGTAAGTCTTTGCAAAATCTAGGAGCTAGAACTGG
TCAGGGCTGGGGCAATTTTTAATTATTGTTACGCAGGTCTTGCCTAGGGGGGGGAGGCC
GTATTATCTTCTAGTGATGTTTGCTGAAAACGCCTATCTGTGCAAGGTTTAACATCGTTA
TTATGAAGCGAAAACTAATTCCCTTTTTTACGCTTCCTCTATTACACTATTCTGCATAGG
AAACCCTTAATAGTTCATTGTCGAGCGAGGAGAACCCTGCATGAATTC

Fig. 45G

```
GTCGAC
AAAAAAAACTGCAAAAATTATCCTGACTGAATGGAAGTCAAAAAGACTGGAAAATGGGATC
AAACAACAAGAAAAAATCAATTTACCCTGCCCATGGCAATAGTTTTAAGGTTAACAAAAA
AAATAGAATTTACCGCAATCGACGGGTAAATTTCCAGAGGATACCCCCAACTCCAGAAGC
AGAAATCTTGCCAGAAAAGCTTTTTTCTGTTACTATACTTAACAAGTAACTACTTTTTCCA
TAGTCCAGGGGCGGCTTTCCAAAAACCAGAGATTGGTGGCTTGCCGCTGCTGTTCTCCTC
TGGAGTAAGGGGAAAAGGTAATTAGTGTTACGGCATTTTACTGACGGGTTAAGTAATCTT
TAACAAAGATTTATGAGCCGTTACCGTAATTGCCCCCACAGGGGAACGCGATGTCTGTGG
ACTCGCCCAGGACGTAATCAATTTTTCTGTACCGATATTAGCGGTGAAAAGTTTTATTCA
ACGTACTAAAATGCCCCGGCGGGAATTAACTTGGGTTCCGGGAAGTCGGGTGCATTAGCC
GTACTAGACTAACCCAATAGTTACTTTGTTTGATTCTTGATTTTGGAGACCGCTGATTTT
ATGAATTC
```

Fig. 45H

```
GTCGAC
GGAAAACAAGCTCAGAATGCTGCGGGGAGAAGGGCAACTCCCCACCAGCCCCAAATTTTT
GCTGGCGATAAATATTTTTCGGTTTAATTGTTCACAAAGCTTTTTGAATTTGAGTTTATA
GAAATTTATTGGCTGGTAATGCTTTTTTGCCCCCCTGCAGGACTTCATTGATCCTTGCCT
ATACCATCAATATCATTGGTCAATAATGATGATGATTGACTAAAACATGTTTAACAAAAT
TTAACGCATATGCTAAATGCGTAAACTGCATATGCCTTGGCTGAGTGTAATTTACGTTAC
AAATTTTAACGAAACGGGAACCCTATATTGATCTCTATCTGGCTTGAAGCGTTGTGAATTC
```

Fig. 45I

```
GTCGACTTTTTTGCTGAGGTACTGAGTACACAGCTAATAAAATTGGGCAATCTCCGCGCC
TCTATGACTTGAAGGAGAGTGTAGGGGTATAGGGGAAAGATATCTTTTATCTACATCACA
TAAATAAAAAATTTAATTTGTCGCTCTGGCTGCATATATTGATGTATTTTTAGCCATAAG
TTTTTTAGTGCCATGTAATTATAGTGATTTTTAGCGATCGCAGAGCATTTTTCCCTGGAT
TTATCGCGATCTCAAAAAAAATTTGCCCGAAGTATGACAGATTGTCATATTTGGTGTCGA
TTTTATTTAAAATGAAATAAGAAAAATAAAACTACAGGTTAGGAGAACGCCATGAATTC
```

Fig. 45J

GTCGACACAACCTAAGACTTCCTTCCAAAAATCCATAGGGCGGTGGAAGCTTAGCTATT
TTTACCATTTTGTTTTGCCACTCAAATATTTACTTAAGGTGAGGTAAAAACTCATCTTTT
TTTTACTAAAAATTGCGGCTAGAAATGTAATTTCGGCAATCCCCCCACCTTCTTTCCTGA
AAACCGAATCTAACCTGGAAGGGGAAATTTTAAGATAGAACCATTCAAGGGTAATCAATT
CCTTCCACACATCAGGAGTTAACATTATGAATTC

Fig. 45K

GTCGACGCACTTCTGGTCAGTTTATAGCAAAAATGCTGGGGAAAGGAAGACAACT
AGGGAAAAAGAACAGGACATCAAATGGTCATTCCCCAGACCCTGGCGTCTTTGCCAGAGT
AATCTCCCTGGCGCGGATGTTACACAAATGTAACGAAAAATATTTTCCCTCTCAGAATTT
AGGCAAAGTGCCCAAACCCATCCTAGGCAAGCAATTCGTCCACCAACAAAAAGCTCTTTT
GGTCAACAGACTTGACAAAAATCTTAACAATACGTTACATTTATTTACATAAGGTTACAA
AATAAAAACCTCAAATACCCAATCAAGGAGATCAACACTATGAATTC

Fig. 45L

GTCGACAAGATTAGCCCTTAGCTTACAAGAAAGGGGCTTTG
GGGCCTAGTTGAATGGCACAAATTTTCCTTCCCTGACTGTTTTTGCGCCATTGTCTAGCT
CAAAGTCAGCCTCCGGCATCCTCTAGAAAGACTTCCATCCCCTGGTTGAGCAAGGGTAAA
CCCCACCACTGCATTGGGAAAACCCTCCTTCCTAGCTCCGGATTCCACCCCCTAAAATTG
ATTTGGTAGTCCTTACACACCCAATAGCCAATATAGAAAATTTTATGAATTC

Fig. 45M

SEQUENCE LISTING

<160> NUMBER OF SEQ ID NOS: 65

<210> SEQ ID NO 1
<211> LENGTH: 463
<212> TYPE: PRT
<213> ORGANISM: Synechocystis PCC6803

<400> SEQUENCE: 1

```
Met Val Ser Leu Thr Pro Asn Pro Ser Tyr Ser Val Ser Leu Leu Leu
1               5                   10                  15

Glu Leu Pro Asn His Ala Gly Thr Leu Ala Ser Val Thr Gln Ala Ile
            20                  25                  30

Ala Asp Ala Gly Gly Ser Phe Gly Gln Ile Ser Leu Ile Glu Ser Asn
        35                  40                  45

Leu Lys Leu Thr Arg Arg Glu Ile Ala Val Asp Ala Ser Ser Ser Glu
    50                  55                  60

His Ala Glu Lys Ile Ile Gly Ala Val Lys Ala Leu Asp Asn Val Lys
65                  70                  75                  80

Leu Leu Lys Val Ser Asp Arg Thr Phe Asp Leu His Arg Gln Gly Lys
                85                  90                  95

Ile Ser Val Val Ser Arg Ile Pro Leu Thr Ser Gln Ser Asp Leu Ala
            100                 105                 110

Met Ala Tyr Thr Pro Gly Val Gly Arg Ile Cys Arg Ala Ile Ala Glu
        115                 120                 125

Asp Pro Glu Lys Val Tyr Ser Leu Thr Ile Lys Ser Asn Thr Val Ala
    130                 135                 140

Val Val Thr Asp Gly Ser Ala Val Leu Gly Leu Gly Asn Leu Gly Pro
145                 150                 155                 160

Glu Ala Ala Leu Pro Val Met Glu Gly Lys Ala Met Leu Phe Lys Glu
                165                 170                 175

Phe Ala Gln Leu Asp Ala Phe Pro Ile Cys Leu Asp Thr Gln Asp Thr
            180                 185                 190

Glu Glu Ile Ile Arg Thr Val Lys Ala Ile Ala Pro Val Phe Gly Gly
        195                 200                 205

Val Asn Leu Glu Asp Ile Ala Ala Pro Arg Cys Phe Glu Ile Glu Ala
    210                 215                 220

Arg Leu Lys Lys Glu Leu Asn Ile Pro Val Phe His Asp Asp Gln His
225                 230                 235                 240

Gly Thr Ala Ile Val Thr Leu Ala Ala Leu Leu Asn Ala Leu Lys Phe
                245                 250                 255

Val Gly Lys Ala Met Ala Ala Val Arg Ile Val Ile Asn Gly Ala Gly
            260                 265                 270

Ala Ala Gly Leu Ala Ile Ala Glu Leu Leu Lys Glu Ser Gly Ala Thr
        275                 280                 285

Asp Ile Trp Ile Cys Asp Ser Lys Gly Ile Val Gly Lys His Arg Thr
    290                 295                 300
```

```
Asp Leu Asn Ser Lys Lys Gln Ser Phe Ala Val Asp Ala Glu Gly Thr
305                 310                 315                 320

Leu Ala Asp Ala Met Ala Gly Ala Asp Val Phe Leu Gly Val Ser Ala
            325                 330                 335

Pro Gly Val Val Thr Lys Glu Met Val Gln Ser Met Ala Lys Asp Pro
            340                 345                 350

Ile Val Phe Ala Met Ala Asn Pro Ile Pro Glu Ile Gln Pro Glu Leu
        355                 360                 365

Ile Gln Glu Asp Ala Ala Val Ile Ala Thr Gly Arg Ser Asp Tyr Pro
    370                 375                 380

Asn Gln Ile Asn Asn Val Leu Ala Phe Pro Gly Val Phe Arg Gly Ala
385                 390                 395                 400

Ile Asp Cys Arg Ala Ser Ile Ile Thr Thr Thr Met Cys Ile Glu Ala
            405                 410                 415

Ala Lys Ala Ile Ala Ser Leu Val His Ser Asn Thr Leu Asp Ser Glu
            420                 425                 430

His Ile Ile Pro Ser Val Phe Asp Asn Arg Val Ala Thr Thr Val Ala
        435                 440                 445

Ser Ala Val Gln Leu Ala Ala Arg Asn Glu Gly Val Ala Gly Gln
    450                 455                 460

<210> SEQ ID NO 2
<211> LENGTH: 24
<212> TYPE: DNA
<213> ORGANISM: Artificial Sequence
<220> FEATURE:
<223> OTHER INFORMATION: Mae-NdeI.fw

<400> SEQUENCE: 2
catatggtta gcctcacccc caat                                        24

<210> SEQ ID NO 3
<211> LENGTH: 25
<212> TYPE: DNA
<213> ORGANISM: Artificial Sequence
<220> FEATURE:
<223> OTHER INFORMATION: MeLongClaI.rv

<400> SEQUENCE: 3
atcgatcggg atggcctatt tatgg                                       25

<210> SEQ ID NO 4
<211> LENGTH: 1545
<212> TYPE: DNA
<213> ORGANISM: Artificial Sequence
<220> FEATURE:
<223> OTHER INFORMATION: sequence of the insert of construct
      pSK9/me-long

<400> SEQUENCE: 4
tatggttagc ctcaccccca atccgagtta tagcgtcagc ctactgttgg aactccccaa    60
ccacgccgga actttggcca gcgttaccca ggcgatcgcc gatgcggggg cagttttgg    120 gcaaatttcc ctgattgaga gtaacttaaa actcacccgg cgggaaattg cggtggatgc    180
ttccagcagt gagcacgccg aaaaaattat tggggcagtg aaagctctgg ataatgtcaa    240
attgctgaag gtgtccgatc gcacctttga tttacaccgt cagggcaaaa ttagcgtggt    300
tagtcgcatt cccctcacct cccaatcgga tttggccatg gcctataccc aggggtggg    360 gcgcatctgt cgggcgatcg ccgaagatcc ggaaaaggtt tattccctga ccattaaaag    420
```

```
caatacggtg gcggtggtga ccgatggcag tgcggtgttg gggttgggta acctggggcc    480
ggaagcggct ttaccagtga tggaaggcaa ggccatgtta ttcaaggaat ttgcccaact    540
ggacgctttt cccatctgtt tggataccca ggatacggag gaaattattc gcaccgtcaa    600
ggcgatcgcc ccggtgtttg gcggcgtaaa tttggaagac attgccgctc cccggtgttt    660
tgaaattgaa gcccggctga aaaagaatt aaatattcct gtatttcacg atgatcagca    720
cggcaccgcc attgttaccc tggccgcttt gttaaatgcc ctcaaatttg ttggtaaagc    780
catggccgct gtccgcattg tcatcaacgg cgctggggct gctgggttgg cgatcgccga    840
attgctcaag gaatccggag ccaccgatat ttggatttgc gactccaagg gcattgtggg    900
caaacatcgc accgatttaa acagcaaaaa acagagcttt gcggtggatg cggaagggac    960
tttagccgat gctatggctg gagctgatgt gttttttaggg gtgagtgcgc cggggggtagt   1020
gaccaaggaa atggtgcaat ccatggccaa ggacccgatt gtgtttgcca tggccaaccc   1080
tatccccgaa attcagccgg aattaatcca agaggatgcg gcggttattg ccacggggcg   1140
cagtgattac cccaaccaaa ttaacaatgt gcttgccttt ccggggggttt tccggggagc   1200
cattgactgt agagctagca ttattaccac caccatgtgc atcgaagcgg ccaaggcgat   1260
cgcctctttg gtgcacagca cacccctaga tagtgagcat attattcctt cggtttttga   1320
caatcgggtc gccactaccg tagccagtgc agtgcagttg gccgcccgca atgaaggggt   1380
ggccggtcaa tagttaatcg ggaattgtta aacctttact ggtcaaccat tcctgattgt   1440
aaagacggga ttggtaacgg gctcctccgt cacaaagtac ggtaacaatg gtatgccccg   1500
gcccaagttt tttggccaat tggtaagccg ctcccacatt aatat                   1545
```

<210> SEQ ID NO 5
<211> LENGTH: 324
<212> TYPE: PRT
<213> ORGANISM: Synechocystis PCC6803

<400> SEQUENCE: 5

```
Met Asn Ile Leu Glu Tyr Ala Pro Ile Ala Cys Gln Ser Trp Gln Val
1               5                   10                  15

Thr Val Val Gly Ala Gly Asn Val Gly Arg Thr Leu Ala Gln Arg Leu
            20                  25                  30

Val Gln Gln Asn Val Ala Asn Val Val Leu Leu Asp Ile Val Pro Gly
        35                  40                  45

Leu Pro Gln Gly Ile Ala Leu Asp Leu Met Ala Ala Gln Ser Val Glu
    50                  55                  60

Glu Tyr Asp Ser Lys Ile Ile Gly Thr Asn Glu Tyr Glu Ala Thr Ala
65                  70                  75                  80

Gly Ser Asp Val Val Ile Thr Ala Gly Leu Pro Arg Arg Pro Gly
                85                  90                  95

Met Ser Arg Asp Asp Leu Leu Gly Lys Asn Ala Asn Ile Val Ala Gln
            100                 105                 110

Gly Ala Arg Glu Ala Leu Arg Tyr Ser Pro Asn Ala Ile Leu Ile Val
        115                 120                 125

Val Thr Asn Pro Leu Asp Val Met Thr Tyr Leu Ala Trp Lys Val Thr
    130                 135                 140

Gly Leu Pro Ser Gln Arg Val Met Gly Met Ala Gly Val Leu Asp Ser
145                 150                 155                 160

Ala Arg Leu Lys Ala Phe Ile Ala Met Lys Leu Gly Ala Cys Pro Ser
                165                 170                 175

Asp Ile Asn Thr Leu Val Leu Gly Gly His Gly Asp Leu Met Leu Pro
```

```
                    180                 185                 190
Leu Pro Arg Tyr Cys Thr Val Ser Gly Val Pro Ile Thr Glu Leu Ile
                195                 200                 205

Pro Pro Gln Thr Ile Glu Glu Leu Val Glu Arg Thr Arg Asn Gly Gly
            210                 215                 220

Ala Glu Ile Ala Ala Leu Leu Gln Thr Gly Thr Ala Tyr Tyr Ala Pro
225                 230                 235                 240

Ala Ser Ser Ala Ala Val Met Val Glu Ser Ile Leu Arg Asn Gln Ser
                245                 250                 255

Arg Ile Leu Pro Ala Ala Thr Tyr Leu Asp Gly Ala Tyr Gly Leu Lys
            260                 265                 270

Asp Ile Phe Leu Gly Val Pro Cys Arg Leu Gly Cys Arg Gly Val Glu
        275                 280                 285

Asp Ile Leu Glu Val Gln Leu Thr Pro Glu Glu Lys Ala Ala Leu His
    290                 295                 300

Leu Ser Ala Glu Ala Val Arg Leu Asn Ile Asp Val Ala Leu Ala Met
305                 310                 315                 320

Val Ser Asp Gly

<210> SEQ ID NO 6
<211> LENGTH: 26
<212> TYPE: DNA
<213> ORGANISM: Artificial Sequence
<220> FEATURE:
<223> OTHER INFORMATION: Mdh-NdeI.fw

<400> SEQUENCE: 6
catatgaata ttttggagta tgctcc                                          26

<210> SEQ ID NO 7
<211> LENGTH: 23
<212> TYPE: DNA
<213> ORGANISM: Artificial Sequence
<220> FEATURE:
<223> OTHER INFORMATION: Mdh-ClaI.rv

<400> SEQUENCE: 7
atcgataagc cctaacctcg gtg                                             23

<210> SEQ ID NO 8
<211> LENGTH: 1027
<212> TYPE: DNA
<213> ORGANISM: Artificial Sequence
<220> FEATURE:
<223> OTHER INFORMATION: sequence of the insert of construct pSK9/mdh

<400> SEQUENCE: 8
tatgaatatt ttggagtatg ctccgatcgc ctgtcagtcc tggcaggtta ccgtggtcgg      60
cgctggcaat gtggggcgga cccttgccca gaggttagtg cagcaaaatg tcgccaacgt     120
agttttgttg acattgtgca caggcttacc ccagggcatt gccttggatt tgatggccgc     180
ccagagcgtg gaggaatacg acagcaaaat cattggcacc aatgaatacg aggccaccgc     240
cggctccgat gtggtggtaa ttaccgctgg tctaccccgc aggcccggca tgagtcggga     300
tgatttgttg ggcaaaaacg ccaacattgt ggcccagggg gcccgggaag cattgcgtta     360
ttcccccaac gccatttga ttgtggtcac caatcccctg gatgtaatga cctatttggc     420
ctggaaagta actggtttac cttcccaacg ggttatgggc atggcggggg tgttggactc     480
ggctcggctc aaggccttca ttgcgatgaa attagggggc tgtccttctg atatcaacac     540
```

```
cttagtgctg ggcgggcacg gagatttgat gctgcccttg ccacgatact gcaccgtcag    600
cggggttccc attaccgaat taataccccc ccaaaccatt gaagagttgg tggagcgtac    660
ccgtaacggt ggggctgaaa ttgccgcctt actacaaacg ggcacagcct attatgcgcc    720
ggcctcttcc gctgcggtga tggtggagtc cattttacgc aatcagtcta gaattctccc    780
cgccgccacc taccttgatg gtgcctatgg attgaaggac attttccttg gagtgccctg    840
ccgtttgggg tgtcgaggag tggaagatat tctcgaagtg caattaaccc ctgaagaaaa    900
agctgccctc catctttctg cagaagcagt tcgccttaat attgatgtgg cgttggccat    960
ggttagcgac ggttaacacg ataacggaca gtgccaatac cgttttttca ccgaggttag   1020
ggcttat                                                              1027
```

<210> SEQ ID NO 9
<211> LENGTH: 24
<212> TYPE: DNA
<213> ORGANISM: Artificial Sequence
<220> FEATURE:
<223> OTHER INFORMATION: Mae-NdeI.fw

<400> SEQUENCE: 9

```
catatggtta gcctcacccc caat                                             24
```

<210> SEQ ID NO 10
<211> LENGTH: 30
<212> TYPE: DNA
<213> ORGANISM: Artificial Sequence
<220> FEATURE:
<223> OTHER INFORMATION: MeShortClaI.rv

<400> SEQUENCE: 10

```
atcgatacaa ttcccgatta actattgacc                                       30
```

<210> SEQ ID NO 11
<211> LENGTH: 26
<212> TYPE: DNA
<213> ORGANISM: Artificial Sequence
<220> FEATURE:
<223> OTHER INFORMATION: MdhRBSClaI.fw

<400> SEQUENCE: 11

```
atcgattttt ctccaccatc aacacc                                           26
```

<210> SEQ ID NO 12
<211> LENGTH: 23
<212> TYPE: DNA
<213> ORGANISM: Artificial Sequence
<220> FEATURE:
<223> OTHER INFORMATION: MdhBglII.rv

<400> SEQUENCE: 12

```
agatctaagc cctaacctcg gtg                                              23
```

<210> SEQ ID NO 13
<211> LENGTH: 2606
<212> TYPE: DNA
<213> ORGANISM: Artificial Sequence
<220> FEATURE:
<223> OTHER INFORMATION: sequence of the insert of construct
      pSK9/me-mdh

<400> SEQUENCE: 13

```
tatggttagc ctcaccccca atccgagtta tagcgtcagc ctactgttgg aactccccaa     60
ccacgccgga actttggcca gcgttaccca ggcgatcgcc gatgcggggg gcagttttgg    120
```

```
gcaaatttcc ctgattgaga gtaacttaaa actcacccgg cgggaaattg cggtggatgc    180
ttccagcagt gagcacgccg aaaaaattat tggggcagtg aaagctctgg ataatgtcaa    240
attgctgaag gtgtccgatc gcacctttga tttacaccgt cagggcaaaa ttagcgtggt    300
tagtcgcatt cccctcacct cccaatcgga tttggccatg cctataccc  cagggtgggg    360 gcgcatctgt cgggcgatcg ccgaagatcc ggaaaaggtt tattccctga ccattaaaag    420
caatacggtg gcggtggtga ccgatggcag tgcggtgttg gggttgggta acctggggcc    480
ggaagcggct ttaccagtga tggaaggcaa ggccatgtta ttcaaggaat ttgcccaact    540
ggacgctttt cccatctgtt tggatacccca ggatacggag gaaattattc gcaccgtcaa    600
ggcgatcgcc ccggtgtttg gcggcgtaaa tttggaagac attgccgctc cccggtgttt    660
tgaaattgaa gcccggctga aaaagaatt  aaatattcct gtatttcacg atgatcagca    720
cggcaccgcc attgttaccc tggccgcttt gttaaatgcc ctcaaatttg ttggtaaagc    780 catgccgct  gtccgcattg tcatcaacgg cgctggggct gctgggttgg cgatcgccga    840
attgctcaag gaatccggag ccaccgatat ttggatttgc gactccaagg gcattgtggg    900
caaacatcgc accgatttaa acagcaaaaa acagagcttt gcggtggatg cggaagggac    960
tttagccgat gctatggctg gagctgatgt gttttaggg  gtgagtgcgc cgggggtagt   1020
gaccaaggaa atggtgcaat ccatggccaa ggacccgatt gtgtttgcca tggccaaccc   1080
tatccccgaa attcagccgg aattaatcca agaggatgcg gcggttattg ccacggggcg   1140
cagtgattac cccaaccaaa ttaacaatgt gcttgccttt ccgggggttt tccggggagc   1200
cattgactgt agagctagca ttattaccac caccatgtgc atcgaagcgg ccaaggcgat   1260
cgcctctttg gtgcacagca acaccctaga tagtgagcat attattcctt cggttttga   1320 caatcgggtc gccactaccg tagccagtgc agtgcagttg gccgcccgca atgaagggt   1380 ggccggtcaa tagttaatcg ggaattgtta aacctttact ggtcaaccat tcctgattgt   1440
aaagacggga ttggtaacgg gctcctccgt cacaaagtac ggtaacaatg gtatgccccg   1500
gcccaagttt tttggccaat tggtaagccg ctcccacatt aatatcgatt tttctccacc   1560
atcaacaccc cggagggtgc catgaatatt ttggagtatg ctccgatcgc ctgtcagtcc   1620 tgcaggtta  ccgtggtcgg cgctggcaat gtggggcgga cccttgccca gaggttagtg   1680
cagcaaaatg tcgccaacgt agttttgttg gacattgtgc caggcttacc ccagggcatt   1740
gccttggatt tgatggccgc ccagagcgtg gaggaatacg acagcaaaat cattggcacc   1800
aatgaatacg aggccaccgc cggctccgat gtggtggtaa ttaccgctgg tctacccgc   1860 aggcccggca tgagtcggga tgatttgttg ggcaaaaacg ccaacattgt ggcccagggg   1920
gcccgggaag cattgcgtta ttcccccaac gccatttga  ttgtggtcac caatccctg   1980 gatgtaatga cctatttggc ctggaaagta actggtttac cttccaacg  ggttatgggc   2040 atggcggggg tgttggactc ggctcggctc aaggccttca ttgcgatgaa attaggggcc   2100
tgtccttctg atatcaacac cttagtgctg gcgcggcacg gagatttgat gctgcccttg   2160
ccacgatact gcaccgtcag cggggttccc attaccgaat taatacccccc ccaaaccatt   2220 gaagagttgg tggagcgtac ccgtaacggt ggggctgaaa ttgccgcctt actacaaacg   2280
ggcacagcct attatgcgcc ggcctcttcc gctgcgtgta tggtggagtc cattttacgc   2340
aatcagtcta gaattctccc cgccgccacc taccttgatg gtgcctatgg attgaaggac   2400
attttccttg gagtgccctg ccgtttgggg tgtcgaggag tggaagatat tctcgaagtg   2460
caattaaccc ctgaagaaaa agctgccctc catctttctg cagaagcagt tcgccttaat   2520
```

```
attgatgtgg cgttggccat ggttagcgac ggttaacacg ataacggaca gtgccaatac    2580
cgttttttca ccgaggttag ggctta                                         2606

<210> SEQ ID NO 14
<211> LENGTH: 6267
<212> TYPE: DNA
<213> ORGANISM: Artificial Sequence
<220> FEATURE:
<223> OTHER INFORMATION: nucleic acid sequence of the vector  pSK9

<400> SEQUENCE: 14
cacctaaatt gtaagcgtta atattttgtt aaaattcgcg ttaaattttt gttaaatcag      60 ctcattttt aaccaatagg ccgaaatcgg caaaatccct tataaatcaa agaatagac      120 cgagataggg ttgagtgttg ttccagtttg gaacaagagt ccactattaa agaacgtgga    180
ctccaacgtc aaagggcgaa aaaccgtcta tcagggcgat ggcccactac gtgaaccatc    240
accctaatca agttttttgg ggtcgaggtg ccgtaaagca ctaaatcgga acctaaaagg    300 gagccccga tttagagctt gacggggaaa gccggcgaac gtggcgagaa aggaagggaa    360
gaaagcgaaa ggagcgggcg ctagggcgct ggcaagtgta gcggtcacgc tgcgcgtaac    420
caccacaccc gccgcgctta atgcgccgct acagggcgcg tcccattcgc cattcaggct    480
gcgcaactgt tgggaagggc gatcggtgcg ggcctcttcg ctattacgcc agctggcgaa    540
agggggatgt gctgcaaggc gattaagttg gtaacgcca gggttttccc agtcacgacg    600
ttgtaaaacg acggccagtg aattgtaata cgactcacta gggcgaat tggaggccag    660 tgctggagga atatgatttt gtcatcctcg actgtgcccc tggttataat ctgttgaccc    720
gcagtggcat tgcggccagc gacttttatc tgttgccggc tcgtcctgaa ccccatcgg    780 tggtggggat gcagttactg gaaagaagaa ttgagaaact gaaggaaagc cataaggcct    840
ccgatgatcc cctgaatatc aatctgatcg gagtggtgtt tattctgtcc ggcggcggtt    900
tgatgagtcg ctactataac caggtaatgc ggcgggtaca aacggatttc accccgggac    960
aactttttca gcagtccatt cccatggatg tcaatgtggc taaggcagtg gatagcttta    1020
tgccggtggt tacctccatg cccaatacgg cgggttcaaa agcttttatt aaattaaccc    1080
aggaattttt acagaaagta gaagcttttg gctaaagcaa agccccccatt gattaacaac    1140 gggagggta ccgaggtgct gctgaagttg cccgcaacag agagtggaac caaccggtga    1200
taccacgata ctatgactga gagtcaacgc catgagcggc tcatttctt attctgagtt    1260 acaacagtcc gcaccgctgt ccggtagctc cttccggtgg gcgcggggca tgactatcgt    1320
cgccgcactt atgactgtct tctttatcat gcaactcgta ggacaggtgc cggcagcgcc    1380
caacagtccc ccggccacgg ggcctgccac catacccacg ccgaaacaag cgccctgcac    1440
cattatgttc cggatctgca tcgcaggatg ctgctggcta ccctgtggaa cacctacatc    1500
tgtattaacg aagcgctaac cgttttttatc aggctctggg aggcagaata aatgatcata    1560
tcgtcaatta ttacctccac ggggagagcc tgagcaaact ggcctcaggc atttgagaag    1620
cacacggtca cactgcttcc ggtagtcaat aaaccggtaa accagcaata gacataagcg    1680
gctatttaac gaccctgccc tgaaccgacg accgggtcga atttgctttc gaatttctgc    1740
cattcatccg cttattatca cttattcagg cgtagcacca ggcgtttaag gcaccaata    1800 actgccttaa aaaaattacg ccccgccctg ccactcatcg cagtactgtt gtaattcatt    1860
aagcattctg ccgacatgga agccatcaca gacggcatga tgaacctgaa tcgccagcgg    1920
catcagcacc ttgtcgcctt gcgtataata tttgcccatg gtgaaaacgg gggcgaagaa    1980
```

```
gttgtccata ttggccacgt ttaaatcaaa actggtgaaa ctcacccagg gattggctga   2040
gacgaaaaac atattctcaa taaacccttt agggaaatag gccaggtttt caccgtaaca   2100
cgccacatct tgcgaatata tgtgtagaaa ctgccggaaa tcgtcgtggt attcactcca   2160
gagcgatgaa aacgtttcag tttgctcatg gaaaacggtg taacaagggt gaacactatc   2220
ccatatcacc agctcaccgt ctttcattgc catacggaat tccggatgag cattcatcag   2280
gcgggcaaga atgtgaataa aggccggata aaacttgtgc ttattttttct ttacggtctt   2340 taaaaaggcc gtaatatcca gctgaacggt ctggttatag gtacattgag caactgactg   2400
aaatgcctca aaatgttctt tacgatgcca ttgggatata tcaacggtgg tatatccagt   2460 gattttttc tccattttag cttccttagc tcctgaaaat ctcgataact caaaaaatac   2520
gcccggtagt gatcttattt cattatggtg aaagttggaa cctcttacct cggtaccct   2580 catcggggggc tgtgttggcc gagacggcac tgaggatttt actctccatg gcattccaag   2640
gaatatctac ccaactcacc tgctccggcg gattgttccg ctcaaaagta ctaatcaagt   2700
cgtcaaaata cttattaaat tttggctgca attgcatagt ccaaaagctg actttcccct   2760
ccatgctctg gggggaattg ctctggcaac tgattaatcc actgagcaac agcccaagac   2820
acgcaaacaa aaaccaacgt cttggcgatc gccatcggca ccatgaaacc atcgtaaaag   2880
ctggggaaag aataaaaaac agtggttcag gaattgcatt gccatggcca cttcacaaac   2940
ctagccaatt ttagcttgac cgcaactttg acagattgtc ttttgacttt gcctggaccg   3000
cctcccataa taccttcgcg tcttgaagac tttatccttg aaaggagaac atatgtttct   3060
cggcaaaaat taattatcga ttggctggaa cctggtcaaa ccagggcttt tcatccattg   3120
gaaaagcgat tttgatcatc tagggtcagg agcaaagatc tgatcaaata ttgatcattt   3180
attaggaaag ctgaactttc accactttat ttttggcttc ctctactttg ggcaaagtca   3240
aagttaggat accggcatcg taattagctt taacttctgt gttttggatt gctccaggta   3300
caggaataac ccggcggaaa ctgccatagc ggaactctgt gcgccgcacc ccatcttttt   3360
cggtgctatg ggtatcctgg cgatcgccgc tgacggtcac cgcatccctg gcggcttgga   3420
tgtccaaatt atcggggtcc atgccaggta attctagttt gagcacatag gcttcttcag   3480
tttcagttag ttctgcttta ggattaaacc cttggcgatc gccgtggcgg tccgtaggga   3540
caaaaacttc ttcaaacagt tggttcatct gctgctggaa attatccatt tcccgcaggg   3600
gattgtaaag aatgagagac ataatgttaa ctcctgatgt gtggaaggaa ttgattaccc   3660
ttgaatggtt ctatcttaaa atttcccctt ccaggttaga ttcggttttc aggaaagaag   3720 gtgggggat tgccgaaatt acatttctag ccgcaatttt tagtaaaaaa aagatgagtt   3780
tttacctcac cttaagtaaa tatttgagtg gcaaacaaa atggtaaaaa tagctaagct   3840
tccaccgccc tatggatttt tggaaggaag tcttaggttg tgaaaaacta taaaaaccaa   3900
ccataggaat ggagaccttt acccaacaag ttgacccccta ggtaacaaat ccaaaccacc   3960
gtaaaaccgc tggcggccaa aatagcgggc ttgcggcctt gccaacccttt ggtaatgcgg   4020 gcatggagat aggcggcaaa tactagccag gtgattaggg cccggtaccc agcttttgtt   4080 cccttttagtg agggttaatt tcgagcttgg cgtaatcatg gtcatagctg tttcctgtgt   4140
gaaattgtta tccgctcaca attccacaca acatacgagc cggaagcata aagtgtaaag   4200
cctggggtgc ctaatgagtg agctaactca cattaattgc gttgcgctca ctgcccgctt   4260
tccagtcggg aaacctgtcg tgccagctgc attaatgaat cggccaacgc gcggggagag   4320
gcggtttgcg tattgggcgc tcttccgctt cctcgctcac tgactcgctg cgctcggtcg   4380
```

```
ttcggctgcg gcgagcggta tcagctcact caaaggcggt aatacggtta tccacagaat    4440
caggggataa cgcaggaaag aacatgtgag caaaaggcca gcaaaggcc aggaaccgta    4500 aaaaggccgc gttgctggcg ttttccata ggctccgccc ccctgacgag catcacaaaa    4560
atcgacgctc aagtcagagg tggcgaaacc cgacaggact ataaagatac caggcgtttc    4620
cccctggaag ctccctcgtg cgctctcctg ttccgaccct gccgcttacc ggatacctgt    4680
ccgcctttct cccttcggga agcgtggcgc tttctcatag ctcacgctgt aggtatctca    4740
gttcggtgta ggtcgttcgc tccaagctgg gctgtgtgca cgaaccccc gttcagcccg    4800 accgctgcgc cttatccggt aactatcgtc ttgagtccaa cccggtaaga cacgacttat    4860
cgccactggc agcagccact ggtaacagga ttagcagagc gaggtatgta ggcggtgcta    4920
cagagttctt gaagtggtgg cctaactacg gctacactag aaggacagta tttggtatct    4980
gcgctctgct gaagccagtt accttcggaa aaagagttgg tagctcttga tccggcaaac    5040
aaaccaccgc tggtagcgt ggttttttg tttgcaagca gcagattacg cgcagaaaaa    5100
aaggatctca agaagatcct ttgatctttt ctacggggtc tgacgctcag tggaacgaaa    5160
actcacgtta agggattttg gtcatgagat tatcaaaaag gatcttcacc tagatccttt    5220
taaattaaaa atgaagtttt aaatcaatct aaagtatata tgagtaaact tggtctgaca    5280
gttaccaatg cttaatcagt gaggcaccta tctcagcgat ctgtctattt cgttcatcca    5340
tagttgcctg actccccgtc gtgtagataa ctacgatacg ggagggctta ccatctggcc    5400
ccagtgctgc aatgataccg cgagacccac gctcaccggc tccagattta tcagcaataa    5460
accagccagc cggaagggcc gagcgcagaa gtggtcctgc aactttatcc gcctccatcc    5520
agtctattaa ttgttgccgg gaagctgag taagtagttc gccagttaat agtttgcgca    5580
acgttgttgc cattgctaca ggcatcgtgg tgtcacgctc gtcgtttggt atggcttcat    5640
tcagctccgg ttcccaacga tcaaggcgag ttacatgatc ccccatgttg tgcaaaaaag    5700
cggttagctc cttcggtcct ccgatcgttg tcagaagtaa gttggccgca gtgttatcac    5760
tcatggttat ggcagcactg cataattctc ttactgtcat gccatccgta agatgctttt    5820
ctgtgactgg tgagtactca accaagtcat tctgagaata gtgtatgcgg cgaccgagtt    5880
gctcttgccc ggcgtcaata cgggataata ccgcgccaca tagcagaact ttaaaagtgc    5940
tcatcattgg aaaacgttct cggggcgaa aactctcaag gatcttaccg ctgttgagat    6000
ccagttcgat gtaacccact cgtgcaccca actgatcttc agcatctttt actttcacca    6060
gcgtttctgg gtgagcaaaa acaggaaggc aaaatgccgc aaaaaaggga ataagggcga    6120
cacggaaatg ttgaatactc atactcttcc tttttcaata ttattgaagc atttatcagg    6180
gttattgtct catgagcgga tacatatttg aatgtattta gaaaaataaa caataggggg    6240
ttccgcgcac atttccccga aaagtgc                                       6267
```

<210> SEQ ID NO 15
<211> LENGTH: 821
<212> TYPE: PRT
<213> ORGANISM: Synechocystis PCC6803

<400> SEQUENCE: 15

```
Met Gly Ser Thr Leu Val Gly Lys Cys Thr Ser Leu Gly Val Phe Ser
1               5                   10                  15

Met Val Thr Ser Pro Phe Ser Leu Ser Pro Phe Gly Gln Ala Arg Ser
            20                  25                  30

Thr Val Thr Gly Asn Pro Leu Asp Pro Thr Glu Leu Asn Gln Met His
```

```
                35                  40                  45
Gly Phe Trp Arg Ala Ala Asn Tyr Leu Ala Val Gly Met Ile Tyr Leu
 50                  55                  60

Arg Asp Asn Pro Leu Leu Arg Glu Pro Leu Gln Pro Glu Gln Ile Lys
 65                  70                  75                  80

His Arg Leu Leu Gly His Trp Gly Ser Ser Pro Gly Ile Ser Phe Leu
                 85                  90                  95

Tyr Thr His Leu Asn Arg Ile Ile Arg Lys Phe Asp Gln Asp Met Leu
            100                 105                 110

Tyr Met Val Gly Pro Gly His Gly Ala Pro Gly Phe Leu Gly Pro Cys
        115                 120                 125

Tyr Leu Glu Gly Ser Tyr Ser Arg Phe Phe Ala Glu Cys Ser Glu Asp
    130                 135                 140

Glu Asp Gly Met Lys Arg Phe Phe Lys Gln Phe Ser Phe Pro Gly Gly
145                 150                 155                 160

Ile Gly Ser His Cys Thr Pro Glu Thr Pro Gly Ser Ile His Glu Gly
                165                 170                 175

Gly Glu Leu Gly Tyr Cys Leu Ser His Ala Tyr Gly Ala Ala Phe Asp
            180                 185                 190

Asn Pro Asn Leu Ile Val Val Gly Leu Ala Gly Asp Gly Glu Ser Glu
        195                 200                 205

Thr Gly Pro Leu Ala Thr Ser Trp His Ser Asn Lys Phe Ile Asn Pro
    210                 215                 220

Ile Arg Asp Gly Ala Val Leu Pro Val Leu His Leu Asn Gly Tyr Lys
225                 230                 235                 240

Ile Asn Asn Pro Ser Val Leu Ser Arg Ile Ser His Glu Glu Leu Lys
                245                 250                 255

Ala Leu Phe Glu Gly Tyr Gly Tyr Thr Pro Tyr Phe Val Glu Gly Ser
            260                 265                 270

Asp Pro Glu Ser Met His Gln Ala Met Ala Ala Thr Leu Asp His Cys
        275                 280                 285

Val Ser Glu Ile His Gln Ile Gln Gln Glu Ala Arg Ser Thr Gly Ile
    290                 295                 300

Ala Val Arg Pro Arg Trp Pro Met Val Val Met Arg Thr Pro Lys Gly
305                 310                 315                 320

Trp Thr Gly Pro Asp Tyr Val Asp Gly His Lys Val Glu Gly Phe Trp
                325                 330                 335

Arg Ser His Gln Val Pro Met Gly Gly Met His Glu Asn Pro Ala His
            340                 345                 350

Leu Gln Gln Leu Glu Ala Trp Met Arg Ser Tyr Lys Pro Glu Glu Leu
        355                 360                 365

Phe Asp Glu Gln Gly Thr Leu Lys Pro Gly Phe Lys Ala Ile Ala Pro
    370                 375                 380

Glu Gly Asp Lys Arg Leu Gly Ser Thr Pro Tyr Ala Asn Gly Gly Leu
385                 390                 395                 400

Leu Arg Arg Gly Leu Lys Met Pro Asp Phe Arg Gln Tyr Gly Ile Asp
                405                 410                 415

Val Asp Gln Pro Gly Thr Ile Glu Ala Pro Asn Thr Ala Pro Leu Gly
            420                 425                 430

Val Phe Leu Arg Asp Val Met Ala Asn Asn Met Thr Asn Phe Arg Leu
        435                 440                 445

Phe Gly Pro Asp Glu Asn Ser Ser Asn Lys Leu His Ala Val Tyr Glu
    450                 455                 460
```

Val Ser Lys Lys Phe Trp Ile Ala Glu Tyr Leu Glu Glu Asp Gln Asp
465                 470                 475                 480

Gly Gly Glu Leu Ser Pro Asp Gly Arg Val Met Glu Met Leu Ser Glu
            485                 490                 495

His Thr Leu Glu Gly Trp Leu Glu Ala Tyr Leu Leu Thr Gly Arg His
        500                 505                 510

Gly Phe Phe Ala Thr Tyr Glu Ser Phe Ala His Val Ile Thr Ser Met
    515                 520                 525

Val Asn Gln His Ala Lys Trp Leu Asp Ile Cys Arg His Leu Asn Trp
530                 535                 540

Arg Ala Asp Ile Ser Ser Leu Asn Ile Leu Met Thr Ser Thr Val Trp
545                 550                 555                 560

Arg Gln Asp His Asn Gly Phe Thr His Gln Asp Pro Gly Phe Leu Asp
                565                 570                 575

Val Ile Leu Asn Lys Ser Pro Asp Val Val Arg Ile Tyr Leu Pro Pro
            580                 585                 590

Asp Val Asn Ser Leu Leu Ser Val Ala Asp His Cys Leu Gln Ser Lys
        595                 600                 605

Asn Tyr Ile Asn Ile Ile Val Cys Asp Lys Ala His Leu Gln Tyr
    610                 615                 620

Gln Asp Met Thr Ser Ala Ile Arg Asn Cys Thr Lys Gly Val Asp Ile
625                 630                 635                 640

Trp Glu Trp Ala Ser Asn Asp Ala Gly Thr Glu Pro Asp Val Met
                645                 650                 655

Ala Ala Ala Gly Asp Ile Pro Thr Lys Glu Ala Leu Ala Thr Ala
            660                 665                 670

Met Leu Arg Gln Phe Phe Pro Asn Leu Arg Ile Arg Phe Val Ser Val
        675                 680                 685

Ile Asp Leu Leu Lys Leu Gln Pro Glu Ser Glu His Pro His Gly Leu
690                 695                 700

Ser Asp Arg Asp Phe Asp Ser Leu Phe Thr Thr Asp Lys Pro Ile Ile
705                 710                 715                 720

Phe Asn Phe His Ala Tyr Pro Trp Leu Ile His Arg Leu Thr Tyr Arg
                725                 730                 735

Arg Thr Asn His Gly Asn Leu His Val Arg Gly Tyr Lys Glu Lys Gly
            740                 745                 750

Asn Ile Asn Thr Pro Met Asp Leu Ala Ile Gln Asn Gln Ile Asp Arg
        755                 760                 765

Phe Ser Leu Ala Ile Asp Val Ile Asp Arg Leu Pro Gln Leu Arg Val
770                 775                 780

Ala Gly Ala His Ile Lys Glu Met Leu Lys Asp Met Gln Ile Asp Cys
785                 790                 795                 800

Thr Asn Tyr Ala Tyr Glu His Gly Ile Asp Met Pro Glu Ile Val Asn
                805                 810                 815

Trp Arg Trp Pro Leu
            820

<210> SEQ ID NO 16
<211> LENGTH: 697
<212> TYPE: PRT
<213> ORGANISM: Synechocystis PCC6803

<400> SEQUENCE: 16

Met Thr Ser Ser Leu Tyr Leu Ser Thr Thr Glu Ala Arg Ser Gly Lys
1               5                   10                  15

-continued

Ser Leu Val Val Leu Gly Ile Leu Asp Leu Ile Leu Lys Thr Thr
            20                  25                  30

Arg Ile Ala Tyr Phe Arg Pro Ile Gln Asp Pro Val Asn Gly Lys
        35                  40                  45

His Asp Asn Asn Ile Ile Leu Val Leu Glu Asn Phe Arg Leu Gln Gln
50                      55                  60

Thr Tyr Thr Asp Ser Phe Gly Leu Tyr Phe His Glu Ala Val Ser Leu
65                  70                  75                  80

Ala Ser Asp Gly Ala Ile Asp Gln Val Leu Asp Arg Ile Leu Ala Lys
                85                  90                  95

Tyr Arg His Leu Ala Asp Gln Val Asp Phe Ile Leu Cys Glu Gly Ser
                100                 105                 110

Asp Tyr Leu Gly Glu Glu Ser Ala Phe Glu Phe Asp Leu Asn Thr Thr
        115                 120                 125

Ile Ala Lys Met Leu Asn Cys Pro Ile Leu Leu Gly Asn Ala Met
130                 135                 140

Gly Asn Thr Ile Ala Asp Ser Leu Gln Pro Ile Asp Met Ala Leu Asn
145                 150                 155                 160

Ser Tyr Asp Gln Glu Ser Cys Gln Val Val Gly Val Ile Ile Asn Arg
        165                 170                 175

Val Gln Pro Glu Leu Ala Thr Glu Ile Gln Ala Gln Leu Glu Gln Arg
    180                 185                 190

Tyr Gly Asp Arg Pro Met Val Leu Gly Thr Ile Pro Gln Asp Ile Met
    195                 200                 205

Leu Lys Ser Leu Arg Leu Arg Glu Ile Val Ser Gly Leu Asn Ala Gln
210                 215                 220

Val Leu Ser Gly Ala Asp Leu Leu Asp Asn Leu Val Tyr His His Leu
225                 230                 235                 240

Val Val Ala Met His Ile Ala His Ala Leu His Trp Leu His Glu Lys
            245                 250                 255

Asn Thr Leu Ile Ile Thr Pro Gly Asp Arg Gly Asp Ile Ile Leu Gly
            260                 265                 270

Val Met Gln Ala His Arg Ser Leu Asn Tyr Pro Ser Ile Ala Gly Ile
        275                 280                 285

Leu Leu Thr Ala Asp Tyr His Pro Glu Pro Ala Ile Met Lys Leu Ile
        290                 295                 300

Glu Gly Leu Pro Asp Ala Pro Pro Leu Leu Thr Ser Thr His Thr
305                 310                 315                 320

His Glu Thr Ser Ala Arg Leu Glu Thr Leu His Pro Ala Leu Ser Pro
                325                 330                 335

Thr Asp Asn Tyr Lys Ile Arg His Ser Ile Ala Leu Phe Gln Gln Gln
                340                 345                 350

Ile Asp Gly Glu Lys Leu Leu Asn Tyr Leu Lys Thr Ile Arg Ser Lys
        355                 360                 365

Gly Ile Thr Pro Lys Leu Phe Leu Tyr Asn Leu Val Gln Ala Ala Thr
370                 375                 380

Ala Ala Gln Arg His Ile Val Leu Pro Glu Gly Glu Glu Ile Arg Ile
385                 390                 395                 400

Leu Lys Ala Ala Ala Ser Leu Ile Asn His Gly Ile Val Arg Leu Thr
            405                 410                 415

Leu Leu Gly Asn Ile Glu Ala Ile Glu Gln Thr Val Lys Ile Asn His
            420                 425                 430

Ile Asp Leu Asp Leu Ser Lys Val Arg Leu Ile Asn Pro Lys Thr Ser
        435                 440                 445

-continued

```
Pro Asp Arg Glu Arg Tyr Ala Glu Thr Tyr Tyr Gln Leu Arg Lys His
    450                 455                 460

Lys Gly Val Thr Leu Ala Met Ala Arg Asp Ile Leu Thr Asp Ile Ser
465                 470                 475                 480

Tyr Phe Gly Thr Met Met Val His Leu Gly Glu Ala Asp Gly Met Val
                485                 490                 495

Ser Gly Ser Val Asn Thr Thr Gln His Thr Val Arg Pro Ala Leu Gln
            500                 505                 510

Ile Ile Lys Thr Gln Pro Gly Phe Ser Leu Val Ser Ser Val Phe Phe
        515                 520                 525

Met Cys Leu Glu Asp Arg Val Leu Val Tyr Gly Asp Cys Ala Val Asn
    530                 535                 540

Pro Asp Pro Asn Ala Glu Gln Leu Ala Glu Ile Ala Leu Thr Ser Ala
545                 550                 555                 560

Ala Thr Ala Lys Asn Phe Gly Ile Glu Pro Arg Val Ala Leu Leu Ser
                565                 570                 575

Tyr Ser Ser Gly Ser Ser Gly Gln Gly Ala Asp Val Glu Lys Val Arg
            580                 585                 590

Gln Ala Thr Ala Ile Ala Lys Glu Arg Glu Pro Asp Leu Ala Leu Glu
        595                 600                 605

Gly Pro Ile Gln Tyr Asp Ala Ala Val Asp Ser Thr Val Ala Ala Gln
    610                 615                 620

Lys Met Pro Gly Ser Ala Val Ala Gly Lys Ala Thr Val Phe Ile Phe
625                 630                 635                 640

Pro Asp Leu Asn Thr Gly Asn Asn Thr Tyr Lys Ala Val Gln Arg Glu
                645                 650                 655

Thr Lys Ala Ile Ala Ile Gly Pro Ile Leu Gln Gly Leu Asn Lys Pro
            660                 665                 670

Val Asn Asp Leu Ser Arg Gly Cys Leu Val Glu Asp Ile Ile Asn Thr
        675                 680                 685

Val Val Ile Thr Ala Leu Gln Val Lys
    690                 695
```

<210> SEQ ID NO 17
<211> LENGTH: 33
<212> TYPE: DNA
<213> ORGANISM: Artificial Sequence
<220> FEATURE:
<223> OTHER INFORMATION: #phk1

<400> SEQUENCE: 17
gtgtctcata tggttacatc cccctttttcc ctt        33

<210> SEQ ID NO 18
<211> LENGTH: 34
<212> TYPE: DNA
<213> ORGANISM: Artificial Sequence
<220> FEATURE:
<223> OTHER INFORMATION: #phk-BglII-rev

<400> SEQUENCE: 18
ggtcacagat ctgttgtccc ccatggccta gcta        34

<210> SEQ ID NO 19
<211> LENGTH: 40
<212> TYPE: DNA
<213> ORGANISM: Artificial Sequence
<220> FEATURE:
<223> OTHER INFORMATION: #pta-BglII-fw

<400> SEQUENCE: 19

```
ccttgcagat ctggatacgt tgaggttatt taaattatga                           40
```

<210> SEQ ID NO 20
<211> LENGTH: 34
<212> TYPE: DNA
<213> ORGANISM: Artificial Sequence
<220> FEATURE:
<223> OTHER INFORMATION: #pta_pPETJ2-XhoI

<400> SEQUENCE: 20

```
cggttgctcg agcatctgga acggttgggt aaat                                 34
```

<210> SEQ ID NO 21
<211> LENGTH: 5385
<212> TYPE: DNA
<213> ORGANISM: Artificial Sequence
<220> FEATURE:
<223> OTHER INFORMATION: nucleic acid sequence of the insert of
      pVZ322-PpetJ-phk-pta

<400> SEQUENCE: 21

```
cccgggtacc cctcatcggg ggctgtgttg gccgagacgg cactgaggat tttactctcc     60
atggcattcc aaggaatatc tacccaactc acctgctccg gcggattgtt ccgctcaaaa    120
gtactaatca agtcgtcaaa atacttatta aattttggct gcaattgcat agtccaaaag    180
ctgactttcc cctccatgct ctgggggaa ttgctctggc aactgattaa tccactgagc     240
aacagcccaa gacacgcaaa caaaaaccaa cgtcttggcg atcgccatcg gcaccatgaa    300
accatcgtaa aagctgggga agaataaaa aacagtggtt caggaattgc attgccatgg     360
ccacttcaca aacctagcca attttagctt gaccgcaact ttgacagatt gtcttttgac    420
tttgcctgga ccgcctccca taatacctt gcgtcttgaa gactttatcc ttgaaaggag     480
aacatatggt tacatccccc ttttcccctta gtccctttgg tcaagctaga tccaccgtca    540
ctggcaatcc ccttgacccg acagaactta accaaatgca cggttttgg cgggcagcca     600
actacttggc agtgggcatg atttatctgc gggataatcc cctttttgcgg gaaccgcttc    660
aaccggaaca gatcaagcat cgcctgttgg gtcactgggg ttctagtccc ggcattagtt    720
ttctctacac ccatctcaac cgcattatca ggaaatttga ccaggatatg ctgtacatgg    780
tggggcctgg ccacggcgca ccaggctttt tggggccctg ctacctagaa gggagctatt    840
ctcgcttttt tgccgagtgt agtgaagatg aggacggcat gaagcgcttt ttcaaacaat    900
tttcctttcc cggtggcatt ggcagtcatt gcactcccga aacccctggt tccatccacg    960
aggggggaga attgggctac tgcctatccc atgcctatgg cgctgccttt gataatccca   1020
atttaattgt ggtcggttta gcggggatg gggagtcgga aacaggcccc ttggctacct    1080
cctggcattc caataagttt attaacccga ttcgggatgg ggcagtttta ccggttctgc   1140
atctcaatgg gtacaagatt aacaatccaa gtgtttatc tcgcattagc catgaagaat   1200
taaaggcttt atttgaaggt tacgttata ccccctactt tgttgaaggc tctgacccgg    1260
aatctatgca ccaagccatg gcagccacgt tggatcattg tgtgagcgaa attcatcaaa    1320
tccaacaaga agctcgtagt acgggcattg ccgtgcgccc ccgttggccc atggttgtga    1380
tgcggactcc caagggatgg acggggcctg actatgttga tggccataag gtagaaggtt    1440
tttggcgatc gcaccaagtt cccatggggg gcatgcacga gaatccagcc catttgcaac    1500
agttggaagc ttggatgcgg agttataagc cggaagaatt gttcgacgag caaggtactt   1560
```

```
taaaaccggg atttaaggcg atcgccccgg agggagataa gcgtttaggc tctactccct    1620
acgccaatgg tggtttgtta cggcggggtt tgaaaatgcc ggactttcgt caatatggta    1680
ttgatgtgga ccaaccaggc accatcgaag ccctaatac tgcacccctg ggagtatttc     1740
tgcgggatgt gatggccaac aacatgacca atttccgcct gttggcccc gatgaaaata     1800
gttccaataa actccatgcc gtctacgagg ttagcaaaaa attctggatt gctgaatatc    1860
tagaagaaga ccaggatggg ggggaattaa gtcccgatgg tcgggtgatg gaaatgttaa    1920
gcgagcacac cttagaaggt tggttagagg cctatctttt aaccgggcgt cacggctttt    1980
tcgccaccta tgaatccttt gcccatgtga tcacttccat ggttaaccaa cacgctaaat    2040
ggttggatat ttgtcgacac ctcaactggc gggcagatat ttcctcgtta aatatcttga    2100
tgacgtccac cgtgtggcga caggatcaca acgggtttac ccaccaagat cccggttttc    2160
tcgatgtcat tctcaataaa agccccgatg tggtgcgaat ttatttaccc cccgatgtta    2220
attctctgct ttccgtagcg gaccattgtt tacagagcaa aaactacatc aacatcatcg    2280
tttgcgataa gcaagcccac ctgcaatacc aggacatgac ttccgctatc cgtaactgca    2340
ctaaaggggt ggacatttgg gaatgggcca gtaatgatgc cggtacggaa ccggatgtgg    2400
tgatggcagc ggcgggggat attcccacca aagaggcctt ggcggccaca gccatgctaa    2460
ggcaattttt tcctaatctg agaattcgct tgtcagcgt gattgatttg ctcaaactgc     2520
aaccggaatc ggagcatccc catggcctga gcgatcggga ttttgactcc ctctttacca    2580
ccgataaacc gattatttt aacttccacg cctatccctg gttaattcat cggttgacct     2640
atcgacggac taaccatggc aatctccatg tgcgggcta caaggaaaag gcaacatca      2700
acacccccat ggatttagcg attcaaaacc agattgaccg tttcagcctc gccattgatg    2760
tgatcgatcg cctgccccaa ttgcgggtgg ccggagccca catcaaggaa atgctcaagg    2820
atatgcagat tgactgcacc aactacgcct acgaacacgg cattgatatg ccagaaatcg    2880
ttaattggcg ctggcccctc tagaccttaa ctaaaatccc tgacatcgtt ctagtttctg    2940
ttccaatagg ttagctaggc catggggac aacagatctg gatacgttga ggttatttaa     3000
attatgacga gttccctta tttaagcacc accgaagccc gcagcggtaa atctctagta     3060
gtattgggca ttttagactt aattctcaaa aaaaccaccc gtattgccta ttttcgtccc    3120
attattcaag acccagttaa tggcaaacat gataacaaca ttattctggt gctgaaaaat    3180
tttcgtctcc aacaaaccta taccgattcc tttggtttgt atttccatga agcggtgagt    3240
ttagcctccg atgagctat tgatcaggta ttagaccgaa ttttggctaa atatcgccat     3300
ttggcagatc aagtagattt tattctctgt gaaggctcag actatttggg ggaggaatcg    3360
gcttttgaat ttgatctcaa caccacgatc gccaagatgt tgaactgccc cattttgctg    3420
ttgggcaatg ccatgggcaa caccattgcc gatagtttgc aacccatcga tatggccctg    3480
aatagctatg accaagagtc ttgtcaggtg gtggggtaa tcattaaccg agtgcagccc      3540
gaattagcca cagaaattca agcccaactg gaacagcgtt atggcgatcg cccgatggtg    3600
ttgggcacta ttccccagga cattatgctc aaaagtctgc gcctgaggga aattgtcagc    3660
gggctcaatg cccaagtact cagcggtgcg gatttgctcg ataacttggt ctatcaccat    3720
ttagtggtgg cgatgcacat tgcccacgcc ctccattggt tgcacgaaaa aaatacccta    3780
attattcccc ctggcgatcg gggcgacatc attctggggg tgatgcaggc ccaccgctcc    3840
ctcaactatc ccagcattgc cggtattttg ctcactgcag attaccatcc cgaaccggcc    3900
attatgaaac taattgaagg gctacccgac gcccctcccc tgttgctgac tagcacccac    3960
```

-continued

```
acccatgaaa cttccgcccg tttggaaact ctccaccctg ccctgagccc tacggataat    4020
tataaaattc gccacagtat tgcgctgttt caacaacaaa ttgatgggga gaaattactc    4080
aattacctta aaaccatccg cagtaaaggt attaccccca aactgtttct ctacaattta    4140
gttcaagccg ccaccgccgc ccaacgacat attgtcctac cggaagggga agaaattcgt    4200
attctcaagg cggccgctag cttaattaac cacggcattg tccgtttgac tttactcggt    4260
aacattgagg cgatcgagca aacggtaaaa attaatcaca ttgacttaga tttgagcaaa    4320
gttcgcctca ttaatcctaa aactagccca gaccgagagc gctacgccga aacctattac    4380
cagctacgta aacataaggg ggtaaccctg gccatggctc gggatatcct caccgatatt    4440
tcctattttg gaacgatgat ggtgcatttg ggagaggccg atggcatggt ttctggctcc    4500
gtcaatacca cccaacatac cgtgcgtcct gctttacaaa ttattaaaac ccagccaggt    4560
ttttccttgg tttcttcagt cttttttatg tgtttagaag accgagtttt ggtctatgga    4620
gattgtgctg ttaatcccga tcccaatgca gaacagttag cagaaattgc ccttacttct    4680
gcggctacgg ccaagaattt tggcattgag cccagggtag ctctattgtc ctattcttcc    4740
ggttcttctg gcaagggc cgatgtggaa aaagtgcggc aagccacggc gatcgccaag    4800
gaaagagagc cagatttagc attggaaggg ccgatccagt atgatgcggc ggtggattcc    4860
acagtggcgg cccaaaaaat gcctgggtca gcggtggcgg gtaaagcaac ggtgtttatt    4920
tttcccgatt taaataccgg taacaatact tacaaggcag tgcaaagaga acaaaggcg    4980
atcgccattg gccccatttt acaaggatta aataaaccag ttaatgatct aagtcggggt    5040
tgtttagtgg aggatattat taatacggtg gtaattacag ctttgcaagt taaataattt    5100
tactcttaat tagttaaaat gatcccttga attaccttga ttttgccctc caaactacca    5160
atagctgggc cgaaaattgg catcatttaa aatcaccaac gtgtccccgg acggagctag    5220
cacaaacaga cccttaccat aggcatagct gaccacttct tggcttaaca ccatggctgc    5280
cactgcacct aaagctttaa catcccggta gcggggcata aactgtttga atttacccaa    5340
ccgttccaga tgctcgagca accgatcttt ctagaagatc tcgag                    5385
```

<210> SEQ ID NO 22
<211> LENGTH: 456
<212> TYPE: PRT
<213> ORGANISM: Synechocystis PCC6803

<400> SEQUENCE: 22

```
Met Asn Thr Ala Lys Thr Val Ala Glu Gln Arg Asp Phe Phe Arg
1               5                   10                  15

Gln Gly Lys Thr Lys Ser Val Gln Asp Arg Leu Thr Ala Leu Ala Lys
            20                  25                  30

Leu Lys Thr Gln Ile Gln Ala Gln Glu Glu Ile Ile Lys Ala Leu
        35                  40                  45

Lys Gln Asp Phe Gly Lys Pro Thr Phe Glu Ser Tyr Val Asn Glu Ile
    50                  55                  60

Leu Gly Val Ile Arg Glu Ile Asn Tyr Tyr Gln Lys His Leu Gln Gln
65                  70                  75                  80

Trp Ser Lys Pro Gln Arg Val Gly Thr Asn Leu Met Val Phe Pro Ala
                85                  90                  95

Ser Ala Gln Leu Arg Pro Glu Pro Leu Gly Val Val Leu Ile Ile Ser
            100                 105                 110

Pro Trp Asn Tyr Pro Phe Tyr Leu Cys Leu Met Pro Leu Ile Gly Ala
        115                 120                 125
```

```
Ile Ala Ala Gly Asn Cys Val Val Lys Pro Ser Glu Tyr Thr Pro
    130             135                 140
Ala Ile Ser Gly Val Ile Thr Arg Leu Ile Gln Asn Val Phe Ser Pro
145             150                 155                 160
Ala Trp Ala Thr Val Val Glu Gly Asp Glu Thr Ile Ser Gln Gln Leu
                165                 170                 175
Leu Gln Glu Lys Phe Asp His Ile Phe Phe Thr Gly Ser Pro Arg Val
            180                 185                 190
Gly Arg Leu Ile Met Ala Ala Ala Glu Gln Leu Thr Pro Val Thr
        195                 200                 205
Leu Glu Leu Gly Gly Lys Ser Pro Cys Val Val Asp Arg Glu Ile Asn
    210                 215                 220
Leu Gln Glu Thr Ala Lys Arg Ile Met Trp Gly Lys Leu Val Asn Ala
225             230                 235                 240
Gly Gln Thr Cys Val Ala Pro Asp Tyr Leu Leu Val Glu Gln Ser Cys
                245                 250                 255
Leu Glu Gln Leu Leu Pro Ala Leu Gln Gln Ala Ile Gln Met Leu Phe
            260                 265                 270
Gly Glu Asn Pro Ala His Ser Pro Asp Tyr Thr Arg Ile Val Asn Gln
        275                 280                 285
Gln Gln Trp Ser Arg Leu Val Ser Leu Leu Ser His Gly Lys Val Ile
    290                 295                 300
Thr Arg Gly Asp His Asn Glu Gly Asp Arg Tyr Ile Ala Pro Thr Leu
305             310                 315                 320
Ile Ile Asp Pro Asp Leu Asn Ser Pro Leu Met Gln Glu Glu Ile Phe
                325                 330                 335
Gly Pro Ile Leu Pro Ile Leu Thr Tyr Gln Ser Leu Ser Glu Ala Ile
            340                 345                 350
Asp Phe Ile Asn Ile Lys Pro Lys Pro Leu Ala Leu Tyr Phe Phe Ser
        355                 360                 365
Asn Asn Arg Gln Lys Gln Glu Glu Ile Leu Gln Ser Thr Ser Ser Gly
    370                 375                 380
Ser Val Cys Leu Asn Asp Ile Leu Leu His Leu Thr Val Thr Asp Leu
385             390                 395                 400
Pro Phe Gly Gly Val Gly Glu Ser Gly Met Gly Arg Tyr His Gly Lys
                405                 410                 415
Ala Thr Phe Asp Thr Leu Ser Asn Tyr Lys Ser Ile Leu Arg Arg Pro
            420                 425                 430
Phe Trp Gly Glu Thr Asn Leu Arg Tyr Ser Pro Tyr Gly Lys Lys Met
        435                 440                 445
Asn Leu Ile Lys Lys Leu Phe Ser
    450                 455

<210> SEQ ID NO 23
<211> LENGTH: 35
<212> TYPE: DNA
<213> ORGANISM: Artificial Sequence
<220> FEATURE:
<223> OTHER INFORMATION: #aldh1-NdeI-fw

<400> SEQUENCE: 23
gtgcctcata tgaatactgc taaaactgtt gttgc                                 35

<210> SEQ ID NO 24
<211> LENGTH: 35
<212> TYPE: DNA
<213> ORGANISM: Artificial Sequence
```

<220> FEATURE:
<223> OTHER INFORMATION: #aldh2-XhoI-rev

<400> SEQUENCE: 24
gatctcctcg aggtaaagaa tcagcatagg tctgg         35

<210> SEQ ID NO 25
<211> LENGTH: 2089
<212> TYPE: DNA
<213> ORGANISM: Artificial Sequence
<220> FEATURE:
<223> OTHER INFORMATION: sequence of the insert of construct
      pVZ322-PpetJ-aldh

<400> SEQUENCE: 25

| | |
|---|---:|
| ctgcaggtcg actctagagg atccccgggt acccctcatc gggggctgtg ttggccgaga | 60 |
| cggcactgag gattttactc tccatggcat tccaaggaat atctacccaa ctcacctgct | 120 |
| ccggcggatt gttccgctca aaagtactaa tcaagtcgtc aaaatactta ttaaattttg | 180 |
| gctgcaattg catagtccaa aagctgactt tcccctccat gctctggggg gaattgctct | 240 |
| ggcaactgat taatccactg agcaacagcc aagacacgc aaacaaaaac caacgtcttg | 300 |
| gcgatcgcca tcggcaccat gaaaccatcg taaaagctgg ggaaagaata aaaaacagtg | 360 |
| gttcaggaat tgcattgcca tggccacttc acaaacctag ccaattttag cttgaccgca | 420 |
| actttgacag attgtctttt gactttgcct ggaccgcctc ccataatacc ttcgcgtctt | 480 |
| gaagacttta tccttgaaag gagaacatat gaatactgct aaaactgttg ttgctgagca | 540 |
| aagggacttt tttcgtcagg gcaaaactaa atcagtccaa gatagattaa cagctctagc | 600 |
| aaaattaaaa acgcaaattc aagcccagga agaggaaatt attaaggccc ttaagcaaga | 660 |
| ttttggtaag cccacctttg aaagctatgt aaacgaaatt tgggggtaa ttagggaaat | 720 |
| taattattat caaaaacatc ttcagcaatg gtctaagccc caacgggtag gtacgaatct | 780 |
| gatggttttt cctgccagtg cccagttaag accagaaccc cttggtgtag tgctaattat | 840 |
| tagcccctgg aattatcctt tttatctttg tttaatgccc ttgatcgggg cgatcgccgc | 900 |
| tggaaattgt gtggtggtaa agccgtcgga atatactcca gctattagtg gggtaattac | 960 |
| cagattaatc caaaatgtat tttccccggc ttgggcaaca gtggtggagg gagatgaaac | 1020 |
| cattagccaa caattgttac aggaaaaatt tgaccatatt tctttaccg gcagccctag | 1080 |
| ggtgggtcgg ttaattatgg cagctgcggc agagcaatta accccagtta cgttggaatt | 1140 |
| gggggggtaaa tctccctgtg tggtggatag ggaaatcaac ctccaggaaa cagccaaacg | 1200 |
| cattatgtgg ggcaagctag tcaatgctgg ccaaacctgt gtggcaccgg attatttatt | 1260 |
| ggtgagcaa tcctgcttag aacaactttt accagctttta caacaggcaa ttcagatgct | 1320 |
| tttcggggaa aatccagccc atagccctga ctacactcgc attgttaacc aacaacaatg | 1380 |
| gtcacggtta gttagtttat taagccatgg caaagtaatt acaaggggag atcataacga | 1440 |
| aggcgatcgc tacattgccc aactttaat catcgatcca gatttaaatt ctcccttaat | 1500 |
| gcaagaggaa atatttggcc caattttgcc aatttaact tatcagagtt tgtcagaagc | 1560 |
| aatagatttt attaacatca aacctaaacc attggcactt tatttttta gcaataatcg | 1620 |
| gcaaaaacag gaggaaattt tgcaatctac cagttccggt agtgtttgtt tgaacgatat | 1680 |
| tttgcttcat ttaactgtga cagacttacc ctttggtggg gtgggagaaa gtggtatggg | 1740 |
| acgctaccat ggcaaggcta cttttgacac attgagcaat tataaaagca ttttacgacg | 1800 |
| acccttttgg ggggaaacta atttacgcta ttctccctat ggcaaaaaaa tgaatttaat | 1860 |

```
caaaaagttg ttctcctagg attattcatg gccgaccgtc cccagttgag tattattatt   1920
cccgtgttta atgaagcaaa aattttacaa aagtctccga ctgaaaatac cagacaatat   1980
ttgggacaat ttaccgagga tcaacggata gaaattttaa ttattgatgg gggcagtcag   2040
gatagcacag tggagttatg ccagacctat gctgattctt tacctcgag              2089
```

```
<210> SEQ ID NO 26
<211> LENGTH: 413
<212> TYPE: PRT
<213> ORGANISM: Synechocystis PCC6803

<400> SEQUENCE: 26

Met Lys Phe Leu Ile Leu Asn Ala Gly Ser Ser Gln Lys Ser Cys
1               5                   10                  15

Leu Tyr Glu Leu Thr Gly Asp Arg Leu Pro Glu Thr Ile Pro Glu Pro
            20                  25                  30

Leu Trp Glu Ala Phe Ile Asp Trp Thr Val Leu Ala Asn Gln Gly Arg
        35                  40                  45

Leu Thr Val Glu Thr Ala Gly Gln Lys Gln Val Ile Ile Leu Glu Thr
    50                  55                  60

Gly Asp Arg Gln Gln Gly Ile Ala Arg Met Leu Asp Thr Leu Val Thr
65                  70                  75                  80

Gly Asp Asp Ala Val Leu Lys Ser Leu Ala Glu Ile Asp Leu Val Gly
                85                  90                  95

His Arg Val Val His Gly Gly Thr Asp His Ala Glu Ala Thr Leu Ile
            100                 105                 110

Thr Pro Glu Val Gln Gln Ala Ile Ala Asp Leu Ile Pro Leu Ala Pro
        115                 120                 125

Ala His Asn Pro Ala His Leu Glu Gly Ile Glu Ala Ile Ser Ala Leu
    130                 135                 140

Leu Val Leu Gly Glu Val Pro Gln Ile Ala Val Phe Asp Thr Ala Phe
145                 150                 155                 160

His Arg Thr Ile Pro Thr Pro Ala Ala Glu Tyr Pro Ile Pro Gln Ala
                165                 170                 175

Trp Thr Asn Leu Gly Ile Arg Arg Tyr Gly Phe His Gly Thr Ser His
            180                 185                 190

Lys Tyr Cys Ala Gln Lys Thr Ala Glu Ile Leu Gly Lys Pro Leu Ala
        195                 200                 205

Asp Leu Lys Leu Ile Thr Cys His Ile Gly Asn Gly Ala Ser Leu Thr
    210                 215                 220

Ala Ile Lys Asn Gly Val Ser Ile Asp Thr Thr Met Gly Phe Thr Pro
225                 230                 235                 240

Leu Glu Gly Leu Met Met Gly Ala Arg Ser Gly Ser Ile Asp Pro Ala
                245                 250                 255

Ile Leu Leu Phe Leu Gln Glu Thr Gln Gly Leu Thr Pro Ala Glu Ile
            260                 265                 270

Asn Thr Thr Leu Asn Lys Lys Ser Gly Leu Leu Gly Val Ser Gly Leu
        275                 280                 285

Ser Ala Asp Leu Arg Thr Ile Leu Gln Ala Lys Ala Glu Gly Asn Glu
    290                 295                 300

Gln Ala Gln Leu Ala Tyr Val Met Tyr Ile His Arg Phe Arg Ser Cys
305                 310                 315                 320

Leu Gly Gln Met Ile Ala Ser Leu Glu Gly Leu Asp Thr Leu Val Phe
                325                 330                 335

Thr Ala Gly Val Gly Glu Asn Ala Ala Thr Val Arg Ala Asp Val Cys
```

```
            340             345             350
Gln Ala Phe Glu Phe Leu Gly Leu Lys Leu Asp Pro Glu Leu Asn Asn
        355                 360                 365

Arg Ser Pro Arg Asp Thr Val Ile Ser His Ser Asp Ser Leu Val Thr
    370                 375                 380

Val Leu Ile Val His Thr Glu Glu Asp Trp Ala Ile Ala Gln Asp Cys
385                 390                 395                 400

Trp His Trp Trp His Ser Gln Gly Gln Arg Lys Gln Ser
                405                 410

<210> SEQ ID NO 27
<211> LENGTH: 23
<212> TYPE: DNA
<213> ORGANISM: Artificial Sequence
<220> FEATURE:
<223> OTHER INFORMATION: #ack-1 fw

<400> SEQUENCE: 27
ccgggacgtg acagaacggg tgg                                          23

<210> SEQ ID NO 28
<211> LENGTH: 23
<212> TYPE: DNA
<213> ORGANISM: Artificial Sequence
<220> FEATURE:
<223> OTHER INFORMATION: #ack-2 rv

<400> SEQUENCE: 28
gcgttggcga tcgccgtcac tag                                          23

<210> SEQ ID NO 29
<211> LENGTH: 2760
<212> TYPE: DNA
<213> ORGANISM: Artificial Sequence
<220> FEATURE:
<223> OTHER INFORMATION: nucleic acid sequence of the insert of
      construct pBlue-ack-Km

<400> SEQUENCE: 29
actagtagtg cagaaatttt gagcgatctg aagccacca ttgcctacgc ccaaacttta    60
cccaacgtta aaccggaaga agtaggatta attggttttt gttttggtgg ttggattgtc   120
tatttagggg ctagtttacc cacagtcaag gccacggctt ccttttacgg cgcgggtatt   180
ccccattggg ctccagggac agcggaaccg cccattacct ataccgataa aattcagggc   240
actttatacg ccttcttcgg cttggaagat accagcattc ccatggcaga tacggagcag   300
attgaacagg ctttaaccaa gtatcaggtg aaccataaaa ttttccgtta cccaggcgca   360
gaccatggct ttttctgtga ccaaagggct agctataacg ccgaagcggc cgccgatgct   420
tggcaaaaag tgaaacaact tttccaaacc gaattgaaat gaattcctg attctcaatg    480 ccggttccag cagtcaaaaa agttgtcttt atgagctgac tggcgatcgc ctaccggaga   540
cgataccgga gcccttatgg gaggctttca ttgattggac ggtgttggca atcaggggc    600 ggttgacctg caggggggg ggggaaagcc acgttgtgtc tcaaaatctc tgatgttaca   660
ttgcacaaga taaaaatata tcatcatgaa caataaaact gtctgcttac ataacagta   720 atacaagggg tgttatgagc catattcaac gggaaacgtc ttgctcgagg ccgcgattaa   780
attccaacat ggatgctgat ttatatgggt ataaatgggc tcgcgataat gtcgggcaat   840
caggtgcgac aatctatcga ttgtatggga agcccgatgc gccagagttg tttctgaaac   900
atggcaaagg tagcgttgcc aatgatgtta cagatgagat ggtcagacta aactggctga   960
```

```
cggaatttat gcctcttccg accatcaagc attttatccg tactcctgat gatgcatggt    1020
tactcaccac tgcgatcccc gggaaaacag cattccaggt attagaagaa tatcctgatt    1080
caggtgaaaa tattgttgat gcgctggcag tgttcctgcg ccggttgcat tcgattcctg    1140
tttgtaattg tccttttaac agcgatcgcg tatttcgtct cgctcaggcg caatcacgaa    1200
tgaataacgg tttggttgat gcgagtgatt tgatgacga gcgtaatggc tggcctgttg    1260
aacaagtctg gaaagaaatg cataagcttt tgccattctc accggattca gtcgtcactc    1320
atggtgattt ctcacttgat aaccttattt ttgacgaggg gaaattaata ggttgtattg    1380
atgttggacg agtcggaatc gcagaccgat accaggatct tgccatccta tggaactgcc    1440
tcggtgagtt ttctccttca ttacagaaac ggcttttttca aaaatatggt attgataatc    1500
ctgatatgaa taaattgcag tttcatttga tgctcgatga gttttctaa tcagaattgg    1560 ttaattggtt gtaacactgg cagagcatta cgctgacttg acgggacggc ggctttgttg    1620
aataaatcga acttttgctg agttgaagga tcagatcacg catcttcccg acaacgcaga    1680
ccgttccgtg gcaaagcaaa agttcaaaat caccaactgg tccacctaca acaaagctct    1740
catcaaccgt ggctccctca ctttctggct ggatgatggg gcgattcagg cctggtatga    1800
gtcagcaaca ccttcttcac gaggcagacc tcagcgcccc cccccccctg caggtcaacc    1860 ccggcgaaa ttaacaccac cctcaataaa aaatccggtt tgctcggagt ctctgggctg    1920
tcggcggatc ttcgtaccat tttgcaggcc aaagcagagg gtaatgaaca agctcaattg    1980
gcttatgtca tgtatatcca tcgcttccgg agttgtttgg ggcaaatgat tgcttccttg    2040
gaaggtttgg atacgttggt gtttaccgcc ggggtggggg aaaatgccgc cactgtgcgg    2100
gcagatgttt gccaagcttt tgaatttcta ggtttaaaac ttgatccaga gttgaataac    2160
cgatcgccaa gggatactgt catttctcac tccgactcct tggtgacggt gttgattgtc    2220
cacaccgaag aagattgggc gatcgcccag gattgttggc actggtggca tagccaggga    2280
cagagaaagc aatcgtaaat tgcgaaaatg ttagaaaatg gctgtgaaga taaatgttga    2340
attaggctaa atttccttgg ctagagtccg catccgccaa cacgtcaacc ccctcagtga    2400
aaaatatcgg caggtgttgg cctgtcccga ttgggccacc gtttatgacg atgtccaacg    2460
accattgcat ctagatattg gctgtgcccg gggtcgcttt ccctcaaaa tggctcaaca    2520 acaccccgac tggaatttt tagggtgga aatccgtcaa cccttggtgc tagaggccaa    2580
cgaaaccggc gatcgtctgg ggttaaaaaa tctccattac ctgtttggca acatcaatgt    2640
ggagccagaa aaattctttt ccgcctttcc ccccactctg caacgggtca gcatccaatt    2700
tcccgatccc tggtttaagc aacgacataa taaacgccga gtggcccaac cagaactagt    2760
```

<210> SEQ ID NO 30
<211> LENGTH: 697
<212> TYPE: PRT
<213> ORGANISM: Synechocystis PCC6803

<400> SEQUENCE: 30

```
Met Thr Ser Ser Leu Tyr Leu Ser Thr Thr Glu Ala Arg Ser Gly Lys
1               5                   10                  15

Ser Leu Val Val Leu Gly Ile Leu Asp Leu Ile Leu Lys Lys Thr Thr
            20                  25                  30

Arg Ile Ala Tyr Phe Arg Pro Ile Ile Gln Asp Pro Val Asn Gly Lys
        35                  40                  45

His Asp Asn Asn Ile Ile Leu Val Leu Glu Asn Phe Arg Leu Gln Gln
    50                  55                  60
```

```
Thr Tyr Thr Asp Ser Phe Gly Leu Tyr Phe His Glu Ala Val Ser Leu
 65                  70                  75                  80

Ala Ser Asp Gly Ala Ile Asp Gln Val Leu Asp Arg Ile Leu Ala Lys
                 85                  90                  95

Tyr Arg His Leu Ala Asp Gln Val Asp Phe Ile Leu Cys Glu Gly Ser
            100                 105                 110

Asp Tyr Leu Gly Glu Glu Ser Ala Phe Glu Phe Asp Leu Asn Thr Thr
        115                 120                 125

Ile Ala Lys Met Leu Asn Cys Pro Ile Leu Leu Gly Asn Ala Met
130                 135                 140

Gly Asn Thr Ile Ala Asp Ser Leu Gln Pro Ile Asp Met Ala Leu Asn
145                 150                 155                 160

Ser Tyr Asp Gln Glu Ser Cys Gln Val Val Gly Val Ile Ile Asn Arg
                165                 170                 175

Val Gln Pro Glu Leu Ala Thr Glu Ile Gln Ala Gln Leu Glu Gln Arg
            180                 185                 190

Tyr Gly Asp Arg Pro Met Val Leu Gly Thr Ile Pro Gln Asp Ile Met
        195                 200                 205

Leu Lys Ser Leu Arg Leu Arg Glu Ile Val Ser Gly Leu Asn Ala Gln
210                 215                 220

Val Leu Ser Gly Ala Asp Leu Leu Asp Asn Leu Val Tyr His His Leu
225                 230                 235                 240

Val Val Ala Met His Ile Ala His Ala Leu His Trp Leu His Glu Lys
                245                 250                 255

Asn Thr Leu Ile Ile Thr Pro Gly Asp Arg Gly Asp Ile Ile Leu Gly
            260                 265                 270

Val Met Gln Ala His Arg Ser Leu Asn Tyr Pro Ser Ile Ala Gly Ile
        275                 280                 285

Leu Leu Thr Ala Asp Tyr His Pro Glu Pro Ala Ile Met Lys Leu Ile
290                 295                 300

Glu Gly Leu Pro Asp Ala Pro Pro Leu Leu Thr Ser Thr His Thr
305                 310                 315                 320

His Glu Thr Ser Ala Arg Leu Glu Thr Leu His Pro Ala Leu Ser Pro
                325                 330                 335

Thr Asp Asn Tyr Lys Ile Arg His Ser Ile Ala Leu Phe Gln Gln Gln
            340                 345                 350

Ile Asp Gly Glu Lys Leu Leu Asn Tyr Leu Lys Thr Ile Arg Ser Lys
        355                 360                 365

Gly Ile Thr Pro Lys Leu Phe Leu Tyr Asn Leu Val Gln Ala Ala Thr
370                 375                 380

Ala Ala Gln Arg His Ile Val Leu Pro Glu Gly Glu Glu Ile Arg Ile
385                 390                 395                 400

Leu Lys Ala Ala Ala Ser Leu Ile Asn His Gly Ile Val Arg Leu Thr
                405                 410                 415

Leu Leu Gly Asn Ile Glu Ala Ile Glu Gln Thr Val Lys Ile Asn His
            420                 425                 430

Ile Asp Leu Asp Leu Ser Lys Val Arg Leu Ile Asn Pro Lys Thr Ser
        435                 440                 445

Pro Asp Arg Glu Arg Tyr Ala Glu Thr Tyr Gln Leu Arg Lys His
450                 455                 460

Lys Gly Val Thr Leu Ala Met Ala Arg Asp Ile Leu Thr Asp Ile Ser
465                 470                 475                 480

Tyr Phe Gly Thr Met Met Val His Leu Gly Glu Ala Asp Gly Met Val
```

```
                            485                 490                 495
Ser Gly Ser Val Asn Thr Thr Gln His Thr Val Arg Pro Ala Leu Gln
                500                 505                 510

Ile Ile Lys Thr Gln Pro Gly Phe Ser Leu Val Ser Ser Val Phe Phe
            515                 520                 525

Met Cys Leu Glu Asp Arg Val Leu Val Tyr Gly Asp Cys Ala Val Asn
        530                 535                 540

Pro Asp Pro Asn Ala Glu Gln Leu Ala Glu Ile Ala Leu Thr Ser Ala
545                 550                 555                 560

Ala Thr Ala Lys Asn Phe Gly Ile Glu Pro Arg Val Ala Leu Leu Ser
                565                 570                 575

Tyr Ser Ser Gly Ser Ser Gly Gln Gly Ala Asp Val Glu Lys Val Arg
                580                 585                 590

Gln Ala Thr Ala Ile Ala Lys Glu Arg Glu Pro Asp Leu Ala Leu Glu
            595                 600                 605

Gly Pro Ile Gln Tyr Asp Ala Ala Val Asp Ser Thr Val Ala Ala Gln
        610                 615                 620

Lys Met Pro Gly Ser Ala Val Ala Gly Lys Ala Thr Val Phe Ile Phe
625                 630                 635                 640

Pro Asp Leu Asn Thr Gly Asn Asn Thr Tyr Lys Ala Val Gln Arg Glu
                645                 650                 655

Thr Lys Ala Ile Ala Ile Gly Pro Ile Leu Gln Gly Leu Asn Lys Pro
            660                 665                 670

Val Asn Asp Leu Ser Arg Gly Cys Leu Val Glu Asp Ile Ile Asn Thr
        675                 680                 685

Val Val Ile Thr Ala Leu Gln Val Lys
    690                 695

<210> SEQ ID NO 31
<211> LENGTH: 21
<212> TYPE: DNA
<213> ORGANISM: Artificial Sequence
<220> FEATURE:
<223> OTHER INFORMATION: #pta-1fw

<400> SEQUENCE: 31
gccattgtgg gggtgggtca g                                          21

<210> SEQ ID NO 32
<211> LENGTH: 22
<212> TYPE: DNA
<213> ORGANISM: Artificial Sequence
<220> FEATURE:
<223> OTHER INFORMATION: #pta-2rv

<400> SEQUENCE: 32
cagtttatgc cccgctaccg gg                                         22

<210> SEQ ID NO 33
<211> LENGTH: 3654
<212> TYPE: DNA
<213> ORGANISM: Artificial Sequence
<220> FEATURE:
<223> OTHER INFORMATION: insert of plasmid pUC-pta-Cm

<400> SEQUENCE: 33
ttggccaaaa aacaaggttt actgggtttt accgctgatg ttttactgga aaatcgagcc    60
atgttgcatc tatttgagaa gatgaacttt cgcatggaac gacgtatgag cgaagggggtt   120 tacgaattaa aaatgttttt tagttgagcc gtcttctttc tgctaattta ttgaaggaat   180
```

```
ttttgatgct ggcgttagta attttaccgc ttcttagatt tattaaaatc tcgtcataaa    240
actttactga ctagcggttt attttctggc taaaagcgct atcacttaag taggtggaat    300
tggcagattt gtagtagttg atacttaact ttttagggaa tatcgctgtg ggaaaaatcg    360
agatcatttt cccagaaaaa tcattgctgg atacgttgag gttatttaaa ttatgacgag    420 ttcccttttat ttaagcacca ccgaagcccg cagcggtaaa tctctagtag tattgggcat    480
tttagactta attctcaaaa aaaccacccg tattgcctat tttcgtccca ttattcaaga    540
cccagttaat ggcaaacatg ataacaacat tattctggtg ctggaaaatt ttcgtctcca    600
acaaacctat accgattcct ttggtttgta tttccatgaa gcggtgagtt tagcctccga    660
tggagctatt gatcaggtat tagaccgaat tttggctaaa tatcgccatt tggcagatca    720
agtagatttt attctctgtg aaggctcaga ctatttgggg gaggaatcgg cttttgaatt    780
tgatctcaac accacgatcg ccaagatgtt gaactgcccc attttgctgt tgggcaatgc    840
catgggcaac accattgccg atagtttgca acccatcgat tttccatggc agctgagaat    900
attgtaggag atcttctaga aagatcctgt gacggaagtt aacttcgcag aataaataaa    960
tcctggtgtc cctgttgata ccgggaagcc ctgggccaac ttttggcgaa aatgagacgt   1020
tgatcggcac gtaagaggtt ccaactttca ccataatgaa ataagatcac taccgggcgt   1080 atttttgag ttatcgagat tttcaggagc taaggaagct aaaatggaga aaaaaatcac   1140
tggatatacc accgttgata tatcccaatg gcatcgtaaa gaacattttg aggcatttca   1200
gtcagttgct caatgtacct ataaccagac cgttcagctg gatattacgg cctttttaaa   1260
gaccgtaaag aaaaataagc acaagtttta tccggccttt attcacattc ttgcccgcct   1320
gatgaatgct catccggaat tccgtatggc aatgaaagac ggtgagctgg tgatatggga   1380
tagtgttcac ccttgttaca ccgttttcca tgagcaaact gaaacgtttt catcgctctg   1440
gagtgaatac cacgacgatt tccggcagtt tctacacata tattcgcaag atgtggcgtg   1500
ttacggtgaa aacctggcct atttccctaa agggtttatt gagaatatgt ttttcgtctc   1560
agccaatccc tgggtgagtt tcaccagttt tgatttaaac gtggccaata tggacaactt   1620
cttcgccccc gttttcacca tgggcaaata ttatacgcaa ggcgacaagg tgctgatgcc   1680
gctggcgatt caggttcatc atgccgtttg tgatggcttc catgtcggca gaatgcttaa   1740
tgaattacaa cagtactgcg atgagtggca gggcggggcg taatttttt aaggcagtta   1800 ttggtgccct taaacgcctg gttgctacgc ctgaataagt gataataagc ggttgactgg   1860
cagaaattcg atcttgctga aaaactcgag ccatccggaa gatctggcgg ccgctctccc   1920
tatagtgagt cgtattacgc cggatggata tggtgttcag gcacaagtgt taaagcagtt   1980 gatttttattc actatgatga aaaaaacaat gaatggaacc tgctccaagt taaaaataga   2040
gataataccg aaaactcatc gagtagtaag attagagata atacaacaat aaaaaaatgg   2100
tttagaactt actcacagcg tgatgctact aattgggaca attttccaga tgaagtatca   2160
tctaagaatt taaatgaaga agacttcaga gcttttgtta aaaattattt ggcaaaaata   2220
atataattcg gctgcagatt accatcccga accggccatt atgaaactaa ttgaagggct   2280
acccgacgcc cctcccctgt tgctgactag cacccacacc catgaaactt ccgcccgttt   2340
ggaaactctc caccctgccc tgagcccctac ggataattat aaaattcgcc acagtattgc   2400 gctgttttcaa caacaaattg atggggagaa attactcaat taccttaaaa ccatccgcag   2460
taaaggtatt accccccaaac tgtttctcta caatttagtt caagccgcca ccgccgccca   2520
acgacatatt gtcctaccgg aaggggaaga aattcgtatt ctcaaggcgg ccgctagctt   2580
```

```
aattaaccac ggcattgtcc gtttgacttt actcggtaac attgaggcga tcgagcaaac    2640
ggtaaaaatt aatcacattg acttagattt gagcaaagtt cgcctcatta atcctaaaac    2700
tagcccagac cgagagcgct acgccgaaac ctattaccag ctacgtaaac ataagggggt    2760
aaccctggcc atggctcggg atatcctcac cgatatttcc tattttggaa cgatgatggt    2820
gcatttggga gaggccgatg gcatggtttc tggctccgtc aataccaccc aacataccgt    2880
gcgtcctgct ttacaaatta ttaaaaccca gccaggtttt tccttggttt cttcagtctt    2940
ttttatgtgt ttagaagacc gagttttggt ctatggagat tgtgctgtta atcccgatcc    3000
caatgcagaa cagttagcag aaattgccct tacttctgcg gctacggcca agaattttgg    3060
cattgagccc agggtagctc tattgtccta ttcttccggt tcttctgggc aaggggccga    3120
tgtggaaaaa gtgcggcaag ccacggcgat cgccaaggaa agagagccag atttagcatt    3180
ggaagggccg atccagtatg atgcggcggt ggattccaca gtggcggccc aaaaaatgcc    3240
tgggtcagcg gtggcgggta agcaacggt gtttattttt cccgatttaa ataccggtaa    3300
caatacttac aaggcagtgc aaagagaaac aaaggcgatc gccattggcc ccatttttaca   3360 aggattaaat aaaccagtta atgatctaag tcggggttgt ttagtggagg atattattaa    3420
tacggtggta attacagctt tgcaagttaa ataatttttac tcttaattag ttaaaatgat    3480
cccttgaatt accttgattt tgccctccaa actaccaata gctgggccga aaattggcat    3540
catttaaaat caccaacgtg tccccggacg gagctagcac aaacagaccc ttaccatagg    3600
catagctgac cacttcttgg cttaacacca tggctgccac tgcacctaaa gctt          3654
```

<210> SEQ ID NO 34
<211> LENGTH: 333
<212> TYPE: PRT
<213> ORGANISM: Synechocystis PCC6803

<400> SEQUENCE: 34

```
Met Lys Ile Ala Phe Phe Ser Ser Lys Ala Tyr Asp Arg Gln Phe Phe
1               5                   10                  15

Gln Gln Ala Asn His Pro His Gln Arg Glu Met Val Phe Phe Asp Ala
            20                  25                  30

Gln Leu Asn Leu Asp Thr Ala Ile Leu Ala Glu Asp Cys Pro Val Ile
        35                  40                  45

Cys Leu Phe Val Asn Asp Gln Ala Pro Ala Pro Val Leu Glu Lys Leu
    50                  55                  60

Ala Ala Gln Gly Thr Lys Leu Ile Ala Leu Arg Ser Ala Gly Tyr Asn
65                  70                  75                  80

Asn Val Asp Leu Lys Thr Ala Ala Asp Leu Gly Leu Lys Val His
                85                  90                  95

Val Pro Ser Tyr Ser Pro His Ala Val Ala Glu His Thr Val Gly Leu
            100                 105                 110

Ile Leu Ala Leu Asn Arg Lys Leu Tyr Arg Ala Tyr Asn Arg Val Arg
        115                 120                 125

Asp Asp Asn Phe Ser Leu Glu Gly Leu Leu Gly Phe Asp Leu His Gly
    130                 135                 140

Thr Thr Val Gly Val Ile Gly Thr Gly Lys Ile Gly Leu Ala Phe Ala
145                 150                 155                 160

Gln Ile Met Asn Gly Phe Gly Cys His Leu Leu Gly Tyr Asp Ala Phe
                165                 170                 175

Pro Asn Asp Lys Phe Thr Ala Ile Gly Gln Ala Leu Tyr Val Ser Leu
            180                 185                 190
```

```
Asn Glu Leu Leu Ala His Ser Asp Ile Ile Ser Leu His Cys Pro Leu
            195                 200                 205
Leu Pro Glu Thr His Tyr Leu Ile Asn Thr Asn Thr Ile Ala Gln Met
    210                 215                 220
Lys Pro Gly Val Met Leu Ile Asn Thr Ser Arg Gly His Leu Ile Asp
225                 230                 235                 240
Thr Gln Ala Val Ile Gln Gly Ile Lys Ser His Lys Ile Gly Phe Leu
                245                 250                 255
Gly Ile Asp Val Tyr Glu Glu Glu Glu Leu Phe Phe Thr Asp His
            260                 265                 270
Ser Asp Thr Ile Ile Gln Asp Asp Thr Phe Gln Leu Gln Ser Phe
        275                 280                 285
Pro Asn Val Met Ile Thr Ala His Gln Gly Phe Phe Thr His Asn Ala
    290                 295                 300
Leu Gln Thr Ile Ala Ala Thr Thr Leu Ala Asn Ile Ala Glu Phe Glu
305                 310                 315                 320
Gln Asn Lys Pro Leu Thr Tyr Gln Val Ile Cys Pro His
                325                 330

<210> SEQ ID NO 35
<211> LENGTH: 23
<212> TYPE: DNA
<213> ORGANISM: Artificial Sequence
<220> FEATURE:
<223> OTHER INFORMATION: #ldh-1fw

<400> SEQUENCE: 35
gcgaactacc caacgctgac cgg                                              23

<210> SEQ ID NO 36
<211> LENGTH: 26
<212> TYPE: DNA
<213> ORGANISM: Artificial Sequence
<220> FEATURE:
<223> OTHER INFORMATION: #ldh-2rv

<400> SEQUENCE: 36
gcatcaagtg ttgggggata tccctg                                           26

<210> SEQ ID NO 37
<211> LENGTH: 2246
<212> TYPE: DNA
<213> ORGANISM: Artificial Sequence
<220> FEATURE:
<223> OTHER INFORMATION: sequence of the insert of pBlue-ldh-Gm

<400> SEQUENCE: 37
ggagctccac cgcggtggcg gccgctctag ctaaagggaa gctgaaaatg catcacagcc      60
aaacacagga gttggaggcc aaaccctaca gttgccccag tgtgagtcaa tatctaccgc    120
tacggcaatc gccagagcta ggggagtatt aaataataca aatgcaggaa gaatcagaaa    180 atttcttta agattggaaa aaatacccct gactaaatag tgctctaaga gcctgtttaa     240
caagcccccc tggcccccaa atttggggtg aagctgggtg aaagtacccc attattgggg    300
gatttagggg gcggaataaa actttccaaa cacgttctaa actacttccc ataatcgtca    360
tgaaaatcgc tttttttagc agtaaagcct atgatcgtca attttccaa caagcaaacc     420 acccccatca acgggaaatg gtctttttg atgcccaact caaccttgat accgctattt    480
tagcggagga ttgccccgtt atttgcctct tcgttaatga ccaagctcct gccccggtgc    540
```

```
tagaaaagtt agctgcccag ggcacaaaat taatcgctct gcgcagtgcg ggctataata    600
atgttgacct caaaacagcc gcagatccgt cgacctgcag ccttgctcta gagctcgaat    660
tgacataagc ctgttcggtt cgtaaactgt aatgcaagta gcgtatgcgc tcacgcaact    720
ggtccagaac cttgaccgaa cgcagcggtg gtaacgcgc agtggcggtt ttcatggctt     780
gttatgactg ttttttttgta cagtctatgc ctcgggcatc caagcagcaa gcgcgttacg   840
ccgtgggtcg atgtttgatg ttatggagca gcaacgatgt tacgcagcag caacgatgtt   900
acgcagcagg gcagtcgccc taaaacaaag ttaggtggct caagtatggg catcattcgc   960
acatgtaggc tcggccctga ccaagtcaaa tccatgcggg ctgctcttga tcttttcggt  1020
cgtgagttcg gagacgtagc cacctactcc caacatcagc cggactccga ttacctcggg  1080
aacttgctcc gtagtaagac attcatcgcg cttgctgcct tcgaccaaga agcggttgtt  1140
ggcgctctcg cggcttacgt tctgcccagg tttgagcagc cgcgtagtga gatctatatc  1200
tatgatctcg cagtctccgg cgagcaccgg aggcagggca ttgccaccgc gctcatcaat  1260
ctcctcaagc atgaggccaa cgcgcttggt gcttatgtga tctacgtgca agcagattac  1320
ggtgacgatc ccgcagtggc tctctataca aagttgggca tacggaaaga agtgatgcac  1380
tttgatatcg acccaagtac cgccacctaa caattcgttc aagccgagat cggcttcccg  1440
gccgcggagt tgttcggtaa attgtcacaa cgccgcggcc aattcgagct cggtacccaa  1500
cgctcggttg ccgccgggcg ttttttattc caccggttgg ttccactctc tgttgcgggc  1560
aacttcagca gcacctcggt accctcccg ttgttaatca atgggggctt tgctttagcc   1620
aaaagcttct actttctgta aaaattcctg ggttaattta ataaaagctt ttgaacccgc  1680
cgtattgggc atggaggtaa ccaccggcat aaagctatcc actgccttag ccacattgac  1740
atccatggga atggactgct gaaaaagttg tcccaactaa agataacgtt aaatttttta  1800
gccttttatt accagatatt tttcctaaaa atgaagcaac gatagtatta acggcactac  1860
cttggtgatc gatagtacga taaatcgtag ctgttactag gttttactaa ccggcgactt  1920
ctgccttttg ttgtcgcatc aacttgacga acttctcgaa cagataatcg gcatcatggg  1980
gtccagggct ggcctccggg tggtactgca ccgagaaaaa gggcaattct ttatggcgta  2040
gccccgccac cgttttatcg ttgaggttga aatgggtaat ttccacttct tcggccaggg  2100
aaccttccgt caccgcaaaa ccatggttct ggctggtaat ttccacctgt tgctccaggc  2160
cacagggttg attgagcccct cgatgaccaa atttgagctt aaaggtctcc gctcccaggg  2220
atatcaagct tatcgatacc gtcgac                                        2246
```

<210> SEQ ID NO 38
<211> LENGTH: 24
<212> TYPE: DNA
<213> ORGANISM: Artificial Sequence
<220> FEATURE:
<223> OTHER INFORMATION: petJ-fw-SalI

<400> SEQUENCE: 38
gtcgacggga attgctctgg caac                                           24

<210> SEQ ID NO 39
<211> LENGTH: 25
<212> TYPE: DNA
<213> ORGANISM: Artificial Sequence
<220> FEATURE:
<223> OTHER INFORMATION: petJ-rev-EcoRI

<400> SEQUENCE: 39

```
gaattcatta gttctccttt caagg                                     25
```

<210> SEQ ID NO 40
<211> LENGTH: 3093
<212> TYPE: DNA
<213> ORGANISM: Zymomonas mobilis

<400> SEQUENCE: 40

```
atgaattctt atactgtcgg tacctattta gcggagcggc ttgtccagat tggtctcaag    60
catcacttcg cagtcgcggg cgactacaac ctcgtccttc ttgacaacct gcttttgaac   120
aaaaacatgg agcaggttta ttgctgtaac gaactgaact gcggtttcag tgcagaaggt   180
tatgctcgtg ccaaaggcgc agcagcagcc gtcgttacct acagcgtcgg tgcgctttcc   240
gcatttgatg ctatcggtgg cgcctatgca gaaaaccttc cggttatcct gatctccggt   300
gctccgaaca acaatgatca cgctgctggt cacgtgttgc atcacgctct tggcaaaacc   360
gactatcact atcagttgga aatggccaag aacatcacgg ccgcagctga agcgatttac   420
accccagaag aagctccggc taaaatcgat cacgtgatta aaactgctct tcgtgagaag   480
aagccggttt atctcgaaat cgcttgcaac attgcttcca tgccctgcgc cgctcctgga   540
ccggcaagcg cattgttcaa tgacgaagcc agcgacgaag cttctttgaa tgcagcggtt   600
gaagaaaccc tgaaattcat cgccaaccgc gacaaagttg ccgtcctcgt cggcagcaag   660
ctgcgcgcag ctggtgctga agaagctgct gtcaaatttg ctgatgctct cggtggcgca   720
gttgctacca tggctgctgc aaaaagcttc ttcccagaag aaaacccgca ttacatcggt   780
acctcatggg gtgaagtcag ctatccgggc gttgaaaaga cgatgaaaga agccgatgcg   840
gttatcgctc tggctcctgt cttcaacgac tactccacca ctggttggac ggatattcct   900
gatcctaaga aactggttct cgctgaaccg cgttctgtcg tcgttaacgg cgttcgcttc   960
cccagcgttc atctgaaaga ctatctgacc cgtttggctc agaaagtttc caagaaaacc  1020
ggtgctttgg acttcttcaa atccctcaat gcaggtgaac tgaagaaagc cgctccggct  1080
gatccgagtg ctccgttggt caacgcagaa atcgcccgtc aggtcgaagc tcttctgacc  1140
ccgaacacga cggttattgc tgaaaccggt gactcttggt tcaatgctca gcgcatgaag  1200
ctcccgaacg gtgctcgcgt tgaatatgaa atgcagtggg gtcacatcgg ttggtccgtt  1260
cctgccgcct tcggttatgc cgtcggtgct ccggaacgtc gcaacatcct catggttggt  1320
gatggttcct tccagctgac ggctcaggaa gtcgctcaga tggttcgcct gaaactgccg  1380
gttatcatct tcttgatcaa taactatggt tacaccatcg aagttatgat ccatgatggt  1440
ccgtacaaca acatcaagaa ctgggattat gccggtctga tggaagtgtt caacggtaac  1500
ggtggttatg acagcggtgc tggtaaaggc ctgaaggcta aaccggtgg cgaactggca  1560
gaagctatca aggttgctct ggcaaacacc gacgcccaa ccctgatcga atgcttcatc  1620
ggtcgtgaag actgcactga agaattggtc aaatggggta gcgcgttgc tgccgccaac  1680
agccgtaagc ctgttaacaa gctcctctag ttttttgggga tcaattcgag ctcggtaccc  1740
aaactagtat gtagggtgag gttatagcta tggcttcttc aacttttat attcctttcg  1800
tcaacgaaat gggcgaaggt tcgcttgaaa agcaatcaa ggatcttaac ggcagcggct  1860
ttaaaaatgc gctgatcgtt tctgatgctt tcatgaacaa atccggtgtt gtgaagcagg  1920
ttgctgacct gttgaaagca cagggtatta attctgctgt ttatgatggc gttatgccga  1980
acccgactgt taccgcagtt ctggaaggcc ttagatcct gaaggataac aattcagact  2040
tcgtcatctc cctcggtggt ggttctcccc atgactgcgc caaagccatc gctctggtcg  2100
```

```
caaccaatgg tggtgaagtc aaagactacg aaggtatcga caaatctaag aaacctgccc   2160
tgcctttgat gtcaatcaac acgacggctg gtacggcttc tgaaatgacg cgtttctgca   2220
tcatcactga tgaagtccgt cacgttaaga tggccattgt tgaccgtcac gttaccccga   2280
tggtttccgt caacgatcct ctgttgatgg ttggtatgcc aaaaggcctg accgccgcca   2340
ccggtatgga tgctctgacc cacgcatttg aagcttattc ttcaacggca gctactccga   2400
tcaccgatgc ttgcgccttg aaggctgcgt ccatgatcgc taagaatctg aagaccgctt   2460
gcgacaacgg taaggatatg ccagctcgtg aagctatggc ttatgcccaa ttcctcgctg   2520
gtatggcctt caacaacgct tcgcttggtt atgtccatgc tatggctcac cagttgggcg   2580
gctactacaa cctgccgcat ggtgtctgca acgctgttct gcttccgcat gttctggctt   2640
ataacgcctc tgtcgttgct ggtcgtctga agacgttgg tgttgctatg ggtctcgata   2700
tcgccaatct cggtgataaa gaaggcgcag aagccaccat tcaggctgtt cgcgatctgg   2760
ctgcttccat tggtattcca gcaaatctga ccgagctggg tgctaagaaa gaagatgtgc   2820
cgcttcttgc tgaccacgct ctgaaagatg cttgtgctct gaccaacccg cgtcagggtg   2880
atcagaaaga gttgaagaa ctcttcctga gcgctttcta atttcaaaac aggaaaacgg   2940
ttttccgtcc tgtcttgatt ttcaagcaaa caatgcctcc gatttctaat cggaggcatt   3000 tgttttgtt tattgcaaaa acaaaaaata ttgttacaaa tttttacagg ctattaagcc   3060
taccgtcata aataatttgc catttgggga tcc                                3093
```

<210> SEQ ID NO 41
<211> LENGTH: 569
<212> TYPE: PRT
<213> ORGANISM: Zymomonas mobilis

<400> SEQUENCE: 41

```
Met Asn Ser Tyr Thr Val Gly Thr Tyr Leu Ala Glu Arg Leu Val Gln
1               5                   10                  15

Ile Gly Leu Lys His His Phe Ala Val Ala Gly Asp Tyr Asn Leu Val
            20                  25                  30

Leu Leu Asp Asn Leu Leu Leu Asn Lys Asn Met Glu Gln Val Tyr Cys
        35                  40                  45

Cys Asn Glu Leu Asn Cys Gly Phe Ser Ala Glu Gly Tyr Ala Arg Ala
    50                  55                  60

Lys Gly Ala Ala Ala Val Val Thr Tyr Ser Val Gly Ala Leu Ser
65                  70                  75                  80

Ala Phe Asp Ala Ile Gly Gly Ala Tyr Ala Glu Asn Leu Pro Val Ile
                85                  90                  95

Leu Ile Ser Gly Ala Pro Asn Asn Asn Asp His Ala Ala Gly His Val
            100                 105                 110

Leu His His Ala Leu Gly Lys Thr Asp Tyr His Tyr Gln Leu Glu Met
        115                 120                 125

Ala Lys Asn Ile Thr Ala Ala Ala Glu Ala Ile Tyr Thr Pro Glu Glu
    130                 135                 140

Ala Pro Ala Lys Ile Asp His Val Ile Lys Thr Ala Leu Arg Glu Lys
145                 150                 155                 160

Lys Pro Val Tyr Leu Glu Ile Ala Cys Asn Ile Ala Ser Met Pro Cys
                165                 170                 175

Ala Ala Pro Gly Pro Ala Ser Ala Leu Phe Asn Asp Glu Ala Ser Asp
            180                 185                 190

Glu Ala Ser Leu Asn Ala Ala Val Glu Glu Thr Leu Lys Phe Ile Ala
        195                 200                 205
```

Asn Arg Asp Lys Val Ala Val Leu Val Gly Ser Lys Leu Arg Ala Ala
    210                 215                 220

Gly Ala Glu Glu Ala Ala Val Lys Phe Ala Asp Ala Leu Gly Gly Ala
225                 230                 235                 240

Val Ala Thr Met Ala Ala Lys Ser Phe Phe Pro Glu Glu Asn Pro
                245                 250                 255

His Tyr Ile Gly Thr Ser Trp Gly Val Ser Tyr Pro Gly Val Glu
                260                 265                 270

Lys Thr Met Lys Glu Ala Asp Ala Val Ile Ala Leu Ala Pro Val Phe
                275                 280                 285

Asn Asp Tyr Ser Thr Thr Gly Trp Thr Asp Ile Pro Asp Pro Lys Lys
    290                 295                 300

Leu Val Leu Ala Glu Pro Arg Ser Val Val Asn Gly Val Arg Phe
305                 310                 315                 320

Pro Ser Val His Leu Lys Asp Tyr Leu Thr Arg Leu Ala Gln Lys Val
                325                 330                 335

Ser Lys Lys Thr Gly Ala Leu Asp Phe Phe Lys Ser Leu Asn Ala Gly
                340                 345                 350

Glu Leu Lys Lys Ala Ala Pro Ala Asp Pro Ser Ala Pro Leu Val Asn
                355                 360                 365

Ala Glu Ile Ala Arg Gln Val Glu Ala Leu Leu Thr Pro Asn Thr Thr
    370                 375                 380

Val Ile Ala Glu Thr Gly Asp Ser Trp Phe Asn Ala Gln Arg Met Lys
385                 390                 395                 400

Leu Pro Asn Gly Ala Arg Val Glu Tyr Glu Met Gln Trp Gly His Ile
                405                 410                 415

Gly Trp Ser Val Pro Ala Ala Phe Gly Tyr Ala Val Gly Ala Pro Glu
                420                 425                 430

Arg Arg Asn Ile Leu Met Val Gly Asp Gly Ser Phe Gln Leu Thr Ala
    435                 440                 445

Gln Glu Val Ala Gln Met Val Arg Leu Lys Leu Pro Val Ile Ile Phe
450                 455                 460

Leu Ile Asn Asn Tyr Gly Tyr Thr Ile Glu Val Met Ile His Asp Gly
465                 470                 475                 480

Pro Tyr Asn Asn Ile Lys Asn Trp Asp Tyr Ala Gly Leu Met Glu Val
                485                 490                 495

Phe Asn Gly Asn Gly Gly Tyr Asp Ser Gly Ala Gly Lys Gly Leu Lys
                500                 505                 510

Ala Lys Thr Gly Gly Glu Leu Ala Glu Ala Ile Lys Val Ala Leu Ala
    515                 520                 525

Asn Thr Asp Gly Pro Thr Leu Ile Glu Cys Phe Ile Gly Arg Glu Asp
    530                 535                 540

Cys Thr Glu Glu Leu Val Lys Trp Gly Lys Arg Val Ala Ala Ala Asn
545                 550                 555                 560

Ser Arg Lys Pro Val Asn Lys Leu Leu
                565

<210> SEQ ID NO 42
<211> LENGTH: 383
<212> TYPE: PRT
<213> ORGANISM: Zymomonas mobilis

<400> SEQUENCE: 42

Met Ala Ser Ser Thr Phe Tyr Ile Pro Phe Val Asn Glu Met Gly Glu
1               5                   10                  15

```
Gly Ser Leu Glu Lys Ala Ile Lys Asp Leu Asn Gly Ser Gly Phe Lys
            20                  25                  30

Asn Ala Leu Ile Val Ser Asp Ala Phe Met Asn Lys Ser Gly Val Val
            35                  40                  45

Lys Gln Val Ala Asp Leu Leu Lys Ala Gln Gly Ile Asn Ser Ala Val
        50                  55                  60

Tyr Asp Gly Val Met Pro Asn Pro Thr Val Thr Ala Val Leu Glu Gly
65                  70                  75                  80

Leu Lys Ile Leu Lys Asp Asn Asn Ser Asp Phe Val Ile Ser Leu Gly
                85                  90                  95

Gly Gly Ser Pro His Asp Cys Ala Lys Ala Ile Ala Leu Val Ala Thr
            100                 105                 110

Asn Gly Gly Glu Val Lys Asp Tyr Glu Gly Ile Asp Lys Ser Lys Lys
        115                 120                 125

Pro Ala Leu Pro Leu Met Ser Ile Asn Thr Thr Ala Gly Thr Ala Ser
130                 135                 140

Glu Met Thr Arg Phe Cys Ile Ile Thr Asp Glu Val Arg His Val Lys
145                 150                 155                 160

Met Ala Ile Val Asp Arg His Val Thr Pro Met Val Ser Val Asn Asp
                165                 170                 175

Pro Leu Leu Met Val Gly Met Pro Lys Gly Leu Thr Ala Ala Thr Gly
            180                 185                 190

Met Asp Ala Leu Thr His Ala Phe Glu Ala Tyr Ser Ser Thr Ala Ala
        195                 200                 205

Thr Pro Ile Thr Asp Ala Cys Ala Leu Lys Ala Ala Ser Met Ile Ala
210                 215                 220

Lys Asn Leu Lys Thr Ala Cys Asp Asn Gly Lys Asp Met Pro Ala Arg
225                 230                 235                 240

Glu Ala Met Ala Tyr Ala Gln Phe Leu Ala Gly Met Ala Phe Asn Asn
                245                 250                 255

Ala Ser Leu Gly Tyr Val His Ala Met Ala His Gln Leu Gly Gly Tyr
            260                 265                 270

Tyr Asn Leu Pro His Gly Val Cys Asn Ala Val Leu Leu Pro His Val
        275                 280                 285

Leu Ala Tyr Asn Ala Ser Val Val Ala Gly Arg Leu Lys Asp Val Gly
290                 295                 300

Val Ala Met Gly Leu Asp Ile Ala Asn Leu Gly Asp Lys Glu Gly Ala
305                 310                 315                 320

Glu Ala Thr Ile Gln Ala Val Arg Asp Leu Ala Ala Ser Ile Gly Ile
                325                 330                 335

Pro Ala Asn Leu Thr Glu Leu Gly Ala Lys Lys Glu Asp Val Pro Leu
            340                 345                 350

Leu Ala Asp His Ala Leu Lys Asp Ala Cys Ala Leu Thr Asn Pro Arg
        355                 360                 365

Gln Gly Asp Gln Lys Glu Val Glu Glu Leu Phe Leu Ser Ala Phe
370                 375                 380

<210> SEQ ID NO 43
<211> LENGTH: 294
<212> TYPE: DNA
<213> ORGANISM: Synechocystis PCC6803

<400> SEQUENCE: 43
gtcgacggga attgctctgg caactgatta atccactgag caacagccca agacacgcaa        60
```

```
acaaaaacca acgtcttggc gatcgccatc ggcaccatga aaccatcgta aaagctgggg      120
aaagaataaa aaacagtggt tcaggaattg cattgccatg gccacttcac aaacctagcc      180 aatttttagct tgaccgcaac tttgacagat tgtcttttga ctttgcctgg accgcctccc    240
ataatacctt cgcgtcttga agactttatc cttgaaagga gaactaatga attc            294

<210> SEQ ID NO 44
<211> LENGTH: 10502
<212> TYPE: DNA
<213> ORGANISM: Artificial Sequence
<220> FEATURE:
<223> OTHER INFORMATION: pVZ321b vector

<400> SEQUENCE: 44
gtcgacgaat tctgccatt catccgctta ttatcactta ttcaggcgta gcaccaggcg       60
tttaagggca ccaataactg ccttaaaaaa attacgcccc gccctgccac tcatcgcagt    120
actgttgtaa ttcattaagc attctgccga catggaagcc atcacagacg gcatgatgaa    180
cctgaatcgc cagcggcatc agcaccttgt cgccttgcgt ataatatttg cccatggtga    240
aaacgggggc gaagaagttg tccatattgg ccacgtttaa atcaaaactg gtgaaactca    300
cccagggatt ggctgagacg aaaaacatat tctcaataaa ccctttaggg aaataggcca    360
ggttttcacc gtaacacgcc acatcttgcg aatatatgtg tagaaactgc cggaaatcgt    420
cgtggtattc actccagagc gatgaaaacg tttcagtttg ctcatggaaa acggtgtaac    480
aagggtgaac actatcccat atcaccagct caccgtcttt cattgccata cggaattccg    540
gatgagcatt catcaggcgg gcaagaatgt gaataaaggc cggataaaac ttgtgcttat    600
ttttctttac ggtctttaaa aaggccgtaa tatccagctg aacggtctgg ttataggtac    660
attgagcaac tgactgaaat gcctcaaaat gttcttacg atgccattgg gatatatcaa    720
cggtggtata tccagtgatt tttttctcca ttttagcttc cttagctcct gaaaatctcg    780
ataactcaaa aaatacgccc ggtagtgatc ttatttcatt atggtgaaag ttggaacctc    840
ttacgtgccg atcaacgtct catttttcgcc aaaagttggc ccagggcttc ccggtatcaa    900
cagggacacc aggattttatt tattctgcga agtgatcttc cgtcacaggt atttattcga    960
agacgaaagg gcctcgtgat acgcctattt ttataggtta atgtcatgat aataatggtt   1020
tcttagacgt caggtggcac ttttcgggga atgtgcgcg gaaccctat ttgttttattt   1080 ttctaaatac attcaaatat gtatccgctc atgagacaat aaccctgata aatgcttcaa   1140
taatattgaa aaaggaagag tatgagtatt caacatttcc gtgtcgccct tattcccttt   1200
tttgcggcat tttgccttcc tgttttttgct cacccagaaa cgctggtgaa agtaaaagat   1260
gctgaagatc agttgggtgc acgagtgggt tacatcgaac tggatctcaa cagcggtaag   1320
atccttgaga gttttcgccc cgaagaacgt tttccaatga tgagcacttt taaagttctg   1380
ctatgtggcg cggtattatc ccgtgttgac gccgggcaag agcaactcgg tcgccgcata   1440
cactattctc agaatgactt ggttgagtac tcaccagtca cagaaaagca tcttacggat   1500
ggcatgacag taagagaatt atgcagtgct gccataacca tgagtgataa cactgcggcc   1560
aacttacttc tgacaacgat cggaggaccg aaggagctaa ccgcttttt gcacaacatg   1620 ggggatcatg taactcgcct tgatcgttgg gaaccggagc tgaatgaagc cataccaaac   1680
gacgagcgtg acaccacgat gcctgcagga gcagaagagc atacatctgg aagcaaagcc   1740
aggaaagcgg cctatggagc tgtgcggcag cgctcagtag gcaattttttc aaaatattgt   1800 taagcctttt ctgagcatgg tatttttcat ggtattacca attagcagga aaataagcca   1860
```

```
ttgaatataa aagataaaaa tgtcttgttt acaatagagt ggggggggtc agcctgccgc    1920
cttgggccgg gtgatgtcgt acttgcccgc cgcgaactcg gttaccgtcc agcccagcgc    1980
gaccagctcc ggcaacgcct cgcgcacccg ctggcggcgc ttgcgcatgg tcgaaccact    2040
ggcctctgac ggccagacat agccgcacaa ggtatctatg gaagccttgc cggttttgcc    2100
ggggtcgatc cagccacaca gccgctggtg cagcaggcgg gcggtttcgc tgtccagcgc    2160
ccgcacctcg tccatgctga tgcgcacatg ctggccgcca cccatgacgg cctgcgcgat    2220 caagggttc agggccacgt acaggcgccc gtccgcctcg tcgctggcgt actccgacag    2280
cagccgaaac ccctgccgct tgcggccatt ctgggcgatg atggataccT tccaaaggcg    2340
ctcgatgcag tcctgtatgt gcttgagcgc cccaccacta tcgacctctg ccccgatttc    2400
cttTgccagc gcccgatagc tacctttgac cacatggcat tcagcggtga cggcctccca    2460
cttgggttcc aggaacagcc ggagctgccg tccgccttcg gtcttgggtt ccgggccaag    2520
cactaggcca ttaggcccag ccatggccac cagcccttgc aggatgcgca gatcatcagc    2580
gcccagcggc tccgggccgc tgaactcgat ccgcttgccg tcgccgtagt catacgtcac    2640
gtccagcttg ctgcgcttgc gctcgccccg cttgagggca cggaacaggc cggggggccag    2700 acagtgcgcc gggtcgtgcc ggacgtggct gaggctgtgc ttgttcttag gcttcaccac    2760
ggggcacccc cttgctcttg cgctgcctct ccagcacggc gggcttgagc accccgccgt    2820
catgccgcct gaaccaccga tcagcgaacg gtgcgccata gttggccttg ctcacaccga    2880
agcggacgaa gaaccggcgc tggtcgtcgt ccacaccccA ttcctcggcc tcggcgctgg    2940
tcatgctcga caggtaggac tgccagcgga tgttatcgac cagtaccgag ctgccccggc    3000
tggcctgctg ctggtcgcct gcgcccatca tggccgcgcc cttgctggca tggtgcagga    3060
acacgataga gcacccggta tcggcggcga tggcctccat gcgaccgatg acctgggcca    3120
tggggccgct ggcgtttttct tcctcgatgt ggaaccggcg cagcgtgtcc agcaccatca    3180
ggcggcggcc ctcggcggcg cgcttgaggc cgtcgaacca ctccggggcc atgatgttgg    3240
gcaggctgcc gatcagcggc tggatcagca ggccgtcagc cacggcttgc cgttcctcgg    3300
cgctgaggtg cgccccaagg gcgtgcaggc ggtgatgaat ggcggtgggc gggtcttcgg    3360
cgggcaggta gatcaccggg ccggtgggca gttcgcccac ctccagcaga tccggcccgc    3420
ctgcaatctg tgcggccagt tgcagggcca gcatggattt accggcacca ccgggcgaca    3480
ccagcgcccc gaccgtaccg gccaccatgt tgggcaaaac gtagtccagc ggtggcggcg    3540
ctgctgcgaa cgcctccaga atattgatag gcttatgggt agccattgat tgcctccttt    3600
gcaggcagtt ggtggttagg cgctggcggg gtcactaccc ccgccctgcg ccgctctgag    3660
ttcttccagg cactcgcgca gcgcctcgta ttcgtcgtcg gtcagccaga acttgcgctg    3720
acgcatccct ttggccttca tgcgctcggc atatcgcgct tggcgtacag cgtcagggct    3780
ggccagcagg tcgccggtct gcttgtcctt ttggtctttc atatcagtca ccgagaaact    3840
tgccggggcc gaaaggcttg tcttcgcgga acaaggacaa ggtgcagccg tcaaggttaa    3900
ggctggccat atcagcgact gaaaagcggc cagcctcggc cttgtttgac gtataaccaa    3960
agccaccggg caaccaatag cccttgtcac ttttgatcag gtagaccgac cctgaagcgc    4020
ttttttcgta ttccataaaa cccccttctg tgcgtgagta ctcatagtat aacaggcgtg    4080
agtaccaacg caagcactac atgctgaaat ctggcccgcc cctgtccatg cctcgctggc    4140
ggggtgccgg tgcccgtgcc agctcggccc gcgcaagctg gacgctgggc agacccatga    4200
ccttgctgac ggtgcgctcg atgtaatccg cttcgtggcc gggcttgcgc tctgccagcg    4260
```

```
ctgggctggc ctcggccatg gccttgccga tttcctcggc actgcggccc cggctggcca      4320
gcttctgcgc ggcgataaag tcgcacttgc tgaggtcatc accgaagcgc ttgaccagcc      4380
cggccatctc gctgcggtac tcgtccagcg ccgtgcgccg gtggcggcta agctgccgct      4440
cgggcagttc gaggctggcc agcctgcggg ccttctcctg ctgccgctgg gcctgctcga      4500
tctgctggcc agcctgctgc accagcgccg ggccagcggt ggcggtcttg cccttggatt      4560
cacgcagcag cacccacggc tgataaccgg cgcgggtggt gtgcttgtcc ttgcggttgg      4620
tgaagcccgc caagcggcca tagtggcggc tgtcggcgct ggccgggtcg gcgtcgtact      4680
cgctggccag cgtccgggca atctgccccc gaagttcacc gcctgcggcg tcggccacct      4740
tgacccatgc ctgatagttc ttcgggctgg tttccactac cagggcaggc tcccggccct      4800
cggctttcat gtcatccagg tcaaactcgc tgaggtcgtc caccagcacc agaccatgcc      4860
gctcctgctc ggcgggcctg atatacacgt cattgccctg ggcattcatc cgcttgagcc      4920
atggcgtgtt ctggagcact tcggcggctg accattcccg gttcatcatc tggccggtgg      4980
tggcgtccct gacgccgata tcgaagcgct cacagcccat ggccttgagc tgtcggccta      5040
tggcctgcaa agtcctgtcg ttcttcatcg ggccaccaag cgcagccaga tcgagccgtc      5100
ctcggttgtc agtggcgtca ggtcgagcaa gagcaacgat gcgatcagca gcaccaccgt      5160
aggcatcatg gaagccagca tcacggttag ccatagcttc cagtgccacc ccgcgacgc      5220 gctccgggcg ctctgcgcgg cgctgctcac ctcggcggct acctcccgca actctttggc      5280
cagctccacc catgccgccc ctgtctggcg ctgggctttc agccactccg ccgcctgcgc      5340
ctcgctggcc tgctgggtct ggctcatgac ctgccgggct tcgtcggcca gtgtcgccat      5400
gctctgggcc agcggttcga tctgctccgc taactcgttg atgcctctgg atttcttcac      5460
tctgtcgatt gcgttcatgg tctattgcct cccggtattc ctgtaagtcg atgatctggg      5520
cgttggcggt gtcgatgttc agggccacgt ctgcccggtc ggtgcggatg ccccggcctt      5580
ccatctccac cacgttcggc cccaggtgaa caccgggcag gcgctcgatg ccctgcgcct      5640
caagtgttct gtggtcaatg cgggcgtcgt ggccagcccg ctctaatgcc cggttggcat      5700
ggtcggccca tgcctcgcgg gtctgctcaa gccatgcctt gggcttgagc gcttcggtct      5760
tctgtgcccc gccttctcc ggggtcttgc cgttgtaccg cttgaaccac tgagcggcgg      5820
gccgctcgat gccgtcattg atccgctcgg agatcatcag gtggcagtgc gggttctcgc      5880
cgccaccggc atggatggcc agcgtatacg gcaggcgctc ggcaccggtc aggtgctggg      5940
cgaactcgga cgccagcgcc ttctgctggt cgagggtcag ctcgaccggc agggcaaatt      6000
cgacctcctt gaacagccgc ccattggcgc gttcatacag gtcggcagca tcccagtagt      6060
cggcgggccg ctcgacgaac tccggcatgt gcccggattc ggcgtgcaag acttcatcca      6120
tgtcgcgggc atacttgcct tcgcgctgga tgtagtcggc cttggccctg gccgattggc      6180
cgcccgacct gctgccggtt ttcgccgtaa ggtgataaat cgccatgctg cctcgctgtt      6240
gcttttgctt ttcggctcca tgcaatggcc ctcggagagc gcaccgcccg aagggtggcc      6300
gttaggccaa tttctcgaag agaaaccggt aagtgcgccc tccctacaa agtagggtcg      6360 ggattgccgc cgctgtgcct ccatgatagc ctacgagaca gcacattaac aatgggtgt       6420 caagatggtt aaggggagca acaaggcggc ggatcggctg ccaagctcg aagaacaacg       6480 agcgcgaatc aatgccgaaa ttcagcgggt gcgggcaagg gaacagcagc aagagcgcaa      6540
gaacgaaaca aggcgcaagg tgctggtggg ggccatgatt ttggccaagg tgaacagcag      6600
cgagtggccg gaggatcggc tcatggcggc aatggatgcg taccttgaac gcgaccacga      6660
```

```
ccgcgccttg ttcggtctgc cgccacgcca gaaggatgag ccgggctgaa tgatcgaccg    6720
agacaggccc tgcggggctg cacacgcgcc cccacccttc gggtaggggg aaaggccgct    6780
aaagcggcta aaagcgctcc agcgtatttc tgcggggttt ggtgtggggt ttagcgggct    6840
ttgcccgcct ttccccctgc cgcgcagcgg tggggcggtg tgtagcctag cgcagcgaat    6900
agaccagcta tccggcctct ggccgggcat attgggcaag ggcagcagcg ccccacaagg    6960
gcgctgataa ccgcgcctag tggattattc ttagataatc atggatggat ttttccaaca    7020
ccccgccagc ccccgcccct gctgggtttg caggtttggg ggcgtgacag ttattgcagg    7080
ggttcgtgac agttattgca gggggcgtg acagttattg caggggttcg tgacagttag     7140
tacgggagtg acgggcactg gctggcaatg tctagcaacg gcaggcattt cggctgaggg    7200
taaaagaact ttccgctaag cgatagactg tatgtaaaca cagtattgca aggacgcgga    7260
acatgcctca tgtggcggcc aggacggcca gccgggatcg ggatactggt cgttaccaga    7320
gccaccgacc cgagcaaacc cttctctatc agatcgttga cgagtattac ccggcattcg    7380
ctgcgcttat ggcagagcag ggaaaggaat tgccgggcta tgtgcaacgg gaatttgaag    7440
aatttctcca atgcgggcgg ctggagcatg gctttctacg ggttcgctgc gagtcttgcc    7500
acgccgagca cctggtcgct ttcagctgta atccgggcag cgcaacggaa cattcatcag    7560
tgtaaaaatg gaatcaataa agccctgcgc agcgcgcagg gtcagcctga atacgcgttt    7620
aatgaccagc acagtcgtga tggcaaggtc agaatagcgc tgaggtctgc ctcgtgaaga    7680
aggtgttgct gactcatacc aggcctgaat cgccccatca tccagccaga agtgaggga    7740 gccacggttg atgagagctt tgttgtaggt ggaccagttg gtgattttga acttttgctt    7800
tgccacggaa cggtctgcgt tgtcgggaag atgcgtgatc tgatccttca actcagcaaa    7860
agttcgattt attcaacaaa gccacgttgt gtctcaaaat ctctgatgtt acattgcaca    7920
agataaaaat atatcatcat gaacaataaa actgtctgct tacataaaca gtaatacaag    7980
gggtgttatg agccatattc aacgggaaac gtcttgctcg aggccgcgat taaattccaa    8040
catggatgct gatttatatg ggtataaatg gctcgcgat aatgtcgggc aatcaggtgc     8100
gacaatctat cgattgtatg ggaagcccga tgcgccagag ttgtttctga acatggcaa     8160 aggtagcgtt gccaatgatg ttacagatga gatggtcaga ctaaactggc tgacggaatt    8220
tatgcctctt ccgaccatca agcattttat ccgtactcct gatgatgcat ggttactcac    8280
cactgcgatc cccgggaaaa cagcattcca ggtattagaa gaatatcctg attcaggtga    8340
aaatattgtt gatgcgctgg cagtgttcct gcgccggttg cattcgattc ctgtttgtaa    8400
ttgtcctttt aacagcgatc gcgtatttcg tctcgctcag gcgcaatcac gaatgaataa    8460
cggtttggtt gatgcgagtg attttgatga cgagcgtaat ggctggcctg ttgaacaagt    8520
ctggaaagaa atgcataagc ttttgccatt ctcaccggat tcagtcgtca ctcatggtga    8580
tttctcactt gataaccttaa ttttgacga ggggaaatta ataggttgta ttgatgttgg    8640
acgagtcgga atcgcagacc gataccagga tcttgccatc ctatggaact gcctcggtga    8700
gttttctcct tcattacaga aacggctttt tcaaaaatat ggtattgata atcctgatat    8760
gaataaattg cagtttcatt tgatgctcga tgagtttttc taatcagaat tggttaattg    8820
gttgtaacac tggcagagca ttacgctgac ttgacgggac ggcggctttg ttgaataaat    8880
cgaacttttg ctgagttgaa ggatcagatc acgcatcttc ccgacaacgc agaccgttcc    8940
gtggcaaagc aaaagttcaa aatcaccaac tggtccacct acaacaaagc tctcatcaac    9000
cgtggctccc tcactttctg gctggatgat ggggcgattc aggcctggta tgagtcagca    9060
```

-continued

| | |
|---|---|
| acaccttctt cacgaggcag acctcagcgc tattctgacc ttgccatcac gactgtgctg | 9120 |
| gtcattaaac gcgtattcag gctgaccctg cgcgctgcgc agggctttat tgattccatt | 9180 |
| tttacactga tgaatgttcc gttgcgctgc ccggattaca gatcctctag atctagaaga | 9240 |
| acagcaaggc cgccaatgcc tgacgatgcg tggagaccga aaccttgcgc tcgttcgcca | 9300 |
| gccaggacag aaatgcctcg acttcgctgc tgcccaaggt tgccgggtga cgcacaccgt | 9360 |
| ggaaacggat gaaggcacga acccagtgga cataagcctg ttcggttcgt aagctgtaat | 9420 |
| gcaagtagcg tatgcgctca cgcaactggt ccagaacctt gaccgaacgc agcggtggta | 9480 |
| acggcgcagt ggcggttttc atggcttgtt atgactgttt ttttgggta cagtctatgc | 9540 |
| ctcgggcatc caagcagcaa gcgcgttacg ccgtgggtcg atgtttgatg ttatggagca | 9600 |
| gcaacgatgt tacgcagcag ggcagtcgcc ctaaaacaaa gttaaacatc atgagggaag | 9660 |
| cggtgatcgc cgaagtatcg actcaactat cagaggtagt tggcgtcatc gagcgccatc | 9720 |
| tcgaaccgac gttgctggcc gtacatttgt acggctccgc agtggatggc ggcctgaagc | 9780 |
| cacacagtga tattgatttg ctggttacgg tgaccgtaag gcttgatgaa caacgcggc | 9840 |
| gagctttgat caacgacctt ttggaaactt cggcttcccc tggagagagc gagattctcc | 9900 |
| gcgctgtaga agtcaccatt gttgtgcacg acgacatcat tccgtggcgt tatccagcta | 9960 |
| agcgcgaact gcaatttgga gaatggcagc gcaatgacat tcttgcaggt atcttcgagc | 10020 |
| cagccacgat cgacattgat ctggctatct tgctgacaaa agcaagagaa catagcgttg | 10080 |
| ccttggtagg tccagcggcg gaggaactct tgatccggt tcctgaacag gatctatttg | 10140 |
| aggcgctaaa tgaaacctta acgctatgga actcgccgcc cgactgggct ggcgatgagc | 10200 |
| gaaatgtagt gcttacgttg tcccgcattt ggtacagcgc agtaaccggc aaaatcgcgc | 10260 |
| cgaaggatgt cgctgccgac tgggcaatgg agcgcctgcc ggcccagtat cagcccgtca | 10320 |
| tacttgaagc tagacaggct tatcttggac aagaagaaga tcgcttggcc tcgcgcgcag | 10380 |
| atcagttgga agaatttgtc cactacgtga aaggcgagat caccaaggta gtcggcaaat | 10440 |
| aatgtctaac aattcgttca agccgacgcc gcttcgcggc gcggcttaac tcaagctcta | 10500 |
| ga | 10502 |

<210> SEQ ID NO 45
<211> LENGTH: 28
<212> TYPE: DNA
<213> ORGANISM: Artificial Sequence
<220> FEATURE:
<223> OTHER INFORMATION: SynADH-SacI-fw

<400> SEQUENCE: 45

| | |
|---|---|
| atgagctctc tggataaaac taataaac | 28 |

<210> SEQ ID NO 46
<211> LENGTH: 27
<212> TYPE: DNA
<213> ORGANISM: Artificial Sequence
<220> FEATURE:
<223> OTHER INFORMATION: SynADH-PstI-rev

<400> SEQUENCE: 46

| | |
|---|---|
| atctgcagat cgaatgtcaa gctttcc | 27 |

<210> SEQ ID NO 47
<211> LENGTH: 1144
<212> TYPE: DNA
<213> ORGANISM: Synechocystis PCC6803

-continued

```
<400> SEQUENCE: 47
gagctctctg gataaaacta ataaactcta ttacccatga ttaaagccta cgctgccctg      60
gaagccaacg gaaaactcca acccttttgaa tacgaccccg gtgccctggg tgctaatgag    120
gtggagattg aggtgcagta ttgtggggtg tgccacagtg atttgtccat gattaataac    180
gaatggggca tttccaatta ccccctagtg ccgggtcatg aggtggtggg tactgtggcc    240
gccatgggcg aaggggtgaa ccatgttgag gtggggggatt tagtggggct gggttggcat    300
tcgggctact gcatgacctg ccatagttgt ttatctggct accacaacct tgtgccacg     360 gcggaatcga ccattgtggg ccactacggt ggctttggcg atcgggttcg ggccaaggga    420
gtcagcgtgg tgaaattacc taaaggcatt gacctagcca gtgccgggcc ccttttctgt    480
ggaggaatta ccgttttcag tcctatggtg gaactgagtt aaagcccac tgcaaaagtg     540 gcagtgatcg gcattggggg cttgggccat ttagcggtgc aatttctccg ggcctggggc    600
tgtgaagtga ctgcctttac ctccagtgcc aggaagcaaa cggaagtgtt ggaattgggc    660
gctcaccaca tactagattc caccaatcca gaggcgatcg ccagtgcgga aggcaaattt    720
gactatatta tctccactgt gaacctgaag cttgactgga acttatacat cagcaccctg    780
gcgccccagg acatttccca ctttgttggg gtggtgttgg agcctttgga tctaaatctt    840
tttccccttt tgatgggaca cgctccgtt tctgcctccc cagtgggtag tcccgccacc     900
attgccacca tgttggactt tgctgtgcgc catgacatta aacccgtggt ggaacaattt    960
agctttgatc agatcaacga ggcgatcgcc catctagaaa gcggcaaagc ccattatcgg   1020
gtagtgctca gccatagtaa aaattagctc tgcaaaggtt gcttctgggt ccgtggaatg   1080
gtcaaacgga gtcgatctca gttttgatac gctctatctg gaaagcttga cattcgatct   1140
gcag                                                                 1144

<210> SEQ ID NO 48
<211> LENGTH: 336
<212> TYPE: PRT
<213> ORGANISM: Synechocystis PCC6803

<400> SEQUENCE: 48

Met Ile Lys Ala Tyr Ala Ala Leu Glu Ala Asn Gly Lys Leu Gln Pro
1               5                   10                  15

Phe Glu Tyr Asp Pro Gly Ala Leu Gly Ala Asn Glu Val Glu Ile Glu
                20                  25                  30

Val Gln Tyr Cys Gly Val Cys His Ser Asp Leu Ser Met Ile Asn Asn
            35                  40                  45

Glu Trp Gly Ile Ser Asn Tyr Pro Leu Val Pro Gly His Glu Val Val
        50                  55                  60

Gly Thr Val Ala Ala Met Gly Glu Gly Val Asn His Val Glu Val Gly
65                  70                  75                  80

Asp Leu Val Gly Leu Gly Trp His Ser Gly Tyr Cys Met Thr Cys His
                85                  90                  95

Ser Cys Leu Ser Gly Tyr His Asn Leu Cys Ala Thr Ala Glu Ser Thr
            100                 105                 110

Ile Val Gly His Tyr Gly Gly Phe Gly Asp Arg Val Arg Ala Lys Gly
        115                 120                 125

Val Ser Val Val Lys Leu Pro Lys Gly Ile Asp Leu Ala Ser Ala Gly
    130                 135                 140

Pro Leu Phe Cys Gly Gly Ile Thr Val Phe Ser Pro Met Val Glu Leu
145                 150                 155                 160
```

```
Ser Leu Lys Pro Thr Ala Lys Val Ala Val Ile Gly Ile Gly Gly Leu
            165                 170                 175
Gly His Leu Ala Val Gln Phe Leu Arg Ala Trp Gly Cys Glu Val Thr
        180                 185                 190
Ala Phe Thr Ser Ser Ala Arg Lys Gln Thr Glu Val Leu Glu Leu Gly
        195                 200                 205
Ala His His Ile Leu Asp Ser Thr Asn Pro Glu Ala Ile Ala Ser Ala
        210                 215                 220
Glu Gly Lys Phe Asp Tyr Ile Ile Ser Thr Val Asn Leu Lys Leu Asp
225                 230                 235                 240
Trp Asn Leu Tyr Ile Ser Thr Leu Ala Pro Gln Gly His Phe His Phe
                245                 250                 255
Val Gly Val Val Leu Glu Pro Leu Asp Leu Asn Leu Phe Pro Leu Leu
            260                 265                 270
Met Gly Gln Arg Ser Val Ser Ala Ser Pro Val Gly Ser Pro Ala Thr
        275                 280                 285
Ile Ala Thr Met Leu Asp Phe Ala Val Arg His Asp Ile Lys Pro Val
        290                 295                 300
Val Glu Gln Phe Ser Phe Asp Gln Ile Asn Glu Ala Ile Ala His Leu
305                 310                 315                 320
Glu Ser Gly Lys Ala His Tyr Arg Val Val Leu Ser His Ser Lys Asn
                325                 330                 335

<210> SEQ ID NO 49
<211> LENGTH: 24
<212> TYPE: DNA
<213> ORGANISM: Artificial Sequence
<220> FEATURE:
<223> OTHER INFORMATION: Gm-ClaI-fw

<400> SEQUENCE: 49
atcgatgctc gaattgacat aagc                                          24

<210> SEQ ID NO 50
<211> LENGTH: 24
<212> TYPE: DNA
<213> ORGANISM: Artificial Sequence
<220> FEATURE:
<223> OTHER INFORMATION: Gm-XhoI-rev

<400> SEQUENCE: 50
actcgagacc gagctcgaat tggc                                          24

<210> SEQ ID NO 51
<211> LENGTH: 2747
<212> TYPE: DNA
<213> ORGANISM: Thermosynechococcus sp.

<400> SEQUENCE: 51
atgaattccc caaccttgac cagtgacccc cccgttcaaa gccttgccga tctggaaggg    60
ctgattgagc gcgtccaacg ggcgcagagt cagtacgccc aatttaccca agagcaagtg   120
gatcacattt tccacgaagc agccatggcg gccaaccaag cccggattcc cctggccaaa   180
caagccgtag ccgaaacggg catgggggtt gtcgaagata agttattaa aaatcacttt    240 gcttcggaat acatctacaa caagtacaaa atgagaaaa cctgcggcgt cattgaggat    300
gaccccatct ttggtatcca aaaaattgct gaaccggtgg ggatcattgc cggtgtggtg    360
ccggtcacga accccacttc aacgaccatc tttaaggcac tgattgccct gaagactcgc    420
aatggcatta tcttttcgcc ccaccccccgg gcaaaggcct gtacggttgc agcggccaag    480
```

```
gtagtgttgg atgcagcggt cgctgccggc gcaccccccg atattattgg ctggattgat    540
gagccgacga ttgaactctc ccaagccctg atgcagcacc cgcagatcaa gctgattttg    600
gccacggggg gaccaggtat ggtcaaggca gcctattcct ctggccatcc ggcgatcggg    660
gtcggggccg ggaataccCC cgtgctcatt gatgccacag ccgatattcc cacggcagtg    720
agttcgattc tcctcagtaa ggcctttgac aatggcatga tctgtgcctc ggagcaggca    780
gtgattgttg tggatgagat ttatgacgca cttaaagctg agtttcaacg gcgaggggcc    840
taccttctct cccctgagga acggcagcag gtggcacaac tactgctgaa ggatggtcgc    900
ctcaatgccg ccattgttgg tcaatcggcc gccaccattg ccgcaatggc caatatccaa    960
gtaccgccag aaacccgggt actcattggc gaggtgagtg aagtggggcc gcaggagcca   1020
ttttcctatg agaaactctg tccggtattg gcgttatatc gggcacccca gttccataaa   1080
ggggtggaga ttgcggccca gttggtgaat tttgggggca aggggcatac atctgtgctc   1140
tataccgatc cccgcaatca agatgatatt gcctatttca ataccgcat gcaaacggcg    1200
cggggttctga ttaacacccc ttcttcccag ggggcaattg gcgatctcta caacttcaag   1260
ttagatccgt cgctaaccct tggttgtggt acgtggggcg gcaacgtcac atcggaaaat   1320
gttggtcccc gtcacttgct gaatattaaa acggtgagcg atcgccggga aaatatgctt   1380
tggtttcggt tgccgcccaa gatctacttc aaacccggct gtttgcccat tgccctgcgg   1440
gagctggcgg ggaaaaaacg cgccttcctc gtgacggata accccctctt tgacttgggg   1500
atcactgaac cgattgtcca taccctcgaa gaactgggca tcaagtatga catcttccat   1560
gaagtggaac cagatccaac cctcagtacc gttaaccgcg gtctagggtt gctgcggcaa   1620
tatcagccgg atgtgattgt tgctgtgggg ggtggctcac ctatgatgc agccaaggtg   1680
atgtggctgt tgtatgagca tccggaggtg gagtttgacg gccttgcgat gcgcttcatg   1740
gatattcgca agcgggtgta tcaactgcct cccttgggtc aaaaggcaat cctggtggct   1800
attcccacca cctcggggac gggttcagag gtgaccccct ttgccgtggt taccgacgat   1860
cgcgtgggga ttaaatatcc cttggcagac tatgcccta cgccaacgat ggcgattgtg   1920
gatcccgact tggtgctgca catgcccaag aaactgacgg cctacggtgg cattgatgcg   1980
ctgacccatg ccctggaggc ctatgtgtcg gtgctctcga cggagtttac ggagggactg   2040
gctctagagg ccattaaact gctctttacc tacctacccc gtgccatcg cttgggggcg   2100
gcggatccgg aggcacggga gaaggtccac tatgcggcga cgatcgctgg catggccttt   2160
gcgaatgcct tcttgggggt ctgccactcg ctggcccaca aactaggctc caccttccac   2220
gtgccccacg gcttggcgaa tgcactcatg atttcccatg tgattcgcta caatgccacg   2280
gatgctcccc tgaagcaggc gatttttccg cagtacaagt atccccaagc gaaggagcgc   2340
tatgcccaaa ttgccgactt cctcgaattg ggggcacga ccccagagga aaaagtggag   2400
cgtctcattg cggcaattga ggatttgaaa gcccaattag aaattcccgc cacgattaag   2460
gaggccctca acagtgagga tcaagcgttc tatgagcagg tggagagcat ggccgaactg   2520
gcctttgacg atcagtgcac gggggccaat ccccgctatc cgctgatcca agacctcaag   2580
gagttgtata tcctggccta tatgggggtgt cggcgggatg cggcagccta ctatggggg   2640
gaggcaacgg ggagttgatg tggcgttata ttcccccctt tgcagctcca gcgaaggtgc   2700
aaatggcggt ggattcctgg ctctggcagc ggagcgatcg cctgcag               2747

<210> SEQ ID NO 52
<211> LENGTH: 885
```

-continued

```
<212> TYPE: PRT
<213> ORGANISM: Thermosynechococcus sp.

<400> SEQUENCE: 52

Met Asn Ser Pro Thr Leu Thr Ser Asp Pro Val Gln Ser Leu Ala
1               5                   10                  15

Asp Leu Glu Gly Leu Ile Glu Arg Val Gln Arg Ala Gln Ser Gln Tyr
            20                  25                  30

Ala Gln Phe Thr Gln Glu Gln Val Asp His Ile Phe His Glu Ala Ala
            35                  40                  45

Met Ala Ala Asn Gln Ala Arg Ile Pro Leu Ala Lys Gln Ala Val Ala
50                  55                  60

Glu Thr Gly Met Gly Val Val Glu Asp Lys Val Ile Lys Asn His Phe
65                  70                  75                  80

Ala Ser Glu Tyr Ile Tyr Asn Lys Tyr Lys Asn Glu Lys Thr Cys Gly
                85                  90                  95

Val Ile Glu Asp Asp Pro Ile Phe Gly Ile Gln Lys Ile Ala Glu Pro
            100                 105                 110

Val Gly Ile Ile Ala Gly Val Val Pro Val Thr Asn Pro Thr Ser Thr
            115                 120                 125

Thr Ile Phe Lys Ala Leu Ile Ala Leu Lys Thr Arg Asn Gly Ile Ile
130                 135                 140

Phe Ser Pro His Pro Arg Ala Lys Ala Cys Thr Val Ala Ala Ala Lys
145                 150                 155                 160

Val Val Leu Asp Ala Ala Val Ala Ala Gly Ala Pro Pro Asp Ile Ile
                165                 170                 175

Gly Trp Ile Asp Glu Pro Thr Ile Glu Leu Ser Gln Ala Leu Met Gln
            180                 185                 190

His Pro Gln Ile Lys Leu Ile Leu Ala Thr Gly Gly Pro Gly Met Val
            195                 200                 205

Lys Ala Ala Tyr Ser Ser Gly His Pro Ala Ile Gly Val Gly Ala Gly
210                 215                 220

Asn Thr Pro Val Leu Ile Asp Ala Thr Ala Asp Ile Pro Thr Ala Val
225                 230                 235                 240

Ser Ser Ile Leu Leu Ser Lys Ala Phe Asp Asn Gly Met Ile Cys Ala
                245                 250                 255

Ser Glu Gln Ala Val Ile Val Val Asp Glu Ile Tyr Asp Ala Leu Lys
            260                 265                 270

Ala Glu Phe Gln Arg Arg Gly Ala Tyr Leu Leu Ser Pro Glu Glu Arg
            275                 280                 285

Gln Gln Val Ala Gln Leu Leu Leu Lys Asp Gly Arg Leu Asn Ala Ala
290                 295                 300

Ile Val Gly Gln Ser Ala Ala Thr Ile Ala Ala Met Ala Asn Ile Gln
305                 310                 315                 320

Val Pro Pro Glu Thr Arg Val Leu Ile Gly Val Ser Glu Val Gly
                325                 330                 335

Pro Gln Glu Pro Phe Ser Tyr Glu Lys Leu Cys Pro Val Leu Ala Leu
            340                 345                 350

Tyr Arg Ala Pro Gln Phe His Lys Gly Val Glu Ile Ala Ala Gln Leu
            355                 360                 365

Val Asn Phe Gly Gly Lys Gly His Thr Ser Val Leu Tyr Thr Asp Pro
370                 375                 380

Arg Asn Gln Asp Asp Ile Ala Tyr Phe Lys Tyr Arg Met Gln Thr Ala
385                 390                 395                 400
```

-continued

```
Arg Val Leu Ile Asn Thr Pro Ser Ser Gln Gly Ala Ile Gly Asp Leu
                405                 410                 415
Tyr Asn Phe Lys Leu Asp Pro Ser Leu Thr Leu Gly Cys Gly Thr Trp
            420                 425                 430
Gly Gly Asn Val Thr Ser Glu Asn Val Gly Pro Arg His Leu Leu Asn
        435                 440                 445
Ile Lys Thr Val Ser Asp Arg Arg Glu Asn Met Leu Trp Phe Arg Val
    450                 455                 460
Pro Pro Lys Ile Tyr Phe Lys Pro Gly Cys Leu Pro Ile Ala Leu Arg
465                 470                 475                 480
Glu Leu Ala Gly Lys Lys Arg Ala Phe Leu Val Thr Asp Lys Pro Leu
                485                 490                 495
Phe Asp Leu Gly Ile Thr Glu Pro Ile Val His Thr Leu Glu Glu Leu
            500                 505                 510
Gly Ile Lys Tyr Asp Ile Phe His Glu Val Glu Pro Asp Pro Thr Leu
        515                 520                 525
Ser Thr Val Asn Arg Gly Leu Gly Leu Leu Arg Gln Tyr Gln Pro Asp
    530                 535                 540
Val Ile Val Ala Val Gly Gly Gly Ser Pro Met Asp Ala Ala Lys Val
545                 550                 555                 560
Met Trp Leu Leu Tyr Glu His Pro Glu Val Glu Phe Asp Gly Leu Ala
                565                 570                 575
Met Arg Phe Met Asp Ile Arg Lys Arg Val Tyr Gln Leu Pro Pro Leu
            580                 585                 590
Gly Gln Lys Ala Ile Leu Val Ala Ile Pro Thr Thr Ser Gly Thr Gly
        595                 600                 605
Ser Glu Val Thr Pro Phe Ala Val Val Thr Asp Asp Arg Val Gly Ile
    610                 615                 620
Lys Tyr Pro Leu Ala Asp Tyr Ala Leu Thr Pro Thr Met Ala Ile Val
625                 630                 635                 640
Asp Pro Asp Leu Val Leu His Met Pro Lys Lys Leu Thr Ala Tyr Gly
                645                 650                 655
Gly Ile Asp Ala Leu Thr His Ala Leu Glu Ala Tyr Val Ser Val Leu
            660                 665                 670
Ser Thr Glu Phe Thr Glu Gly Leu Ala Leu Glu Ala Ile Lys Leu Leu
        675                 680                 685
Phe Thr Tyr Leu Pro Arg Ala Tyr Arg Leu Gly Ala Ala Asp Pro Glu
    690                 695                 700
Ala Arg Glu Lys Val His Tyr Ala Ala Thr Ile Ala Gly Met Ala Phe
705                 710                 715                 720
Ala Asn Ala Phe Leu Gly Val Cys His Ser Leu Ala His Lys Leu Gly
                725                 730                 735
Ser Thr Phe His Val Pro His Gly Leu Ala Asn Ala Leu Met Ile Ser
            740                 745                 750
His Val Ile Arg Tyr Asn Ala Thr Asp Ala Pro Leu Lys Gln Ala Ile
        755                 760                 765
Phe Pro Gln Tyr Lys Tyr Pro Gln Ala Lys Glu Arg Tyr Ala Gln Ile
    770                 775                 780
Ala Asp Phe Leu Glu Leu Gly Gly Thr Thr Pro Glu Glu Lys Val Glu
785                 790                 795                 800
Arg Leu Ile Ala Ala Ile Glu Asp Leu Lys Ala Gln Leu Glu Ile Pro
                805                 810                 815
Ala Thr Ile Lys Glu Ala Leu Asn Ser Glu Asp Gln Ala Phe Tyr Glu
            820                 825                 830
```

```
Gln Val Glu Ser Met Ala Glu Leu Ala Phe Asp Asp Gln Cys Thr Gly
        835                 840                 845

Ala Asn Pro Arg Tyr Pro Leu Ile Gln Asp Leu Lys Glu Leu Tyr Ile
    850                 855                 860

Leu Ala Tyr Met Gly Cys Arg Arg Asp Ala Ala Tyr Tyr Gly Gly
865                 870                 875                 880

Glu Ala Thr Gly Ser
            885

<210> SEQ ID NO 53
<211> LENGTH: 294
<212> TYPE: DNA
<213> ORGANISM: Synechocystis PCC6803

<400> SEQUENCE: 53
gtcgacggga attgctctgg caactgatta atccactgag caacagccca agacacgcaa       60
acaaaaacca acgtcttggc gatcgccatc ggcaccatga aaccatcgta aaagctgggg      120
aaagaataaa aaacagtggt tcaggaattg cattgccatg ccacttcac aaacctagcc       180 aattttagct tgaccgcaac tttgacagat tgtcttttga ctttgcctgg accgcctccc      240 ataataccctt cgcgtcttga agactttatc cttgaaagga gaactaatga attc           294

<210> SEQ ID NO 54
<211> LENGTH: 608
<212> TYPE: DNA
<213> ORGANISM: Synechocystis PCC6803

<400> SEQUENCE: 54
gtcgactgtc cgaccaattg gttcatcaaa gttgatttac ccacattggg acggccgaca       60
atggccacaa agccggaacg aaaacccgca ggagcctggg gaatagttgc aatggttgcg      120
gtggtgttgg gaatatccat gaaaaaaatc aagcctaaaa attccttagt ttatggaggg      180
tcaagcggaa aaacgttaaa aactccactg agttaatcaa ccagaggaaa aagtcaagga      240
ggtaaactat ccgcctggaa aacggcttgc cagcttgaca aaaaaatatg ttgggttaac      300
cccactgtgc cattcggtaa tccttcatct tggcccttgt ggaatcccctt aatgattcgt     360 catcatggtg atattgattt tttgggtatc ttttttagcta tgcggctgta ggagcgtggt     420
attggtttcg gcggtaacgc cccagcctag aaccacaaaa attattattt attcccgaac      480
cttgtcacca tttgcggcgt ctaaaggccc actcgttagg acacggtgta aaaaaaattg      540
acgactgcac taccctattc tccaccatca atgacttagt ctaagacatt tttgggaaag      600
atgaattc                                                              608

<210> SEQ ID NO 55
<211> LENGTH: 581
<212> TYPE: DNA
<213> ORGANISM: Synechocystis PCC6803

<400> SEQUENCE: 55
gtcgacgctg atgtgacggt taagggaggc ggaattaaac tgggtaagga cgtaaatttt       60
aacgatttct gagttgatgc aattactgac gggaatatcg atgaggcgat actttccggc      120
caagggaact gcgggtttgg ctctgagttt ggttaaagga tagaggcggg tcccggcccc      180
accgcccagg ataatcgcta agacacgttt cacaagcaga cctctcgatt gccaacaaca      240
cacttcgaag tcaagtttag aaccgagggg gacatctgga aagggaatct ggacggaaat      300
tccggctaac cagcgggttt taatgcccca agcaagaatg gcgatcgccg ttgggattcg      360
```

```
gagctgagtt gtcagatcac tgtgggggta cggataaccg aaatggcaaa ggtcggaaac    420
tgccgctgag taaactgtcc ctggcttcgt atgatgatgg ggttaccccc attgctgggg    480
cgctgggcaa atctggggag ctgactaggt tcctggaagt tttgctaatc cactaaattt    540
cctaacaatc ctaaacatta aatctaaaga cctatgaatt c                        581

<210> SEQ ID NO 56
<211> LENGTH: 590
<212> TYPE: DNA
<213> ORGANISM: Synechocystis PCC6803

<400> SEQUENCE: 56
gtcgacccaa caacattagt ccgtcctccc gttggcgatc gcgctgtttg gctctgaccc     60
atcgccgctg atattgccaa gcttggcagt agggcacaag tccgaacgat aataaacgac    120
aggaaggatt ggccatggcg ctacaaagga acggaatca  aactaaagtt caaagttggc    180
agaaattaag aaacgtaaag agatgcaaag gaaagtcaaa atcacctgac cgattaggtc    240
ttattcaata catagtgcta atctgaagat agtcttagga gttaattatt taccaccaca    300
attttctgga aaactttacc tctaccctag ggatgattaa aagtaaacta gagaataaca    360
aggttgggtt tataattcat caccaagctc aaatttatgg tgttttttca atgatccatg    420
cttttgatat ctttagcaga aaggcatttt aagtaatgat tccacctcac tgtttctcgg    480
aaaaattgcc caatctaact tagttttttat aacttaagtt tagatctgcg gaaaaccaac    540
cattgctcat tttttattaa tttttacgaag ggagaattta gtatgaattc                590

<210> SEQ ID NO 57
<211> LENGTH: 572
<212> TYPE: DNA
<213> ORGANISM: Synechocystis PCC6803

<400> SEQUENCE: 57
gtcgacagaa tccttgccca gatgcaggcc ttctggcgat cgccatggtg agcaacgatt     60
gcggctttag cgttccagtg gatatttgct gggggttaat gaaacattgt ggcggaaccc    120
agggacaatg tgaccaaaaa attcagggat atcaataagt attaggtata tggatcataa    180
ttgtatgccc gactattgct taaactgact gaccactgac cttaagagta atggcgtgca    240
aggcccagtg atcaatttca ttattttttca ttatttcatc tccattgtcc ctgaaaatca    300
gttgtgtcgc ccctctacac agcccagaac tatggtaaag gcgcacgaaa aaccgccagg    360
taaactcttc tcaaccccca aaacgccctc tgtttaccca tggaaaaaac gacaattaca    420
agaaagtaaa acttatgtca tctataagct tcgtgtatat taacttcctg ttacaaagct    480
ttacaaaact ctcattaatc ctttagacta agtttagtca gttccaatct gaacatcgac    540
aaatacataa ggaattataa ccaaatgaat tc                                    572

<210> SEQ ID NO 58
<211> LENGTH: 273
<212> TYPE: DNA
<213> ORGANISM: Synechocystis PCC6803

<400> SEQUENCE: 58
gtcgacatca ggaattgtaa ttagaaagtc caaaaattgt aatttaaaaa acagtcaatg     60
gagagcattg ccataagtaa aggcatcccc tgcgtgataa gattaccttc agaaaacaga    120
tagttgctgg gttatcgcag attttttctcg caaccaaata actgtaaata ataactgtct    180
ctggggcgac ggtaggcttt atattgccaa atttcgcccg tgggagaaag ctaggctatt    240
```

```
caatgtttat ggaggactga cctagatgaa ttc                                    273

<210> SEQ ID NO 59
<211> LENGTH: 408
<212> TYPE: DNA
<213> ORGANISM: Synechocystis PCC6803

<400> SEQUENCE: 59
gtcgacattt cttaaaatta agctgttat  agcaacaaca ttgattaatt tctatctaat        60
ttttgacggt gcccattgct atcagttgta agttgatgaa aatgctgtaa attttgtaa       120 caaagttcaa ctttgtcttg acttttgtaa gtctttgcaa aatctaggag ctagaactgg      180
tcagggctgg ggcaattttt aattattgtt acgcaggtct tgcctagggg gggggaggcc      240
gtattatctt ctagtgatgt tgctgaaaaa cgcctatctg tgcaaggttt aacatcgtta      300
ttatgaagcg aaaactaatt cccttttta cgcttcctct attacactat tctgcatagg       360
aaacccttaa tagttcattg tcgagcgagg agaaccctgc atgaattc                   408

<210> SEQ ID NO 60
<211> LENGTH: 614
<212> TYPE: DNA
<213> ORGANISM: Synechocystis PCC6803

<400> SEQUENCE: 60
gtcgacaaaa aaactgcaaa aattatcctg actgaatgga agtcaaaaag actggaaaat       60
gggatcaaac aacaagaaaa aatcaattta ccctgcccat ggcaatagtt ttaaggttaa      120
caaaaaaaat agaatttacc gcaatcgacg ggtaaatttc cagaggatac ccccaactcc      180
agaagcagaa atcttgccag aaaagctttt tctgttacta tacttaacaa gtaactactt      240
tttccatagt ccaggggcgg cttttccaaaa accagagatt ggtggcttgc cgctgctgtt      300
ctcctctgga gtaaggggaa aagtaatta  gtgttacggc atttttactga cgggttaagt     360 aatctttaac aaagatttat gagccgttac cgtaattgcc cccacagggg aacgcgatgt      420
ctgtggactc gcccaggacg taatcaattt ttctgtaccg atattagcgg tgaaaagttt      480
tattcaacgt actaaaatgc cccggcggga attaacttgg gttccgggaa gtcgggtgca      540
ttagccgtac tagactaacc caatagttac tttgtttgat tcttgatttt ggagaccgct      600
gattttatga attc                                                        614

<210> SEQ ID NO 61
<211> LENGTH: 367
<212> TYPE: DNA
<213> ORGANISM: Synechocystis PCC6803

<400> SEQUENCE: 61
gtcgacggaa acaagctca gaatgctgcg gggagaaggg caactcccca ccagccccaa        60
atttttgctg gcgataaata ttttcggtt taattgttca caaagctttt tgaatttgag      120
tttatagaaa tttattggct ggtaatgctt ttttgccccc ctgcaggact tcattgatcc      180
ttgcctatac catcaatatc attggtcaat aatgatgatg attgactaaa acatgtttaa      240
caaaatttaa cgcatatgct aaatgcgtaa actgcatatg ccttggctga gtgtaattta      300
cgttacaaat tttaacgaaa cgggaaccct atattgatct ctatctggct tgaagcgttg      360
tgaattc                                                                367

<210> SEQ ID NO 62
<211> LENGTH: 359
```

-continued

```
<212> TYPE: DNA
<213> ORGANISM: Synechocystis PCC6803

<400> SEQUENCE: 62
gtcgactttt ttgctgaggt actgagtaca cagctaataa aattgggcaa tctccgcgcc      60
tctatgactt gaaggagagt gtaggggtat aggggaaaga tatcttttat ctacatcaca     120
taaataaaaa atttaatttg tcgctctggc tgcatatatt gatgtatttt tagccataag     180 tttttttagtg ccatgtaatt atagtgattt ttagcgatcg cagagcattt ttccctggat    240
ttatcgcgat ctcaaaaaaa atttgcccga agtatgacag attgtcatat ttggtgtcga     300
ttttatttaa aatgaaataa gaaaaataaa actacaggtt aggagaacgc catgaattc      359

<210> SEQ ID NO 63
<211> LENGTH: 273
<212> TYPE: DNA
<213> ORGANISM: Synechocystis PCC6803

<400> SEQUENCE: 63
gtcgacacaa cctaagactt ccttccaaaa atccataggg cggtggaagc ttagctattt      60
ttaccatttt gttttgccac tcaaatattt acttaaggtg aggtaaaaac tcatcttttt     120
tttactaaaa attgcggcta gaaatgtaat ttcggcaatc cccccacctt ctttcctgaa     180
aaccgaatct aacctggaag gggaaatttt aagatagaac cattcaaggg taatcaattc    240
cttccacaca tcaggagtta acattatgaa ttc                                  273

<210> SEQ ID NO 64
<211> LENGTH: 342
<212> TYPE: DNA
<213> ORGANISM: Synechocystis PCC6803

<400> SEQUENCE: 64
gtcgacgcac ttctggtcag tttatagcaa aaatgctggg gaaaggaaga caactaggga     60 aaagaacag gacatcaaat ggtcattccc cagaccctgg cgtctttgcc agagtaatct      120
ccctggcgcg gatgttacac aaatgtaacg aaaaatattt tccctctcag aatttaggca    180
aagtgcccaa acccatccta ggcaagcaat tcgtccacca acaaaaagct cttttggtca    240
acagacttga caaaaatctt aacaatacgt tacatttatt tacataaggt tacaaaataa    300
aaacctcaaa tacccaatca aggagatcaa cactatgaat tc                       342

<210> SEQ ID NO 65
<211> LENGTH: 273
<212> TYPE: DNA
<213> ORGANISM: Synechocystis PCC6803

<400> SEQUENCE: 65
gtcgacaaga ttagccctta gcttacaaga aaggggcttt ggggcctagt tgaatggcac      60
aaattttcct tccctgactg ttttttgcgcc attgtctagc tcaaagtcag cctccggcat   120
cctctagaaa gacttccatc ccctggttga gcaagggtaa accccaccac tgcattggga    180
aaaccctcct tcctagctcc ggattccacc ccctaaaatt gatttggtag tccttacaca    240
cccaatagcc aatatagaaa attttatgaa ttc                                  273
```

METABOLICALLY ENHANCED PHOTOAUTOTROPHIC ETHANOL PRODUCING HOST CELLS, METHOD FOR PRODUCING THE HOST CELLS, CONSTRUCTS FOR THE TRANSFORMATION OF THE HOST CELLS, AND METHOD OF PRODUCING ETHANOL USING THE HOST CELLS

CROSS REFERENCE TO RELATED APPLICATIONS

This is a continuation application of PCT Application No. PCT/EP2009/060526, filed Aug. 13, 2009, which is incorporated by reference herein in its entirety.

REFERENCE TO SEQUENCE LISTING

The instant application contains a Sequence Listing which has been submitted via EFS-Web and is incorporated herein by reference in its entirety. Said ASCII copy is named "SequenceListing", was created on Feb. 13, 2012, lists 65 sequences and is 127 KB in size.

FIELD OF THE INVENTION

This invention is related to the field of ethanol production using metabolically enhanced cells. The PCT patent application PCT/EP2009/000892 filed on Feb. 9, 2009 is incorporated by reference herein in its entirety.

BACKGROUND OF THE INVENTION

Without new methods for biofuel production, the world will continue to depend on fossil fuels for transportation. Accelerating demand, diminishing reserves and geopolitical risks have in recent years dramatically driven up the cost of fossil fuels. Use of fossil fuels also releases carbon dioxide into the atmosphere, which may cause deleterious environmental effects. Many governments have prescribed a reduction in the use of fossil fuels in favor of alternative renewable biofuels in an effort to stem the release of carbon dioxide from transportation vehicles.

Ethanol can be used as renewable biofuel but methods do not currently exist that can produce ethanol in sufficient quantities and at a price that could lead to a widespread adoption of ethanol as a major alternative to fossil fuels in the worldwide transportation fuel market.

The patent and scientific literature cited herein establishes the knowledge that is available to those with skill in the art. The issued U.S. and foreign patents, published U.S. and foreign patent applications, and all other publications cited herein are hereby incorporated by reference. Additionally, all amino acid and nucleic acid sequences with the respective amino acid sequences encoded thereby identified by database accession number are hereby incorporated by reference.

Aspects of the invention utilize techniques and methods common to the fields of molecular biology, microbiology and cell culture. Useful laboratory references for these types of methodologies are readily available to those skilled in the art. See, for example, Molecular Cloning: A Laboratory Manual (Third Edition), Sambrook, J., et al. (2001) Cold Spring Harbor Laboratory Press; Current Protocols in Microbiology (2007) Edited by Coico, R, et al., John Wiley and Sons, Inc.; The Molecular Biology of Cyanobacteria (1994) Donald Bryant (Ed.), Springer Netherlands; Handbook Of Microalgal Culture: Biotechnology And Applied Phycology (2003) Richmond, A.; (ed.), Blackwell Publishing; and "The cyanobacteria, molecular Biology, Genomics and Evolution", Edited by Antonia Herrero and Enrique Flores, Caister Academic Press, Norfolk, UK, 2008.

Definitions

As used herein, the term "metabolically enhanced" refers to any change in the endogenous genome of a wild type cell or to the addition of non-endogenous genetic code to a wild type cell, e.g., the introduction of a heterologous gene. More specifically, such changes are made by the hand of man through the use of recombinant DNA technology or mutagenesis. The changes can involve protein coding sequences or non-protein coding sequences such as regulatory sequences as promoters or enhancers.

The term "nucleic acid" is intended to include nucleic acid molecules, e.g., polynucleotides which include an open reading frame encoding a polypeptide, and can further include non-coding regulatory sequences, and introns in the case of eukaryotic organisms for example algae. In addition, the terms are intended to include one or more genes that map to a functional locus. In addition, the terms are intended to include a specific gene for a selected purpose. The gene can be endogenous to the host cell or can be recombinantly introduced into the host cell.

The phrase "operably linked" means that the nucleotide sequence of the nucleic acid molecule or gene of interest is linked to the regulatory sequence(s) in a manner which allows for expression (e.g., enhanced, increased, constitutive, basal, attenuated, decreased or repressed expression) of the nucleotide sequence and expression of a gene product encoded by the nucleotide sequence (e.g., when the recombinant nucleic acid molecule is included in a recombinant vector, as defined herein, and is introduced into a microorganism).

The term "recombinant nucleic acid molecule" includes a nucleic acid molecule (e.g., a DNA molecule) that has been altered, enhanced or engineered such that it differs in nucleotide sequence from the native or natural nucleic acid molecule from which the recombinant nucleic acid molecule was derived (e.g., by addition, deletion or substitution of one or more nucleotides). Advantageously, a recombinant nucleic acid molecule (e.g., a recombinant DNA molecule) includes an isolated nucleic acid molecule or gene of the present invention The terms "host cell" and "recombinant host cell" are intended to include a cell suitable for metabolic manipulation, e.g., which can incorporate heterologous polynucleotide sequences, e.g., which can be transformed. The cell can be a prokaryotic or a eukaryotic cell. The term is intended to include progeny of the cell originally transformed. In particular embodiments, the cell is a prokaryotic cell, e.g., a cyanobacterial cell. Particularly, the term recombinant host cell is intended to include a cell that has already been selected or engineered to have certain desirable properties and suitable for further enhancement using the compositions and methods of the invention.

The term "promoter" is intended to include a polynucleotide segment that can transcriptionally control a gene-of-interest, e.g., a pyruvate decarboxylate gene that it does or does not transciptionally control in nature. In one embodiment, the transcriptional control of a promoter results in an increase in expression of the gene-of-interest. In another embodiment, a promoter is placed 5' to the gene-of-interest. A promoter can be used to replace the natural promoter, or can be used in addition to the natural promoter. A promoter can be endogenous with regard to the host cell in which it is used or it can be a heterologous polynucleotide sequence introduced into the host cell, e.g., exogenous with regard to the host cell in which it is used. Promoters of the invention may also be inducible, meaning that certain exogenous stimuli (e.g., nutrient starvation, heat shock, mechanical stress, light exposure, etc.) will induce the promoter leading to the transcription of the gene behind.

The term "about" is used herein to mean approximately, in the region of, roughly, or around. When the term "about" is used in conjunction with a numerical value/range, it modifies that value/range by extending the boundaries above and below the numerical value(s) set forth. In general, the term "about" is used herein to modify a numerical value(s) above and below the stated value(s) by a variance of 20%.

As used herein, the phrase "increased activity" refers to any metabolic enhancement resulting in increased levels of enzyme in a host cell. As known to one of ordinary skill in the art, enzyme activity may be increased by increasing the level of transcription, either by modifying promoter function or by increasing gene copy number, increasing translational efficiency of an enzyme messenger RNA, e.g., by modifying ribosomal binding, or by increasing the stability of an enzyme protein, at which the half-life of the protein is increased, will lead to more enzyme molecules in the cell. All of these represent non-limiting examples of increasing the activity of an enzyme. (mRNA Processing and Metabolism: Methods and Protocols, Edited by Daniel R. Schoenberg, Humana Press Inc., Totowa, N.J.; 2004; ISBN 1-59259-750-5; Prokaryotic Gene Expression (1999) Baumberg, S., Oxford University Press, ISBN 0199636036; The Structure and Function of Plastids (2006) Wise, R. R. and Hoober J. K., Springer, ISBN 140203217X; The Biomedical Engineering Handbook (2000) Bronzino, J. D., Springer, ISBN 354066808X).

In one aspect the invention also provides nucleic acids, which are at least 60%, 70%, 80% 90% or 95% identical to the promoter nucleic acids disclosed therein and to the nucleic acids, which encode proteins, for example enzymes for ethanol formation or host cell enzymes involved in the conversion or formation of acetyl CoA, acetaldehyde or pyruvate. The invention also provides amino acid sequences for enzymes for ethanol formation or host cell enzymes involved in the conversion or formation of acetyl-CoA, acetaldehyde or pyruvate or for formation of reserve compounds, which are at least 60%, 70%, 80% 90% or 95% identical to the amino acid sequences disclosed therein.

The percentage of identity of two nucleic acid sequences or two amino acid sequences can be determined using the algorithm of Thompson et al. (CLUSTALW, 1994 Nucleic Acid Research 22: 4673-4, 680). A nucleotide sequence or an amino acid sequence can also be used as a so-called "query sequence" to perform searches against public nucleic acid or protein sequence databases in order, for example, to identify further unknown homologous genes, which can also be used in embodiments of this invention. In addition, any nucleic acid sequences or protein sequences disclosed in this patent application can also be used as a "query sequence" in order to identify yet unknown sequences in public databases, which can encode for example new enzymes, which could be useful in this invention. Such searches can be performed using the algorithm of Karlin and Altschul (1999 Proceedings of the National Academy of Sciences U.S.A. 87: 2,264 to 2,268), modified as in Karlin and Altschul (1993 Proceedings of the National Academy of Sciences U.S.A. 90: 5,873 to 5,877). Such an algorithm is incorporated in the NBLAST and XBLAST programs of Altschul et al. (1999 Journal of Molecular Biology 215: 403 to 410). Suitable parameters for these database searches with these programs are, for example, a score of 100 and a word length of 12 for BLAST nucleotide searches as performed with the NBLAST program. BLAST protein searches are performed with the XBLAST program with a score of 50 and a word length of 3. Where gaps exist between two sequences, gapped BLAST is utilized as described in Altschul et al. (1997 Nucleic Acid Research, 25: 3,389 to 3,402).

Database entry numbers given in the following are for the CyanoBase, the genome database for cyanobacteria (http://bacteria.kazusa.or.jp/cyanobase/index.html); Yazukazu et al. "CyanoBase, the genome database for *Synechocystis* sp. Strain PCC6803: status for the year 2000", Nucleic Acid Research, 2000, Vol. 18, page 72.

It is one object of embodiments of the invention to provide a metabolically enhanced host cell, which can be used for production of ethanol.

This object is reached by providing a metabolically enhanced host cell according to base claim 1. Further embodiments of the metabolically enhanced host cell, as well as constructs for producing the metabolically enhanced host cells and a method for producing ethanol using the metabolically enhanced host cells are subject matters of further claims.

Embodiment of metabolic knockout and/or overexpression of metabolic pathway enzymes One aspect of the invention provides a metabolically enhanced photoautotrophic, ethanol producing host cell comprising:
at least two first metabolic enhancements reducing the enzymatic activity or affinity of at least two endogenous host cell enzymes involved in acetate and lactate fermentation, the first metabolic enhancements resulting in an enhanced level of biosynthesis of acetaldehyde, pyruvate, acetyl-CoA or precursors thereof compared to the respective wild type host cell,
at least one second metabolic enhancement different from the first metabolic enhancement comprising an overexpressed enzyme for the formation of ethanol.

Acetaldehyde, pyruvate and acetyl-coA or their precursors are important metabolic intermediates for energy production in cells. In photoautotrophic cells, which use light, $CO_2$, and water as a source of energy to produce carbohydrates via photosynthesis, acetaldehyde, pyruvate, acetyl-CoA and their precursors can be formed by conversion of organic molecules obtained via $CO_2$ fixation in the Calvin-cycle, for example 3-phosphoglycerate. Pyruvate, acetyl-CoA and their precursors are important metabolic intermediates obtained e.g. by photosynthetic $CO_2$ fixation in photoautotrophic cells. Acetaldehyde is a metabolic intermediate of the anoxygenic fermentation pathway in many photoautotrophic cells.

Precursors of pyruvate and acetyl-CoA are organic compounds, which can be converted into these important metabolic intermediates via the enzymatic action of enzymes of the photoautotrophic cell. For example the organic compounds 2-phosphoglycerate, 3-phosphoglycerate or phosphoenolpyruvate can be converted into pyruvate by enzymes of the glycolytic pathway in photoautotrophic cells.

The metabolically enhanced photoautotrophic ethanol producing host cell comprises at least two different metabolic enhancements, a first and a second metabolic enhancement. The first metabolic enhancement changes the enzymatic activity or affinity of at least two endogenous host cell enzymes involved in acetate and lactate fermentation, resulting in a higher level of biosynthesis of acetyl-CoA, acetaldehyde, pyruvate or precursors thereof. The endogenous host enzyme is already present in an unmodified wild type host cell and its activity or affinity is changed by the first metabolic enhancement in order to increase the level of biosynthesis of metabolic intermediates, which are also present in the wild type host cell and which can be used to form ethanol.

Furthermore the metabolically enhanced photoautotrophic ethanol producing host cell comprises a second metabolic enhancement in the form of at least one overexpressed enzyme, which can form ethanol, for example from the above-mentioned important metabolic intermediates. In a further embodiment the overexpressed enzyme for ethanol formation can catalyze the last step of ethanol formation leading to the final product ethanol. The overexpressed enzyme for ethanol formation can also catalyze the penultimate step of ethanol formation resulting in a metabolic intermediate, which can further be converted by another enzyme for ethanol formation into the final product ethanol.

The enzyme for ethanol formation can, for example, be an endogenous enzyme already present in a wild type photoautotrophic host cell, which is not metabolically enhanced. In this case the activity or affinity of the enzyme for ethanol formation can be enhanced by the second metabolic enhancement, for example by metabolic engineering or random mutagenesis. This can, for example, be done by metabolically modifying the amino acid sequence of the enzyme by site directed or random mutagenesis of the gene encoding this endogenous enzyme, thereby enhancing its activity for formation of ethanol. Another possibility is to increase the number of gene copies encoding for the enzyme in the host cell or simply by enhancing the rate of transcription of the gene already present in the wild type cell to increase the abundance of its messenger RNA in the second metabolic enhancement. This can be done for example by replacing or mutating the endogenous promoter controlling the transcription of the endogenous gene encoding the enzyme for ethanol formation.

Alternatively or additionally a heterologous enzyme for ethanol formation can be introduced into the host cell by the second metabolic enhancement, if that enzyme is not present in a metabolically unmodified wild type host cell. This can be done, for example, by introducing a construct, for example a DNA vector into the host cell including a heterologous gene encoding the overexpressed enzyme for ethanol formation. In the case that an endogenous enzyme for ethanol formation is already present in a photoautotrophic wild type host cell, the heterologous enzyme for ethanol formation can enhance the activity of the endogenous enzyme resulting in a higher rate of ethanol formation.

The enzymatic activity and the affinity of an enzyme for its substrate are important kinetic features. The enzymatic activity is given by the parameter $V_{max}$, which reflects the maximal velocity of an enzymatic reaction occurring at high substrate concentrations when the enzyme is saturated with its substrate. The affinity is given by the Michaelis-Menten constant $K_m$ which is the substrate concentration required for an enzyme to reach one-half of its maximum velocity. In order to increase the enzymatic activity $V_{max}$ has to be increased, whereas for increasing the affinity $K_m$ has to be reduced. Regarding a further explanation of enzyme kinetics we refer to the chapter "enzyme kinetics" in the textbook "Biochemistry" by Donald Voet and Judith Voet (John Wiley & Sons, 1990, pages 335 to 340).

The higher level of biosynthesis of acetyl-CoA, acetaldehyde, pyruvate or precursors thereof results in a change of the flux of the acetyl-CoA, acetaldehyde, pyruvate or precursors thereof in the direction of the at least one overexpressed enzyme for ethanol formation so that formation of ethanol can be increased in comparison to a photoautotrophic ethanol producing host cell harboring only the second metabolic enhancement, but lacking the first metabolic enhancement.

Acetyl-CoA, acetaldehyde, pyruvate or precursors thereof are transient metabolic intermediates, which are often rapidly processed into other metabolites by the photoautotrophic host cell and therefore a change in the level of biosynthesis of these metabolic intermediates can be hard to detect in photoautotrophic host cells featuring the first metabolic enhancement but lacking the second metabolic enhancement.

A first metabolic enhancement therefore results in a higher level of biosynthesis of acetyl-CoA, acetaldehyde, pyruvate or precursors thereof compared to the respective wild type host cell, if after introduction of the second metabolic enhancement a higher level of ethanol formation can be detected in a cell harboring the first and second metabolic enhancement than in a cell only harboring the second metabolic enhancement but lacking the first metabolic enhancement. This even applies if a change in the level of biosynthesis of these metabolic intermediates could not be detected in the photoautotrophic host cell harboring the first metabolic enhancement but lacking the second metabolic enhancement in comparison to the respective wild-type photoautotrophic host cell, which does not harbor the first and second metabolic enhancement.

In particular, the metabolically enhanced photoautotrophic host cell can comprise more than two first metabolic enhancements and can also comprise more than one second metabolic enhancement. For example the first metabolic enhancements can comprise at least three metabolic enhancements, which are lactate dehydrogenase phosphotransacetylase and acetate kinase.

The inventors found out that by reducing the enzymatic affinity or activity of lactate dehydrogenase and an enzyme selected from phosphotransacetylase and acetate kinase the level of in particular pyruvate can be increased. Pyruvate is an important substrate for ethanologenic enzymes such as pyruvate decarboxylase, so that the pyruvate can be used for ethanol production.

The metabolically enhanced photoautotrophic host cell shows a high production of ethanol due to the fact that the ethanol forming enzyme is overexpressed due to the second metabolic enhancement leading to a high enzymatic activity for ethanol formation and that at the same time a higher level of biosynthesis of acetaldehyde, pyruvate, acetyl-CoA or their precursors is formed in the cells compared to the respective wild type cells due to the first metabolic enhancements. Acetaldehyde, pyruvate, acetyl-CoA or their precursors serve as substrates for the ethanol production. These metabolic intermediates can either be a direct substrate for a first overexpressed enzyme for the formation of ethanol or for another second overexpressed enzyme for ethanol formation, which then catalyzes the formation of a substrate for the first overexpressed enzyme for ethanol formation.

In yet a further embodiment of the host cell of the invention, the at least one overexpressed enzyme for the formation of ethanol is an alcohol dehydrogenase.

An alcohol dehydrogenase catalyzes the reduction of a substrate to ethanol. This reaction is normally dependent on the cofactor NADH. Alternatively there are alcohol dehydrogenases which are NADPH-dependent.

Furthermore, the alcohol dehydrogenase can be a thermaphilic alcohol dehydrogenase. Thermophilic alcohol dehydrogenase can, for example, be obtained from a host cell which can normally grow well at temperatures above 45° C. Thermophilic alcohol dehydrogenases can be more stable and probably more active at higher temperatures than alcohol dehydrogenases obtained from mesophilic host cells, which normally grow at temperatures below 45° C. One possible example for such a thermophilic alcohol dehydrogenase is the alcohol dehydrogenase AdhE obtained from the thermophilic cyanobacterium *Thermosynechococcus* sp. or from *E. coli*

(see FIG. 44A for the nucleic acid sequence and FIG. 44B for the amino acid sequence of ThAdhE protein sequence BAC07780).

One possible substrate for alcohol dehydrogenase can be acetyl-CoA, which for example can be directly converted to ethanol by the above-mentioned alcohol dehydrogenase AdhE from *Thermosynechococcus* or *E. coli*. Overexpressing such an alcohol dehydrogenase in a metabolically enhanced host cell has the advantage that only one enzyme has to be overexpressed in order to enhance the level of ethanol production. In the case that the level of biosynthesis of acetyl-CoA of the host cell is increased due to overexpression of acetyl-coenzyme A forming enzymes and due to the reduction of enzymatic activity of acetyl-CoA converting enzymes, a high level of ethanol formation can result.

In a further embodiment of the invention, a metabolically enhanced host cell can be provided, which further comprises:

pyruvate decarboxylase converting pyruvate to acetaldehyde, wherein the alcohol dehydrogenase converts the acetaldehyde to ethanol.

In this case, the substrate for the alcohol dehydrogenase is provided by a further second overexpressed enzyme, for example pyruvate decarboxylase, which is introduced into the host cell via a further second metabolic enhancement. Due to the fact that the level of biosynthesis of pyruvate of the host cell is increased due to the above-mentioned enhancements of the pyruvate forming and converting enzymatic activities by way of the first metabolic enhancement, more acetaldehyde is formed via the enzymatic activity of pyruvate decarboxylase. Therefore there is an increased synthesis of acetaldehyde, which is then further converted by alcohol dehydrogenase, the first overexpressed enzyme for ethanol formation to ethanol resulting in a higher intracellular or extracellular ethanol level in the host cell. The alcohol dehydrogenase, as well as the pyruvate decarboxylase can be obtained from alcohol-fermenting organisms such as the bacteria *Zymomonas mobilis*, *Zymobacter palmae* or other prokaryots carrying genes encoding pyruvate decarboxylases with comparable or better enzymatic features as well as the yeast *Saccharomyces cerevisiae* or other eukaryotes carrying genes encoding pyruvate decarboxylases with comparable or better enzymatic features.

In another embodiment of the invention the metabolically enhanced host cell comprises two second metabolic enhancements, one comprising alcohol dehydrogenases Adh converting acetaldehyde into ethanol and another second metabolic enhancement comprising a CoA-dependent acetaldehyde dehydrogenase converting acetyl-CoA into acetaldehyde.

In yet a further embodiment of the invention the metabolically enhanced host cell harbors a pyruvate decarboxylase enzyme as the only second metabolic enhancement. Such a single second metabolic enhancement is particularly advantageous in metabolically enhanced host cells, which already have an endogenous alcohol dehydrogenase enzyme. The inventors surprisingly found that the activity of such an endogenous alcohol dehydrogenase enzyme can be high enough in order to convert all or almost all of the acetaldehyde formed by the overexpressed pyruvate decarboxylase enzyme into ethanol.

For example all cyanobacterial host cells harbor at least one endogenous alcohol dehydrogenase enzyme. A preferred example is the cyanobacterium *Synechocystis* in particular *Synechocystis* PCC6803 or nitrogen fixing cyanobacteria such as *Nostoc/Anabaena* spec. PCC7120 and *Anabaena variabilis* ATCC 29413.

In a further embodiment of the invention the metabolically enhanced photoautotrophic ethanol producing host cell is an aquatic organism. This aquatic organism can, for example, be a fresh water species living in lakes, rivers, streams or wetlands. Alternatively the aquatic organism can be a marine organism, which lives in salty water, for example oceans. The aquatic organism also can be a fresh water species, which shows a high tolerance for brackish water or even salt water. The inventors also found fresh water strains that can grow in marine media with the same growth rate as in fresh water media.

In a further embodiment the metabolically enhanced host cell is selected from a group consisting of: algae and bacteria.

Algae are a diverse group of simple plant-like organisms which include unicellular or multicellular forms. Algae are photosynthetically active organisms, in particular photoautotrophs, which produce organic compounds from inorganic molecules such as $CO_2$ and water using light as an external source of energy.

Algae are considered to be eukaryotic organisms in particular protists. Protists are relatively simple eukaryotic organisms which are unicellular or multicellular without highly specialized tissues.

In particular, protist algae can include Chlorophytes, which are green algae, such as *Ulva chlatrata*, Rhodophytes, which are red algae or heterokontophytes, which are brown algae. A preferred green algal species is *Chlorella*. Another example of a green algae is *Chlamydomonas*, which are unicellular flagellates. A particular well known example of *Chlamydomonas* is *Chlamydomonas reinhardtii*, which is a motile single-celled green algae found in, for example, fresh water. *Chlamydomonas reinhardtii* is also known to produce minor amounts of ethanol via fermentation under dark conditions (Gfeller and Gibbs, Fermentative Metabolism of *Chlamydomonas reinhardtii*, Plant Psychology (1984) 75, pages 212 to 218).

In a further embodiment of the invention a metabolically enhanced photoautotrophic, ethanol producing host cell is provided, which comprises:

at least one first metabolic enhancement enhancing the enzymatic activity or affinity of the endogenous host cell enzymes selected from a group consisting of malic enzyme and malate dehydrogenase, at least one second metabolic enhancement different from the at least two first metabolic enhancements comprising an overexpressed enzyme for the formation of ethanol, the first and second metabolic enhancements resulting in an increased rate of ethanol production compared to the respective photoautotrophic, ethanol producing host cell harboring the second metabolic enhancement but lacking the first metabolic enhancements.

In the case that the enzymatic activity of malate dehydrogenase, an enzyme of the citric acid cycle and malic enzyme, an enzyme of the intermediate steps of metabolism is enhanced, for example by co-overexpression, malate dehydrogenase can stimulate the conversion of oxaloacetate to pyruvate via malate. Malate dehydrogenase catalyzes the conversion of oxaloacetate to malate using NADH:

Malic enzyme catalyzes the conversion of malate into pyruvate using $NADP^+$:

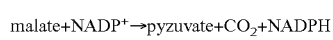

Alternatively the enzymatic activity or affinity of only one of the enzymes malic enzyme or malate dehydrogenase can be enhanced, by for example overexpression.

In yet another embodiment of the invention a metabolically enhanced photoautotrophic, ethanol producing host cell is provided, which comprises:

at least one first metabolic enhancement enhancing the enzymatic activity or affinity of the endogenous host cell enzymes aldehyde dehydrogenase, at least one second metabolic enhancement different from the at least one first metabolic enhancement comprising an overexpressed enzyme for the formation of ethanol, the first and second metabolic enhancements resulting in an increased rate of ethanol production compared to the respective photoautotrophic, ethanol producing host cell harboring the second metabolic enhancement but lacking the first metabolic enhancement.

An enzyme of the fermentation pathway, which can be overexpressed is for example the aldehyde dehydrogenase enzyme, which can convert acetate to acetaldehyde and vice versa, thereby increasing the level of biosynthesis of acetaldehyde in the host cell. Alternatively also other aldehyde dehydrogenase enzymes could be overexpressed in order to increase the level of biosynthesis of acetaldehyde in the host cell.

In a further embodiment of the invention a metabolically enhanced photoautotrophic, ethanol producing host cell is provided, which comprises:

at least two first metabolic enhancements enhancing the enzymatic activity or affinity of the endogenous host cell enzymes phosphoketolase and phosphoacetyltransacetylase, at least one second metabolic enhancement different from the at least two first metabolic enhancements comprising an overexpressed enzyme for the formation of ethanol, the first and second metabolic enhancements resulting in an increased rate of ethanol production compared to the respective photoautotrophic, ethanol producing host cell harboring the second metabolic enhancement but lacking the first metabolic enhancements.

According to a further aspect of the invention the enzymatic activity or affinity of the enzyme phosphoketolase (EC 4.1.2.-, putative phosphoketolase in *Synechocystis* PCC 6803 slr 0453) is enhanced in a first metabolic enhancement in order to increase the level of biosynthesis of precursor molecules for the generation of acetyl-CoA and acetaldehyde. Phosphoketolase catalyses the formation of acetyl phosphate and glyceraldehyde 3-phosphate, a precursor of 3-phosphoglycerate from xylulose-5-phosphate which is an intermediate of the Calvin cycle. The concomitant enhancement of the enzymatic activity or affinity of the enzyme phosphoacetyltransacetylase, which catalyzes the interconversion of acetylphosphate and acetyl-CoA can enhance the level of, for example, acetyl-CoA and pyruvate. In particular the acetylphosphate produced by the overexpressed phosphoketolase can be further converted to acetyl-CoA via the enzymatic action of the overexpressed phosphoacetyltransacetylase. Without being bound by an theory, an enhanced level of acetyl-CoA might lead to a feed back effect and slow down the conversion of pyruvate to acetyl-CoA.

Any of the above mentioned enhancements, for example but not limiting the different ethanologenic enzymes for the second metabolic enhancement or the various different promoters, which are described in relation to the at least two first metabolic enhancements reducing the enzymatic activity or affinity of at least two endogenous host cell enzymes involved in acetate and lactate fermentation can also be used in conjunction with the enhancement of the enzymatic activity or affinity of malic enzyme and/or malate dehydrogenase, or aldehyde dehydrogenase or phosphoketolase and phosphoacetyltransacetylase.

Further in another embodiment of the invention, the metabolically enhanced host cell harboring any of the above disclosed first metabolic enhancements can also comprise overexpressed enzymes as a first metabolic enhancement or overexpressed ethanologenic enzymes for ethanol formation as a second metabolic enhancement, which are under the transcriptional control of various inducible or constitutive promoters, wherein the promoters are selected from a group consisting of:

rbcLS, ntcA, nblA, isiA, petJ, petE, sigB, lrtA, htpG, hspA, clpB1, hliB, ggpS, psbA2, psaA, nirA and crhC.

The promoters hspA, clpB1, and hliB can be induced by heat shock (raising the growth temperature of the host cell culture from 30° C. to 40° C.), cold shock (reducing the growth temperature of the cell culture from 30° C. to 20° C.), oxidative stress (for example by adding oxidants such as hydrogen peroxide to the culture), or osmotic stress (for example by increasing the salinity). The promoter sigB can be induced by stationary growth, heat shock, and osmotic stress. The promoters ntcA and nblA can be induced by decreasing the concentration of nitrogen in the growth medium and the promoters psaA and psbA2 can be induced by low light or high light conditions. The promoter htpG can be induced by osmotic stress and heat shock. The promoter crhC can be induced by cold shock. An increase in copper concentration can be used in order to induce the promoter petE, whereas the promoter petJ is induced by decreasing the copper concentration.

All the above promoter elements can be combined with any of the genes encoding any of the enzymes of the invention by using standard molecular cloning techniques. In particular the promoters, which can be used for the present invention include, but are not limited to:

(1) FIG. 45A depicts the nucleotide sequence of the petJ promoter (*Synechocystis* sp. PCC 6803) (petJ gene: sll1796 (encoding for cytochrome c553; induced expression under copper starvation);

Reference.:

J Biol Chem. 2004 February 20;279(8): 7229-33. Epub 2003 December.

The efficient functioning of photosynthesis and respiration in *Synechocystis* sp. PCC 6803 strictly requires the presence of either cytochrome c6 or plastocyanin.

Durán R V, Hervás M, De La Rosa M A, Navarro J A.

(2) FIG. 45B depicts the nucleotide sequence of the sigB promoter (*Synechocystis* sp. PCC 6803)

sigB gene: sll0306 (encoding for RNA polymerase group 2 sigma factor) induced expression after heat shock, in stationary growth phase/nitrogen starvation and darkness)

References:

Arch Microbial. 2006 October;186(4):273-86. Epub 2006 Jul. 26.

a. The heat shock response in the cyanobacterium *Synechocystis* sp. Strain PCC 6803 and regulation of gene expression by HrcA and SigB.

b. Singh A K, Summerfield T C, Li H, Sherman L A

FEBS Lett. 2003 November 20;554(3):357-62.

c. Antagonistic dark/light-induced SigB/SigD, group 2 sigma factors, expression through redox potential and their roles in cyanobacteria.

d. Imamura S, Asayama M, Takahashi H, Tanaka K, Takahashi H, Shirai M

J Biol Chem. 2006 February 3;281(5):2668-75. Epub 2005 Nov. 21.

e. Growth phase-dependent activation of nitrogen-related genes by a control network of group 1 and group 2 sigma factors in a cyanobacterium.

f. Imamura S, Tanaka K, Shirai M, Asayama M.

(3) FIG. 45C depicts the nucleotide sequence of the htpG promoter (*Synechocystis* sp. PCC 6803) htpG gene: sll0430: (encoding for heat shock protein 90, molecular chaperone) induced expression after heat shock Reference:

Plant Physiol. 1998 May;117(1):225-34.

g. Transcriptional and posttranscriptional control of mRNA from lrtA, a light-repressed transcript in *Synechococcus* sp. PCC 7002.

h. Samartzidou, H, Widger W R (4) FIG. 45D shows the nucleotide sequence of the lrtA promoter (*Synechocystis* sp. PCC 6803) lrtA gene: sll0947 (encoding the light repressed protein A homolog induced expression after light to dark transition)

Reference:

Plant Physiol. 1998 May;117(1):225-34. Transcriptional and posttranscriptional control of mRNA from lrtA, a light-repressed transcript in *Synechococcus* sp. PCC 7002.

i. Samartzidou H, Widger W R (5) the nucleotide sequence of the psbA2 promoter (*Synechocystis* sp. PCC 6803) (see FIG. 45E) psbA2 gene: slr1311 (encoding the photosystem II D1 protein) induced expression after dark to light transition Reference:

Biochem Biophys Res Commun. 1999 February 5;255(1): 47-53.

j. Light-dependent and rhythmic psbA transcripts in homologous/heterologous cyanobacterial cells.

k. Agrawal G K, Asayama M, Shirai M.

(6) FIG. 45F shows the nucleotide sequence of the rbcL promoter (*Synechocystis* sp. PCC 6803) rbcL gene: slr0009 (encoding the ribulose biphosphate carboxylase/oxygenase large subunit constitutive strong expression under continuous light conditions Reference:

Plant Mol Biol. 1989 December;13(6):693-700 l. Influence of light on accumulation of photosynthesis-specific transcripts in the cyanobacterium *Synechocystis* 6803.

m. Mohamed A, Janssen C.

(7) FIG. 45G depicts the nucleotide sequence of the psaA promoter (*Synechocystis* sp. PCC6803); PsaA gene: slr1834 (encoding P700 apoprotein subunit Ia) induced expression under low white light and orange light, to expression level under high light and red light, repressed in darkness References:

Plant Cell Physiol. 2005 September;46(9):1484-93. Epub 2005 Jun. 24.

Regulation of photosystem I reaction center genes in *Synechocystis* sp. strain PCC 6803 during Light acclimation.

Herranen M, Tyystjärvi T, Aro E M.

Plant Cell Physiol. 2006 July;47(7):878-90. Epub 2006 May 16.

Characterization of high-light-responsive promoters of the psaAB genes in *Synechocystis* sp. PCC 6803.

Muramatsu M, Hihara Y.

(8) FIG. 45H shows the nucleotide sequence of the ggpS promoter (*Synechocystis* sp. PCC6803); ggpS gene: sll1566 (encoding glucosylglycerolphosphate synthase) induced expression after salt stress Reference:

Plant Physiol. 2004 October;136(2):3290-300. Epub 2004 Sep. 10.

Gene expression profiling reflects physiological processes in salt acclimation of *Synechocystis* sp. strain PCC 6803.

Marin K, Kanesaki Y, Los D A, Murata N, Suzuki I, Hagemann M.

J. Bacteriol. 2002 June;184(11):2870-7.

Salt-dependent expression of glucosylglycerol-phosphate synthase, involved in osmolyte synthesis in the cyanobacterium *Synechocystis* sp. strain PCC 6803.

Marin K, Huckauf J, Fulda S, Hagemann M.

(9) FIG. 45I depicts the nucleotide sequence of the nirA promoter (*Synechocystis* sp. PCC6803); nirA gene: slr0898 (encoding ferredoxin-nitrite reductase) induced expression after transition from ammonia to nitrate.

Reference:

Appl. Environ Microbiol. 2005 October;71(10):5678-84.

Application of the *Synechococcus* nirA promoter to establish an inducible expression system for engineering the *Synechocystis* tocopherol pathway.

Qi Q, Hao M, Ng W O, Slater S C, Baszis S R, Weiss J D, Valentin H E.

J. Bacteriol. 1998 August;180(16):4080-8 cis-acting sequences required for NtcB-dependent, nitrite-responsive positive regulation of the nitrate assimilation operon in the cyanobacterium *Synechococcus* sp. strain PCC 7942.

Maeda S, Kawaguchi Y, Ohe T A, Omata T.

(10) FIG. 45J depicts the nucleotide sequence of the petE promoter (*Anabaena* sp. PCC7120); petE gene: all0258 (encoding plasocyanin precursor) induced expression at elevated copper concentrations Reference:

Microbiology. 1994 May;140 (Pt 5):1151-9.

Cloning, sequencing and transcriptional studies of the genes for cytochrome c-553 and plastocyanin from *Anabaena* sp. PCC 7120.

n. Ghassemian M, Wong B, Ferreira F, Markley J L, Straus N A.

Proc Natl Acad Sci U S A. 2001 February 27;98(5):2729-34. Epub 2001 Feb. 20.

Expression of the *Anabaena* hetR gene from a copper-regulated promoter leads to heterocyst differentiation under repressing conditions.

o. Buikema W J, Haselkorn R.

(11) FIG. 45K shows the nucleotide sequence of the hspA promoter (*Synechocystis* sp. PCC6803); hspA gene: sll1514 16.6 kDa small heat shock protein, molecular chaperone multi-stress responsible promoter (heat, cold, salt and oxidative stress)

Reference:

Curr Microbiol. 2004 September;49(3):192-8.

Expression of the heat shock gene hsp16.6 and promoter analysis in the cyanobacterium, *Synechocystis* sp. PCC 6803.

Fang F, Barnum S R.

J Exp Bot. 2006;57(7):1573-8. Epub 2006 Mar. 30.

The heat shock response of *Synechocystis* sp. PCC 6803 analyzed by transcriptomics and proteomics.

Suzuki I, Simon W J , Slabas A R.

(12) FIG. 45L depicts the nucleotide sequence of the hliB promoter (*Synechocystis* sp. PCC6803); hliB gene: ssr2595: high light-inducible polypeptide HliB, CAB/ELIP/HLIP superfamily multi-stress responsible promoter (heat, cold, salt and oxidative stress)

Reference:

J Biol Chem. 2001 January 5;276(1):306-14.

The high light-inducible polypeptides in *Synechocystis* PCC6803. Expression and function in high light.

He Q, Dolganov N, Bjorkman O, Grossman A R.

Arch Microbiol. 2007 April;187(4):337-42. Epub 2007 Feb. 10.

The response regulator RpaB binds the high light regulatory 1 sequence upstream of the high-light-inducible hliB gene from the cyanobacterium *Synechocystis* PCC 6803.

Kappell A D, van Waasbergen L G.

(13) FIG. 45M shows the nucleotide sequence of the clpB1 promoter (*Synechocystis* sp. PCC6803); clpB1 gene: slr1641: ATP-dependent Clp protease, Hsp 100, ATP-binding subunit ClpB multi-stress responsible promoter (heat, cold, salt and oxidative stress)

Reference:

Microbiology. 2004 May;150(Pt 5):1271-81.

Effects of high light on transcripts of stress-associated genes for the cyanobacteria *Synechocystis* sp. PCC 6803 and *Prochlorococcus* MED4 and MIT9313.

Mary I, Tu C J, Grossman A, Vaulot D.

J Exp Bot. 2006;57(7):1573-8. Epub 2006 Mar. 30.

The heat shock response of *Synechocystis* sp. PCC 6803 analysed by transcriptomics and proteomics.

Suzuki I, Simon W J, Slabas A R.

EMBODIMENTS OF THE INVENTION

In the following the inventions will be explained in more detail with reference to figures and certain embodiments:

FIG. 1 shows some general metabolic pathways in cyanobacteria as a non-limiting example. In particular the Calvin cycle as the light independent part of the photosynthesis is shown starting with the carbon dioxide fixation reaction catalyzed by the enzyme RubisCO. Further the glycolysis pathway, the pentose phosphate pathway and the citric acid cycle are shown. The general metabolic pathways depict boxed and circled enzymes, whose activity or affinity can be changed as part of at least one first metabolic enhancement of an endogenous host enzyme of the cyanobacterial host cell. Boxed enzymes either have been overexpressed compared to the respective wild type cyanobacterial cells or are prime candidates for overexpression. Circled enzymes either have been knocked out or down regulated or are prime targets for knock-out or down-regulation. The main reason for the knock-out or overexpression is to enhance the level of pyruvate biosynthesis in the metabolically enhanced cell by knocking-out or reducing the activity or affinity of enzymes consuming pyruvate or its metabolites and to enhance the enzymatic activity of enzymes producing pyruvate or its precursors such as phosphoenolpyruvate (PEP). The cyanobacterial host cell can comprise more than one first metabolic enhancement. For example enzymes enhancing the level of pyruvate biosynthesis such as enolase, phosphoketolase or malic enzyme can be overexpressed and the activity or affinity of enzymes consuming pyruvate, such as the enzymes of fermentative pathway such as lactate dehydrogenase, phosphoacetyltransacetylase and acetate kinase can be reduced or abolished by knock-out of the respective genes in one cyanobacterial host cell.

Figure 2:
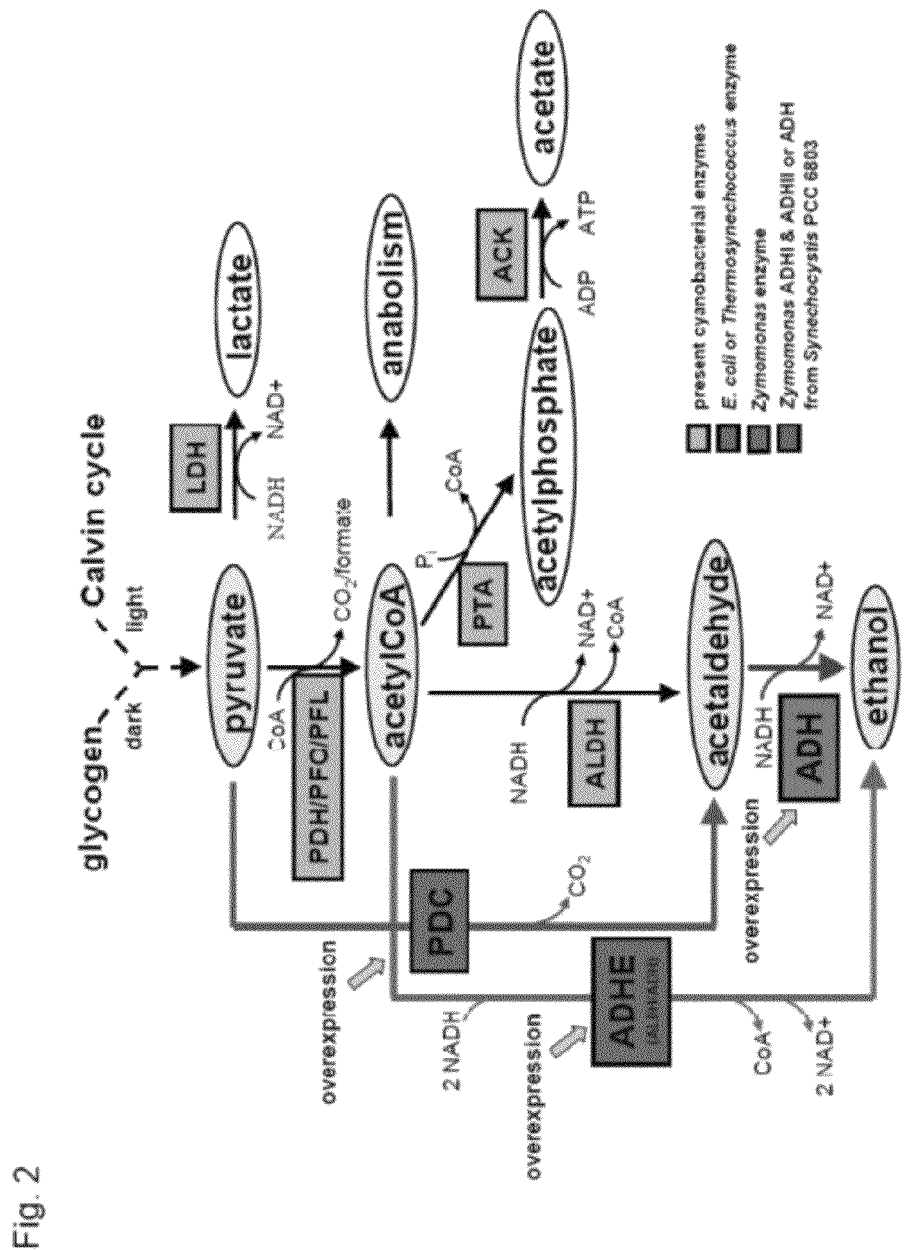
FIG. 2 shows a flow chart including some ethanologenic enzymes for ethanol production.

FIG. 2 shows in a more detailed way the last steps of ethanol synthesis in metabolically enhanced cyanobacteria.

Figure 3:
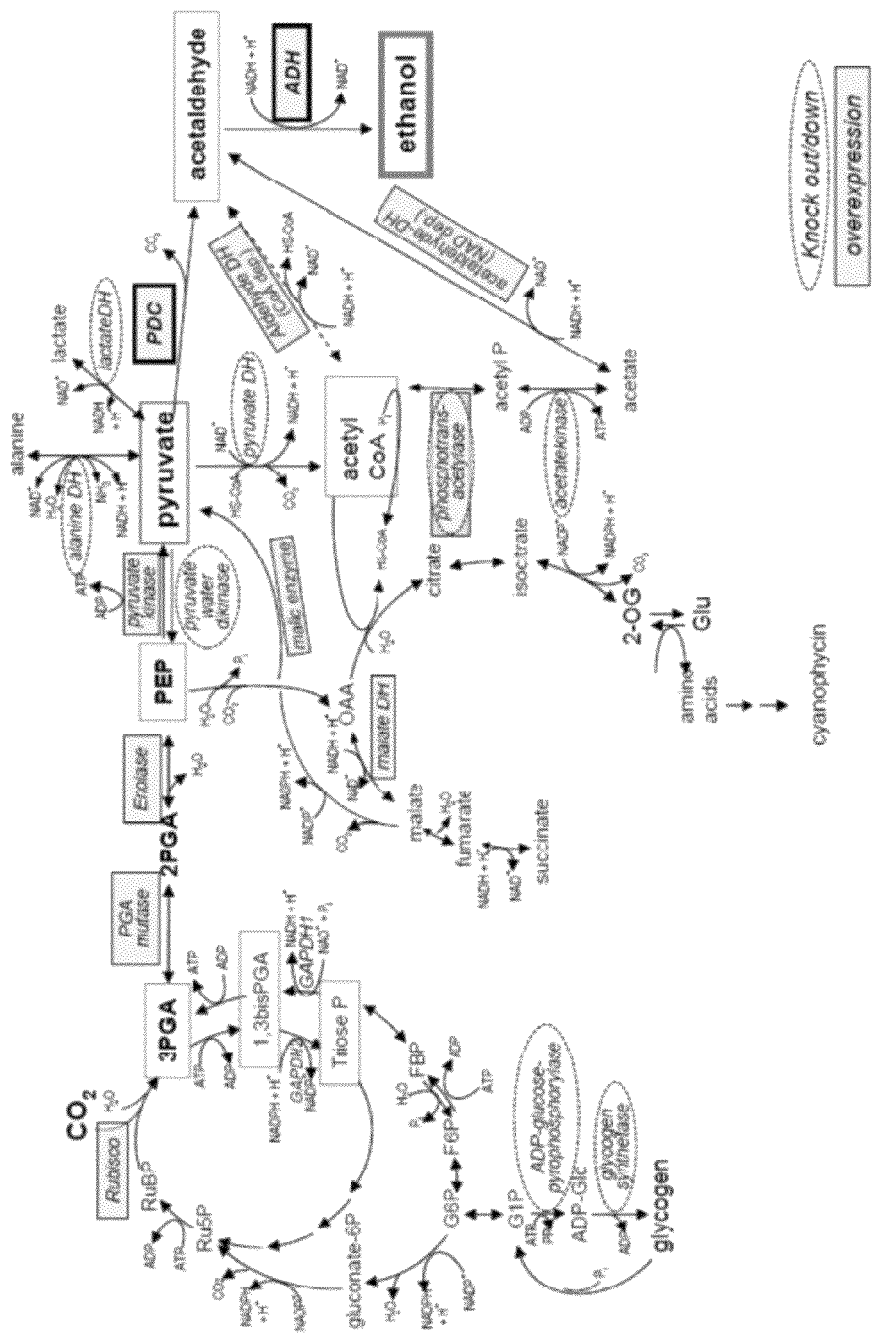
FIGS. 1 and 3 depict general schemes of metabolic pathways in Cyanobacteria with marked enzymes for overexpression and down-regulation or knock-out for the increase of biosynthesis of different metabolic intermediates, in particular acetyl-CoA and pyruvate.

FIG. 3 depicts a further non-limiting representation of metabolic pathways of a cyanobacterium. In contrast to the FIG. 1 a NAD dependent acetaldehyde dehydrogenase is shown, which can convert acetate into acetaldehyde, which then can be converted into ethanol by Adh enzyme. Such an aldehyde dehydrogenase can be overexpressed in order to increase the level of acetaldehyde for ethanol production.

1. General Construction of DNA-vectors for overexpression

DNA sequences encoding genes of interest were amplified by polymerase chain reaction (PCR) using specific primers. When the genomic sequence did not contain appropriate restriction sites for cloning, primers were designed containing restriction sites. Genomic DNA from *Synechocystis* sp. PCC 6803 was used as template. The amplified PCR fragments were digested with the appropriate restriction enzymes and cloned into either a self replicating plasmid (pVZ series) or an integrative plasmid (pSK series). As promoters either the genomic 5' region of the specific gene itself was used or alternative an inducible promoter like PpetJ. (PpetJ, pVZ, pSK, for description see below mentioned adh/pdc constructs). An antibiotic resistance cassette for selection of positive clones is present on the appropriate plasmid. The structures and sequences of all used DNA-vectors are described below.

Metabolic engineering of constructs as well as PCRs, ligations into cloning vectors, insertions of antibiotic resistance cassettes and transformations into *E. coli* were done using standard procedures (state of the art) or according to the manufacturer instructions.

All pVZ plasmids were transferred to *Synechocystis* sp. PCC 6803 by the below described "general Protocol for conjugation". The pSK, pUC or pBluescript constructs were transferred to *Synechocystis* sp. PCC 6803 by the below described "general protocol for transformation".

General Protocol for transformation

All pSK or pBluescript constructs were transferred to *Synechocystis* sp. PCC 6803 by transformation.

Host cells are mutagenized by transformation of the DNA-vectors (pSK, pUC or pBluescript constructs) using the natural competence of *Synechocystis* sp. PCC 6803 for DNA uptake and its system for homologous recombination.

10 ml of exponentially growing culture of *Synechocystis* spec. were spun down at room temperature (RT) and the supernatant was removed. The pellet was resuspended in 0.5-1.0 ml of BG11 medium and 1-10 µg plasmid DNA (pSK-constructs carrying ethanologenic genes and an antibiotic cassette for screening for homologous recombination or pUC- and pBluescript knock-out-constructs carrying gene of interest and an antibiotic cassette for screening for homologous recombination) were added. The cells were incubated on a table-top shaker for 5-6 hours in the light at 28° C. 0.2 ml of the transformation mixture were plated on a BG11 agar. The plates were incubated in the light at 28° C. over night. For selection of mutant clones the appropriate antibiotics were put under the agar (0.4 ml of kanamycin (1 mg/mL) or 0.4 ml chloramphenicol (1.4 mg/mL) or 0.2 ml gentamycin (1 mg/mL), respectively).

After approx. 2 weeks incubation in the light at 28° C., colonies were picked and plated to plates containing the appropriate antibiotic. Thereafter, the concentrations of the antibiotic were increased stepwise when the cells were transferred onto another agar plate or into liquid culture (for kanamycin from initially 5 to 150 µg/ml BG11, for chloramphenicol from initially 1 to 15 µg/ml BG11 medium and for gentamycin from initially 1 to 5 µg/ml BG11) in order to get fully segregated (homozygous) mutants. Transfers were done every week.

When mutants grew on the final antibiotic concentration, individual clones were checked for full segregation of the mutant gene by PCR.

BG11 media recipe:
$NaNO_3$: 1.5 g
$K_2HPO_4$: 0.04 g
$MgSO_4.7H_2O$: 0.075 g
$CaCl_2.2H_2O$: 0.036 g
Citric acid: 0.006 g
Ferric ammonium citrate: 0.006 g
EDTA (disodium salt): 0.001 g
$NaCO_3$: 0.02 g
Trace metal mix A5 1.0 ml (see below)
Distilled water: 1.0 L
Trace metal mix A5:
$H_3BO_3$: 2.86 g
$MnCl_2.4H_2O$: 1.81 g
$ZnSO_4.7H^2O$: 0.222 g
$NaMoO_4.2H_2O$: 0.39 g
$CuSO_4.5H_2O$: 0.079 g
$Co(NO_3)_2.6H_2O$: 49.4 mg
Distilled water: 1.0 L 2. General Protocol for conjugation All pVZ self replicating plasmids were transferred into cyanobacterial cells by conjugation.

Protocol:

Cyanobacterial culture:

*Synechocystis* PCC6803 wild type or mutants strains (with the appropriate antibiotic) cultivated in BG11 medium until OD750 nm 0.2-0.8

*E. coil* cultures:

inoculation of overnight cultures of strains *E. coli* XL-1 carrying plasmid (pVZ) and *E. coil* J53 (RP4) in LB medium containing the appropriate antibiotics (50 µl/ml ampicillin for J53 and antibiotic for pVZ).

preparation of well growing culture (for each conjugation 10 ml of XL-1 (pVZ plasmid) and 10 ml of J53 (RP4) is needed): inoculate 0.25 ml overnight culture in 9.75 ml LB+antibiotic, grow for 2.5 h/37° C.

spin down the well grown *E. coil* cultures (10 min at 2500 rpm).

"wash"/resuspend cells in 1 ml of LB without antibiotics.

for each conjugation mix 1 ml of resuspended XL-1 (pVZ) and 1 ml J53 (RP4), spin down, remove supernatant and resuspend-pellet in 100 µl LB medium and incubate without shaking 1 h at 30° C.

then add 1.9 ml *Synechocystis* culture, shake slightly and centrifuge.

Resuspend the pellet in 30 µl BG-11 and drop it on an HATF (nitrocellulose membrane) filter, which is located on a prepared dried plate (of 20 ml 2× BG-11 and 20 ml 2% cyanoagar and 2 ml LB medium).

Leave the plate for 2 days under low light conditions in cyano cultivation chamber at 28° C.

After incubation splash the bacteria on the filter with 300 µl BG-11 and plate it carefully on 1%-cyano agar plate with antibiotic (for pVZ). After 10 days (or a little more) first transconjugants are visible.

Figures 1B, 4:
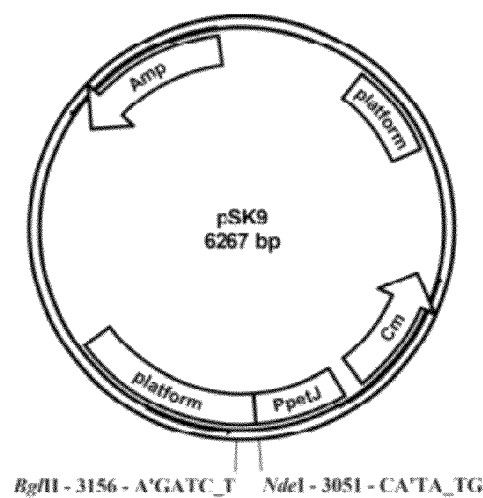

3. Protocols for generation of *Synechocystis* sp. PCC 6803 mutants overexpressing the following genes as first metabolic enhancements:

3a) co-overexpression of both malic enzyme and malate dehydrogenase and single overexpression of either malic enzyme or malate dehydrogenase 3b) co-overexpression of both phosphoketolase and phosphoracetyltransacetylase 3c) aldehyde dehydrogenase 3a) Construction of DNA-vectors for overexpression of malic enzyme and malate dehydrogenase 3a.1) Construction of DNA-vectors for overexpression of malic enzyme ORF slr0721 encoding mal enzyme 1 (EC 1.1.1.38), Ac. No p72661, has the amino acid sequence as shown in FIG. 4.

For over-expression of malic enzyme, the encoding me gene together with its gene-specific terminator region was PCR-amplified using the following primer:

Mae-NdeI.fw: 5'-CATATGGTTAGCCTCACCCCCAAT-3', primer contains a NdeI restriction site for cloning (marked in bold letters) (SEQ ID NO. 2)

MeLongClaI.rv: 5'-ATCGATCGGGATGGCCTATT-TATGG-3', primer contains a ClaI restriction site for cloning (marked in bold letters)

(SEQ ID NO. 3)

The PCR fragment was amplified by a High-Fidelity DNA Polymerase (Phusion™; Finnzymes), adenylated (BIO-TAQ™ DNA-Polymerase; BIOLINE), cloned into the pDrive vector (Qiagen) and restricted with NdeI/ClaI (Fermentas). This fragment was cloned into the pSK9 vector, digested with NdeI/ClaI. The gene is incorporated into a non-coding genome region of *Synechocystis* sp. PCC 6803 via the integrated platform. The expression of the enzyme is under control of the copper dependent promoter PpetJ. (The nucleotide sequence and a schematic representation of the non-public pSK9 vector are given on FIGS. 4-1A. and 4-1B, respectively.)

Figure 5:
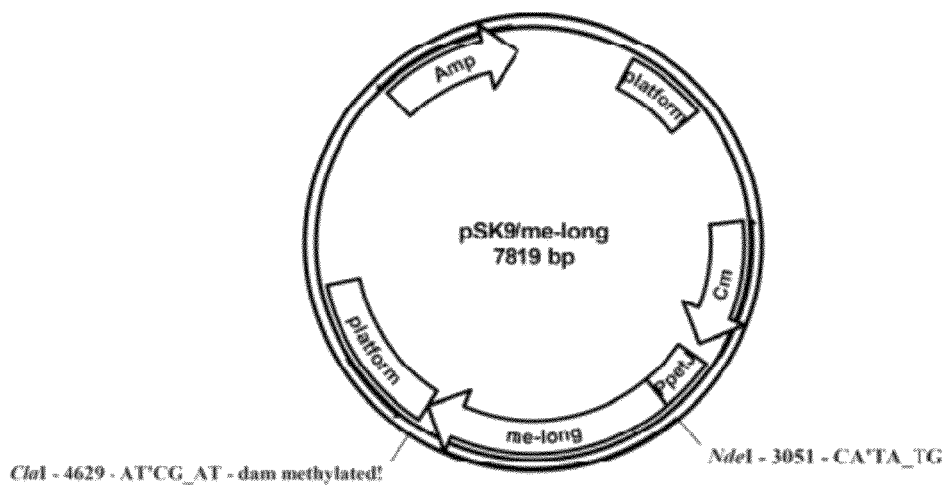

The construct used, designated as pSK9/me-long, has the structure depicted in FIG. 5. The sequence of the insert of construct pSK9/me-long is shown in FIG. 6.

3a.2) Construction of DNA-vector for over-expression of malate dehydrogenase

ORF sll0891 encodes malate dehydrogenase (EC 1.1.1.37), Ac. No Q55383 with the amino acid sequence as depicted in FIG. 7.

For over-expression of malate dehydrogenase a construct was generated including start-codon and the gene specific termination loop of the mdh gene using the following primers:

Mdh-NdeI.fw: 5'-CATATGAATATTTTGGAGTAT-GCTCC-3, primer contains a NdeI restriction site for cloning (marked in bold letters)

(SEQ ID NO. 6)

Mdh-ClaI.rv: 5'-ATCGATAAGCCCTAACCTCGGTG-3, primer contains a ClaI restriction site for cloning (marked in bold letters)

(SEQ ID NO. 7)

The PCR fragment was amplified by a High-Fidelity DNA Polymerase (Phusion™; Finnzymes), adenylated (BIO-TAQ™ DNA-Polymerase; BIOLINE), cloned into the pDrive vector (Qiagen) and restricted with NdeI/ClaI (Fermentas). This fragment was cloned into the pSK9 vector, digested with NdeI/ClaI. The expression of the enzyme is under the control of the copper dependent promoter PpetJ.

Figure 8:
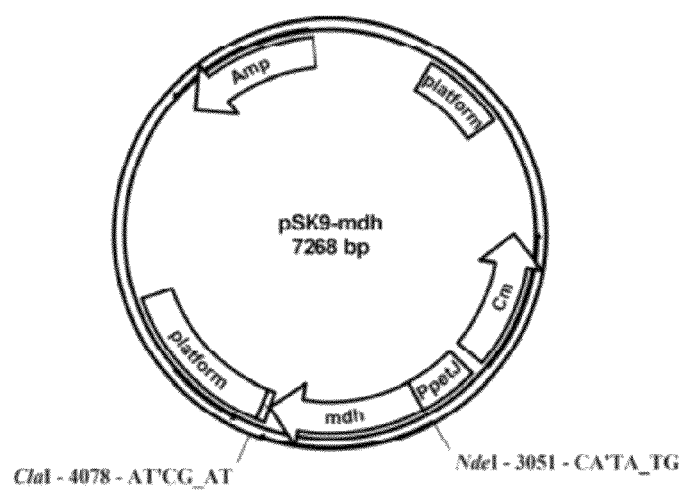

The construct used, designated as pSK9/mdh has the general structure as presented in FIG. 8 and the sequence of the insert of construct pSK9/mdh is shown in FIG. 9.

3a.3) Construction of DNA-vector for co-over-expression of malic enzyme and malate dehydrogenase This construct was generated for co-over-expression of malic enzyme and malate dehydrogenase. These genes were amplified by PCR using primers including the start and stop-codon of the me gene (PCR fragment I) and including the ribosome binding site (RBS) and termination loop of the mdh gene (PCR fragment II). The co-expression of the enzymes is under the control of the copper dependent promoter PpetJ.

The following primers were used for amplification
PCR fragment I:
Mae-NdeI.fw: 5'-CAT ATG GTTAGCCTCACCCCCAAT-3', primer contains a NdeI restriction site for cloning (marked in bold letters)
(SEQ ID NO. 9)
MeShortClaI.rv: 5'-ATCGATACAATTCCCGATTAAC-TATTGACC-3', primer contains a ClaI restriction site for cloning (marked in bold letters)
(SEQ ID NO. 10)
PCR fragment II:
MdhRBSClaI.fw: 5'-ATCGATTTTTCTCCACCATCAA-CACC-3', primer contains a ClaI restriction site for cloning (marked in bold letters)
(SEQ ID NO. 11)
MdhBglII.rv: 5'-AGATCTAAGCCCTAACCTCGGTG-3', primer contains a BglII restriction site for cloning (marked in bold letters)
(SEQ ID NO. 12)

The PCR fragments were amplified by a High-Fidelity DNA Polymerase (Phusion™; Finnzymes), adenylated (BIOTAQ™ DNA-Polymerase, BIOLINE), cloned into the pDrive vector (Qiagen) and restricted with NdeI/ClaI and ClaI/BglII (Fermentas), respectively. These fragments were cloned into the pSK9 vector, first digested with NdeI/ClaI for integration of malic enzyme and secondly with ClaI/BglII for integration of malate dehydrogenase.

Figure 10:
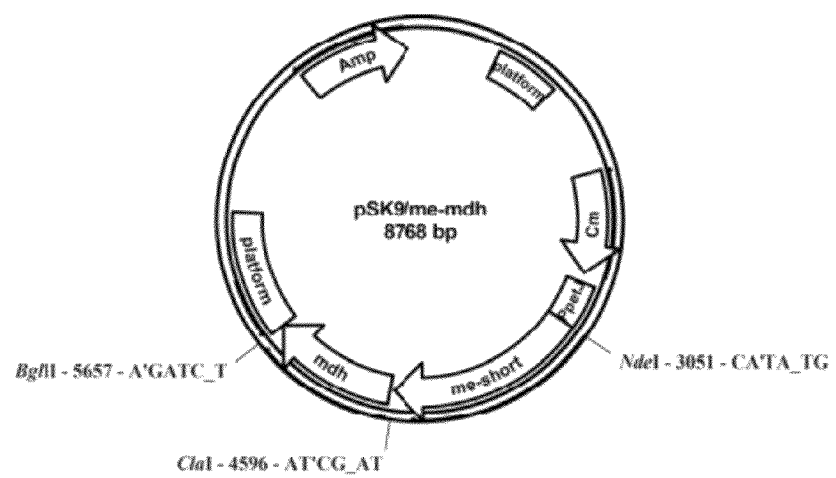

The construct used, designated as pSK9/me-mdh has the structure depicted in FIG. 10. The sequence of the insert of construct (pSK9/me-mdh) is as presented in FIG. 11.

3a.4) Plasmid pSK9 structure and sequence

Figure 12:
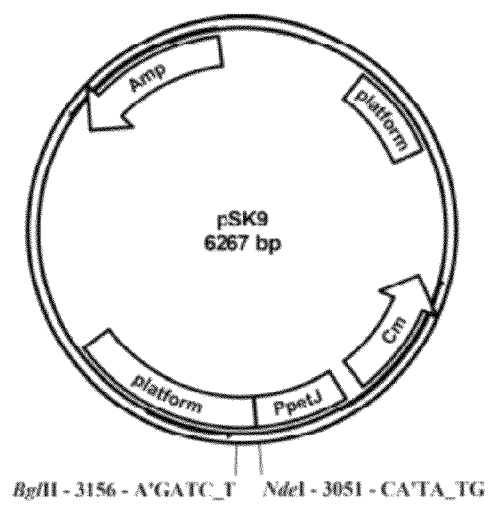

The non-public pSK9 vector was generated in the lab of V. V. Zinchenko (Moscow, Russia) and is shown in FIG. 12. FIG. 13 depicts the nucleic acid sequence of the vector.

Using the plasmids coding for the ethanologenic enzymes and the methods as described in the section 5)
"Generation of self-replicating (extrachromosomal) vectors for the inducible overexpression of ethanologenic enzymes in cyanobacterial mutant strains" the following mutants have been generated comprising a first metabolic mutation and as second metabolic enhancements overexpressed Pdc enzymes and SynAdh enzymes:

PCC6803 PpetJ-me: Synechocystis spec. PCC6803 was first transformed with pSK9/me-long, resulting in a fully segregated mutant PCC6803 PpetJ-me.

PCC6803 PpetJ-me/pVZ325-PpetJ-PDC-synADH: Self-replicating plasmid pVZ325-PpetJ-PDC-synADH was then introduced into mutant PCC6803 PpetJ-me by conjugation, thereby creating a mutant cyanobacterial strain harboring overexpressed malic enzyme as a first metabolic enhancement and overexpressed Pdc enzyme and SynAdh enzyme as second metabolic enhancements.

PCC6803 PpetJ-mdh: Synechocystis spec. PCC6803 was first transformed with pSK9/mdh, resulting in a fully segregated mutant PCC6803 PpetJ-mdh.

PCC6803 PpetJ-mdh/pVZ325-PpetJ-PDC-synADH: Self-replicating plasmid pVZ325-PpetJ-PDC-synADH was then introduced into mutant PCC6803 PpetJ-mdh by conjugation, thereby creating a mutant cyanobacterial strain harboring overexpressed malate dehydrogenase enzyme as a first metabolic enhancement and overexpressed Pdc enzyme and SynAdh enzyme as second metabolic enhancements.

PCC6803 PpetJ-me-mdh: Synechocystis spec. PCC6803 was first transformed with pSK9/me-mdh, resulting in a fully segregated mutant PCC6803 PpetJ-me-mdh.

PCC6803 PpetJ-me-mdh/pVZ321b-PpetJ-PDC-ADHII: Self-replicating plasmid pVZ321b-PpetJ-PDC-ADHII was then introduced into mutant PCC6803 PpetJ-me-mdh by conjugation, thereby creating a mutant cyanobacterial strain harboring overexpressed malic enzyme and malate dehydrogenase as first metabolic enhancements and overexpressed Pdc enzyme and SynAdh enzyme as second metabolic enhancements.

PCC6803 pVZ321b-PpetJ-PDC-ADHII and PCC6803 pVZ325-PpetJ-PDC-synADH: Self-replicating plasmids pVZ321b-PpetJ-PDC-ADHII or pVZ325-PpetJ-PDC-synADH, respectively, were introduced into Synechocystis spec. PCC6803 wild type by conjugation, thereby treating a mutant cyanobacterial strain harboring overexpressed Pdc enzyme and either AdhII or SynAdh enzyme as second metabolic enhancements, but lacking the first metabolic enhancement.

3b) Generation of a Synechocystis PCC6803 mutant overexpressing phosphoketolase and phosphoacetyltransacetylase as first metabolic enhancements A DNA-vector for co-overexpression of phosphoketolase and phosphoacetyltransacetylase was constructed as follows:

FIG. 14 shows the amino acid sequence of ORF slr0453 encoding the probable phosphoketolase (phk), (EC 4.1.2.-), Ac. No P74690. ORF slr2132 encodes a phosphoacetyltransacetylase (pta), EC 2.3.1.8, Ac No. P73662, having the amino acid sequence depicted in FIG. 15.

The phosphoketolase and phosphoacetyltransacetylase genes were amplified by PCR using the following primers:

```
phosphoketolase (phk)              (SEQ ID NO. 17)
#phk1 5'-GTGTCTCATATGGTTACATCCCCCTTTTCCCTT-3'
(NdeI site inserted)

#phk-BglII-rev                     (SEQ ID NO. 18)
5'-GGTCACAGATCTGTTGTCCCCCATGGCCTAGCTA-3' phosphoacetyltransacetylase (pta)
pta-BglII-fw                      (SEQ ID NO. 19)
5'-CCTTGCAGATCTGGATACGTTGAGGTTATTTAAATTATGA-3' pta_pPETJ2-XhoI                   (SEQ ID NO. 20)
5'-CGGTTGCTCGAGCATCTGGAACGGTTGGGTAAAT-3'
```

All primers contain restriction sites for cloning (marked in bold letters).

PCR fragments were cut with the appropriate restriction enzymes and ligated downstream of the PpetJ promoter into pIC-PpetJ as followed:
5'-XhoI-pIC-PpetJ-NdeI-3'
5'-NdeI-phk-BglII-3'
5'-BglII-pts-XhoI-3'

The entire PpetJ-phk-pta fragment was cut out of the cloning plasmid pIC20H with SmaI/NruI and ligated into SmaI site of the E. coli-Synechocystis shuttle vector pVZ322 (self replicating plasmid).

Figure 16:
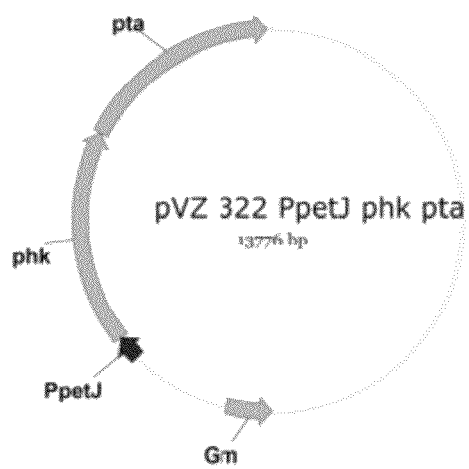

The construct named pVZ322-PpetJ-phk-pta, has the structure shown in FIG. 16 and the nucleic acid sequence of the insert of pVZ322-PpetJ-phk-pta is as presented in FIG. 17.

Plasmid pVZ322-PetJ-phk-pta was transferred into Synechocystis PCC6803 by conjugation as described. Confirmation of the resulting mutant, PCC6803 pVZ-PpetJ-phk-pta, was performed by PCR.

3c) Generation of a Synechocystis PCC6803 mutant overexpressing aldehyde dehydrogenase as a first metabolic enhancement A DNA-vector for overexpression of aldehyde dehydrogenase was constructed as follows:

The amino acid sequence of ORF slr0091 encoding an aldehyde dehydrogenase (aldh), EC 1.2.1.3, Ac No. BAA10564 Q55811 is shown in FIG. 18.

A construct was generated for overexpression of aldehyde dehydrogenase under control of the inducible promoter PpetJ.

The construct includes the petJ promoter, the 1369 bp aldehyde dehydrogenase fragment containing the entire coding sequence from ORF slr0091 and 205 bp downstream of the gene (terminator region). The aldehyde dehydrogenase (aldh) gene was amplified by PCR using the following primer:

```
#aldh1-NdeI-fw                          (SEQ ID NO. 23)
5'-GTGCCTCATATGAATACTGCTAAAACTGTTGTTGC-3' aldh2-XhoI-rev                         (SEQ ID NO. 24)
5'-GATCTCCTCGAGGTAAAGAATCAGCATAGGTCTGG-3'
```

Primers contain a NdeI or XhoI restriction site, respectively, for cloning (marked in bold letters).

The PCR fragment was digested with NdeI/XhoI and ligated downstream of the PpetJ promoter into pIC-PpetJ. The entire PpetJ-aldehyde dehydrogenase fragment was cut out of this plasmid with PstI/XhoI and ligated into the *E. coli-Synechocystis* shuttle vector pVZ322 (self replicating plasmid).

Figure 19:
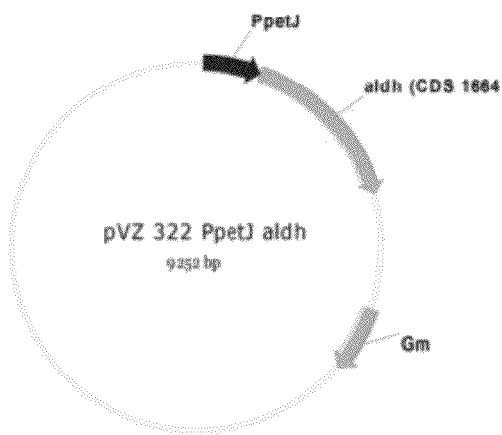

The construct used, named pVZ322-PpetJ-aldh, has the structure as depicted in FIG. 19. The sequence of the insert of construct pVZ322-PpetJ-aldh is presented in FIG. 20.

Plasmid pVZ322-PpetJ-aldh was transferred into *Synechocystis* PCC6803 by conjugation as described. Confirmation of the resulting mutant, PCC6803 pVZ-PpetJ-aldh, was performed by PCR 4) Protocols for generation of *Synechocystis* sp. PCC 6803 triple Δack/Δpta/Δldh knock-out mutant affecting lactate dehyrogenase (ldh), acetate kinase (ack) and phosphoacetyltransacetylase (pta) as first metabolic enhancements In the following the construction of DNA-vectors for generation of the Δack/Δpta/Δldh triple knock-out mutant is described:

4a) Construction of a DNA-vector for generation of an acetate kinase mutant

ORF sll1299 encodes a putative acetate kinase (EC 2.7.2.1), Ac No. P73162, with the amino acid sequence as shown in FIG. 21.

A 2316 bp fragment containing the entire coding sequence from acetate kinase (sll1299) was amplified by PCR using the following primer:

```
                                        (SEQ ID NO. 27)
#ack-1 fw: 5'-CCGGGACGTGACAGAACGGGTGG -3'

(SEQ ID NO. 28)
#ack-2 rv: 5'-GCGTTGGCGATCGCCGTCACTAG-3'
```

The PCR fragment was digested with SpeI and cloned into pBluescript SK+ vector. Cloning vector pBluescript II® SK+ (Ac. No X52328) was from Stratagene, La Jolla, Calif., USA. The kanamycin resistance cassette was used from the DNA vector pUC4K (Ac. No X06404) and ligated into the HpaI restriction sites of slr1299.

Figure 22:
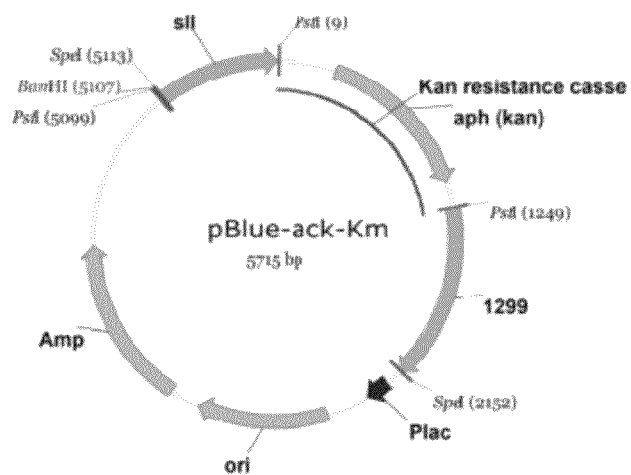

FIG. 22 depicts the structure of the knock-out-construct, named pBlue-ack-Km and the nucleic acid sequence of the insert of construct pBlue-ack-Km is shown in FIG. 23.

4b) Construction of a DNA-vector for generation of a phosphoacetyltransacetylase (phosphoacyltransferase) mutant ORF slr2132 encodes a phosphoacetyltransacetylase (EC 2.3.1.8), Ac No. P73662 having the amino acid sequence as shown in FIG. 24.

A 2869 bp by fragment containing the entire coding sequence from phosphoacetyltransacetylase (slr2132) was amplified by PCR using the following primer:

```
                                        (SEQ ID NO. 31)
#pta-1fw: 5'- GCCATTGTGGGGGTGGGTCAG -3'

(SEQ ID NO. 32)
#pta-2rv: 5'- CAGTTTATGCCCCGCTACCGGG -3',
```

The PCR fragment was digested with MfeI/HindIII and cloned into EcoRI/HindIII sites of cloning vector pUC19 (Ac. No M77789). The chloramphenicol resistance cassette was used from plasmid pACYC184 (Ac. No X06403) and ligated into the ClaI/PstI restriction sites of slr2132.

Figure 25:
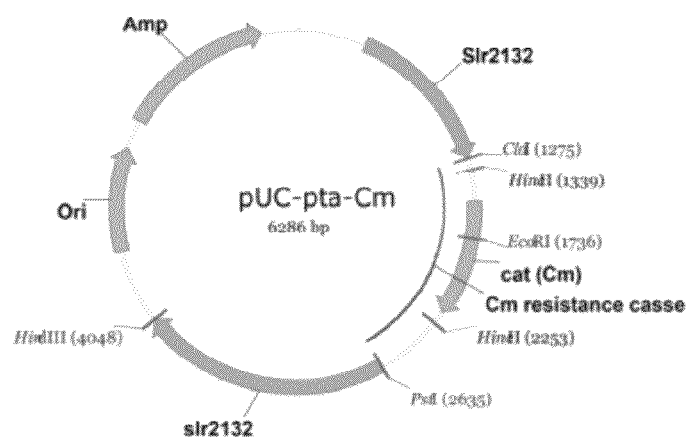

The knock-out-construct pUC-pta-Cm has the structure depicted in FIG. 25 and the sequence of the insert of plasmid pUC-pta-Cm is presented in FIG. 26.

4c) Construction of DNA-vectors for generation of a lactate dehydrogenase mutant ORF slr1556 encodes a putative lactate dehydrogense (EC 1.1.1.28), annotated as 2-hydroxyaciddehydrogenase homolog (P74586) with the amino acid sequence shown in FIG. 27.

A 1931 bp fragment containing the entire coding sequence from lactate dehydrogenase (slr1556) was amplified by PCR using the following primers:

```
                                        (SEQ ID NO. 35)
ldh-1fw: 5'-GCGAACTACCCAACGCTGACCGG-3' ldh-2rv: 5'-GCATCAAGTGTTGGGGGATATCCCTG-3',
```

(SEQ ID NO. 36) containing an EcoRV restriction site for cloning (marked in bold letters).

Figure 28:
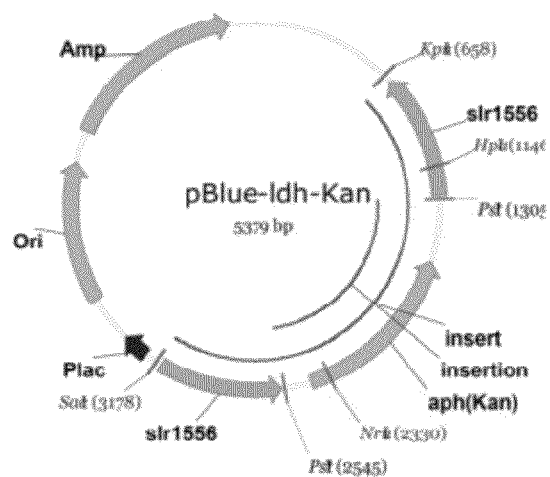

The PCR fragment was digested with NheI/EcoRV and cloned into pBluescript SK+ vector using XbaI/EcoRV. A kanamycin resistance cassette was cut out of vector pUC4K with BamHI and ligated into the BglII/BclI restriction sites of slr1556, resulting in plasmid pBlue-ldh-Kan (see FIG. 28).

Figure 29:
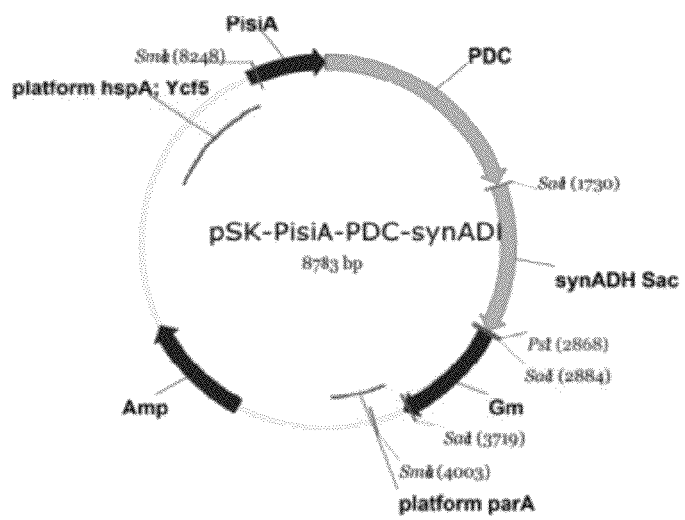

Plasmid pBlue-ldh-Kan was used for construction of an alternative lactate dehydrogenase knock-out vector, in which the kanamycin resistance cassette was substituted by a gentamycin resistance cassette. The Gm cassette was cut out of plasmid pSK-PisiA-PDC-synADH (shown in FIG. 29) by PstI and SmaI (1135 bp fragment) and ligated into the PstI and HpaI sites of pBlue-ldh-Kan.

Figure 30:
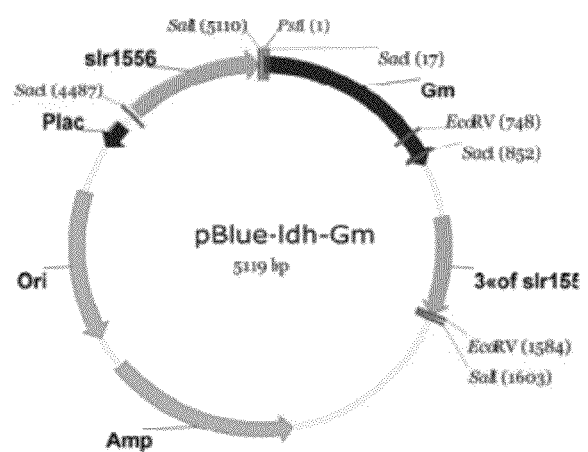

The knock-out construct pBlue-ldh-Gm has the structure as shown in FIG. 30 and the sequence of the insert of pBlue-ldh-Gm is depicted in FIG. 31.

4d) Generation of the triple knock out mutant Δack/Δpta/Δldh by transformation of the DNA-vectors (knock-out-constructs) using the natural competence of *Synechocystis* spec. PCC 6803 for DNA uptake and its system for homologous recombination.

The generation of a triple Δack/Δpta/Δldh knock-out mutant was done in three steps. In a first transformation with construct pBlue-ack-Kan gene sll1299 encoding the putative acetate kinase was knocked out in the wild type of *Synechocystis*, and the corresponding mutant Δack was selected. In a second step, gene slr2132 encoding a phosphoacetyltransacetylase was knocked out in the Δack mutant by transformation with construct pUC-pta-Cm and Δack/Δpta double mutants were selected. Finally a Δack/Δpta double mutant was transformed with construct pBlue-ldh-Gm in order to generate the triple knock-out mutant Δack/Δpta/Δldh. The transformations were done as described above in the "General Protocol for transformation"(.

When mutants grew on the final antibiotic concentration, individual clones were checked for full segregation of the mutant gene by PCR. In mutant Δack/Δpta/Δldh no wt genes of either ack, pta or ldh could be detected.

5) Generation of self-replicating (extrachromosomal) vectors for the inducible overexpression of ethanologenic enzymes in cyanobacterial mutant strains as second metabolic enhancements The construction of certain vectors including the petJ promoter were done by using the following general protocol:

EcoRI/BamHI restriction of the pCB4-LR(TF)pa shuttle vector in order to cut off the pdc and adh genes. This shuttle vector was constructed by Dr. John Coleman, University of Toronto, Toronto, Canada.

ligation of the pdc/adh containing EcoRI/BamHI fragment into the cloning vector pDrive (EcoRI/BamHI). The pDrive vector (Qiagen, Hilden, Germany, GenBank no.: DQ996013) was already described above.

amplification of the petJ-promoter using chromosomal DNA from Synechocystis sp. PCC 6803 and the following primers (amplified promoter sequence include the ribosome binding site of the petJ-gene):

```
                                          (SEQ ID NO. 38)
petJ-fw-SalI  5'-GTCGACGGGAATTGCTCTGGCAAC-3'

(SEQ ID NO. 39)
petJ-rev-EcoRI  5'-GAATTCATTAGTTCTCCTTTCAAGG-3'
```

Figure 32:
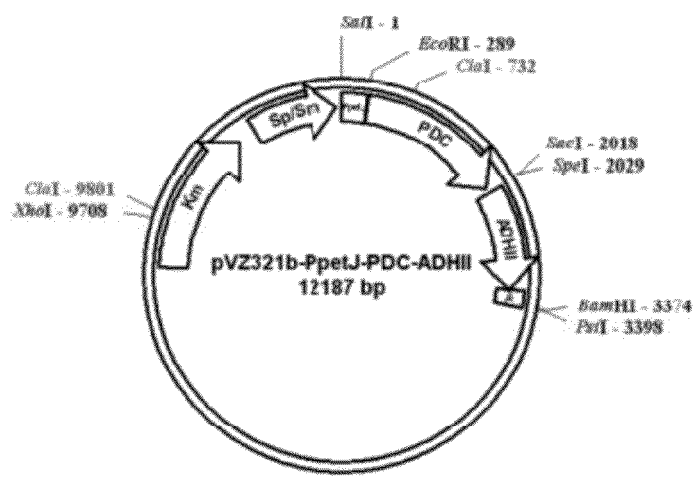

The forward primer included the SalI restriction site and the reverse primer included a EcoRI restriction site for cloning.

ligation of the SalI/EcoRI cut petJ-promoter fragment into the pDrive-pdc/adh (SalI/EcoRI) generating the construct pDrive-PpetJ-pdc/adh SalI/PstI restriction of pDrive-PpetJ-pdc/adh and ligation of the corresponding promoter-pdc/adh fusions into the self replicating broad-host range vector pVZ321b (SalI/PstI), a derivate of the pVZ321 (constructed by V. V. Zinchenko Moscow, Russia; described above) with an additional streptomycin resistance cassette/cartridge introduced into the XbaI site of pVZ321.

pVZ321 Gen Bank no.: AF100176 available in the NCBI data base on the world wide web at ncbi.nlm.nih.gov/entrez/viewer.fcgi?db=nuccore&id=4323382.

endproduct of the cloning procedure is the pVZ-vector pVZ321b-PpetJ-pdc/adh (plasmid map and sequences see FIG. 32)

Remark: In all following nt sequences of genes restriction sites (marked in yellow or blue) for clonings as well as translation starts (start codons, marked in green) and translation stops (stop codons, marked in red) are color coded.

Figure 34:
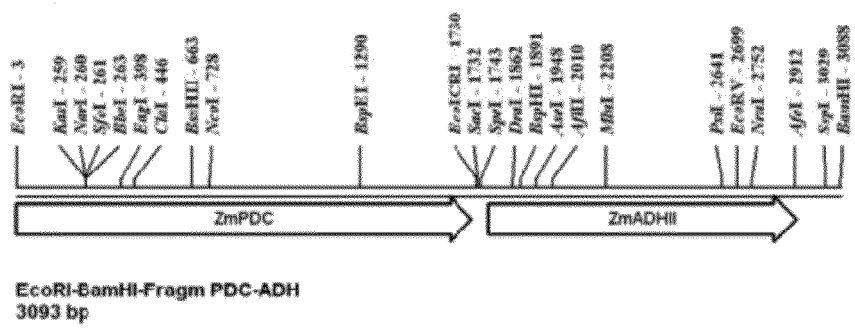

Nucleotide and amino acid sequences of adhII and pdc genes from Zymomonas mobilis (source shuttle vector pCB4-LR(TF)pa [John Coleman]; fully sequenced by Allen Place on demand of Algenol Inc. and shown in FIG. 33). The restriction sites in the AdhII and Pdc encoding genes are shown in FIG. 34.

The amino acid sequences of Zymomonas mobilis ZmPdc protein and Zymomonas mobilis ZmAdhII protein are depicted in FIGS. 35 and 36, respectively.

The nucleic acid sequence of the petJ promoter (Synechocystis sp. PCC6803) is shown in FIG. 37 (petJ gene: sll1796 (encoding for cytochrome c553); induced expression under copper starvation).

Reference:
J Biol Chem. 2004 February 20;2079(8):7229-33. Epub 2003 Dec. 5.

The efficient functioning of photosynthesis and respiration in Synechocystis sp. PCC 6803 strictly requires the presence of either cytochrome c6 or plastocyanin.

Durán R V, Hervás M, De La Rosa M A, Navarro J A.

Figure 39:
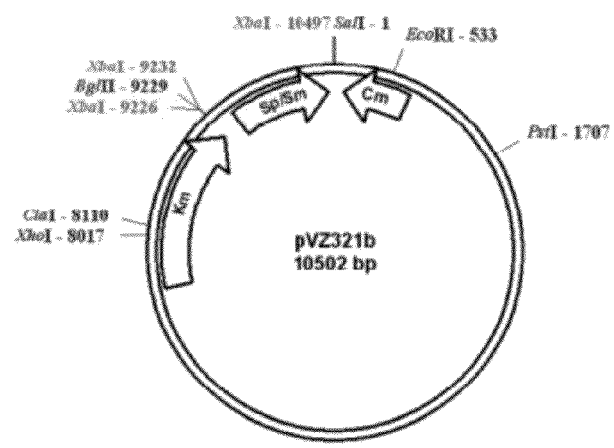

The pVZ321b vector (derivate of pVZ321) was constructed by Anne Karradt, Humboldt-University Berlin, Plant Biochemistry Department (Prof. Lockau), Berlin and has the nucleic acid sequence as depicted in FIG. 38 and the structure as shown in the plasmid map of FIG. 39.

Introduction of Adh from Synechocystis sp. PCC 6803 (SynADH)

Figure 40:
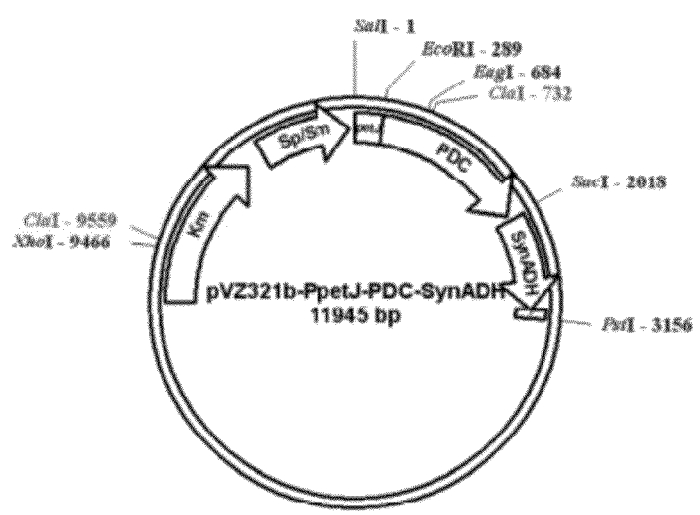

In order to create expression construct as described above but with a different alcohol dehydrogenase, the adh encoding sequence was cut out by SacI/PstI digestion of the corresponding pVZ321b-PpetJ-pdc/adh construct. The adh-gene of Synechocystis containing the restriction sites SacI/PstI that were introduced by used primer (see below) was ligated into the "adh free" pVZ construct (SacI/PstI) resulting in a derivate that expresses the ZmPdc together with SynAdh under control of the petJ-promoter (shown in FIG. 40).

```
SynADH-SacI-fw                            (SEQ ID NO. 45)
5'-ATGAGCTCTCTGGATAAAACTAATAAAC-3'

SynADH-PstI-rev                           (SEQ ID NO. 46)
5'-ATCTGCAGATCGAATGTCAAGCTTTCC-3'
```

The alcohol dehydrogenase SynAdh (Zn-dependent alcohol dehydrogenase) adh gene (slr1192) from Synechocystis sp. PCC 6803 is depicted in FIG. 41 and the corresponding amino acid sequence Syn Adh is shown in FIG. 42.

Generation of pVZ325 (introduction of Gm resistance cassette into pVZ321b)

For the ethanologenic pVZ321b constructs described above, which mediate Streptomycin (St) as well as Kanamycin (Km) resistance, a derivate was created in which the Km resistance was replaced by introduction Gentamycin (Gm) resistance cassette.

The Gm resistance cassette from pVZ322 (V. Zinchenko) was amplified by PCR using the following primer pair:

```
Gm-ClaI-fw                                (SEQ ID NO. 48)
5'-ATCGATGCTCGAATTGACATAAGC-3'

Gm-XhoI-rev                               (SEQ ID NO. 49)
5'-ACTCGAGACCGAGCTCGAATTGGC-3'
```

The resultant PCR product was ligated into the pJET1.2/blunt cloning vector (Fermentas). The Gm resistance cassette was cut out from pJET-Gm using the restriction sites ClaI and XhoI (introduced by the forward and reverse primer, respectively) and ligated into the pVZ321b-PpetJ-PDC-SynADH (ClaI/XhoI). Note: The ClaI restriction site within the PDC coding sequence is methylated by Dam-methylase system of E. coli and therefore not cleavable by ClaI restriction endonuclease.

Figure 43:
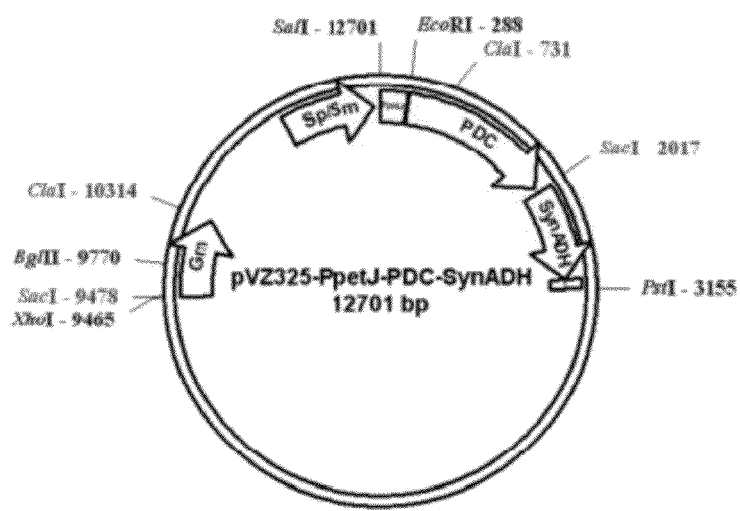

Due to the introduction of the Gm resistance cassette into the pVZ321b the Km resistance is inactivated but the resultant pVZ-derivate (pVZ325) now confers resistance against Gm as well as Streptomycin to the recipient (see FIG. 43).

6. Characterization of the mutant strains harboring at least one first metabolic enhancement regarding pyruvate levels and characterization of mutant strains additionally containing second metabolic enhancements regarding the ethanol production rate Metabolic mutant strains having a first metabolic enhancement were characterized regarding their growth properties and the extra-cellular metabolite pyruvate in comparison to wild type strains.

Metabolic mutant strains having a first metabolic enhancement and in addition also transformed with Pdc and Adh enzyme as a second metabolic enhancement were characterized regarding growth properties and ethanol production rates in comparison to the appropriate reference strain(s) expressing Pdc and Adh enzyme, but lacking the metabolic mutation (first metabolic enhancement).

6.1 Cultivation of cyanobacterial wild type and mutant strains

Wild type and mutant strains of Synechocystis PCC 6803 were grown as batch cultures in BG11 medium at 27-28° C. For cultivation of mutants the appropriate antibiotics were added to the medium (kanamycin 75 mg/l; chloramphenicol 10 mg/l; gentamycin 3 mg/l or streptomycin 10 mg/l). In order to avoid premature induction of gene expression in mutants having constructs with the PpetJ promoter, these mutants were grown in culture medium supplemented with excess copper (5×Cu).

Prior to the characterization experiments, two rounds of pre-cultures were grown in BG11 medium (no excess of Cu), aerated with 0.5% CO2 in air and stirred with a magnetic stir bar (150 rpm). In each round, the pre-culture was started at an OD750 of 0.5 and grown up to an OD750 of 2.0.

For characterization experiments, wild type and mutant strains were grown in BG11 medium. Mutants having constructs with PpetJ (overexpression or mutants expressing Pdc and Adh enzymes) were transferred to BG11 lacking Cu in order to induce gene expression. The total culture volume was 300 mL in a 500 mL Schott-Flask; the initial OD750 was 1.0. Cultures were aerated with 0.5% CO2 in air and stirred with a magnetic stir bar (150 rpm).

All mutants were characterized under constant light conditions (75-100 $\mu E\ m^{-2}\ s^{-1}$). The length of the light path through the culture for a 300 mL culture in a 500 mL Schott-Flask was 7.5 cm (diameter of the vessel; illumination took place from one side). In fast growing cultures, the light intensity was increased during the growth experiment (75-100 $\mu E\ m^{-2}\ s^{-1}$ up to OD4; then 200 $\mu E\ m^{-2}\ s^{-1}$).

6.2 Characterization of the growth properties

For characterization experiments, metabolic mutants and the appropriate reference strains were cultured as described. Growth was followed for about 14 days by measuring optical density (daily) and chlorophyll concentration (every second day). Photosynthetic $O_2$ production was determined several times during the exponential growth phase using a Clark electrode as followed:

6.3 Measurement of photosynthetic oxygen evolution and ethanol production rate (short term experiment)

Cells are washed 2× with fresh growth medium by centrifugation (3000× g, 10 min, room temperature) and resuspension. The cells are finally resuspended in growth medium to a chlorophyll concentration of 10 to 15 µg chlorophyll/ml. Chlorophyll is measured as described by N. Tandeau De Marsac and J. Houmard in: Methods in Enzymology, Vol. 169, 318-328. L. Packer, ed., Academic Press, 1988. The cells are filled into the chamber of a Rank Brothers oxygen electrode (Digital Model 10, Rank Brothers, Cambridge, England) and sodium bicarbonate is added to a final concentration of 25 mM. The thickness of the culture was 1 cm so that the length of the light path travelling through the cultures was also 1 cm.

and the rate of the photosynthetic oxygen evolution is measured for example with a chart recorder REC 112, Amersham Pharmacia Biotech connected to the electrode. The chamber of the oxygen electrode is maintained at a constant temperature (in most cases 28° C.) with a circulating, temperature-controlled water bath (RM6, Lauda Brinkmann). The chamber is translucent and illuminated from the outside. The excitation light for photosynthesis experiments is provided by a slide projector with a 150-watt lamp (Osram, Xenophot HLX Germany). For measurements under standard conditions the light intensity was adjusted to 400 $\mu E\ m^{-2}\ s^{-1}$. Light intensities at the oxygen electrode were determined and the distance between light source and the chamber of the oxygen electrode were adjusted accordingly. When the illumination is switched on, photosynthesis starts and an increase of oxygen concentration in the chamber can be observed. After a short period of time the plotted curve is linear. From the linear part of the plotted curve the rate (=photosynthetic oxygen evolution vs. time) is determined. The entire measurement of oxygen is finished after not more than 10 minutes. After completion of this measurement illumination of the sample in the chamber is continued under unchanged conditions. Over a period of one hour samples of 0.15 ml are taken in defined intervals (in most cases every 10 minutes). Immediately after removal samples are centrifuged (14,000× g, 10 min, 4° C.) and the supernatant is stored on ice. After completion of the sampling, the ethanol concentration in the supernatants is measured as described herein. The ethanol concentration versus time is plotted. Using the linear equation the rate of the increase of the ethanol content in v/v in the assay per hour is calculated. The rate of ethanol production is usually given in the dimension $\mu$mol ethanol $*h^{-1}*$ mg chlorophyll$^{-1}$, the chlorophyll content measured at the beginning of the experiment is then used.

For the calibration of the electrode the signal difference of air-saturated water (100% saturation) and oxygen free water (zero point) is measured. Oxygen free water is obtained by adding sodium dithionite (approximately 1 mg/ml). The measured amplitude is equated with the solubility of oxygen in water at 28° C. and a pressure of 1013.5 hPa (7.75 mg oxygen/L).

6.4 Determination of ethanol production

For characterization of mutants expressing PDC and ADH, ethanol was measured daily during the growth experiment according to the afore described optical enzymatic method ("Ethanol UV method" test kit by Boehringer Mannheim/R-Biopharm, Darmstadt, Germany). Ethanol production of metabolic mutants expressing PDC and ADH was compared to the appropriate reference strain expressing PDC and ADH as a second metabolic enhancement, but lacking the respective metabolic mutation, the first metabolic enhancement.

Principle of ethanol quantification:

Ethanol is oxidized by nicotinamide-adenine dinucleotide (NAD$^+$) to acetaldehyde in a reaction, which is catalyzed by the enzyme alcohol dehydrogenase (ADH) (reaction 1). The acetaldehyde, which is formed in the reaction, is quantitatively oxidized to acetic acid by the enzyme aldehyde dehydrogenase (Al-DH) (reaction 2).

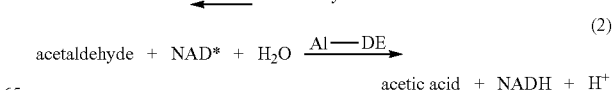

In reactions (1) and (2) reduced nicotinamide-adenine dinucleotide (NADH) is formed. The amount of NADH formed is proportionate to the amount of ethanol in the sample. NADH is easily quantified by means of its light absorbance. The absorbance is usually measured at 340 nm, Hg 365 nm or Hg 334 nm.

Procedure:

Preparation of solutions: Solution 1: 1.3 mg/ml NAD and 0.27 U aldehyde dehydrogenase in potassium diphosphate buffer, pH 9.0. Solution 2: Suspension of alcohol dehydrogenase (ADH) with approx. 4000 U/ml. Alternatively, the chemicals and solutions of the ethanol determination kit of Boehringer Mannheim/R-Biopharm (Cat. No. 10 176 290 035) can be used.

Sample and solution 1 are mixed in a ratio of 3 ml solution 1 and 0.1 ml sample (if necessary the sample is diluted with water). After approx. 3 min the absorbance is measured ($A_1$). The reaction is then started by the addition of ADH suspension (solution 2, 0.050 ml for 3 ml solution 1 and 0.1 ml sample). After completion of the reaction (approx. 5 to 10 min) the absorbance is measured again ($A_2$). The absorption measurements can be performed using a photometer or a microplate reader. For plate reader measurements all volumes are downscaled.

From the measured absorbance difference $\Delta A=(A_2-A_1)$ the ethanol concentration in the sample is calculated with the equation:

$$c = \frac{V \times MG}{\varepsilon \times d \times v \times 2 \times 1000} \times \Delta A$$

c, ethanol concentration [q/L]; V, total volume [mL]; MG, molecular weight of ethanol (46.07 g/mol); e, extinction coefficient (6.3 L×mmol$^{-1}$×cm$^{-1}$ at 340 nm); d, light path [cm]; v, sample volume [mL]

Literature:

Protocol of the kit Ethanol, UV method for the determination of ethanol in foodstuff and other materials, Cat. No. 10176290035, R-Biopharm AG, Darmstadt, Germany.

H.-O. Beutler (1984) in: Methods in Enzymatic Analysis (Bergmeyer, H. U. ed.) 3$^{rd}$ ed. Vol. VI, pp. 598-606, Verlag Chemie, Weinheim, Germany.

6.5 Determination of extracellular pyruvate

The extracellular content of pyruvate was measured at 3 times during a 14 days cultivation periode (usually at day 5, 9, 14) using the optical enzymatic test of Häusler et al. (2000), Anal. Biochem, 281:1-8.

This method allows for the quantification of pyruvate and phosphoenolpyruvate in one test.

Protocol:

Quantifications are based on the reduction of pyruvate to lactate by lactate dehydrogenase (LDH) at the expense of NADH which is oxidized to NAD+. In the first step, pyruvate was assayed. After completion of this reaction, pyruvate kinase is added. Pyruvate kinase converts phosphoenolpyruvate to pyruvate and thus allows for determination of phosphoenolpyruvate.

To 450 µl master mix (9 µl 20 mM NADH, 12 µl 1 M MgCl2, 46 µl 1 M KCl, 12 µl 100 mM ADP, 360 µl 100 mM HEPES, 10 µl H2O) 520 µl sample (if necessary diluted with H2O) are added. Two µl LDH are added to start the reaction. The oxidation of NADH is observed as a decrease of absorbance at 340 nm. Either the difference of the absorbances at 340 nm minus 380 nm is measured by difference spectroscopy (turbid or colored samples; $\varepsilon340-380=4.83$ 1×cm×mmol−1) or the absorbance at 340 nm is measured against water ($\varepsilon340=6.28$ 1×cm×mmol−1). After complete reaction of pyruvate, 2 µl pyruvate kinase are added to the assay. NADH oxidation is measured as before. From the differences of the absorbances at the start and the end of the reactions, the amount of oxidized NADH (=amount of pyruvate, and phosphoenolpyruvate, respectively) is calculated.

Chemicals and solutions:

1. Lactate dehydrogenase suspension from bovine heart (L-LDH, Sigma L2625-2.5KU, suspension with 5629.5 U/ml), diluted 1:10
2. Pyruvate Kinase from rabbit muscle (PK, Serve 34085, suspension with 4000 U/ml), diluted 1:20
3. 100 mM HEPES/NaOH (pH 7.5)
4. 1 M MgCl2
5. 100 mM ADP
6. NADH (Sigma, N6005) 20 mM in H2O
7. 1 M KCl 6.6 Characterization of the metabolic mutants overexpressing both malic enzyme and malate dehydrogenase or overexpressing either malic enzyme or malate dehydrogenase Mutants PCC6803 PetJ-me, PpetJ-mdh and PpetJ-me/mdh were examined in comparison to the *Synechocystis* wild-type strain under constant light conditions as described. Expression of me and mdh genes was induced by copper starvation.

Results:

No significant differences could be detected in cell growth, chlorophyll content and photosynthetic oxygen production between *Synechocystis* PCC6803 wild type and mutants PCC6803 PpetJ-me, PpetJ-mdh and PpetJ-me/mdh, respectively.

An enhanced extracellular pyruvate level was detected in the medium of all three mutants following induction of gene expression by copper starvation. The following table shows the extracellular pyruvate concentrations measured 7 and 14 days after induction in comparison to the wild type.

|  | 7 days | | 14 days | |
| --- | --- | --- | --- | --- |
|  | OD$_{750}$ | pyruvate [mM] | OD$_{750}$ | pyruvate [mM] |
| PCC6803 Wt | 5.5 | 0.002 | 8.9 | 0.004 |
| PpetJ-me | 4.3 | 0.005 | 8.8 | 0.032 |
| PpetJ-mdh | 5.0 | 0.006 | 9.1 | 0.030 |
| PpetJ-me-mdh | 5.2 | 0.009 | 8.3 | 0.061 |

The higher extracellular pyruvate levels measured in the induced PCC6803 PpetJ-me, PpetJ-mdh and PpetJ-me/mdh mutants (compared to wildtype) suggest that overexpression of malic enzyme or malate dehydrogenase leads to a higher pyruvate level within the cyanobacterial cells.

Mutants PCC6803 PpetJ-me/pVZ325-PpetJ-PDC-synADH, PCC6803 PpetJ-mdh/pVZ325-PpetJ-PDC-synADH and PCC6803 PpetJ-me/mdh/pVZ321b-PpetJ-PDC-ADHII expressing ethanologenic genes were examined regarding their growth properties and ethanol production rates in comparison to the reference strains PCC6803 pVZ325-PpetJ-PDC-synADH and PCC6803 pVZ321b-PpetJ-PDC-ADHII. The expression of me, mdh and the ethanologenic genes was induced by copper starvation. The cultivation conditions under constant light were as described.

Results

Mutants PCC6803 expressing me, mdh or both genes exhibited significantly higher ethanol production rates compared to the reference strains.

The following table shows the ethanol production rate relative to cell growth (given as the slope of ethanol production [%] $OD_{750\,nm}$ and day.

|  | EtOH production rate [%/$OD_{750\,nm}$ * d] |
|---|---|
| PCC6803 pVZ325-PpetJ-PDC-synADH | 0.0014 |
| PCC6803 PpetJ-me pVZ325-PpetJ-PDC-synADH | 0.0024 |
| PCC6803 pVZ321b-PpetJ-PDC-ADHII | 0.0016 |
| PCC6803 PpetJ-me-mdh pVZ321b-PpetJ-PDC-ADHII | 0.0025 |

At two consecutive days during the logarithmic growth phase, photosynthetic capacity and ethanol production was measured in the oxygen electrode as described.

In these short-term measurements photosynthetic activity is measured under optimized conditions (saturating light and carbon supply). Results represent the maximal photosynthetic capacity of cells rather than the real photosynthetic activity during cultivation.

Values are the means of two consecutive measurements.

|  | PS capacity [µmol $O_2$/ mg Chl * h] | EtOH production [µmol EtOH/ mg Chl * h] | µmol EtOH/ µmol $O_2$ |
|---|---|---|---|
| PCC6803 pVZ325-PpetJ-PDC-synADH | 141 | 3.6 | 0.025 |
| PCC6803 PpetJ-me pVZ325-PpetJ-PDC-synADH | 115 | 5.0 | 0.043 |
| PCC6803 PpetHJ-mdh pVZ325-PpetJ-PDC-synADH | 97 | 3.4 | 0.035 |

|  | PS capacity [µmol $O_2$/ mg Chl * h] | EtOH production [µmol EtOH/ mg Chl * h] | µmol EtOH/ µmol $O_2$ |
|---|---|---|---|
| PCC6803 pVZ321b-PpetJ-PDC-ADHII | 109 | 2.1 | 0.019 |
| PCC6803 PpetJ-me-mdh pVZ321b-PpetJ-PDC-ADHII | 103 | 3.1 | 0.030 |

These results clearly show that by increasing the enzymatic activity of either malic enzyme or malate dehydrogenase by overexpression or co-overexpression of both enzymes (first metabolic enhancements), the ethanol production rate of photoautotrophic host cells, in particular cyanobacterial cells can be increased compared to the respective wild-type cyanobacterial cells lacking these first metabolic enhancements.

6.7 Characterization of the metabolic mutant overexpressing both phosphoketolase and phosphoacetyltransacetylase The mutant PCC6803 pVZ-PpetJ-phk-pta was characterized regarding its growth properties and extracellular pyruvate in comparison to wild type strain *Synechocystis* PCC6803.

Results:

No significant differences could be detected in cell growth, chlorophyll content and photosynthetic oxygen production between the *Synechocystis* PCC6803 wild type and the mutant.

Excretion of pyruvate into the medium could be detected at the end of the log phase and was increased in the mutant compared to the wild type. The optical density at 750 nm ($OD_{750\,nm}$) and the concentration of pyruvate in the medium are given at two time points at the end of the log phase. These results clearly indicate that overexpression of both phosphoketolase and phosphoacetyltransacetylase as first metabolic enhancements results in an enhanced level of pyruvate, which can be used by ethanologenic enzymes (second metabolic enhancement) for enhanced ethanol production.

|  | 9 days | | 14 days | |
|---|---|---|---|---|
|  | $OD_{750\,nm}$ | pyruvate [mM] | $OD_{750\,nm}$ | pyruvate [mM] |
| PCC6803 wt | 7.85 | 0.006 | 9.52 | 0.010 |
| PCC6803 pVZ-PpetJ-phk-pta | 7.37 | 0.009 | 9.38 | 0.020 |

6.8 Characterization of the metabolic mutant overexpressing aldehyde dehydrogenase The mutant PCC6803 pVZ-PpetJ-aldh was characterized regarding its growth properties and extracellular pyruvate in comparison to wild type strain *Synechocystis* PCC6803.

Results:

No significant differences could be detected in cell growth, chlorophyll content and photosynthetic oxygen production between the *Synechocystis* PCC6803 wild type and the mutant.

Excretion of pyruvate into the medium could be detected at the end of the log phase and was increased in the mutant compared to the wild type. The optical density at 750 nm ($OD_{750\,nm}$) and the concentration of pyruvate in the medium are given at time points at the end of the log phase. These results show that an enhancement in pyruvate production can be achieved by overexpressing aldehyde dehydrogenase as a first metabolic enhancement.

|  | 9 days | | 14 days | |
|---|---|---|---|---|
|  | $OD_{750\,nm}$ | pyruvate [mM] | $OD_{750\,nm}$ | pyruvate [mM] |
| PCC6803 wt | 7.84 | 0.005 | 9.22 | 0.005 |
| PCC6803 pVZ-PpetJ-aldh | 8.14 | 0.005 | 8.50 | 0.021 |

6.9 Characterization of the metabolic triple Δack/Δpta/Δldh knock-out mutant affecting lactate dehydrogenase (ldh), acetate kinase (ack) and phosphoacetyltransacetylase (pta) as first metabolic enhancements The triple knock-out mutant Δack/Δpta/Δldh was characterized regarding its growth properties and extracellular pyruvate in comparison to wild type strain *Synechocystis* PCC6803.

Results:

No significant differences could be detected in cell growth, chlorophyll content and photosynthetic oxygen production between the *Synechocystis* PCC6803 wild type and triple knock-out mutant Δack/Δpta/Δldh.

Excretion pyruvate into the medium could be detected at the end of the log phase and was increased in the mutant compared to the wild type. The optical density at 750 nm ($OD_{750\,nm}$) and the concentration of pyruvate in the medium are given at two time points at the end of the log phase.

|  | 11 days | | 15 days | |
| --- | --- | --- | --- | --- |
|  | $OD_{750\,nm}$ | pyruvate [mM] | $OD_{750\,nm}$ | pyruvate [mM] |
| PCC6803 wt | 8.3 | 0.003 | 11.5 | 0.005 |
| Δack/Δpta/Δldh | 6.7 | 0.010 | 9.8 | 0.015 |

The scope of protection of the invention is not limited to the examples given hereinabove. The invention is embodied in each novel characteristic and each combination of characteristics, which particularly includes every combination of any features which are stated in the claims, even if this feature or this combination of features is not explicitly stated in the claims or in the examples.

We claim:

1. A metabolically enhanced photoautotrophic, ethanol producing *Synechocystis* host cell comprising:
 a. three first metabolic enhancements that reduce the enzymatic activity or affinity of endogenous host cell enzymes involved in acetate and lactate fermentation, wherein said enzymes are lactate dehydrogenase, phosphotransacetylase and acetate kinase, wherein the first metabolic enhancements comprise disrupting host cell genes that encode lactate dehydrogenase, phosphotransacetylase and acetate kinase, wherein the host cell genes are disrupted by homologous recombination, wherein the first metabolic enhancements result in biosynthesis of at least 3 times greater production of acetaldehyde, pyruvate, acetyl-CoA or precursors thereof after at least 15 days of culture compared to biosynthesis of acetaldehyde, pyruvate, acetyl-CoA or precursors thereof by the respective wild type *Synechocystis* host cell, and b. at least one second metabolic enhancement different from the three first metabolic enhancements comprising at least one overexpressed enzyme selected from the group consisting of pyruvate decarboxylase and alcohol dehydrogenase for the formation of ethanol, wherein said alcohol dehydrogenase has at least 95% sequence identity to SEQ ID NO: 42 or at least 95% sequence identity to SEQ ID NO: 48.

2. A metabolically enhanced *Synechocystis* host cell according to claim 1, wherein at least one of the gene disruptions is caused by insertion of a biocide resistance gene into the respective gene.

3. A metabolically enhanced *Synechocystis* host cell according to claim 2, wherein said gene disruption by the insertion of a biocide resistance gene into the respective gene is fully segregated.

4. A metabolically enhanced *Synechocystis* host cell according to claim 1, further comprising pyruvate decarboxylase and alcohol dehydrogenase, wherein the pyruvate decarboxylase converts pyruvate to acetaldehyde and the alcohol dehydrogenase converts the acetaldehyde to ethanol.

5. A metabolically enhanced *Synechocystis* host cell according to claim 1, wherein the only second metabolic enhancement is an overexpressed pyruvate decarboxylase from *Zymomonas mobilis*.

6. A metabolically enhanced host cell according to claim 1, further comprising at least one endogenous alcohol dehydrogenase.

7. A metabolically enhanced *Synechocystis* host cell according to claim 1, further comprising a gene encoding the at least one overexpressed enzyme selected from the group consisting of pyruvate decarboxylase and alcohol dehydrogenase for the formation of ethanol, wherein the gene encoding the at least one overexpressed enzyme for the formation of ethanol is under the transcriptional control of a promoter endogenous to the *Synechocystis* host cell.

8. A metabolically enhanced *Synechocystis* host cell according to claim 1, further comprising a gene encoding the at least one overexpressed enzyme selected from the group consisting of pyruvate decarboxylase and alcohol dehydrogenase for the formation of ethanol, wherein the gene encoding the at least one overexpressed enzyme for the formation of ethanol is under the transcriptional control of a heterologous promoter.

9. A metabolically enhanced *Synechocystis* host cell according to claim 7, wherein the gene encoding the at least one overexpressed enzyme selected from the group consisting of pyruvate decarboxylase and alcohol dehydrogenase for the formation of ethanol is under the transcriptional control of an inducible promoter.

10. A metabolically enhanced *Synechocystis* host cell according to claim 9, wherein the inducible promoter is induced under conditions of nutrient starvation, by stationary growth phase, by heat shock, by cold shock, by oxidative stress, by salt stress, by light or by darkness.

11. A metabolically enhanced *Synechocystis* host cell according to claim 9, wherein the inducible promoter is selected from the group consisting of: rbcLS, ntcA, nblA, isiA, petJ, petE, sigB, lrtA, htpG, hspA, clpB1, hliB, ggpS, psbA2, psaA, nirA and crhC.

12. A metabolically enhanced photoautotrophic, ethanol producing *Synechocystis* host cell comprising:

a. at least two first metabolic enhancements that enhance the enzymatic activity or affinity of malic enzyme and malate dehydrogenase, wherein the first metabolic enhancements comprise overexpressing malic enzyme and malate dehydrogenase, and b. at least one second metabolic enhancement different from the at least two first metabolic enhancements comprising at least one overexpressed enzyme selected from the group consisting of pyruvate decarboxylase and alcohol dehydrogenase for the formation of ethanol, wherein the first and second metabolic enhancements result in a rate of ethanol production at least 1.5 times greater than the rate of ethanol production by the respective photoautotrophic, ethanol producing host cell harboring the second metabolic enhancement but lacking the first metabolic enhancements 13. A metabolically enhanced photoautotrophic, ethanol producing *Synechocystis* host cell according to claim 12, wherein the at least one overexpressed enzyme for the formation of ethanol is a pyruvate decarboxylase from *Zymomonas mobilis*.

14. A metabolically enhanced photoautotrophic, ethanol producing *Synechocystis* host cell according to claim 12, wherein the at least one overexpressed enzyme for the formation of ethanol is an alcohol dehydrogenase from *Synechocystis*.

15. A metabolically enhanced *Synechocystis* host cell according to claim 12, wherein the at least one overexpressed enzyme for the formation of ethanol is an alcohol dehydrogenase from *Zymomonas mobilis*.

16. A metabolically enhanced *Synechocystis* host cell according to claim 13, further comprising an alcohol dehydrogenase from *Synechocystis*.

17. A metabolically enhanced *Synechocystis* host cell according to claim 13, further comprising an alcohol dehydrogenase from *Zymomonas mobilis*.

18. A method for the production of ethanol comprising the method steps of:

a. providing and culturing metabolically enhanced *Synechocystis* host cells according to claim 1 in a growth medium under the exposure of light and $CO_2$, the *Synechocystis* host cells accumulating ethanol while being cultured, and b. separating the ethanol from the *Synechocystis* host cells and/or the growth medium.

19. A method according to claim 18, wherein in method step a. *Synechocystis* host cells are provided, which comprise a metabolically enhanced gene encoding at least one overexpressed pyruvate decarboxylase or alcohol dehydrogenase for the formation of ethanol under the transcriptional control of an inducible promoter, which can be induced by exposure to an exogenous stimulus, the method step a. further comprising:

culturing the *Synechocystis* host cells under the absence of the exogenous stimulus or under a low presence of the exogenous stimulus, and thereafter providing or enhancing the exogenous stimulus, thereby inducing or enhancing ethanol production.

20. A construct for the transformation of a *Synechocystis* host cell by disrupting host genes encoding endogenous host cell enzymes involved in acetate and lactate fermentation, wherein said enzymes are lactate dehydrogenase, phosphotransacetylase and acetate kinase, comprising:
   at least one heterologous nucleic acid sequence comprising a promoter and a biocide resistance conferring gene under the transcriptional control of the promoter, wherein
   the heterologous nucleic acid sequence is flanked at its 5' and 3' ends by nucleic acid sequences, which are able to bind to at least parts of said host genes encoding lactate dehydrogenase, phosphotransacetylase and acetate kinase.

21. A construct according to claim 20, wherein the heterologous nucleic acid sequence further comprises a gene that encodes at least one overexpressed enzyme selected from the group consisting of pyruvate decarboxylase and alcohol dehydrogenase for ethanol formation.

* * * * *

UNITED STATES PATENT AND TRADEMARK OFFICE
CERTIFICATE OF CORRECTION

PATENT NO.        : 8,404,466 B2
APPLICATION NO.   : 13/372456
DATED             : March 26, 2013
INVENTOR(S)       : Kerstin Baier et al.

It is certified that error appears in the above-identified patent and that said Letters Patent is hereby corrected as shown below:

In the Specifications:

Column 22, line 45, delete "48" and insert --49--.

Column 22, line 48, delete "49" and insert --50--.

Signed and Sealed this
Twenty-first Day of May, 2013

Teresa Stanek Rea
*Acting Director of the United States Patent and Trademark Office*